US011332518B2

(12) United States Patent
Fernandez-Salas et al.

(10) Patent No.: US 11,332,518 B2
(45) Date of Patent: May 17, 2022

(54) IMMUNO-BASED BOTULINUM TOXIN SEROTYPE A ACTIVITY ASSAYS

(71) Applicant: Allergan, Inc., Irvine, CA (US)

(72) Inventors: Ester Fernandez-Salas, San Mateo, CA (US); Joanne Wang, Irvine, CA (US); Patton E. Garay, Long Beach, CA (US); Lina Wong, Irvine, CA (US); D. Dianne Hodges, Tustin, CA (US); Kei Roger Aoki, Coto De Caza, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 17/376,416

(22) Filed: Jul. 15, 2021

(65) Prior Publication Data

US 2021/0340229 A1 Nov. 4, 2021

Related U.S. Application Data

(60) Division of application No. 17/124,747, filed on Dec. 17, 2020, which is a continuation of application No. 16/920,031, filed on Jul. 2, 2020, now abandoned, which is a continuation of application No. 15/400,618, filed on Jan. 6, 2017, now Pat. No. 10,703,806, which is a division of application No. 13/649,923, filed on Oct. 11, 2012, now abandoned, which is a continuation of application No. 13/475,553, filed on May 18, 2012, now Pat. No. 9,249,216, which is a division of application No. 12/403,531, filed on Mar. 13, 2009, now Pat. No. 8,198,034.

(60) Provisional application No. 61/036,723, filed on Mar. 14, 2018.

(51) Int. Cl.
 *C07K 16/12* (2006.01)
 *G01N 33/68* (2006.01)
 *G01N 33/566* (2006.01)
 *G01N 33/50* (2006.01)
 *C12Q 1/37* (2006.01)
 *G01N 33/569* (2006.01)

(52) U.S. Cl.
 CPC ............ *C07K 16/1282* (2013.01); *C12Q 1/37* (2013.01); *G01N 33/5014* (2013.01); *G01N 33/566* (2013.01); *G01N 33/56911* (2013.01); *G01N 33/6854* (2013.01); *C07K 2317/34* (2013.01); *C07K 2317/56* (2013.01); *C07K 2317/565* (2013.01); *C07K 2317/77* (2013.01); *C07K 2317/92* (2013.01); *G01N 2333/33* (2013.01); *G01N 2333/705* (2013.01); *G01N 2333/952* (2013.01)

(58) Field of Classification Search
 None
 See application file for complete search history.

(56) References Cited

U.S. PATENT DOCUMENTS

| | | |
|---|---|---|
| 5,962,637 A | 10/1999 | Shone et al. |
| 6,043,042 A | 3/2000 | Shone et al. |
| 6,337,386 B1 | 1/2002 | Shone et al. |
| 6,673,215 B2 | 1/2004 | DeWent |
| 7,183,066 B2 | 2/2007 | Fernandez-Salas et al. |
| 7,208,285 B2 | 4/2007 | Steward et al. |
| 7,223,577 B2 | 5/2007 | Steward et al. |
| 7,332,567 B2 | 2/2008 | Steward et al. |
| 7,374,896 B2 | 5/2008 | Steward et al. |
| 7,399,607 B2 | 7/2008 | Williams et al. |
| 7,419,676 B2 | 9/2008 | Dolly et al. |
| 7,485,654 B2 | 2/2009 | Takayama |
| 7,495,069 B2 | 2/2009 | Steward et al. |
| 7,514,088 B2 | 4/2009 | Steward |
| 7,598,027 B2 | 10/2009 | Fernandez-Salas et al. |
| 7,632,655 B2 | 12/2009 | Williams |
| 7,635,574 B2 | 12/2009 | Williams |
| 7,638,294 B2 | 12/2009 | Williams |
| 7,645,570 B2 | 1/2010 | Fernandez-Salas et al. |
| 7,674,601 B2 | 3/2010 | Williams |
| 7,678,550 B1 | 3/2010 | Steward |
| 7,709,608 B2 | 5/2010 | Steward |
| 7,718,766 B2 | 5/2010 | Steward |
| 7,749,759 B2 | 7/2010 | Fernandez-Salas |
| 7,838,260 B2 | 11/2010 | Steward |
| 7,846,722 B2 | 12/2010 | Williams et al. |

(Continued)

FOREIGN PATENT DOCUMENTS

| | | |
|---|---|---|
| AU | 2011/253597 A1 | 12/2011 |
| MY | 142256 A | 11/2010 |

(Continued)

OTHER PUBLICATIONS

Rheaume et al., Toxins, 2015, 7, 2354-2370. published: Jun. 24, 2015. (Year: 2015).*

(Continued)

*Primary Examiner* — Nita M. Minnifield
(74) *Attorney, Agent, or Firm* — Foley Hoag LLP

(57) ABSTRACT

The present specification discloses SNAP-25 compositions, methods of making α-SNAP-25 antibodies that bind an epitope comprising a carboxyl-terminus at the $P_1$ residue from the BoNT/A cleavage site scissile bond from a SNAP-25 cleavage product, α-SNAP-25 antibodies that bind an epitope comprising a carboxyl-terminus at the $P_1$ residue from the BoNT/A cleavage site scissile bond from a SNAP-25 cleavage product, methods of detecting BoNT/A activity, and methods of detecting neutralizing α-BoNT/A antibodies.

30 Claims, 11 Drawing Sheets

Specification includes a Sequence Listing.

(56) References Cited

U.S. PATENT DOCUMENTS

| | | | |
|---|---|---|---|
| 7,998,749 B2 | 8/2011 | Gilmore | |
| 8,022,172 B2 | 9/2011 | Williams | |
| 8,067,231 B2 | 11/2011 | Fernandez-Salas | |
| 8,124,357 B2* | 2/2012 | Fernandez-Salas | G01N 33/5058 435/7.21 |
| 8,187,834 B2 | 5/2012 | Foster | |
| 8,198,034 B2* | 6/2012 | Fernandez-Salas | A61P 25/04 435/7.1 |
| 8,263,747 B2 | 9/2012 | Marks | |
| 8,299,218 B2 | 10/2012 | Marks | |
| 8,361,789 B2 | 1/2013 | Zhu et al. | |
| 8,455,203 B2 | 6/2013 | Wang et al. | |
| 8,455,247 B2 | 6/2013 | Zhu et al. | |
| 8,497,081 B2 | 7/2013 | Fernandez-Salas et al. | |
| 8,501,469 B2 | 8/2013 | Zhu et al. | |
| 8,507,271 B2 | 8/2013 | Zhu et al. | |
| 8,535,941 B2* | 9/2013 | Fernandez-Salas | G01N 33/5058 435/325 |
| 8,618,261 B2* | 12/2013 | Ester | G01N 33/56911 530/387.1 |
| 8,691,566 B1 | 4/2014 | Zhu et al. | |
| 8,753,831 B2* | 6/2014 | Kalkum | C07K 14/705 435/7.94 |
| 8,999,649 B2 | 4/2015 | Chapman et al. | |
| 9,180,081 B2 | 11/2015 | Dake et al. | |
| 9,211,248 B2 | 12/2015 | Dake et al. | |
| 9,249,216 B2* | 2/2016 | Fernandez-Salas | G01N 33/56911 |
| 9,625,447 B2 | 4/2017 | Zhu et al. | |
| 10,125,350 B2* | 11/2018 | Eisele | C12N 5/0619 |
| 10,345,306 B2* | 7/2019 | Wang | C12N 9/52 |
| 10,527,620 B2* | 1/2020 | Broide | C07K 16/18 |
| 10,703,806 B2* | 7/2020 | Fernandez-Salas | A61P 25/00 |
| 10,725,025 B2 | 7/2020 | Jatzke et al. | |
| 10,775,366 B2* | 9/2020 | Kalkum | G01N 33/5308 |
| 10,781,421 B2* | 9/2020 | Eisele | G01N 33/5058 |
| 10,900,955 B2* | 1/2021 | Bruenn | G01N 33/5014 |
| 10,900,967 B2* | 1/2021 | Wang | G01N 33/5014 |
| 2004/0220386 A1 | 11/2004 | Steward | |
| 2006/0252765 A1 | 11/2006 | Takayama et al. | |
| 2007/0122858 A1 | 5/2007 | Fernandez-Salas et al. | |
| 2007/0243565 A1 | 10/2007 | Williams et al. | |
| 2007/0275477 A1 | 11/2007 | Gilmore et al. | |
| 2008/0003240 A1 | 1/2008 | Fernandez-Salas et al. | |
| 2008/0064054 A1 | 3/2008 | Fernandez-Salas et al. | |
| 2008/0096248 A1 | 4/2008 | Steward | |
| 2008/0160561 A1* | 7/2008 | Fernandez-Salas | G01N 33/5058 435/29 |
| 2008/0161543 A1 | 7/2008 | Steward | |
| 2008/0166739 A1 | 7/2008 | Steward et al. | |
| 2008/0171348 A1 | 7/2008 | Steward et al. | |
| 2008/0176249 A1 | 7/2008 | Steward et al. | |
| 2008/0176336 A1 | 7/2008 | Steward et al. | |
| 2008/0182799 A1 | 7/2008 | Fernandez-Salas et al. | |
| 2008/0213796 A1 | 9/2008 | Steward et al. | |
| 2008/0220456 A1 | 9/2008 | Williams et al. | |
| 2008/0241881 A1 | 10/2008 | Steward | |
| 2008/0293084 A1 | 11/2008 | Williams et al. | |
| 2008/0293085 A1 | 11/2008 | Williams et al. | |
| 2008/0305509 A1 | 12/2008 | Williams et al. | |
| 2008/0305510 A1 | 12/2008 | Williams et al. | |
| 2009/0042231 A1 | 2/2009 | Steward et al. | |
| 2009/0053746 A1 | 2/2009 | Steward et al. | |
| 2009/0117572 A1 | 5/2009 | Fernandez-Salas et al. | |
| 2009/0191583 A1 | 7/2009 | Fernandez-Salas et al. | |
| 2009/0317839 A1 | 12/2009 | Fernandez-Salas et al. | |
| 2010/0203559 A1* | 8/2010 | Ester | G01N 33/56911 435/7.92 |
| 2010/0233741 A1 | 9/2010 | Wang et al. | |
| 2010/0233802 A1* | 9/2010 | Zhu | C12N 5/0618 435/325 |
| 2010/0280222 A1 | 11/2010 | Steward | |
| 2012/0122128 A1* | 5/2012 | Fernandez-Salas | G01N 33/6854 435/7.94 |
| 2012/0149105 A1 | 6/2012 | Zhu et al. | |
| 2012/0149106 A1 | 6/2012 | Zhu et al. | |
| 2012/0156776 A1 | 6/2012 | Zhu et al. | |
| 2012/0164728 A1 | 6/2012 | Zhu et al. | |
| 2012/0208271 A1 | 8/2012 | Zhu et al. | |
| 2012/0208272 A1 | 8/2012 | Zhu et al. | |
| 2012/0214231 A1 | 8/2012 | Zhu et al. | |
| 2012/0225426 A1* | 9/2012 | Tanner | C12Q 1/6886 435/6.11 |
| 2012/0225436 A1 | 9/2012 | Fernandez-Salas | |
| 2012/0231538 A1* | 9/2012 | Fernandez-Salas | G01N 33/542 435/325 |
| 2013/0040368 A1* | 2/2013 | Fernandez-Salas | C12Q 1/37 435/220 |
| 2013/0202636 A1 | 8/2013 | Dake et al. | |
| 2013/0236963 A1 | 9/2013 | Zhu et al. | |
| 2014/0093957 A1 | 4/2014 | Zhu et al. | |
| 2016/0114014 A1 | 4/2016 | Dake et al. | |
| 2016/0289731 A1 | 10/2016 | Eisele et al. | |
| 2017/0218334 A1 | 8/2017 | Zhu et al. | |
| 2017/0283487 A1* | 10/2017 | Fernandez-Salas | G01N 33/56911 |
| 2019/0023771 A1* | 1/2019 | Bruenn | C07K 16/1282 |
| 2020/0369749 A1* | 11/2020 | Fernandez-Salas | A61P 25/00 |
| 2020/0392212 A1* | 12/2020 | Fernandez-Salas | A61P 27/02 |
| 2021/0171614 A1* | 6/2021 | Fernandez-Salas | C12Q 1/37 |
| 2021/0172952 A1* | 6/2021 | Wang | G01N 33/573 |
| 2021/0255174 A1* | 8/2021 | Kalkum | G01N 33/573 |
| 2021/0340229 A1* | 11/2021 | Fernandez-Salas | G01N 33/56911 |

FOREIGN PATENT DOCUMENTS

| | | | | |
|---|---|---|---|---|
| WO | WO-1994/000481 A1 | 1/1994 | | |
| WO | WO-95/33850 A1 | 12/1995 | | |
| WO | WO-01060347 A2 | 8/2001 | | |
| WO | WO-2002/007773 A1 | 1/2002 | | |
| WO | WO-2003/072049 A2 | 9/2003 | | |
| WO | WO-03080672 A1 | 10/2003 | | |
| WO | WO-2005/084361 A2 | 9/2005 | | |
| WO | WO-2005/084410 A2 | 9/2005 | | |
| WO | WO-2005/120546 A2 | 12/2005 | | |
| WO | WO-2006/042149 A2 | 4/2006 | | |
| WO | WO-2006/094263 A2 | 9/2006 | | |
| WO | WO-2006/107921 A2 | 10/2006 | | |
| WO | WO-2007/059528 A2 | 5/2007 | | |
| WO | WO-2008/082885 A2 | 7/2008 | | |
| WO | WO-2008/082889 A2 | 7/2008 | | |
| WO | WO-2009/015385 A1 | 1/2009 | | |
| WO | WO-09039356 A1 | 3/2009 | | |
| WO | WO-2009/114748 A1 | 9/2009 | | |
| WO | WO-2009114748 A1 * | 9/2009 | | A61P 25/00 |
| WO | WO-2010/078242 A1 | 7/2010 | | |
| WO | WO-2010105234 A1 * | 9/2010 | | C07K 16/1282 |
| WO | WO-2010105236 A1 * | 9/2010 | | G01N 33/53 |
| WO | WO-2013108088 A1 * | 7/2013 | | A01K 97/00 |

OTHER PUBLICATIONS

Adler, et al., The Current and Scientific and Legal Status of Alternative Methods to the LD50 Test for Botulinum Neurotoxin Potency Testing, ATLA 38: 315-330 (2010).

Amersdorfer et al., "Molecular Characterization of Murine Humoral Immune Response to Botulinum Neurotoxin Type A Binding Domain as Assessed by Using Phage Antibody Libraries," Infect. Immun., 65(9): 3743-3752 (1997).

Antonucci et al., "Long-Distance Retrograde Effects of Botulinum Neurotoxin A," J Neurosci, 28(14): 3689-3696 (2008).

Bateman et al., "Gangliosides Confer Sensitivity to Botulinum Neurotoxin A," Soc Neurosci Abstr, 27(2): 1876 (2001).

(56) References Cited

OTHER PUBLICATIONS

Bendig, Mary, Humanization of Rodent Monoclonal Antibodies by CDR Grafting, A Companion to Methods in Enzymology, 1995, 83-93, 8.
Blitzer et al., "Botulinum toxin (BOTOX) for the treatment of "spastic dysphonia" as part of a trial of toxin injections for the treatment of other cranial dystonias," Laryngoscope, 96(11): 1300-1301 (1986).
Bomba-Warczak et al., "Interneuronal Transfer and Distal Action of Tetanus Toxin and Botulinum Neurotoxins of A and D in Central Neurons," Cell Rep, 16(7): 1974-1987 (2016).
Boyd, et al., "The Effect of Botulinum Neurotoxins on the Release of Insulin from the Insulinoma Cell Lines HIT-5 and RINm5F," J. Biol. Chem., 270(31): 18216-18218 (1995).
Caldas et al., "Humanization of the anti-CD18 antibody 6.7: an unexpected effect of a framework residue in binding to antigen," Mol. Immunol., 39(15): 941-952 (2003).
Campsi et al., "Cellular senescence: when bad things happen to good cells," Nat Rev Mol Cell Biol, 8(9): 729-740 (2007).
Capek et al., "Sensing the Deadliest Toxin: Technologies for Botulinum Detection," Toxins, 2: 24-53 (2010).
Casset et al. (Biochem. Biophys. Res. Common. Jul. 18, 2003; 307 (1): 198-205).
Chang et al. (Structure. Jan. 7, 2014; 22 (1): 9-21).
Chiao et al., "Monoclonal Antibody-Based Enzyme Immunoassay for Detection of Botulinum Neurotoxin Type A," Hybridoma, 27(1): 43-47 (2008).
Chien et al., "Significant structural and functional change of an antigen-binding site by a distant amino acid substitution: proposal of a structural mechanism," Proc. Natl. Acad. Sci. USA, 86(14): 5532-5536 (1989).
Coelho et al., "Spread of OnabotulinumtoxinA Afer Bladder Injection. Experimental Study Using the Distribution of Cleaved SNAP-25 as the Marker of the Toxin Action," European Urology, 61 (6): 1178-1184 (2012).
Colman, "Effects of Amino Acid Sequence Changes on Antibody-Antigen Interactions," Research Immunology, 145:33-36 (1994).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol., 169(6): 3076-3084 (2002).
Declaration of Ester Fernandez-Salas (21 pages) (2016).
Declaration of Mrs. Brünn and Dr. Fink (5 pages) (2017).
Dolimbek et al. (Mol. Immunol. Feb. 2007; 44 (5): 1029-41).
Dong et al., "SV2 Is the Protein Receptor for Botulinum Neurotoxin A," Science, 312(5773): 592-596 (2006).
Dong et al., "Using Fluorescent Sensors to Detect Botulinum Neurotoxin Activity in Vitro and in Living Cells," PNAS, 101(41): 14701-14706 (2004).
Ekong et al., "Recombinant SINAP-25 is an effective substrate for Clostridium botulinum type A toxin endopeptidase activity in vitro," Microbiology, 143: 3337-3347 (1997).
Eubanks et al., "An in vitro and in vivo disconnect uncovered through high-throughput identification of botulinum neurotoxin A antagonists," PNAS, 104(15): 2602-2607 (2007).
Extended European Search Report for EP Application No. 21156222 dated May 28, 2021.
Fernandez-Salas et al., Toxicon, (Jun. 1, 2008) vol. 51, No. Suppl. 1, pp. 3. Meeting Info.: 6th International Conference on Basic and Therapeutic Aspects of Botulinum and Tetanus Toxins. Baveno, Italy. Jun. 12-15, 2008 (Year: 2008).
Fernandez-Salas et al., "A sensitive and robust Western Blot cell-based assay to measure the activity of botulinum neurotoxin serotype A," Abstract Toxins. 51: 1-54 Abstract p. 11 (2008).
Fernandez-Salas et al., "Botulinum Neurotoxin Serotype a Specific Cell-Based Potency Assay to Replace the Mouse Bioassay," (PLoS One. 2012; 7 (11): e49516; pp. 1-13).
Fernandez-Salas et al., "Identification of FGFR3 as a putative receptor for botulinum neurotoxin type A uptake in neuronal cells," Basic and Therapeutic Aspects of Botulinum and Tetanus Toxins International Conference 2005, Abstract P76: 2 page (2005).
Fernandez-Salas et al., "Identification of the fibroblast growth factor receptor FGFR3 as a component of the receptor complex for botulinum neurotoxin type A," Basic and Therapeutic Aspects of Botulinum and Tetanus Toxins (Toxins) 2008, 51 (Suppl1): 3 ABS-6 (2008).
Fernandez-Salas et al., "Is light chain subcellular localization a factor influencing botulinum toxin duration of action?" Basic and Therapeutic Aspects of Botulinum and Tetanus Toxins International Conference 2005, Abstract S20: 1 page (2005).
Fernandez-Salas et al., "Is the Light Chain Subcellular Localization an Important Factor in Botulinum Toxin Duration of Action," Movement Disorders, 19(Suppl. 8): S23-S34 (2004).
Fernandez-Salas et al., "Plasma membrane localization signals in the light chain of botulinum neurotoxin serotype A," Society of Neuroscience Society for Neuroscience Abstract Viewer and Itinerary Planner, Abstract No. 9.2: 1 page (2003).
Fernandez-Salas et al., "Plasma Membrane Localization Signals in the Light Chain of Botulinum Neurotoxin," PNAS, 101(9): 3208-3213 (2004).
Ferreira et al. "Comparison of the Mouse Bioassay and Enzyme-Linked Immunosorbent Assay Procedures for the Detection of Type A Botulinal Toxin in Food," J. Food Prot. 67(1): 203-206 (2004).
Ferreira et al., "Detection of Botulinal Neurotoxins A, B, E, and F by Amplified Enzyme-Linked Immunosorbent Assay: Collaborative Study," Journal of AOAC International, 86(2): 314-331 (2003).
Foran et al., "Botulinum Neurotoxin C1 Cleaves Both Syntaxin and SNAP-25 in Intact and Permeabilized Chromaffin Cells: Correlation With Its Blockade of Catecholamine Release," Biochemistry, 35: 2630-2636 (1996).
Garcia-Rodriguez et al., "Molecular Evolution of Antibody Cross-Reactivity for Two Subtypes of Type A Botulinum Neurotoxin," Nature Bioltech, 25(1): 107-116 (2007).
Gaynor et al., "Presumed Activation of Herpetic Keratouveitis After Argon Laser Peripheral Iridotomy," American Journal of Ophthalmology, vol. 130, No. 5 (2000).
Gilmore et al., "A coupled FRET-fluorescence polarization assay of BoNT proteolytic activity with a fully recombinant substrate," Basic and Therapeutic Aspects of Botulinum and Tetanus Toxins International Conference 2005, Abstract P65: 2 pages (2005).
Giusti et al., "Somatic diversification of S107 from an antiphosphocholine to an anti-DNA autoantibody is due to a single base change in its heavy chain variable region," Proc. Natl. Acad. Sci. USA., 84(9): 2926-2930 (1987).
Gonelle-Gispert et al., "SNAP-25a and -25b isoforms are both expressed in insulin-secreting cells and can function in insulin secretion," Biochem. J., 339:159-165 (1999).
Grate et al., "Advances in Assays and Analytical Approaches for Botulinum-Toxin Detection," Trends in Analytical Chemistry, 29(10): 1137-1156 (2010).
Guan et al., "Regulatory Prespective on Development of Non-Animal Based Potency Assays for Assessment of BoNT Therapeutics," FDA; Oct. 2009.
Gussow et al., "Humanization of monoclonal antibodies," Methods in Enzymology, 203: 99-121 (1991).
Hakami et al., "Gaining Ground: Assays for Therapeutics Against Botulinum Neruotoxin;," Trends in Microbiology, 18(4): 164-172 (2010).
Hallis et al., "Development of novel assays for botulinum type A and B neurotoxins based on their endopeptidase activities," J. Clin. Microbiol., 34(8): 1934-1938 (1996).
Holm et al., "Functional mapping and single chain construction of the anti-cytokeratin 8 monoclonal antibody TS1," Mol. Immunol., 44(6): 1075-1084 (2007).
Huber et al., "The Intercostal NMJ Assay—A New Alternative to the Conventional LD50 Assay for the Determination of the Therapeutic Potency of Botulinum Toxin Preparations," Altern to Lab Animals, 36: 141-152 (2008).
Jones et al., "Development of Improved SNAP-25 Endopeptidase Immunoassays for Botulinum Type A and E Toxins," J. Immunol. Methods, 329: 92-101 (2008).

(56) References Cited

OTHER PUBLICATIONS

Keller et al., "Persistence of botulinum neurotoxin action in cultured spinal cord cells," FEBS Letters, 456: 137-142 (1999).
Keller et al., "Uptake of Botulinum Neurotoxin into Cultured Neurons," Biochemistry, 43: 526-532 (2004).
Klebe et al., "Neuroblastoma: Cell Culture Analysis of a Differentiating Stem Cell System," The Journal of Cell Biology, 43(2): Abstract 165 (1969).
Leese et al., "Duplication of Neuronal Binding Domains Derived From Clostridial Neurotoxins Greatly Enhances Intraneuronal Delivery of Therapeutics," Abstract Toxicon, 156: S2-S120 Abstract p. S68 (2018).
Lindstrom et al., "Laboratory Diagnostics of Botulism," Clin Microbiol Rev, 19(2): 298-314 (2006).
MacCallum et al. (J. Mol. Biol. Oct. 11, 1996; 262 (5): 732-745).
Manufacturer's specification sheet for MC-6053.
Marconi et al., "A protein-chip Membrane-Capture Assay for Botulinum Neurotoxin Activity," Toxicol. App. Pharmacol., 233(3): 439-446 (2008).
Marini et al., "SiMa, a New Neuroblastoma Cell Line Combining Poor Prognostic Cytogenetic Markers with High Adrenergic Differentiation," Cancer Genet. Cytogenet., 112(2): 161-164 (1999).
Mariuzza et al., "The Structural Basis of Antigen-Antibody Recognition," Ann. Rev. Biophys. Biophys. Chem., 16: 139-159 (1987).
Nabokina et al., "Intracellular Location of SNAP-25 in Human Neutrophils," Biochem Biophys. Res. Comm., 239: 592-597 (1997).
NIH Publication., "Workshop on Alternative Methods for Botulinum Toxin Testing," National Institutes of Health: 173 pages (2008).
Padlan et al., "Structure of an Antibody-Antigen-Complex: Crystal Structure of the HyHEL-10 Fab-Lysoyme Complex," Proc Natl Acad Sci, 86:5938-5942 (1989).
PCT, Written Opinion of the International Searching Authority (PCT/US2009/037046); dated Mar. 3, 2009.
Pellet et al., "A neuronal cell-based botulinim neurotoxin assay for highly sensitive and specific detection of neutralizing serum antibodies," FEBS Lett, 581 (25): 4803-4804 (2007).
Pellett, "Progress in Cell Based Assays for Botulinum Neurotoxin Detection," Curr Top Microbiol Immunol, 364: 257-285 (2013).
Pier et al., "Botulinum Neurotoxin subtype A2 enters neuronal cells faster than subtype A1," FEBS Letters, 585(1): 199-206 (2011).
Pier et al., "Recombinant Holotoxoid Vaccine against Botulism." Infect Immun, 76(1): 437-442 (2007).
Purkiss et al., "Clostridium botulinum Neurotoxins Act with a Wide Range of Potencies on SH-SY5Y Human Neuroblastoma Cells," Neurotoxicology, 22:447-53 (2001).
Rasooly et al., "Development of an In Vitro Assay as an Alternative to the Mouse Bioassay for Clostridium botulinum Neurotoxin Type A," App. Environ. Microbiol., 74(14): 4309-4313 (2008).
Razai et al., "Molecular Evolution of Antibody Affinity for Sensitive Detection of Botulinum Neurotoxin Type A," J. Mol. Biol., 351:158-169 (2005).
Read Out: ECL Signals of Cleaved Snap25 Experimental Data B (2007).
Research & Diagnostic Antibodies, "Anti-SNAP-25 Monoclonal Antibody 4F3-2C1," (1 page) (2015).
Rheaume et al., "A Highly Specific Monoclonal Antibody for Botulinum Neurotoxin Type A-Cleaved SNAP25," Toxins, 7(7): 2354-2370 (2015).
Rudikoff et al., "Single amino acid substitution altering antigen-binding specificity," Proc. Natl. Acad. Sci. USA, 79: 1979-1983 (1982).
Schmidt et al., "Fluorigenic Substrates for the Protease Activites of Botulinum Neurotoxins, Serotypes A, B, and F," Applied Environmental Microbiology, 69(1): 297-303 (2003).
Schulte-Baukloh et al., "Persistence of the Synaptosomal-Associated Protein-25 Cleavage Product After Intradetrusor Botulinum Toxin A Injections in Patients with Myelomeningocele Showing an Inadequate Response to Treatment," BJU Int., 100(5):1075-1080 (2007).
Sesardic et al., "Botulinum Toxin: Applying the 3Rs to Product Potency Testing; National Centre for the Replacement," Refinement and Reduction of Animal in Research; NC3Rs #15 Botulinum Toxin; Applying the 3Rs (Mar. 2009).
Sheridan et al., "Primary cell culture for evaluation of botulinum neurotoxin antagonists," Toxicon, 45(3): 377-382 (2005).
Shimazaki et al., "Phosphorylation of 25-kDa Synaptosome-Associated Protein. Possible Involvement in Protein Kinase C-mediated Regulation of Neurotransmitter Release," J. Biol. Chem., 271(24):14548-14533 (1996).
Shone et al., "The 5th International Conference on Basic and Therapeutic Aspects of Botulinum and Tetanus Neurotoxins. Workshop Review: Assays and Detection," Neurotoxicity Research, 9(2,3): 205-216 (2006).
Stahl et al. (J. Biomol. Screen. Apr. 2007; 12 (3): 370-7).
Steward et al., "A sensitive cell-based Fluorescence Resonance Energy Transfer assay for Clostridial neurotoxins," Allergan Inc.: 1 page (2005).
Sørenson et al., "Differential Control of the Releasable Vesicle Pools by SNAP-25 Splice Variants and SNAP-23," Cell, 114(1): 75-86 (2003).
Tamura et al,, "Structural Correlates of an Anticarcinoma Antibody: Identification of Specificity-Determining Residues (SDRs) and Development of a Minimally Immunogenic Antibody Variant by Retention of SDRs Only," J Immunol,, 164:1432-1441 (2000).
U.S. Appl. No. 11/608,912, filed Dec. 11, 2006, Allergan, Inc.
U.S. Appl. No. 12/203,531, filed Mar. 13, 2009, Fernandez-Salas.
Vadakkanchery et al. (J. Neurochem. 1999; 72: 327-37).
Vajdos et al., "Comprehensive Functional Maps of the Antigen-binding Site of an Anti-ErbB2 Antibody Obtained with Shotgun Scanning Mutagenesis," J. Mol. Biol., 320(2): 415-428 (2002).
Welch et al., "Sensitivity of embryonic rat dorsal root ganglia neurons to Clostridium botulinum neurotoxins," Toxicon, 38: 245-258 (2000).
Westerink et al., "The PC12 cell as a model for neurosecretion : PC12 cells as model for neurosecretion," ACTA Physiol, 192(2): 273-285 (2008).
Western Blot: Anti-Snap25-197 Experimental Data A.
Wictome et al., "Development of an In Vitro Bioassay for Clostridium botulinum Type B Neurotoxin in Foods That Is More Sensitive than the Mouse Bioassay," Appl. Environ. Microbiol., 65(9): 3787-3792 (1999).
Williams et al., "GFP-SNAP25 fluorescence release assay of BoNT proteolytic activity," Basic and Therapeutic Aspects of Botulinum and Tetanus Toxins International Conference 2005, Abstract P67: 2 pages (2005).
Williamson et al., "Clostridial Neurotoxins and Substrate Proteolysis in Intact Neurons," J. Biol. Chem., 271(13) : 7694-7699 (1996).
Winkler et al., "Changing the Antigen Binding Specificity by Single Point Mutations of an Anti-p24 (HIV-1) Antibody," J. Immunol., 165(8): 4505-4514 (2000).
Wu et al., "Humanization of a murine monoclonal antibody by simultaneous optimization of framework and CDR residues," J. Mol. Biol., 294(1): 151-162 (1999).
Yowler et al., "Botulinum Neurotoxin A Activity Is Dependent upon the Presence of Specific Gangliosides in Neuroblastoma Cells Expressing Synaptotagmin I*," The Journal of Biological Chemistry, 277(36):32815-23819 (2002).
Yu et al. (PLoS One. 2012; 7 (3): e33340; pp. 1-15).

\* cited by examiner

FIG. 5.

IMMUNO-BASED BOTULINUM TOXIN SEROTYPE A ACTIVITY ASSAYS

This application is a divisional of U.S. patent application Ser. No. 17/124,747, filed Dec. 17, 2020, which is a continuation of U.S. patent application Ser. No. 16/920,031, filed Jul. 2, 2020, which is a continuation of U.S. patent application Ser. No. 15/400,618, filed Jan. 6, 2017, now U.S. Pat. No. 10,703,806, which is a divisional application of U.S. patent application Ser. No. 13/649,923, filed Oct. 11, 2012, now abandoned, which is a continuation of U.S. patent application Ser. No. 13/475,553, filed May 18, 2012, now U.S. Pat. No. 9,249,216, which is a divisional application of U.S. patent application Ser. No. 12/403,531, filed Mar. 13, 2009, now U.S. Pat. No. 8,198,034, which claims priority pursuant to 35 U.S.C. § 119(e) to U.S. Provisional Patent Application Ser. No. 61/036,723, filed Mar. 14, 2008, each of which is incorporated entirely herein by reference.

SEQUENCE LISTING

The application contains a Sequence Listing that has been filed electronically in the form of a text file, created Aug. 17, 2020, and named "18383-US-CIP1CON1-NTB-SubstituteSequenceListing.txt" (313573 bytes), the contents of which are incorporated herein by reference in their entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, Cosmetic and Clinical Applications of Botulinum Toxin (Slack, Inc., 2004). Clostridial toxins commercially available as pharmaceutical compositions include, BoNT/A preparations, such as, e.g., BOTOX® (Allergan, Inc., Irvine, Calif.), DYSPORT®/RELOXIN®, (Ipsen Ltd., Slough, England), PURTOX® (Mentor Corp., Santa Barbara, Calif.), XEOMIN® (Merz Pharmaceuticals, GmbH., Frankfurt, Germany), NEURONOX® (Medy-Tox, Inc., Ochang-myeon, South Korea), BTX-A (Biogen-tech Ltd., University, Yantai, Shandong, China); and BoNT/B preparations, such as, e.g., MYOBLOC®/NEUROBLOC® (Solstice Neurosciences, Inc., South San Francisco, Calif.). As an example, BOTOX® is currently approved in the U.S. for the treatment of cervical dystonia in adults to decrease the severity of abnormal head position and neck pain associated with cervical dystonia; for the treatment of severe primary axillary hyperhidrosis that is inadequately managed with topical agents; and for the treatment of strabismus and blepharospasm associated with dystonia, including benign essential blepharospasm or VII nerve disorders in patients 12 years of age and above.

At present the mouse $LD_{50}$ bioassay, a lethality test, remains the "gold standard" used by all pharmaceutical manufacturers to express the potency of their preparations. S. S. Arnon et al., JAMA 285: 1059-1070 (2001). In fact, the units on the pharmaceutical preparations' labels are mouse $LD_{50}$ units and the number of animals needed to produce statistically useful $LD_{50}$ data is large. The advantage of the mouse $LD_{50}$ bioassay is that it measures all the steps necessary for botulinum toxin uptake (e.g., toxin binding to a cell surface receptor, internalization of the toxin-receptor complex, light chain translocation into the cytoplasm, light chain cleavage of substrate), instead of merely determining the activity for only part of this intoxication process, such as, e.g., in vitro assays that only measure light chain enzymatic activity. Unfortunately, the mouse $LD_{50}$ bioassay suffers from many drawbacks including high operational cost due to the large numbers of laboratory animals required, a lack of specificity since all BoNT serotypes will cause the same measurable end-point, and the potential for inaccuracy unless large animal groups are used. In addition, animal rights groups have exerted pressure on regulatory agencies in the U.S. (FDA/NICEA™/ICCVAM) and Europe (MHRA and EDQM), and on pharmaceutical companies manufacturing botulinum neurotoxin products to reduce animal testing and more importantly replace the mouse $LD_{50}$ bioassay for product release. The regulatory agencies are engaging pharmaceutical companies to apply the three "Rs" principle to the potency testing of botulinum neurotoxins: Reduce, Refine, Replace. D. Straughan, Progress in Applying the Three Rs to the Potency Testing of Botulinum Toxin Type A, Altern. Lab. Anim. 34(3): 305-313 (2006). In recent years, several steps have been already taken to reduce and refine the mouse $LD_{50}$ bioassay in order to standardize the protocol and produce more consistent data using fewer animals per assay.

Thus, a simple, reliable, validated and governmental agency acceptable botulinum toxin activity assay that can evaluate the integrity of all the steps necessary in botulinum toxin uptake would be of significant value because such a non-animal based assay would alleviate the need for animal testing and all the disadvantages, costs and ethical concerns associated with this type of animal-based assay. The present specification provides novel compositions, cells, and methods for assaying the activity of a botulinum toxin A useful for various industries, such as, e.g., the pharmaceutical and food industries, and provides related advantages as well. Such compositions, cells, and methods do not use live animals or tissues taken from live animals, but can evaluate all the steps necessary for neurotoxin action.

DETAILED DESCRIPTION OF THE DRAWINGS

FIGS. 1A-1B are schematics of the current paradigm of neurotransmitter release and Clostridial toxin intoxication in a central and peripheral neuron. FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed. FIG. 1B shows a schematic of the intoxication mechanism for tetanus and botulinum toxin activity in a central and peripheral neuron. This intoxication process can be described as comprising four steps: 1) receptor binding, where Clostridial toxin binds to a Clostridial receptor complex and initiates the intoxication process; 2) complex internalization, where after toxin binding, a vesicle containing a toxin/receptor system complex is endocytosed into the cell; 3) light chain translocation, where multiple events are thought to occur, including changes in the internal pH of the vesicle, formation of a channel pore comprising the $H_N$ domain of Clostridial toxin heavy chain, separation of the Clostridial toxin light chain from the heavy chain, and release of the light chain and 4) enzymatic target modification, where the light chain of Clostridial toxin proteolytically cleaves its target SNARE substrates, such as, e.g., SNAP-25, VAMP or Syntaxin, thereby preventing vesicle docking and neurotransmitter release.

FIGS. 2A-2B show a comparison of BoNT/A uptake in four cell lines by Western blot analysis. FIG. 2A shows a graph of SNAP-25 cleavage product detected based on amount of BoNT/A used to treat the cell line. The data were analyzed in SigmaPlot using a 4 parameter logistic model and $EC_{50}$ values were obtained for each cell line. Ranking of SNAP-25 cleavage product signals detected was: SiMa>>Neuro-2a>LA1-55n>PC12. FIG. 2B shows the signal-to-noise ratios of the raw signals at 300 pM vs. 0 pM and 1.2 pM vs. 0 pM were calculated for the assay. SiMa cells generated the highest signal-to-noise ratios and the lowest $EC_{50}$ values.

Figure 5:
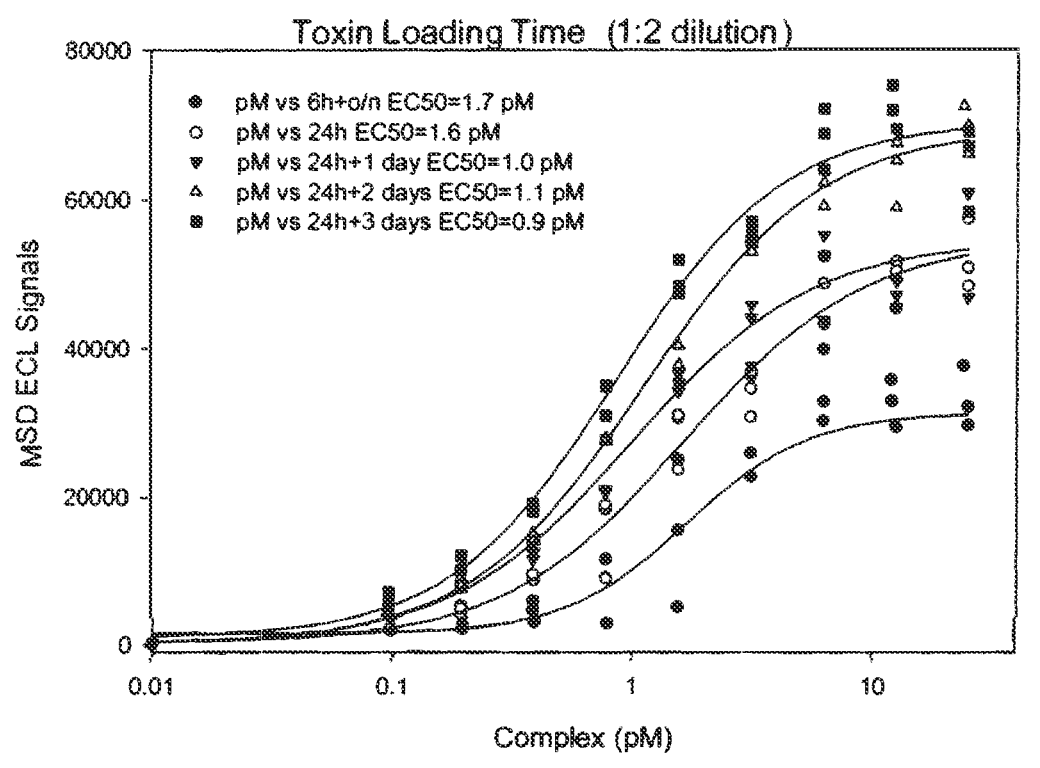

FIG. 5 shows optimization of BoNT/A treatment of cells comprising an established cell line useful in an immuno-based method of detecting BoNT/A activity disclosed in the present specification. The results indicate an $EC_{50}$ of less than 2 pM was achieved with any of the BoNT/A treatments tested.

DETAILED DESCRIPTION

Figure 1A:
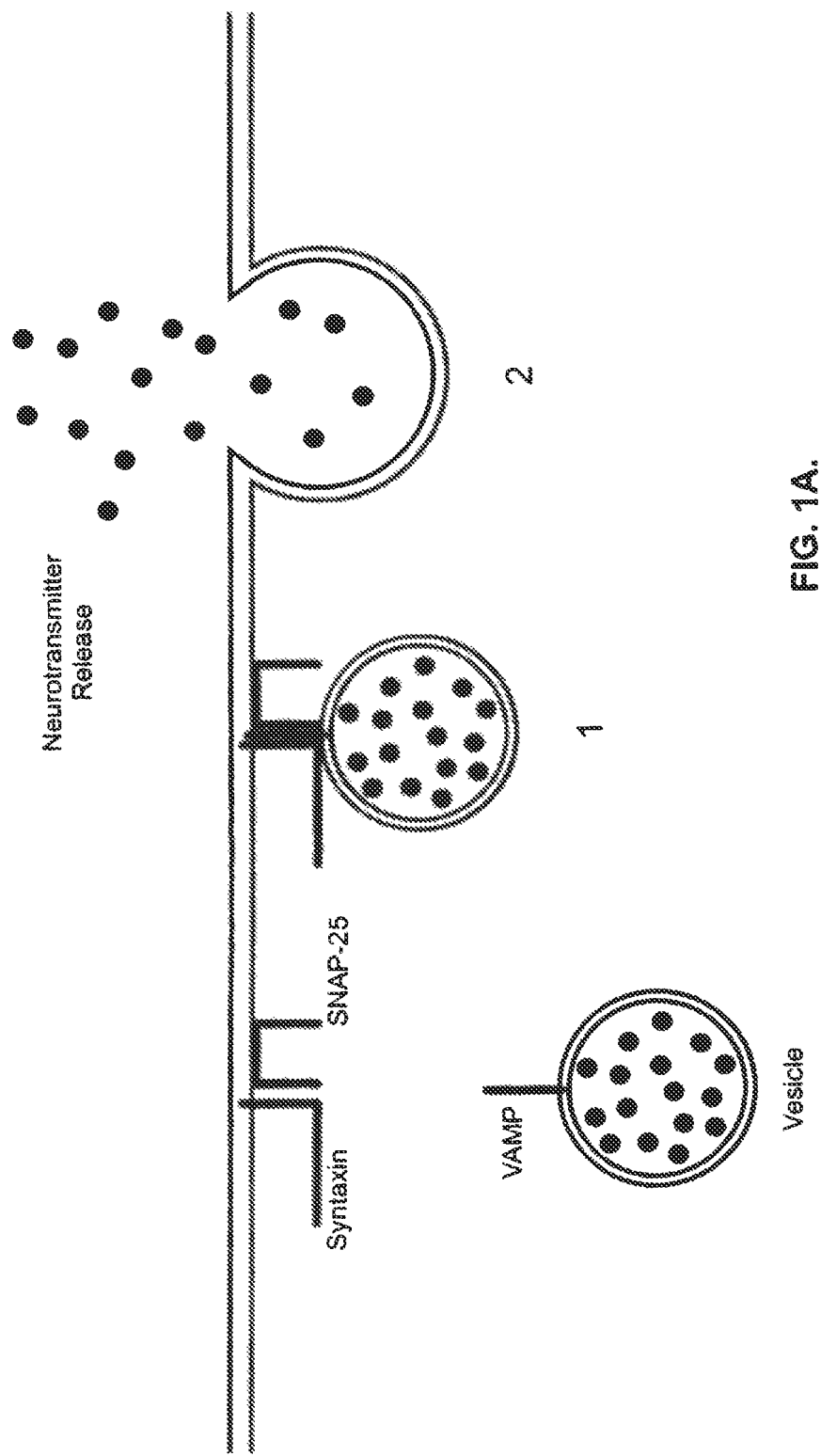

The present specification provides novel assays for determining the presence or absence of an active BoNT/A in a sample and for determining the activity/potency of a BoNT/A preparation. The novel cell-based assays disclosed in the present specification rely on cells, reagents and detection methods that enable the assay to detect picomolar quantities of BoNT/A in a sample. The cell-based assays disclosed in the present specification reduce the need for animal toxicity studies, yet serve to analyze multiple functions BoNT/A, namely, binding and cellular uptake of toxin, translocation into the cell cytosol, and protease activity. As discussed further below, the novel methods and compositions can be used to analyze crude and bulk samples as well as highly purified di-chain toxins and formulated toxin products and further are amenable to automated high throughput assay formats.

Thus, one aspect disclosed in the present specification provides compositions for producing α-SNAP-25 antibodies that can bind an epitope comprising a carboxyl-terminus at the $P_1$ residue from the BoNT/A cleavage site scissile bond from a SNAP-25 cleavage product. Compositions can comprise an adjuvant and a composition including a SNAP-25 antigen, a carrier linked to a SNAP-25 antigen, or a carrier linked to a flexible spacer linked to a SNAP-25 antigen, where the flexible linker intervenes between the SNAP-25 antigen and the carrier. It is envisioned that any and all SNAP-25 antigens that triggers an immune response that produce a α-SNAP-25 antibody that can bind an epitope comprising a carboxyl-terminus at the $P_1$ residue from the BoNT/A cleavage site scissile bond from a SNAP-25 cleavage product can be useful as a SNAP-25 antigen, including, without limitation, a SNAP-25 antigen derived from a naturally occurring SNAP-25, a SNAP-25 antigen derived from a non-naturally occurring SNAP-25, and a SNAP-25 antigen comprising an immunoreactive fragment of the SNAP-25, the SNAP-25 from a naturally occurring SNAP-25 or a non-naturally occurring SNAP-25. SNAP-25 antigens useful for producing α-SNAP-25 antibodies that can bind an epitope comprising a carboxyl-terminus at the $P_1$ residue from the BoNT/A cleavage site scissile bond from a SNAP-25 cleavage product include, without limitation, SNAP-25 antigens comprising a SNAP-25 peptide having a carboxylated C-terminal glutamine linked to a carrier peptide, including, without limitation SEQ ID NO: 38. Other compositions useful for making α-SNAP-25 antibodies that can bind an epitope comprising a carboxyl-terminus at the $P_1$ residue from the BoNT/A cleavage site scissile bond from a SNAP-25 cleavage product include, without limitation, a composition comprising a carrier linked to a flexible linker linked to a SNAP-25 antigen a carboxylated C-terminal glutamine, wherein the flexible linker intervenes between the SNAP-25 antigen and the carrier. It is envisioned that any and all adjuvants can be useful in such a composition, including, without limitation, polyethylene glycol (PEG), monomethoxypolyethylene glycol (mPEG), polyvinyl alcohol (PVA), complete and incomplete Freund's adjuvant.

Another aspect disclosed in the present specification provides methods of producing an α-SNAP-25 antibody that can bind an epitope comprising a carboxyl-terminus at the $P_1$ residue from the BoNT/A cleavage site scissile bond from a SNAP-25 cleavage product. Aspects of this method comprise the steps of (a) administering to an animal a composition disclosed in the present specification; (b) collecting from the animal a sample containing an α-SNAP-25 antibody or α-SNAP-25 antibody-producing cell; and (c) isolating the α-SNAP-25 antibody from the sample. The methods disclosed are useful for making either α-SNAP-25 monoclonal antibodies that can bind an epitope comprising a carboxyl-terminus glutamine from the BoNT/A cleavage site scissile bond from a SNAP-25 cleavage product or α-SNAP-25 polyclonal antibodies that can bind an epitope comprising a carboxyl-terminus glutamine from the BoNT/A cleavage site scissile bond from a SNAP-25 cleavage product.

Still another aspect disclosed in the present specification provides α-SNAP-25 antibodies that can bind an epitope comprising a carboxyl-terminus at the $P_1$ residue from the BoNT/A cleavage site scissile bond from a SNAP-25 cleavage product. Such α-SNAP-25 antibodies include both naturally-occurring and non-naturally-occurring antibodies, as well as, monoclonal α-SNAP-25 antibodies or polyclonal α-SNAP-25 antibodies. Monoclonal α-SNAP-25 antibodies useful as α-SNAP-25 antibodies that bind an epitope comprising a carboxyl-terminus at the $P_1$ residue from the BoNT/A cleavage site scissile bond from a SNAP-25 cleavage product, include, without limitation, the monoclonal α-SNAP-25 antibodies produced from hybridoma cell lines 1 D3B8, 2C9B10, 2E2A6, 3C1A5 and 3C3E2.

Yet another aspect disclosed in the present specification provides methods of detecting BoNT/A activity. Aspects of this method comprise the steps of (a) treating a cell from an established cell line with a sample comprising a BoNT/A, wherein the cell from an established cell line is susceptible to BoNT/A intoxication; (b) isolating from the treated cell a SNAP-25 component comprising a SNAP-25 cleavage product having a carboxyl-terminus at the $P_1$ residue of the BoNT/A cleavage site scissile bond; (c) contacting the SNAP-25 component with an α-SNAP-25 antibody that can bind an epitope comprising a carboxyl-terminus at the $P_1$ residue from the BoNT/A cleavage site scissile bond from a SNAP-25 cleavage product; and (d) detecting the presence of an antibody-antigen complex comprising the α-SNAP-25 antibody and the SNAP-25 cleavage product; wherein detection by the antibody-antigen complex is indicative of BoNT/A activity. The α-SNAP-25 antibody of step c can optionally be linked to a solid phase support.

Yet another aspect disclosed in the present specification provides methods of detecting BoNT/A activity. Aspects of this method comprise the steps of (a) treating a cell from an established cell line with a sample comprising a BoNT/A, wherein the cell from an established cell line can uptake a BoNT/A; (b) isolating from the treated cell a SNAP-25 component comprising a SNAP-25 having a carboxyl-terminus at the $P_1$ residue of the BoNT/A cleavage site scissile bond; (c) contacting the SNAP-25 component with an α-SNAP-25 antibody that can bind an epitope comprising a carboxyl-terminus at the $P_1$ residue from the BoNT/A cleavage site scissile bond from a SNAP-25 cleavage product; and (d) detecting the presence of an antibody-antigen complex comprising the α-SNAP-25 antibody and the SNAP-25 cleavage product; wherein detection by the antibody-antigen complex is indicative of BoNT/A activity. The α-SNAP-25 antibody of step c can optionally be linked to a solid phase support.

A further aspect disclosed in the present specification provides methods of determining BoNT/A immunoresistance in a mammal. Aspects of this method comprise the steps of (a) adding a BoNT/A to a test sample obtained from a mammal being tested for the presence or absence of α-BoNT/A neutralizing antibodies; (b) treating a cell from an established cell line with the test sample, wherein the cell from an established cell line is susceptible to BoNT/A intoxication; (c) isolating from the treated cells a SNAP-25 component comprising a SNAP-25 cleavage product having a carboxyl-terminus at the $P_1$ residue of the BoNT/A cleavage site scissile bond; (d) contacting the SNAP-25 component with an α-SNAP-25 antibody that can bind an epitope comprising a carboxyl-terminus at the $P_1$ residue from the BoNT/A cleavage site scissile bond from a SNAP-25 cleavage product; (e) detecting the presence of an antibody-antigen complex comprising the α-SNAP-25 antibody and the SNAP-25 cleavage product; (f) repeating steps a-e with a negative control sample instead of a test sample; and (g) comparing the amount of antibody-antigen complex detected in step (e) to the amount of antibody-antigen complex detected in step (f), wherein detection of a lower amount of antibody-antigen complex detected in step (e) relative to the amount of antibody-antigen complex detected in step (f) is indicative of the presence of α-BoNT/A neutralizing antibodies. The α-SNAP-25 antibody of step d can optionally be linked to a solid phase support. The control sample in step f can also include a positive control sample, in addition to the negative control sample.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct serotypes of botulinum toxins (BoNTs), which have been identified by investigating botulism outbreaks in man (BoNT/A, BoNT/B, BoNT/E and BoNT/F), animals (BoNT/C1 and BoNT/D), or isolated from soil (BoNT/G). While all seven botulinum toxin serotypes have similar structure and biological properties, each also displays heterogeneous characteristics, such as, e.g., different pharmacological properties. In contrast, tetanus toxin (TeNT) is produced by a uniform group of *C. tetani*. Two other species of Clostridia, *C. baratii* and *C. butyricum*, also produce toxins similar to BoNT/F and BoNT/E, respectively.

Clostridial toxins are each translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring protease produced in the environment. This post-translational processing yields a di-chain molecule comprising an approximately 50 kDa light chain (LC) and an approximately 100 kDa heavy chain (HC) held together by a single disulfide bond and noncovalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC($H_N$) that facilitates release of the LC from intracellular vesicles into the cytoplasm of the target cell; and 3) a binding domain found within the carboxyl-terminal half of the HC($H_C$) that determines the binding activity and binding specificity of the toxin to the receptor complex located at the surface of the target cell.

Figure 1B:
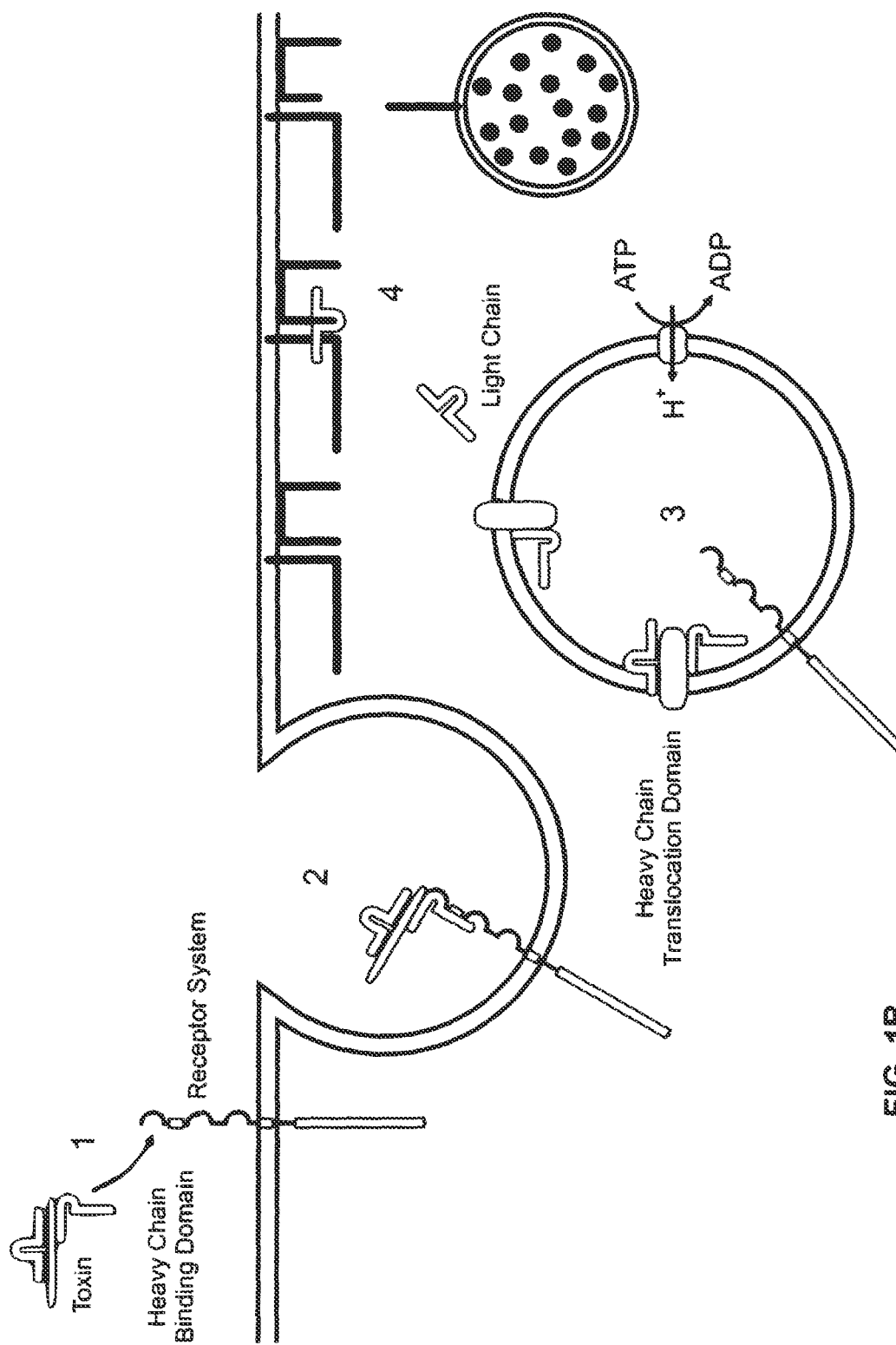

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (FIGS. 1A-1B). The process is initiated when the HC domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate important pH-dependent structural rearrangements that increase hydrophobicity, promote pore formation, and facilitate separation of the heavy and light chains of the toxin. Once separated, the light chain endopeptidase of the toxin is released from the intracellular vesicle into the cytosol where it appears to specifically target core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl terminal region, releasing a nine or twenty six amino acid fragment, respectively, and BoNT/C1 also cleaves SNAP-25 near the carboxyl terminus releasing an eight amino acid fragment. The botulinum serotypes BoNT/B, BoNT/D, BoNT/F and BoNT/G, and tetanus toxin, act on the conserved central portion of VAMP, and release the amino terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release,* 82(5) Biochimie. 427-446 (2000); Kathryn Turton et al., *Botulinum and Tetanus Neurotoxins: Structure, Function and Therapeutic Utility,* 27(11) Trends Biochem. Sci. 552-558. (2002); Giovanna Lalli et al., *The Journey of Tetanus and Botulinum Neurotoxins in Neurons,* 11(9) Trends Microbiol. 431-437, (2003).

Aspects of the present disclosure comprise, in part, a composition for producing α-SNAP-25 antibodies that can bind an epitope comprising a carboxyl-terminus at the $P_1$ residue from the BoNT/A cleavage site scissile bond from a SNAP-25 cleavage product. Other aspects of the present disclosure comprise, in part, an immune response inducing composition for producing α-SNAP-25 antibodies that can bind an epitope comprising a carboxyl-terminus at the $P_1$ residue from the BoNT/A cleavage site scissile bond from a SNAP-25 cleavage product. As used herein, the term "immune response inducing composition" refers to a composition comprising a SNAP-25 antigen which, when administered to an animal, stimulates an immune response against the SNAP-25 antigen, thereby producing α-SNAP-25 antibodies that can bind an epitope comprising a carboxyl-terminus at the $P_1$ residue from the BoNT/A cleavage site scissile bond from a SNAP-25 cleavage product. The term "immune response" refers to any response by the immune system of an animal to an immune response inducing composition. Exemplary immune responses include, but are not limited to, cellular as well as local and systemic humoral immunity, such as, e.g., CTL responses, including antigen-specific induction of CD8+ CTLs, helper T-cell responses, including T-cell proliferative responses and cytokine release, and B-cell responses including, e.g., an antibody producing response. The term "inducing an immune response" refers to administration of an immune response inducing composition or a polynucleotide encoding the immune response inducing composition, where an immune response is affected, i.e., stimulated, initiated or induced.

A composition comprises a SNAP-25 antigen. As used herein, the term "antigen" refers to a molecule that elicits an immune response and includes, without limitation, peptides, polysaccharides and conjugates of lipids, such as, e.g., lipoproteins and glycolipids. As used herein, the term "SNAP-25 antigen" refers to any antigen which has a carboxyl-terminus at the $P_1$ residue of the BoNT/A cleavage site scissile bond that can elicit an immune response. A SNAP-25 antigen used in an immune response inducing composition must be large enough to be substantially unique in sequence, thus reducing the possibility of producing antibodies that are cross reactive against antigens other than SNAP-25. In addition, a SNAP-25 antigen used in an immune response inducing composition must be small enough to only trigger an immune response substantially against a SNAP-25 having a carboxyl-terminus at the $P_1$ residue of the BoNT/A cleavage site scissile bond, thus increasing the possibility of producing α-SNAP-25 antibodies that can distinguish a SNAP-25 having a carboxyl-terminus at the $P_1$ residue of the BoNT/A cleavage site scissile bond from a SNAP-25 lacking a carboxyl-terminus at the $P_1$ residue of the BoNT/A cleavage site scissile bond. Furthermore, it is also very desirable to generate α-SNAP-25 antibodies of a single amino acid sequence in a good yield that are reproducibly selective and which bind with acceptable avidity in order to permit the design of a highly sensitive assay.

The sequence surrounding a BoNT/A cleavage site present in SNAP-25 is denoted as $P_5\text{-}P_4\text{-}P_3\text{-}P_2\text{-}P_1\text{-}P_1'\text{-}P_2'\text{-}P_3'\text{-}P_4'\text{-}P_5'$, with $P_1\text{-}P_1'$ representing the scissile bond. Upon cleavage by BoNT/A, the resulting cleavage products produced comprise a fragment including the $P_5\text{-}P_4\text{-}P_3\text{-}P_2\text{-}P_1$ sequence and a fragment including the $P_1'\text{-}P_2'\text{-}P_3'\text{-}P_4'\text{-}P_5'$. Thus, as used herein, the term "SNAP-25 having a carboxyl-terminus at the $P_1$ residue of the BoNT/A cleavage site scissile bond" refers to any SNAP-25 having the $P_1$ residue as its carboxyl-terminal amino acid. For example, $Q_{197}\text{-}R_{198}$ of human SNAP-25 (SEQ ID NO: 5) represents the $P_1\text{-}P_1'$ scissile bond for the BoNT/A cleavage site. As such, "SNAP-25 having a carboxyl-terminus glutamine of the BoNT/A cleavage site scissile bond" would be any SNAP-25 cleavage product having a glutamine at its carboxyl-terminal amino acid where the glutamine represents $Q_{197}$ of the scissile bond. As another example, $K_{204}\text{-}H_{205}$ of Torpedo marmorata SNAP-25 (SEQ ID NO: 16) represents the $P_1\text{-}P_1'$ scissile bond for the BoNT/A cleavage site. As such, "SNAP-25 having a carboxyl-terminus lysine of the BoNT/A cleavage site scissile bond" would be any SNAP-25 cleavage product having a lysine at its carboxyl-terminal amino acid where the lysine represents $K_{204}$ of the scissile bond.

The SNAP-25 antigen having a carboxyl-terminus at the $P_1$ residue of the BoNT/A cleavage site scissile bond from the BoNT/A cleavage site can be modified to enhance the immunogenicity of a SNAP-25 antigen, a hapten, or any other antigenic compound that is immunogenic, non-immunogenic, or weakly immunogenic when not associated with the modification. In an aspect of this embodiment, the carboxyl-terminal $P_1$ residue from the scissile bond of a SNAP-25 antigen can be carboxylated. Carboxylation increases the desired immunogenic properties of a SNAP-25 antigen in two respects. First, because charged amino acids enhance immunogenicity, adding a $COO^-$ group to the carboxyl-terminal residue will increase the overall immunogenicity of a SNAP-25 antigen. Second, because the $P_1$ residue of the BoNT/A cleavage site scissile bond is in a charged state upon cleavage, adding a $COO^-$ group to the carboxyl-terminal residue will better mimic the actual antigen that the α-SNAP-25 antibodies disclosed in the present specification are designed to bind.

In an aspect of this embodiment, the amino-terminal residue from a SNAP-25 antigen can be modified by the addition of an amino acid adapted to attach the SNAP-25 antigen to a carrier protein, such as, e.g., a keyhole limpet hemocyanin (KLH), an ovalbumin (OVA), a thyroglobulin (THY), a bovine serum albumin (BSA), a soybean trypsin inhibitor (STI), or a multiple attachment peptide (MAP). For example, a cysteine residue can be placed at the amino-terminus in order to conjugate the carrier protein KLH.

Thus, an embodiment, a SNAP-25 antigen having a carboxyl-terminus at the $P_1$ residue of the BoNT/A cleavage site scissile bond can be, e.g., at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30 amino acids in length. In another embodiment, a SNAP-25 antigen having a carboxyl-terminus at the $P_1$ residue of the BoNT/A cleavage site scissile bond can be, e.g., at most 5, at most 6, at most 7, at most 8, at most 9, at most 10, at most 11, at most 12, at most 13, at most 14, at most 15, at most 16, at most 17, at most 18, at most 19, at most 20, at most 25, or at most 30 amino acids in length. In still another embodiment, a SNAP-25 antigen having a carboxyl-terminus at the $P_1$ residue of the BoNT/A cleavage site scissile bond can be, e.g., between 7-12 amino acids, between 10-15 amino acids, or between 13-18 amino acids.

In another embodiment, the SNAP-25 antigen having a carboxyl-terminus at the $P_1$ residue of the BoNT/A cleavage site scissile bond comprises SEQ ID NO: 32. In aspects of this embodiment, the SNAP-25 antigen having a carboxyl-terminus at the $P_1$ residue of the BoNT/A cleavage site scissile bond comprises SEQ ID NO: 33, SEQ ID NO: 34, SEQ ID NO: 35, SEQ ID NO: 36, SEQ ID NO: 37, SEQ ID NO: 147 or SEQ ID NO: 148. In a further embodiment, the SNAP-25 antigen having a carboxyl-terminus at the $P_1$ residue of the BoNT/A cleavage site scissile bond comprises SEQ ID NO: 38.

In yet another embodiment, the SNAP-25 antigen having a carboxyl-terminus at the $P_1$ residue of the BoNT/A cleavage site scissile bond comprises SEQ ID NO: 39. In aspects of this embodiment, the SNAP-25 antigen having a carboxyl-terminus at the $P_1$ residue of the BoNT/A cleavage site scissile bond comprises SEQ ID NO: 40, SEQ ID NO: 41, SEQ ID NO: 42, SEQ ID NO: 43 or SEQ ID NO: 44. In a further embodiment, the SNAP-25 antigen having a carboxyl-terminus at the $P_1$ residue of the BoNT/A cleavage site scissile bond comprises SEQ ID NO: 45.

It is envisioned that any and all SNAP-25 antigens that triggers an immune response that produces α-SNAP-25 antibodies that bind an epitope comprising a carboxyl-terminus at the $P_1$ residue from the BoNT/A cleavage site scissile bond from a SNAP-25 cleavage product can be useful as a SNAP-25 antigen. Thus, amino acid sequence variants comprising SEQ ID NO: 32, SEQ ID NO: 33, SEQ ID NO: 34, SEQ ID NO: 35, SEQ ID NO: 36, SEQ ID NO: 37, SEQ ID NO: 39, SEQ ID NO: 40, SEQ ID NO: 41, SEQ ID NO: 42, SEQ ID NO: 43, SEQ ID NO: 44, SEQ ID NO: 147 or SEQ ID NO: 148 can be useful as a SNAP-25 antigen to trigger an immune response that produces α-SNAP-25 antibodies that bind an epitope comprising a carboxyl-terminus at the $P_1$ residue from the BoNT/A cleavage site scissile bond from a SNAP-25 cleavage product. Thus, in an embodiment, a SNAP-25 antigen can substitute at least 1, at least 2, at least 3, at least 4, or at least 5 amino acid substitutions, deletions or additions to the SNAP-25 antigens comprising SEQ ID NO: 32, SEQ ID NO: 33, SEQ ID NO: 34, SEQ ID NO: 35, SEQ ID NO: 36, SEQ ID NO: 37, SEQ ID NO: 39, SEQ ID NO: 40, SEQ ID NO: 41, SEQ ID NO: 42, SEQ ID NO: 43, SEQ ID NO: 44, SEQ ID NO: 147 or SEQ ID NO: 148. In still another embodiment, a SNAP-25 antigen can have at least 70%, at least 75%, at least 80%, at least 85%, at least 90%, or at least 95% amino acid identity to the SNAP-25 antigens comprising SEQ ID NO: 32, SEQ ID NO: 33, SEQ ID NO: 34, SEQ ID NO: 35, SEQ ID NO: 36, SEQ ID NO: 37, SEQ ID NO: 39, SEQ ID NO: 40, SEQ ID NO: 41, SEQ ID NO: 42, SEQ ID NO: 43, SEQ ID NO: 44, SEQ ID NO: 147 or SEQ ID NO: 148.

It is envisioned that one or more carriers may be linked to a SNAP-25 antigen in order to enhance the immunogenicity of a SNAP-25 antigen that is immunogenic, non-immunogenic, or weakly immunogenic when not associated with the carrier. Non-limiting examples, include, e.g., a keyhole limpet hemocyanin (KLH), an ovalbumin (OVA), a thyroglobulin (THY), a bovine serum albumin (BSA), a soybean trypsin inhibitor (STI), or a multiple attachment peptide (MAP). As is well known in the art, a non-antigenic or weakly antigenic antigen can be made antigenic by coupling the antigen to a carrier. Various other carrier and methods for coupling an antigen to a carrier are well known in the art. See, e.g., Harlow and Lane, supra, 1998a; Harlow and Lane, supra, 1998b; and David W. Waggoner, Jr. et al., Immunogenicity-enhancing carriers and compositions thereof and methods of using the same, U.S. Patent Publication No. 20040057958 (Mar. 25, 2004). An epitope can also be generated by expressing the epitope as a fusion protein. Methods for expressing polypeptide fusions are well known to those skilled in the art as described, for example, in Ausubel et al., Current Protocols in Molecular Biology (Supplement 47), John Wiley & Sons, New York (1999). As the carboxyl-terminal end of the SNAP-25 antigen must be the $P_1$ residue of the BoNT/A cleavage site scissile bond, a carrier must be linked to the amino end of the SNAP-25 antigen.

It is envisioned that one or more flexible spacers may be linked to a SNAP-25 antigen in order to enhance the immunogenicity of a SNAP-25 antigen that is immunogenic, non-immunogenic, or weakly immunogenic when not associated with the flexible linkers. A flexible spacer increases the overall peptide length of the SNAP-25 antigen and provides flexibility, thereby facilitating the proper presentation of the SNAP-25 antigen to the immune cells. As a non-limiting example, a composition can comprise a SNAP-25 antigen linked to one or more flexible spacers in tandem to better present SNAP-25 antigen to immune cells, thereby facilitating the immune response.

A flexible space comprising a peptide is at least one amino acid in length and comprises non-charged amino acids with small side-chain R groups, such as, e.g., glycine, alanine, valine, leucine or serine. Thus, in an embodiment a flexible spacer can be, e.g., at least 1, at least 2, at least 3, at least 4, at least 5, at least 6, at least 7, at least 8, at least 9, or at least 10 amino acids in length. In another embodiment, a flexible spacer can be, e.g., at least 1, at most 2, at most 3, at most 4, at most 5, at most 6, at most 7, at most 8, at most 9, or at most 10 amino acids in length. In still another embodiment, a flexible spacer can be, e.g., between 1-3 amino acids, between 2-4 amino acids, between 3-5 amino acids, between 4-6 amino acids, or between 5-7 amino acids. Non-limiting examples of a flexible spacer include, e.g., a G-spacers such as GGG, GGGG (SEQ ID NO: 55), and GGGGS (SEQ ID NO: 56) or an A-spacers such as AAA, AAAA (SEQ ID NO: 57) and AAAAV (SEQ ID NO: 58). A flexible spacer is linked in-frame to the SNAP-25 antigen as a fusion protein.

As discussed above, a flexible spacer is used, in part, to increase the overall peptide length of the SNAP-25 antigen. For example, a 5-10 amino acid SNAP-25 antigen can have its overall length increased by linking a 3-5 amino acid flexible space to the amino-end of the SNAP-25 antigen. As another example, a 5-10 amino acid SNAP-25 antigen can have its overall length increased by linking a 4-6 amino acid flexible space to the amino-end of the SNAP-25 antigen. As another example, a 5-10 amino acid SNAP-25 antigen can have its overall length increased by linking a 7-10 amino acid flexible space to the amino-end of the SNAP-25 antigen. As another example, a 7-12 amino acid SNAP-25 antigen can have its overall length increased by linking a 1-3 amino acid flexible space to the amino-end of the SNAP-25 antigen. As another example, a 7-12 amino acid SNAP-25 antigen can have its overall length increased by linking a 4-6 amino acid flexible space to the amino-end of the SNAP-25 antigen. The increased length provided by the flexible spacer allows for the selection of a small sized SNAP-25 antigen, thereby increasing the likelihood that the SNAP-25 antigen will only trigger an immune response substantially against a SNAP-25 having a carboxyl-terminus at the $P_1$ residue of the BoNT/A cleavage site scissile bond, thus increasing the possibility of producing α-SNAP-25 antibodies that can distinguish a SNAP-25 having a carboxyl-terminus at the $P_1$ residue of the BoNT/A cleavage site scissile bond from a SNAP-25 lacking a carboxyl-terminus at the $P_1$ residue of the BoNT/A cleavage site scissile bond.

It is envisioned that compositions disclosed in the present specification can optionally comprise a SNAP-25 antigen disclosed in the present specification and one or more adjuvants. As used herein, the term "adjuvant" when used in reference to a SNAP-25 composition refers to any substance or mixture of substances that increases or diversifies the immune response to a SNAP-25 antigen. An adjuvant can, for example, serve to reduce the number of immunizations or the amount of antigen required for protective immunization. The use of adjuvants in an immune response inducing composition is well known. The main objective of these adjuvants is to allow an increase in the immune response. Non-limiting adjuvants include, e.g., liposomes, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide ($Al(OH)_3$) is a commonly used adjuvant. Currently, the only FDA-approved adjuvant for use in humans is aluminum salts (Alum) which are used to "depot" antigens by precipitation of the antigens. Adjuvants provided above are merely exemplary. In fact, any adjuvant may be used in a SNAP-25 composition disclosed in the present specification as long as the adjuvant satisfies the requisite characteristics for inducing an immune response.

A carrier disclosed in the present specification may also act as an adjuvant. Specific adjuvants and methods of making and using are described in, e.g., Gupta et al. Vaccine, 11: 993-306, 1993; Arnon, R. (Ed.) Synthetic Vaccines 1:83-92, CRC Press, Inc., Boca Raton, Fla., 1987; and David W. Waggoner, Jr. et al., Immunogenicity-Enhancing Carriers and Compositions Thereof and Methods of Using the Same, U.S. Patent Publication No. 20040057958 (Mar. 25, 2004). Additional adjuvants include any compound described in Chapter 7 (pp 141-227) of "Vaccine Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the antigenic compound into the cytoplasm of a cell such as listeriolysin, streptolysin or a mixture thereof.

Thus, in an embodiment, a SNAP-25 composition comprises a SNAP-25 antigen having a carboxylated carboxyl-terminal glutamine linked to a carrier peptide. In aspects of this embodiment, a SNAP-25 antigen having a carboxylated carboxyl-terminal glutamine comprises SEQ ID NO: 32, SEQ ID NO: 33, SEQ ID NO: 34, SEQ ID NO: 35, SEQ ID NO: 36, SEQ ID NO: 37, SEQ ID NO: 147 or SEQ ID NO: 148. In another aspect of this embodiment, a SNAP-25 antigen comprises SEQ ID NO: 38. In aspects of this embodiment, the carrier peptide is a keyhole limpet hemocyanin (KLH), an ovalbumin (OVA), a thyroglobulin (THY), a bovine serum albumin (BSA), a soybean trypsin inhibitor (STI) or a multiple attachment peptide (MAP).

In another embodiment, a SNAP-25 composition comprises a SNAP-25 antigen having a carboxylated carboxyl-terminal lysine linked to a carrier peptide. In aspects of this embodiment, SNAP-25 antigen having a carboxylated carboxyl-terminal lysine comprises SEQ ID NO: 39, SEQ ID NO: 40, SEQ ID NO: 41, SEQ ID NO: 42, SEQ ID NO: 43 or SEQ ID NO: 44. In another aspect of this embodiment, a SNAP-25 antigen comprises SEQ ID NO: 45. In aspects of this embodiment, the carrier peptide is a keyhole limpet hemocyanin (KLH), an ovalbumin (OVA), a thyroglobulin (THY), a bovine serum albumin (BSA), a soybean trypsin inhibitor (STI) or a multiple attachment peptide (MAP).

In yet another embodiment, a SNAP-25 composition comprises a SNAP-25 antigen having a carboxylated C-terminal glutamine linked to one or more flexible linkers and a carrier peptide wherein the flexible linkers intervene between the SNAP-25 antigen and the carrier peptide. In aspects of this embodiment, SNAP-25 antigen having a carboxylated carboxyl-terminal glutamine comprises SEQ ID NO: 32, SEQ ID NO: 33, SEQ ID NO: 34, SEQ ID NO: 35, SEQ ID NO: 36, SEQ ID NO: 37, SEQ ID NO: 147 or SEQ ID NO: 148. In another embodiment, a SNAP-25 antigen comprises SEQ ID NO: 46. In aspects of this embodiment, the carrier peptide is a keyhole limpet hemocyanin (KLH), an ovalbumin (OVA), a thyroglobulin (THY), a bovine serum albumin (BSA), a soybean trypsin inhibitor (STI) or a multiple attachment peptide (MAP). In aspects of this embodiment, the flexible linker is a G-spacer or an A-spacer.

In still another embodiment, a SNAP-25 composition comprises a SNAP-25 antigen having a carboxylated C-terminal lysine linked to a flexible linker and a carrier peptide wherein the flexible linker intervenes between the SNAP-25 antigen and the carrier peptide. In aspects of this embodiment, SNAP-25 antigen having a carboxylated carboxyl-terminal lysine comprises SEQ ID NO: 39, SEQ ID NO: 40, SEQ ID NO: 41, SEQ ID NO: 42, SEQ ID NO: 43 or SEQ ID NO: 44. In another aspect of this embodiment, a SNAP-25 antigen comprises SEQ ID NO: 47. In aspects of this embodiment, the carrier peptide is a keyhole limpet hemocyanin (KLH), an ovalbumin (OVA), a thyroglobulin (THY), a bovine serum albumin (BSA), a soybean trypsin inhibitor (STI) or a multiple attachment peptide (MAP). In aspects of this embodiment, the flexible linker is a G-spacer or an A-spacer.

Aspects of the present disclosure comprise, in part, a method for producing α-SNAP-25 antibodies that bind an epitope comprising a carboxyl-terminus at the $P_1$ residue from the BoNT/A cleavage site scissile bond from a SNAP-25 cleavage product. An α-SNAP-25 antibody that binds an epitope comprising a carboxyl-terminus at the $P_1$ residue from the BoNT/A cleavage site scissile bond from a SNAP-25 cleavage product can be produced by a wide variety of methods that are well known in the art. Specific protocols for making and using antibodies as well as detecting, and measuring antibody binding specificity, binding affinity and binding avidity are known in the art. See, e.g., ANTIBODIES: A LABORATORY MANUAL (Edward Harlow & David Lane, eds., Cold Spring Harbor Laboratory Press, 2nd ed. 1998a); and USING ANTIBODIES: A LABORATORY MANUAL: PORTABLE PROTOCOL No. I (Edward Harlow & David Lane, Cold Spring Harbor Laboratory Press, 1998b); Molecular Cloning, A Laboratory Manual, 2001; and Current Protocols in Molecular Biology, 2004; David Anderson et al., Therapeutic Polypeptides, Nucleic Acids Encoding Same, and Methods of Use, U.S. Pat. No. 7,034,132 (Apr. 25, 2005); and Beatriz M. Carreno et al., Antibodies Against CTLA4, U.S. Pat. No. 7,034,121 (Apr. 25, 2006).

As a non-limiting example, α-SNAP-25 polyclonal antibodies that bind an epitope comprising a carboxyl-terminus at the $P_1$ residue from the BoNT/A cleavage site scissile bond from a SNAP-25 cleavage product can be produced by injecting an animal, such as, e.g., a rabbit, a goat, a mouse or another mammal, with one or more injections of a composition disclosed in the present specification. As another non-limiting example, α-SNAP-25 polyclonal antibodies that bind an epitope comprising a carboxyl-terminus at the $P_1$ residue from the BoNT/A cleavage site scissile bond from a SNAP-25 cleavage product can be produced by injecting an egg, such as, e.g., a chicken egg, with one or more injections of a composition disclosed in the present specification. The antibody titer in the immunized animal can be monitored over time by standard techniques, such as with an enzyme linked immunosorbent assay (ELISA) using immobilized antigen or a cell-based activity assay. If desired, polyclonal antibodies for an α-SNAP-25 antibody that binds an epitope comprising a carboxyl-terminus at the $P_1$ residue from the BoNT/A cleavage site scissile bond from a SNAP-25 cleavage product can be isolated from the mammal (e.g., from the blood) and further purified by well known techniques, such as protein A affinity chromatography to obtain the IgG fraction, or by affinity purification against the peptide used for producing the antibodies.

As another non-limiting example, α-SNAP-25 monoclonal antibody that binds an epitope comprising a carboxyl-terminus at the $P_1$ residue from the BoNT/A cleavage site scissile bond from a SNAP-25 cleavage product can be produced using a hybridoma method. See e.g., Chapter 6 Monoclonal Antibodies, pp. 196-244, Harlow & Lane, supra, 1998a; and Chapter 7 Growing Hybridomas, pp. 245-282, Harlow & Lane, supra, 1998a; and Goding, pp. 59-103, Monoclonal Antibodies: Principles and Practice, Academic Press, (1986). In this method, a host animal, such as, e.g., a mouse, a hamster, or another appropriate host animal, is typically exposed to one or more injections of a SNAP-25 antigen disclosed in the present specification to elicit lymphocytes that produce or are capable of producing α-SNAP-25 antibodies that will specifically bind to a SNAP-25 having a carboxyl-terminus at the $P_1$ residue of the BoNT/A cleavage site scissile bond. The antibody titer in the immunized animal can be monitored over time by standard techniques, such as with an enzyme linked immunosorbent assay (ELISA) using immobilized antigen or a cell-based activity assay. Alternatively, the lymphocytes can be immunized in vitro using a suitable cell culture line. At an appropriate time after immunization, e.g., when the antibody titers are highest, antibody-producing cells are isolated from the animal. Generally, either peripheral blood lymphocytes are used, if cells of human origin are desired, or spleen cells or lymph node cells are used, if non-human mammalian sources are desired. The isolated antibody-producing cells are fused with an immortal cell line using a suitable fusing agent, such as polyethylene glycol, to form a hybridoma cell. Immortalized cell lines are usually transformed mammalian cells, particularly myeloma cells of rodent, bovine and human origin. Typically, a murine myeloma cell line is fused with splenocytes harvested from an appropriately immunized mouse to produce the hybridoma. Preferred immortal cell lines are mouse myeloma cell lines that are sensitive to culture medium containing hypoxanthine, aminopterin and thymidine (HAT). Any of a number of myeloma cell lines can be used as a fusion partner according to standard techniques, e.g., the P3-NS1/1-Ag4-1, P3-x63-Ag8.653 or Sp2/O-Ag14 myeloma lines. Hybridoma cells resulting from the fusion are then selected using HAT medium, which kills unfused and unproductively fused myeloma cells (unfused splenocytes die after several days in culture because they are not transformed). The culture medium in which the hybridoma cells are grown can then be assayed for the presence of α-SNAP-25 monoclonal antibodies that bind an epitope comprising a carboxyl-terminus at the $P_1$ residue from the BoNT/A cleavage site scissile bond from a SNAP-25 cleavage product. For example, hybridoma supernatants can be screened using α-SNAP-25 positive media in an immunoprecipitation assay, in vitro binding assay, such as, e.g., a radioimmunoassay (RIA) or an enzyme-linked immunosorbent assay (ELISA), or in a cell-based activity assay. Such techniques and assays are known in the art. See e.g., Chapter 11 Immunoprecipitation, pp. 421-470, Harlow & Lane, supra, 1998a; Chapter 12 Immunoblotting, pp. 471-510, Harlow & Lane, supra, 1998a; Chapter 14 Immunoassays, pp. 553-612, Harlow & Lane, supra, 1998a. Additional studies can then be done to determine whether the antibody is also unreactive to a SNAP-25 lacking a carboxyl-terminus at the $P_1$ residue of the BoNT/A cleavage site scissile bond. The binding affinity of an α-SNAP-25 monoclonal antibody can also be determined, e.g., by Scatchard analysis. See, e.g., Peter J. Munson and David Rodbard, Ligand: A Versatile Computerized Approach For Characterization of Ligand-Binding Systems, 107(1) Anal. Biochem. 220-239 (1980). After the desired hybridoma cells are identified, limiting dilution procedures are used to isolate clones originating from a single cell until a clonal cell line expressing the desired monoclonal antibody is obtained. Those antibodies sufficiently selective for a SNAP-25 having a carboxyl-terminus at the $P_1$ residue of the BoNT/A cleavage site scissile bond and bind with sufficiently high avidity are chosen for further characterization and study.

Another alternative for preparing an α-SNAP-25 monoclonal antibody that binds an epitope comprising a carboxyl-terminus at the $P_1$ residue from the BoNT/A cleavage site scissile bond from a SNAP-25 cleavage product is by screening a recombinant combinatorial immunoglobulin library, such as, e.g., an antibody phage display library, with a SNAP-25 peptide and isolate immunoglobulin library members that bind a SNAP-25 having a carboxyl-terminus at the $P_1$ residue of the BoNT/A cleavage site scissile bond. Kits for generating and screening phage display libraries are commercially available, such as, e.g., the Recombinant Phage Antibody System (Amersham GE Healthcare, Piscataway, N.J.); and the SurfZAP™ Phage Display Kit (Stratagene, La Jolla, Calif.). Additionally, examples of methods and reagents useful in generating and screening antibody display library can be found in, for example, Ladner et al. U.S. Pat. No. 5,223,409; Borrebaeck et al. U.S. Pat. No. 5,712,089; Griffiths et al. U.S. Pat. No. 5,885,793; Griffiths et al. U.S. Pat. No. 5,962,255; McCafferty et al. U.S. Pat. No. 5,969,108; Griffiths et al. U.S. Pat. No. 6,010,884; Jespers et al. U.S. Pat. No. 6,017,732; Borrebaeck et al. U.S. Pat. No. 6,027,930; Johnson et al. U.S. Pat. No. 6,140,471; McCafferty et al. U.S. Pat. No. 6,172,197, each of which is hereby incorporated by reference in its entirety.

Aspects of the present disclosure comprise, in part, collecting a sample containing an α-SNAP-25 antibody or α-SNAP-25 antibody-producing cells. As used herein, the term "sample containing an α-SNAP-25 antibody or α-SNAP-25 antibody-producing cell" refers to any biological matter that contains or potentially contains at least one α-SNAP-25 antibody that bind an epitope comprising a carboxyl-terminus at the $P_1$ residue from the BoNT/A cleavage site scissile bond from a SNAP-25 cleavage product. It is envisioned that any and all samples that can contain an α-SNAP-25 antibody that binds an epitope comprising a carboxyl-terminus at the $P_1$ residue from the BoNT/A cleavage site scissile bond from a SNAP-25 cleavage product can be used in this method, including, without limitation, blood, plasma, serum and lymph fluid. It is also envisioned that any cell capable of producing an α-SNAP-25 antibody that binds an epitope comprising a carboxyl-terminus at the $P_1$ residue from the BoNT/A cleavage site scissile bond from a SNAP-25 cleavage product can be used in this method, including, without limitation, a CD8 cells, a CTL cell, a helper T-cell and a B-cell. A variety of well known methods can be used for collecting from an individual a sample containing the α-SNAP-25 antibody or α-SNAP-25 antibody-producing cell, see, e.g., Harlow & Lane, supra, 1998a; and Harlow & Lane, supra, 1998b. Similarly, a variety of well known methods can be used for processing a sample to isolate an α-SNAP-25 antibody that binds an epitope comprising a carboxyl-terminus at the $P_1$ residue from the BoNT/A cleavage site scissile bond from a SNAP-25 cleavage product. A procedure for collecting a sample can be selected based on the type of antibody to be isolated. As a non-limiting example, when isolating an α-SNAP-25 polyclonal antibodies that bind an epitope comprising a carboxyl-terminus at the $P_1$ residue from the BoNT/A cleavage site scissile bond from a SNAP-25 cleavage product, an appropriate sample can be a blood sample containing such α-SNAP-25 antibodies, whereas when isolating an α-SNAP-25 monoclonal antibodies that bind an epitope comprising a carboxyl-terminus at the $P_1$ residue from the BoNT/A cleavage site scissile bond from a SNAP-25 cleavage product, an appropriate sample can be an α-SNAP-25 antibody-producing cell such as a spleen cell or hybridoma.

Aspects of the present disclosure comprise, in part, isolating an α-SNAP-25 antibody that binds an epitope comprising a carboxyl-terminus at the $P_1$ residue from the BoNT/A cleavage site scissile bond from a SNAP-25 cleavage product from the sample. Methods of isolating an such α-SNAP-25 antibodies, such as, e.g., α-SNAP-25 polyclonal antibodies that bind an epitope comprising a carboxyl-terminus at the $P_1$ residue from the BoNT/A cleavage site scissile bond from a SNAP-25 cleavage product or α-SNAP-25 monoclonal antibodies that bind an epitope comprising a carboxyl-terminus at the $P_1$ residue from the BoNT/A cleavage site scissile bond from a SNAP-25 cleavage product are well known to those skilled in the art. See, e.g., Harlow and Lane, supra, 1998a; and Harlow and Lane, supra, 1998b. For example, such α-SNAP-25 polyclonal antibodies can be isolated from the sample by well known techniques, such as, e.g., affinity chromatography using protein A or protein G, which provide primarily the IgG fraction of immune serum. Subsequently, or alternatively, a specific SNAP-25 antigen can be immobilized on a column or magnetic beads to purify the α-SNAP-25 polyclonal antibodies that bind an epitope comprising a carboxyl-terminus at the $P_1$ residue from the BoNT/A cleavage site scissile bond from a SNAP-25 cleavage product by immunoaffinity chromatography. An α-SNAP-25 monoclonal antibody that binds an epitope comprising a carboxyl-terminus at the $P_1$ residue from the BoNT/A cleavage site scissile bond from a SNAP-25 cleavage product can be isolated from the culture medium or ascites fluid by conventional immunoglobulin purification procedures such as, e.g., protein A-Sepharose, hydroxylapatite chromatography, gel electrophoresis, dialysis, or affinity chromatography.

Thus, in an embodiment, a method of producing an α-SNAP-25 antibody that binds an epitope comprising a carboxyl-terminus at the $P_1$ residue from the BoNT/A cleavage site scissile bond from a SNAP-25 cleavage product comprises the steps (a) administering to an animal a composition comprising a SNAP-25 antigen having a carboxylated C-terminal glutamine linked to a carrier peptide; (b) collecting from the animal a sample containing an α-SNAP-25 antibody or α-SNAP-25 antibody-producing cell; and (c) isolating the α-SNAP-25 antibody component from the sample. In an aspect of this embodiment, the α-SNAP-25 antibody that binds an epitope comprising a carboxyl-terminus at the $P_1$ residue from the BoNT/A cleavage site scissile bond from a SNAP-25 cleavage product is a polyclonal antibody. In another aspect of this embodiment, an α-SNAP-25 antibody that binds an epitope comprising a carboxyl-terminus at the $P_1$ residue from the BoNT/A cleavage site scissile bond from a SNAP-25 cleavage product is a monoclonal antibody. In a further aspect of this embodiment, an α-SNAP-25 monoclonal antibody that binds an epitope comprising a carboxyl-terminus at the $P_1$ residue from the BoNT/A cleavage site scissile bond from a SNAP-25 cleavage product produced is an IgG subtype. In other aspects of this embodiment, SNAP-25 composition further comprises an adjuvant, such as, e.g., polyethylene glycol (PEG), monomethoxypolyethylene glycol (mPEG), or polyvinyl alcohol (PVA).

In another embodiment, a method of producing α-SNAP-25 antibodies that bind an epitope comprising a carboxyl-terminus at the $P_1$ residue from the BoNT/A cleavage site scissile bond from a SNAP-25 cleavage product comprises the steps (a) administering to an animal a composition comprising a SNAP-25 peptide having a carboxylated C-terminal glutamine linked to a flexible linker and a carrier peptide wherein the flexible linker intervenes between the SNAP-25 peptide and the carrier peptide; (b) collecting from the animal a sample containing an α-SNAP-25 antibody or α-SNAP-25 antibody-producing cell; and (c) isolating the α-SNAP-25 antibody from the sample. In an aspect of this embodiment, the α-SNAP-25 antibodies that bind an epitope comprising a carboxyl-terminus at the $P_1$ residue from the BoNT/A cleavage site scissile bond from a SNAP-25 cleavage product is a polyclonal antibody. In another aspect of this embodiment, α-SNAP-25 antibodies that bind an epitope comprising a carboxyl-terminus at the $P_1$ residue from the BoNT/A cleavage site scissile bond from a SNAP-25 cleavage product is a monoclonal antibody. In a further aspect of this embodiment, an α-SNAP-25 monoclonal antibody that binds an epitope comprising a carboxyl-terminus at the $P_1$ residue from the BoNT/A cleavage site scissile bond from a SNAP-25 cleavage product produced in an IgG subtype. In other aspects of this embodiment, SNAP-25 composition further comprises an adjuvant, such as, e.g., polyethylene glycol (PEG), monomethoxypolyethylene glycol (mPEG), or polyvinyl alcohol (PVA).

Aspects of the present disclosure comprise, in part, an isolated α-SNAP-25 antibody that selectively binds to a SNAP-25 epitope having a carboxyl-terminus at the $P_1$ residue of the BoNT/A cleavage site scissile bond. As used herein, the term "isolated" refers to separating a molecule from its natural environment by the use of human intervention. As used herein, the term "antibody" refers to a molecule generated by an immune system that was made in response to a particular antigen that specifically binds to that antigen, and includes both naturally occurring antibodies and non-naturally occurring antibodies. As used herein, the term "α-SNAP-25" is synonymous with "anti-SNAP-25" and refers to an antibody that binds to a SNAP-25 antigen. For example, an antibody can be a polyclonal antibody, a monoclonal antibody, a dimer, a multimer, a multispecific antibody, a humanized antibody, a chimeric antibody, bi-functional antibody, a cell-associated antibody like an Ig receptor, a linear antibody, a diabody, or a minibody, so long as the fragment exhibits the desired biological activity, and single chain derivatives of the same. An antibody can be a full-length immunoglobulin molecule comprising the $V_H$ and $V_L$ domains, as well as a light chain constant domain ($C_L$) and heavy chain constant domains, $C_{H1}$, $C_{H2}$ and $C_{H3}$, or an immunologically active fragment of a full-length immunoglobulin molecule, such as, e.g., a Fab fragment, a $F(ab')_2$ fragment, a Fe fragment, a Fd fragment, a Fv fragment. An antibody can be derived from any vertebrate species (e.g., human, goat, horse, donkey, murine, rat, rabbit, or chicken), and can be of any type (e.g., IgG, IgE, IgM, IgD, and IgA), class (e.g., IgA, IgD, IgE, IgG, and IgM) or subclass (IgG1, IgG2, IgG3, IgG4, IgA1 and IgA2). For general disclosure on the structure of naturally occurring antibodies, non-naturally occurring antibodies, and antigenic compound-binding fragments thereof, see, e.g., Pluckthun in The Pharmacology of Monoclonal Antibodies, vol. 113, Rosenburg and Moore eds., Springer-Verlag, New York, pp. 269-315 (1994); Borrabeck, Antibody Engineering, 2nd ed. (Oxford University Press 1995), each of which is hereby incorporated by reference in its entirety.

Naturally-occurring antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The complete antigen-recognition and antigen-binding site is contained within the variable domains of the antibody, i.e., the Fv fragment. This fragment includes a dimer of one heavy chain variable domain ($V_H$) and one light chain variable domain ($V_L$) in tight, non-covalent association. Each domain comprises four framework regions (FR), which largely adopting a β-sheet configuration, connected by three hypervariable regions, which form loops connecting, and in some cases form part of, the β-sheet structure. Each hypervariable region comprises an amino acid sequence corresponding to a complementarity determining region (CDRs). Collectively, it the three-dimensional configuration of the six CDR regions that define an antigen-binding site on the surface of the $V_H$-$V_L$ dimmer that confers antigen-binding specificity. See e.g., Cyrus Chothia, et al., *Conformations of Immunoglobulin Hypervariable Regions*, Nature 342(6252): 877-883 (1989); Elvin A. Kabat, et al *Sequences of Proteins of Immunological Interest,* 5th Ed. Public Health Service, National Institutes of Health, Bethesda, Md. (1991), each of which is incorporated by reference in its entirety. The constant domains of the antibody are not involved directly in binding an antibody to an antigen, but exhibit various effector functions, such as participation of the antibody in antibody dependent cellular cytotoxicity.

A target antigen generally has one or more binding sites, also called epitopes, which are recognized by the CDR-formed antigen-binding site. As used herein, an "epitope" is synonymous with "antigenic determinant" and refers to the site on a target antigen, such as, e.g., a peptide, polysaccharide or lipid-containing molecule, capable of specific binding to an immunoglobulin or T-cell receptor or otherwise interacting with a molecule. Each antibody that specifically binds to a different epitope has a different structure. Thus, one antigen may have more than one corresponding antibody.

Polyclonal antibodies refer to a heterogeneous population of antibody molecules that contain at least two species of antibody capable of binding to a particular antigen. By definition, a polyclonal antibody includes two different antibodies that bind to at least two different epitopes. As used herein, the term "monoclonal antibody" or "monoclonal antibodies" refer to a substantially homogeneous population of antibody molecules that contain only one species of antibody capable of binding a particular antigen i.e., the individual antibodies comprising the population are identical except for possible naturally occurring mutations that may be present in minor amounts. By definition, a monoclonal antibody binds to a single epitope. Monoclonal antibodies are highly specific, being directed against a single antigenic site. Furthermore, in contrast to polyclonal antibodies, each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) Nature 256:495, or may be made by recombinant DNA methods (see for example: U.S. Pat. Nos. 4,816,567; 5,807,715). The monoclonal antibodies may also be isolated from phage antibody libraries using the techniques described in Clackson et al (1991) Nature, 352:624-628; Marks et al (1991) J. Mol. Biol., 222:581-597; for example.

Thus, in an embodiment, an α-SNAP-25 antibody comprises a heavy chain variable domain ($V_H$) and a light chain variable domain ($V_L$) that selectively binds to a SNAP-25 having a carboxyl-terminus at the $P_1$ residue of the BoNT/A cleavage site scissile bond. In an aspect of this embodiment, the heavy chain variable domain ($V_H$) is SEQ ID NO: 72, SEQ ID NO: 74, SEQ ID NO: 76, SEQ ID NO: 80, or SEQ ID NO: 82. In another aspect of this embodiment, the light chain variable domain ($V_L$) is SEQ ID NO: 84, SEQ ID NO: 86, SEQ ID NO: 88, SEQ ID NO: 90, or SEQ ID NO: 92.

In another embodiment, an α-SNAP-25 antibody comprises a heavy chain variable domain ($V_H$) CDR1 region, a CDR2 region, a CDR3 region, or any combination thereof that selectively binds to a SNAP-25 having a carboxyl-terminus at the $P_1$ residue of the BoNT/A cleavage site scissile bond. In an aspect of this embodiment, the heavy chain variable domain ($V_H$) CDR1 region is SEQ ID NO: 93, SEQ ID NO: 94, SEQ ID NO: 95, SEQ ID NO: 118, SEQ ID NO: 119, or SEQ ID NO: 120. In another aspect of this embodiment, the heavy chain variable domain ($V_H$) CDR2 region is SEQ ID NO: 96, SEQ ID NO: 97, SEQ ID NO: 98, SEQ ID NO: 99, SEQ ID NO: 121, SEQ ID NO: 122, or SEQ ID NO: 123. In yet another aspect of this embodiment, the heavy chain variable domain ($V_H$) CDR3 region is SEQ ID NO: 100, SEQ ID NO: 101, SEQ ID NO: 102, or SEQ ID NO: 124.

In another embodiment, an α-SNAP-25 antibody comprises a light chain variable domain ($V_L$) CDR1 region, a CDR2 region, a CDR3 region, or any combination thereof that selectively binds to a SNAP-25 having a carboxyl-terminus at the $P_1$ residue of the BoNT/A cleavage site scissile bond. In an aspect of this embodiment, the light chain variable domain ($V_L$) CDR1 region is SEQ ID NO: 103, SEQ ID NO: 104, SEQ ID NO: 105, SEQ ID NO: 106, SEQ ID NO: 107, SEQ ID NO: 125, SEQ ID NO: 126, SEQ ID NO: 127, SEQ ID NO: 128, or SEQ ID NO: 129. In another aspect of this embodiment, the light chain variable domain ($V_L$) CDR2 region is SEQ ID NO: 108, SEQ ID NO: 109, SEQ ID NO: 110, SEQ ID NO: 111, or SEQ ID NO: 112. In yet another aspect of this embodiment, the light chain variable domain ($V_L$) CDR3 region is SEQ ID NO: 113, SEQ ID NO: 114, SEQ ID NO: 115, SEQ ID NO: 116, or SEQ ID NO: 117.

In yet another embodiment, an α-SNAP-25 antibody specifically binds an epitope comprising a SNAP-25 having a carboxyl-terminus at the $P_1$ residue of the BoNT/A cleavage site scissile bond. In an aspect of this embodiment, the epitope comprises SEQ ID NO: 32, SEQ ID NO: 33, SEQ ID NO: 34, SEQ ID NO: 35, SEQ ID NO: 36, SEQ ID NO: 37, SEQ ID NO: 147 or SEQ ID NO: 148. In an aspect of this embodiment, the epitope comprises SEQ ID NO: 39, SEQ ID NO: 40, SEQ ID NO: 41, SEQ ID NO: 42, SEQ ID NO: 43, or SEQ ID NO: 44.

As discussed above, the sequence surrounding a BoNT/A cleavage site present in SNAP-25 is denoted $P_5$-$P_4$-$P_3$-$P_2$-$P_1$-$P_1'$-$P_2'$-$P_3'$-$P_4'$-$P_5'$, with $P_1$-$P_1'$ representing the scissile bond. Upon cleavage by BoNT/A, the resulting cleavage products produced comprise a fragment including the $P_5$-$P_4$-$P_3$-$P_2$-$P_1$ sequence and a fragment including the $P_1'$-$P_2'$-$P_3'$-$P_4'$-$P_5'$. As used herein, the term "α-SNAP-25 antibodies that bind an epitope comprising a carboxyl-terminus at the $P_1$ residue from the BoNT/A cleavage site scissile bond from a SNAP-25 cleavage product" refers to α-SNAP-25 antibodies that selectively bind to any SNAP-25 cleavage product fragment comprising the $P_5$-$P_4$-$P_3$-$P_2$-$P_1$ sequence, but not to any SNAP-25 cleavage product fragment comprising the $P_1'$-$P_2'$-$P_3'$-$P_4'$-$P_5'$ sequence or to any SNAP-25 having an intact $P_1$-$P_1'$ scissile bond of a BoNT/A cleavage site. As used herein, the term "α-SNAP-25$_{197}$ antibody" refers to an antibody that selectively binds to a SNAP-25 having a carboxyl-terminus $P_1$ residue that corresponds to glutamine 197 of SEQ ID NO: 5. As used herein, the term "α-SNAP-25$_{204}$ antibody" refers to an antibody that selectively binds to a SNAP-25 having a carboxyl-terminus $P_1$ residue that corresponds to lysine 204 of SEQ ID NO: 16.

As used herein, the term "selectively" refers to having a unique effect or influence or reacting in only one way or with only one thing. As used herein, the term "selectively binds," when made in reference to an antibody, refers to the discriminatory binding of the antibody to the indicated target epitope such that the antibody does not substantially cross react with non-target epitopes. The minimal size of a peptide epitope, as defined herein, is about five amino acids, and a peptide epitope typically comprises at least 5, at least 6, at least 7, at least 8, at least 9, at least 10, at least 15, or at least 20 amino acids. A peptide epitope may be discontinuous, i.e., it comprises amino acid residues that are not adjacent in the primary structure of the peptide but are brought together into an epitope by way of the secondary, tertiary, or quaternary structure of the peptide. Furthermore, it is also noted that an epitope might comprise a portion of a molecule other than an amino acid sequence, such as, e.g., a carbohydrate moiety, a lipid moiety like lipoproteins or glycolipids, or a chemically-modified amino acid moiety like a phosphorylated amino acid. In aspects of this embodiment, an α-SNAP-25 antibody that selectively binds to a SNAP-25 epitope having a carboxyl-terminus at the $P_1$ residue of the BoNT/A cleavage site scissile bond can selectively bind a SNAP-25 epitope having a carboxyl-terminus at the $P_1$ residue of the BoNT/A cleavage site scissile bond comprising at least 5, at least 6, at least 7, at least 8, at least 9, at least 10, at least 15, or at least 20 amino acids. In other aspects of this embodiment, an α-SNAP-25 antibody that selectively binds to a SNAP-25 epitope having a carboxyl-terminus at the $P_1$ residue of the BoNT/A cleavage site scissile bond can selectively bind a SNAP-25 epitope having a carboxyl-terminus at the $P_1$ residue of the BoNT/A cleavage site scissile bond comprising at most 5, at most 6, at most 7, at most 8, at most 9, at most 10, at most 15, or at most 20 amino acids.

Selective binding includes binding properties such as, e.g., binding affinity, binding specificity, and binding avidity. See David J. King, Applications and Engineering of Monoclonal Antibodies, pp. 240 (1998). Binding affinity refers to the length of time the antibody resides at its epitope binding site, and can be viewed as the strength with which an antibody binds its epitope. Binding affinity can be described an antibody's equilibrium dissociation constant (KD), which is defined as the ratio Kd/Ka at equilibrium. Where Ka is the antibody's association rate constant and kd is the antibody's dissociation rate constant. Binding affinity is determined by both the association and the dissociation and alone neither high association or low dissociation can ensure high affinity. The association rate constant (Ka), or on-rate constant (Kon), measures the number of binding events per unit time, or the propensity of the antibody and the antigen to associate reversibly into its antibody-antigen complex. The association rate constant is expressed in $M^{-1} s^{-1}$, and is symbolized as follows: [Ab]×[Ag]×Kon. The larger the association rate constant, the more rapidly the antibody binds to its antigen, or the higher the binding affinity between antibody and antigen. The dissociation rate constant (Kd), or off-rate constant (Koff), measures the number of dissociation events per unit time propensity of an antibody-antigen complex to separate (dissociate) reversibly into its component molecules, namely the antibody and the antigen. The dissociation rate constant is expressed in $s^{-1}$, and is symbolized as follows: [Ab+Ag]×Koff. The smaller the dissociation rate constant, the more tightly bound the antibody is to its antigen, or the higher the binding affinity between antibody and antigen. The equilibrium dissociation constant (KD) measures the rate at which new antibody-antigen complexes formed equals the rate at which antibody-antigen complexes dissociate at equilibrium. The equilibrium dissociation constant is expressed in M, and is defined as Koff/Kon=[Ab]× [Ag]/[Ab+Ag], where [Ab] is the molar concentration of the antibody, [Ag] is the molar concentration of the antigen, and [Ab+Ag] is the molar concentration of the antibody-antigen complex, where all concentrations are of such components when the system is at equilibrium. The smaller the equilibrium dissociation constant, the more tightly bound the antibody is to its antigen, or the higher the binding affinity between antibody and antigen.

Thus, in an embodiment, the binding affinity of an α-SNAP-25 antibody that selectively binds to a SNAP-25 epitope having a carboxyl-terminus at the $P_1$ residue of the BoNT/A cleavage site scissile bond can have an association rate constant of, e.g., less than $1\times10^5$ $M^{-1}$ $s^{-1}$, less than $1\times10^6$ $M^{-1}$ $s^{-1}$, less than $1\times10^7$ $M^{-1}$ $s^{-1}$, or less than $1\times10^8$ $M^{-1}$ $s^{-1}$. In another embodiment, the binding affinity of an α-SNAP-25 antibody that selectively binds to a SNAP-25 epitope having a carboxyl-terminus at the $P_1$ residue of the BoNT/A cleavage site scissile bond can have an association rate constant of, e.g., more than $1\times10^5$ $M^{-1}$ $s^{-1}$, more than $1\times10^6$ $M^{-1}$ $s^{-1}$, more than $1\times10^7$ $M^{-1}$ $s^{-1}$, or more than $1\times10^8$ $M^{-1}$ $s^{-1}$. In other aspects, the binding affinity of an α-SNAP-25 antibody that selectively binds to a SNAP-25 epitope having a carboxyl-terminus at the $P_1$ residue of the BoNT/A cleavage site scissile bond can have an association rate constant between $1\times10^5$ $M^{-1}$ $s^{-1}$ to $1\times10^8$ $M^{-1}$ $s^{-1}$, $1\times10^6$ $M^{-1}$ $s^{-1}$ to $1\times10^8$ $M^{-1}$ $s^{-1}$, $1\times10^5$ $M^{-1}$ $s^{-1}$ to $1\times10^7$ $M^{-1}$ $s^{-1}$, or $1\times10^6$ $M^{-1}$ $s^{-1}$ to $1\times10^7$ $M^{-1}$ $s^{-1}$.

In another embodiment, the binding affinity of an α-SNAP-25 antibody that selectively binds to a SNAP-25 epitope having a carboxyl-terminus at the $P_1$ residue of the BoNT/A cleavage site scissile bond can have a dissociation rate constant of less than $1\times10^{-3}$ $s^{-1}$, less than $1\times10^{-4}$ $s^{-1}$, or less than $1\times10^{-5}$ $s^{-1}$. In other aspects of this embodiment, the binding affinity of an α-SNAP-25 antibody that selectively binds to a SNAP-25 epitope having a carboxyl-terminus at the $P_1$ residue of the BoNT/A cleavage site scissile bond can have a dissociation rate constant of, e.g., less than $1.0\times10^{-4}$ $s^{-1}$, less than $2.0\times10^{-4}$ $s^{-1}$, less than $3.0\times10^{-4}$ $s^{-1}$, less than $4.0\times10^{-4}$ $s^{-1}$, less than $5.0\times10^{-4}$ $s^{-1}$, less than $6.0\times10^{-4}$ $s^{-1}$, less than $7.0\times10^{-4}$ $s^{-1}$, less than $8.0\times10^{-4}$ $s^{-1}$, or less than $9.0\times10^{-4}$ $s^{-1}$. In another embodiment, the binding affinity of an α-SNAP-25 antibody that selectively binds to a SNAP-25 epitope having a carboxyl-terminus at the $P_1$ residue of the BoNT/A cleavage site scissile bond can have a dissociation rate constant of, e.g., more than $1\times10^{-3}$ $s^{-1}$, more than $1\times10^{-4}$ $s^{-1}$, or more than $1\times10^{-5}$ $s^{-1}$. In other aspects of this embodiment, the binding affinity of an α-SNAP-25 antibody that selectively binds to a SNAP-25 epitope having a carboxyl-terminus at the $P_1$ residue of the BoNT/A cleavage site scissile bond can have a disassociation rate constant of, e.g., more than $1.0\times10^{-4}$ $s^{-1}$, more than $2.0\times10^{-4}$ $s^{-1}$, more than $3.0\times10^{-4}$ $s^{-1}$, more than $4.0\times10^{-4}$ $s^{-1}$, more than $5.0\times10^{-4}$ $s^{-1}$, more than $6.0\times10^{-4}$ $s^{-1}$, more than $7.0\times10^{-4}$ $s^{-1}$, more than $8.0\times10^{-4}$ $s^{-1}$, or more than $9.0\times10^{-4}$ $s^{-1}$.

In another embodiment, the binding affinity of an α-SNAP-25 antibody that selectively binds to a SNAP-25 epitope having a carboxyl-terminus at the $P_1$ residue of the BoNT/A cleavage site scissile bond can have an equilibrium disassociation constant of less than 0.500 nM. In aspects of this embodiment, the binding affinity of an α-SNAP-25 antibody that selectively binds to a SNAP-25 epitope having a carboxyl-terminus at the $P_1$ residue of the BoNT/A cleavage site scissile bond can have an equilibrium disassociation constant of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In another embodiment, the binding affinity of an α-SNAP-25 antibody that selectively binds to a SNAP-25 epitope having a carboxyl-terminus at the $P_1$ residue of the BoNT/A cleavage site scissile bond can have an equilibrium disassociation constant of more than 0.500 nM. In aspects of this embodiment, the binding affinity of an α-SNAP-25 antibody that selectively binds to a SNAP-25 epitope having a carboxyl-terminus at the $P_1$ residue of the BoNT/A cleavage site scissile bond can have an equilibrium disassociation constant of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

In yet another embodiment, the binding affinity of an α-SNAP-25 antibody that selectively binds to a SNAP-25 epitope having a carboxyl-terminus at the $P_1$ residue of the BoNT/A cleavage site scissile bond can have an association rate constant of for the intact SNAP-25 of, e.g., less than $1\times10^0$ $M^{-1}$ $s^{-1}$, less than $1\times10^1$ $M^{-1}$ $s^{-1}$, less than $1\times10^2$ $M^{-1}$ $s^{-1}$, less than $1\times10^3$ $M^{-1}$ $s^{-1}$, or less than $1\times10^4$ $M^{-1}$ $s^{-1}$. In another embodiment, the binding affinity of an α-SNAP-25 antibody that selectively binds to a SNAP-25 epitope having a carboxyl-terminus at the $P_1$ residue of the BoNT/A cleavage site scissile bond can have an association rate constant of for the intact SNAP-25 of, e.g., at most $1\times10^0$ $M^{-1}$ $s^{-1}$, at most $1\times10^1$ $N^{-1}$ $s^{-1}$, at most $1\times10^2$ $M^{-1}$ $s^{-1}$, at most $1\times10^3$ $M^{-1}$ $s^{-1}$, or at most $1\times10^4$ $M^{-1}$ $s^{-1}$.

Binding specificity is the ability of an antibody to discriminate between a molecule containing its epitope and a molecule that does not contain that epitope. One way to measure binding specificity is to compare the Kon association rate of the antibody for a molecule containing its epitope relative to the Kon association rate of the antibody for a molecule that does not contain that epitope. For example, comparing the association rate constant (Ka) of an α-SNAP-25 antibody for a SNAP-25 epitope having a carboxyl-terminus at the $P_1$ residue of the BoNT/A cleavage site scissile bond relative to a SNAP-25 not comprising that epitope, such as, e.g., a SNAP-25 epitope lacking a carboxyl-terminus at the $P_1$ residue of the BoNT/A cleavage site scissile bond or a SNAP-25 epitope having an intact $P_1$-$P_1$' scissile bond of a BoNT/A cleavage site. In aspects of this embodiment, an α-SNAP-25 antibody that selectively binds to a SNAP-25 epitope having a carboxyl-terminus at the $P_1$ residue of the BoNT/A cleavage site scissile bond has an association rate constant (Ka) for a SNAP-25 not comprising its epitope(s) of, e.g., less than $1\times10^0$ $M^{-1}$ $s^{-1}$, less than $1\times10^1$ $M^{-1}$ $s^{-1}$, less than $1\times10^2$ $M^{-1}$ $s^{-1}$, less than $1\times10^3$ $M^{-1}$ $s^{-1}$ or less than $1\times10^4$ $M^{-1}$ $s^{-1}$. In other aspects of this embodiment, an α-SNAP-25 antibody that selectively binds to a SNAP-25 epitope having a carboxyl-terminus at the P$_1$ residue of the BoNT/A cleavage site scissile bond has an association rate constant (Ka) for a SNAP-25 not comprising its epitope(s) of, e.g., at most 1×10$^0$ M$^{-1}$ s$^{-1}$, at most 1×10$^1$ M$^{-1}$ s$^{-1}$, at most 1×10$^2$ M$^{-1}$ s$^{-1}$, at most 1×10$^3$ M$^{-1}$ s$^{-1}$ or at most 1×10$^4$ M$^{-1}$ s$^{-1}$.

In yet aspects of this embodiment, an α-SNAP-25 antibody that selectively binds to a SNAP-25 epitope having a carboxyl-terminus at the P$_1$ residue of the BoNT/A cleavage site scissile bond has an association rate constant (Ka) for its epitope relative to a SNAP-25 not comprising that epitope of, e.g., at least 2-fold more, at least 3-fold more, at least 4-fold more, at least 5-fold more, at least 6-fold more, at least 7-fold more, at least 8-fold more, or at least 9-fold more. In further aspects of this embodiment, an α-SNAP-25 antibody that selectively binds to a SNAP-25 epitope having a carboxyl-terminus at the P$_1$ residue of the BoNT/A cleavage site scissile bond has an association rate constant (Ka) for its epitope relative to a SNAP-25 not comprising that epitope of, e.g., at least 10-fold more, at least 100-fold more, at least 1,000-fold more or at least 10,000-fold more. In yet other aspects of this embodiment, an α-SNAP-25 antibody that selectively binds to a SNAP-25 epitope having a carboxyl-terminus at the P$_1$ residue of the BoNT/A cleavage site scissile bond has an association rate constant (Ka) for its epitope relative to a SNAP-25 not comprising that epitope of, e.g., at most 1-fold more, at most 2-fold more, at most 3-fold more, at most 4-fold more, at most 5-fold more, at most 6-fold more, at most 7-fold more, at most 8-fold more, or at most 9-fold more. In yet other aspects of this embodiment, an α-SNAP-25 antibody that selectively binds to a SNAP-25 epitope having a carboxyl-terminus at the P$_1$ residue of the BoNT/A cleavage site scissile bond has an association rate constant (Ka) for its epitope relative to a SNAP-25 not comprising that epitope of, e.g., at most 10-fold more, at most 100-fold more, at most 1,000-fold more or at most 10,000-fold more.

The binding specificity of an α-SNAP-25 antibody that selectively binds to a SNAP-25 epitope having a carboxyl-terminus at the P$_1$ residue of the BoNT/A cleavage site scissile bond can also be characterized as a ratio that such an α-SNAP-25 antibody can discriminate its SNAP-25 epitope relative to a SNAP-25 not comprising that epitope, such as, e.g., a SNAP-25 epitope lacking a carboxyl-terminus at the P$_1$ residue of the BoNT/A cleavage site scissile bond or a SNAP-25 epitope having an intact P$_1$-P$_1$' scissile bond of a BoNT/A cleavage site. In aspects of this embodiment, an α-SNAP-25 antibody that selectively binds to a SNAP-25 epitope having a carboxyl-terminus at the P$_1$ residue of the BoNT/A cleavage site scissile bond has a binding specificity ratio for its SNAP-25 epitope relative to a SNAP-25 not comprising that epitope of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1. In yet other aspects of this embodiment, an α-SNAP-25 antibody that selectively binds to a SNAP-25 epitope having a carboxyl-terminus at the P$_1$ residue of the BoNT/A cleavage site scissile bond has a binding specificity ratio for its SNAP-25 epitope relative to a SNAP-25 lacking a carboxyl-terminus at the P$_1$ residue of the BoNT/A cleavage site scissile bond of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1. In still other aspects of this embodiment, an α-SNAP-25 antibody that selectively binds to a SNAP-25 epitope having a carboxyl-terminus at the P$_1$ residue of the BoNT/A cleavage site scissile bond has a binding specificity ratio for its SNAP-25 epitope relative to a SNAP-25 having an intake P$_1$-P$_1$' scissile bond of a BoNT/A cleavage site of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

Binding avidity, also known as functional affinity, refers to the sum total of the functional binding strength between a multivalent antibody and its antigen. Antibody molecules can have more than one binding site (e.g., 2 for IgG, 10 for IgM), and many antigens contain more than one antigenic site. While binding avidity of an antibody depends on the binding affinities of the individual antibody binding sites, binding avidity is greater than the binding affinity as all the antibody-antigen interactions must be broken simultaneously for the antibody to dissociate completely. It is envisioned that an α-SNAP-25 antibody that selectively binds to a SNAP-25 epitope having a carboxyl-terminus at the P$_1$ residue of the BoNT/A cleavage site scissile bond can selectively bind to any and all epitopes for that antibody.

Thus, in an embodiment, an α-SNAP-25 antibody is an α-SNAP-25 antibody that selectively binds to a SNAP-25 epitope having a carboxyl-terminus at the P$_1$ residue of the BoNT/A cleavage site scissile bond. In aspects of this embodiment, an α-SNAP-25 antibody is an α-SNAP-25 antibody that selectively binds to a SNAP-25 epitope having a carboxyl-terminus glutamine or an α-SNAP-25 antibody that selectively binds to a SNAP-25 epitope having a carboxyl-terminus lysine. In other aspects of this embodiment, an α-SNAP-25 antibody is an α-SNAP-25 antibody that selectively binds to a SNAP-25 epitope having a carboxyl-terminus P$_1$ residue that corresponds to glutamine 197 of SEQ ID NO: 5 or an α-SNAP-25 antibody that selectively binds to a SNAP-25 epitope having a carboxyl-terminus P$_1$ residue that corresponds to lysine 204 of SEQ ID NO: 16. In still other aspects of this embodiment, an α-SNAP-25 antibody is an α-SNAP-25 antibody that selectively binds to a SNAP-25 epitope having a carboxyl-terminal amino acid sequence of SEQ ID NO: 32, SEQ ID NO: 33, SEQ ID NO: 34, SEQ ID NO: 35, SEQ ID NO: 36, SEQ ID NO: 37, SEQ ID NO: 39, SEQ ID NO: 40, SEQ ID NO: 41, SEQ ID NO: 42, SEQ ID NO: 43, SEQ ID NO: 44, SEQ ID NO: 147 or SEQ ID NO: 148.

Aspects of the present disclosure comprise, in part, an immuno-based method of detecting BoNT/A activity. The immuno-based methods disclosed in the present specification can be evaluated by several parameters including, e.g., accuracy, precision, limit of detection (LOD), limits of quantitation (LOQ), linear range, specificity, selectivity, linearity, ruggedness, and system suitability. The accuracy of a method is the measure of exactness of an analytical method, or the closeness of agreement between the measured value and the value that is accepted as a conventional true value or an accepted reference value. The precision of a method is the degree of agreement among individual test results, when the procedure is applied repeatedly to multiple samplings of a homogeneous sample. As such, precision evaluates 1) within assay variability; 2) within-day variability (repeatability); and 3) between-day variability (intermediate precision); and 4) between-lab variability (reproducibility). Coefficient of variation (CV %) is a quantitative measure of precision expressed relative to the observed or theoretical mean value.

An immuno-based method disclosed in the present specification must be able to detect, over background, the presence of an α-SNAP-25 antibody-antigen complex comprising a SNAP-25 having a carboxyl-terminus at the P$_1$ residue of the BoNT/A cleavage site scissile bond. The limit of detection (LOD) of a method refers to the concentration of analyte which gives rise to a signal that is significantly different from the negative control or blank and represents the lowest concentration of analyte that can be distinguished from background.

Thus, in an embodiment, the immuno-based method disclosed in the present specification can detect the LOD of BoNT/A at an amount that is significantly different from a negative control or blank. In aspect of this embodiment, the immuno-based method disclosed in the present specification has an LOD of, e.g., 10 ng or less, 9 ng or less, 8 ng or less, 7 ng or less, 6 ng or less, 5 ng or less, 4 ng or less, 3 ng or less, 2 ng or less, 1 ng or less of a BoNT/A. In still other aspects of this embodiment, the immuno-based method disclosed in the present specification has an LOD of, e.g., 900 pg or less, 800 pg or less, 700 pg or less, 600 pg or less, 500 pg or less, 400 pg or less, 300 pg or less, 200 pg or less, 100 pg or less of a BoNT/A. In further aspects of this embodiment, the immuno-based method disclosed in the present specification has an LOD of, e.g., 90 pg or less, 80 pg or less, 70 pg or less, 60 pg or less, 50 pg or less, 40 pg or less, 30 pg or less, 20 pg or less, 10 pg or less of a BoNT/A. In other aspects of this embodiment, the immuno-based method disclosed in the present specification has an LOD of, e.g., 9 pg or less, 8 pg or less, 7 pg or less, 6 pg or less, 5 pg or less, 4 pg or less, 3 pg or less, 2 pg or less, 1 pg or less of a BoNT/A. In yet other aspects of this embodiment, the immuno-based method disclosed in the present specification has an LOD of, e.g., 0.9 pg or less, 0.8 pg or less, 0.7 pg or less, 0.6 pg or less, 0.5 pg or less, 0.4 pg or less, 0.3 pg or less, 0.2 pg or less, 0.1 pg or less of a BoNT/A.

In another aspect of this embodiment, the immuno-based method disclosed in the present specification has an LOD of, e.g., 10 nM or less or less, 9 nM or less, 8 nM or less, 7 nM or less, 6 nM or less, 5 nM or less, 4 nM or less, 3 nM or less, 2 nM or less, or 1 nM or less of a BoNT/A. In other aspects of this embodiment, the immuno-based method disclosed in the present specification has an LOD of, e.g., 900 pM or less, 800 pM or less, 700 pM or less, 600 pM or less, 500 pM or less, 400 pM or less, 300 pM or less, 200 pM or less, or 100 pM or less of a BoNT/A. In other aspects of this embodiment, the immuno-based method disclosed in the present specification has an LOD of, e.g., 100 pM or less, 90 pM or less, 80 pM or less, 70 pM or less, 60 pM or less, 50 pM or less, 40 pM or less, 30 pM or less, 20 pM or less, or 10 pM or less of a BoNT/A. In yet other aspects of this embodiment, the immuno-based method disclosed in the present specification has an LOD of, e.g., 10 pM or less of a BoNT/A, 9 pM or less, 8 pM or less, 7 pM or less, 6 pM or less, 5 pM or less, 4 pM or less, 3 pM or less, 2 pM or less, or 1 pM or less of a BoNT/A. In still other aspects of this embodiment, the immuno-based method disclosed in the present specification has an LOD of, e.g., 1000 fM or less, 900 fM or less, 800 fM or less, 700 fM or less, 600 fM or less, 500 fM or less, 400 fM or less, 300 fM or less, 200 fM or less, or 100 fM or less of a BoNT/A. In still other aspects of this embodiment, the immuno-based method disclosed in the present specification has an LOD of, e.g., 100 fM or less, 90 fM or less, 80 fM or less, 70 fM or less, 60 fM or less, 50 fM or less, 40 fM or less, 30 fM or less, 20 fM or less, or 10 fM or less of a BoNT/A. In still other aspects of this embodiment, the immuno-based method disclosed in the present specification has an LOD of, e.g., 10 fM or less, 9 fM or less, 8 fM or less, 7 fM or less, 6 fM or less, 5 fM or less, 4 fM or less, 3 fM or less, 2 fM or less, or 1 fM or less of a botulinum neurotoxin A.

The limits of quantitation (LOQ) are the lowest and the highest concentrations of analyte in a sample or specimen that can be measured with an acceptable level of accuracy and precision. The lower limit of quantitation refers to the lowest dose that a detection method can measure consistently from the background. The upper limit of quantitation is the highest dose that a detection method can measure consistently before saturation of the signal occurs. The linear range of the method is the area between the lower and the upper limits of quantitation. The linear range is calculated by subtracting lower limit of quantitation from the upper limit of quantitation. As used herein, the term "signal to noise ratio for the lower asymptote" refers to the signal detected in the method at the lower limit of detection divided by the background signal. As used herein, the term "signal to noise ratio for the upper asymptote" refers to the signal detected in the method at the upper limit of detection divided by the background signal.

Thus, in an embodiment, the immuno-based method disclosed in the present specification can detect the LOQ of BoNT/A at an amount that is significantly different from a negative control or blank. In aspect of this embodiment, the immuno-based method disclosed in the present specification has an LOQ of, e.g., 10 ng or less, 9 ng or less, 8 ng or less, 7 ng or less, 6 ng or less, 5 ng or less, 4 ng or less, 3 ng or less, 2 ng or less, 1 ng or less of a BoNT/A. In still other aspects of this embodiment, the immuno-based method disclosed in the present specification has an LOQ of, e.g., 900 pg or less, 800 pg or less, 700 pg or less, 600 pg or less, 500 pg or less, 400 pg or less, 300 pg or less, 200 pg or less, 100 pg or less of a BoNT/A. In further aspects of this embodiment, the immuno-based method disclosed in the present specification has an LOQ of, e.g., 90 pg or less, 80 pg or less, 70 pg or less, 60 pg or less, 50 pg or less, 40 pg or less, 30 pg or less, 20 pg or less, 10 pg or less of a BoNT/A. In other aspects of this embodiment, the immuno-based method disclosed in the present specification has an LOQ of, e.g., 9 pg or less, 8 pg or less, 7 pg or less, 6 pg or less, 5 pg or less, 4 pg or less, 3 pg or less, 2 pg or less, 1 pg or less of a BoNT/A. In yet other aspects of this embodiment, the immuno-based method disclosed in the present specification has an LOQ of, e.g., 0.9 pg or less, 0.8 pg or less, 0.7 pg or less, 0.6 pg or less, 0.5 pg or less, 0.4 pg or less, 0.3 pg or less, 0.2 pg or less, 0.1 pg or less of a BoNT/A.

In another aspect of this embodiment, the immuno-based method disclosed in the present specification has an LOQ of, e.g., 10 nM or less, 9 nM or less, 8 nM or less, 7 nM or less, 6 nM or less, 5 nM or less, 4 nM or less, 3 nM or less, 2 nM or less, or 1 nM or less of a BoNT/A. In other aspects of this embodiment, the immuno-based method disclosed in the present specification has an LOQ of, e.g., 900 pM or less, 800 pM or less, 700 pM or less, 600 pM or less, 500 pM or less, 400 pM or less, 300 pM or less, 200 pM or less, or 100 pM or less of a BoNT/A. In other aspects of this embodiment, the immuno-based method disclosed in the present specification has an LOQ of, e.g., 100 pM or less, 90 pM or less, 80 pM or less, 70 pM or less, 60 pM or less, 50 pM or less, 40 pM or less, 30 pM or less, 20 pM or less, or 10 pM or less of a BoNT/A. In yet other aspects of this embodiment, the immuno-based method disclosed in the present specification has an LOQ of, e.g., 10 pM or less of a BoNT/A, 9 pM or less, 8 pM or less, 7 pM or less, 6 pM or less, 5 pM or less, 4 pM or less, 3 pM or less, 2 pM or less, or 1 pM or less of a BoNT/A. In still other aspects of this embodiment, the immuno-based method disclosed in the present specification has an LOQ of, e.g., 1000 fM or less, 900 fM or less, 800 fM or less, 700 fM or less, 600 fM or less, 500 fM or less, 400 fM or less, 300 fM or less, 200 fM or less, or 100 fM or less of a BoNT/A. In still other aspects of this embodiment, the immuno-based method disclosed in the present specification has an LOQ of, e.g., 100 fM or less, 90 fM or less, 80 fM or less, 70 fM or less, 60 fM or less, 50 fM or less, 40 fM or less, 30 fM or less, 20 fM or less, or 10 fM or less of a BoNT/A. In still other aspects of this embodiment, the immuno-based method disclosed in the present specification has an LOQ of, e.g., 10 fM or less, 9 fM or less, 8 fM or less, 7 fM or less, 6 fM or less, 5 fM or less, 4 fM or less, 3 fM or less, 2 fM or less, or 1 fM or less of a BoNT/A.

An immuno-based assay useful to practice aspect of the disclosed methods must have a precision of no more than 50%. In aspects of this embodiment, an immuno-based assay has a precision of no more than 50%, no more than 40%, no more than 30%, or no more than 20%. In other aspects of this embodiment, an immuno-based assay has a precision of no more than 15%, no more than 10%, or no more than 5%. In other aspects of this embodiment, an immuno-based assay has a precision of no more than 4%, no more than 3%, no more than 2%, or no more than 1%.

An immuno-based assay useful to practice aspect of the disclosed methods must have an accuracy of at least 50%. In aspects of this embodiment, an immuno-based assay has an accuracy of at least 50%, at least 60%, at least 70%, or at least 80%. In other aspects of this embodiment, an immuno-based assay has an accuracy of at least 85%, at least 90%, or at least 95%. In other aspects of this embodiment, an immuno-based assay has an accuracy of at least 96%, at least 97%, at least 98%, or at least 99%.

An immuno-based method disclosed in the present specification must have a signal to noise ratio for the lower asymptote that is statistically significant and a signal to noise ratio for the upper asymptote that is statistically significant. In aspects of this embodiment, an immuno-based method disclosed in the present specification has a signal to noise ratio for the lower asymptote of, e.g., at least 3:1, at least 4:1, at least 5:1, at least 6:1, at least 7:1, at least 8:1, at least 9:1, at least 10:1, at least 15:1 or at least 20:1. In other aspects of this embodiment, an immuno-based method has a signal to noise ratio for the upper asymptote of, e.g., at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1.

The specificity of a method defines the ability of the method to measure the analyte of interest to the exclusion of other relevant components, such as, e.g., partially-active or inactive analyte. The selectivity of a method describes the ability of an analytical method to differentiate various substances in a sample. The linearity of a method is its ability to elicit results that are directly, or by a well defined mathematical transformation, proportional to the concentration of analyte in the sample. Thus in an embodiment, an immuno-based method disclosed in the present specification can distinguish a fully-active BoNT/A from a partially-active BoNT/A having, e.g., 70% or less, 60% or less, 50% or less, 40% or less, 30% or less, 20% or less, or 10% or less the activity of a fully-active BoNT/A.

The ruggedness of the method is the reproducibility of the test results obtained for identical samples under normal (but variable) test conditions. Robustness of a procedure is a measure of its capacity to remain unaffected by small but deliberate variations in the method parameters and provides an indication of its reliability in normal usage. Thus, whereas ruggedness evaluates unavoidable changes, robustness evaluates deliberate changes. Typical parameters evaluated by ruggedness and robustness include the effects of freeze/thaw, incubation times, incubation temperature, longevity of reagent, sample preparation, sample storage, cell passage number, lots of toxin, variability between purifications, and variability between nicking reactions. Robustness parameters for cell-based assays include the cell bank (beginning, middle and end of freeze), cell passage level, cell seeding density, cell stock density (how many days in culture), cell age in flask (waiting time to seeding), incubation time, different plates, excessive amounts of serum, and source of reagents. The system suitability of the method is the determination of assay performance, including the performance of reagents and instruments, over time by analysis of a reference standard. System suitability is stressed in FDA guidance referring to the fact that equipment, electronics, assay performance, and samples to be analyzed, constitute an integrated system. System suitability can be evaluated by testing for parallelism, which is when plotting the log dose versus the response, serial dilutions of the reference and serial dilutions of the samples should give rise to parallel curves.

Aspects of the present disclosure comprise, in part, a cell from an established cell line. As used herein, the term "cell" refers to any eukaryotic cell susceptible to BoNT/A intoxication by a BoNT/A or any eukaryotic cell that can uptake a BoNT/A. The term cell encompasses cells from a variety of organisms, such as, e.g., murine, rat, porcine, bovine, equine, primate and human cells; from a variety of cell types such as, e.g., neuronal and non-neuronal; and can be isolated from or part of a heterogeneous cell population, tissue or organism. As used herein, the term "established cell line" is synonymous with "immortal cell line," or "transformed cell line" and refers to a cell culture of cells selected for indefinite propagation from a cell population derived from an organism, tissue, or organ source. By definition, an established cell line excludes a cell culture of primary cells. As used herein, the term "primary cells" are cells harvested directly from fresh tissues or organs and do not have the potential to propagate indefinitely. An established cell line can comprise a heterogeneous population of cells or a uniform population of cells. An established cell line derived from a single cell is referred to as a clonal cell line. An established cell line can be one whose cells endogenously express all component necessary for the cells to undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. Alternatively, an established cell line can be one whose cells have had introduced from an exogenous source at least one component necessary for the cells to undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. Also referred to as a genetically-engineered cell line, cells from such an established cell line may, e.g., express an exogenous FGFR2, an exogenous FGFR3, an exogenous SV2, an exogenous SNAP-25, or any combination thereof.

Aspects of the present disclosure comprise, in part, a cell from an established cell line susceptible to BoNT/A intoxication. As used herein, the terms "cell(s) susceptible to BoNT/A intoxication," "cell(s) susceptible to BoNT/A intoxication by a BoNT/A," or "cell(s) from an established cell line susceptible to BoNT/A intoxication by a BoNT/A" refer to cell(s) that can undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. By definition, cell(s) susceptible to of BoNT/A intoxication must express, or be engineered to express, at least one BoNT/A receptor and at least one SNAP-25 substrate. As used herein, the terms "cell(s) that can uptake BoNT/A" or "cell(s) comprising an established cell line that can uptake BoNT/A" refer to cells that can undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. By definition, cell(s) that can uptake BoNT/A must express, or be engineered to express, at least one BoNT/A receptor and at least one SNAP-25 substrate.

Thus in an embodiment, cells from an established cell line are susceptible to BoNT/A intoxication. In aspects of this embodiment, cells from an established cell line are susceptible to BoNT/A intoxication by, e.g., about 500 pM or less, about 400 pM or less, about 300 pM or less, about 200 pM or less, or about 100 pM or less of a BoNT/A. In other aspects of this embodiment, cells from an established cell line are susceptible to BoNT/A intoxication by, e.g., about 90 pM or less, about 80 pM or less, about 70 pM or less, about 60 pM or less, about 50 pM or less, about 40 pM or less, about 30 pM or less, about 20 pM or less A, or about 10 pM or less of a BoNT/A. In still other aspects, cells from an established cell line are susceptible to BoNT/A intoxication by, e.g., about 9 pM or less, about 8 pM or less, about 7 pM or less, about 6 pM or less, about 5 pM or less, about 4 pM or less, about 3 pM or less, about 2 pM or less, or about 1 pM or less of a BoNT/A. In yet other aspects, cells from an established cell line are susceptible to BoNT/A intoxication by, e.g., about 0.9 pM or less, about 0.8 pM or less, about 0.7 pM or less, about 0.6 pM or less, about 0.5 pM or less, about 0.4 pM or less, about 0.3 pM or less, about 0.2 pM, or about 0.1 pM or less of a BoNT/A. As used herein, the term "about" when qualifying a value of a stated item, number, percentage, or term refers to a range of plus or minus ten percent of the value of the stated item, percentage, parameter, or term.

In another embodiment, cells comprising an established cell line can uptake a BoNT/A. In aspects of this embodiment, cells comprising an established cell line can uptake, e.g., about 500 pM or less, about 400 pM or less, about 300 pM or less, about 200 pM or less, or about 100 pM or less of a BoNT/A. In other aspects of this embodiment, cells comprising an established cell line possess the ability to uptake about 90 pM or less, about 80 pM or less, about 70 pM or less, about 60 pM or less, about 50 pM or less, about 40 pM or less, about 30 pM or less, about 20 pM or less, or about 10 pM or less of a BoNT/A. In still other aspects, cells comprising an established cell line possess the ability to uptake about 9 pM or less, about 8 pM or less, about 7 pM or less, about 6 pM or less, about 5 pM or less, about 4 pM or less, about 3 pM or less, about 2 pM or less, or about 1 pM or less of a BoNT/A. In yet other aspects, cells comprising an established cell line possess the ability to uptake about 0.9 pM or less, about 0.8 pM or less, about 0.7 pM or less, about 0.6 pM or less, about 0.5 pM or less, about 0.4 pM or less, about 0.3 pM or less, about 0.2 pM or less, or about 0.1 pM or less of a BoNT/A.

Aspects of the present disclosure comprise, in part, a BoNT/A. As used herein, the term "BoNT/A" is synonymous with "botulinum neurotoxin serotype A" or "botulinum neurotoxin type A" and refers to both a naturally-occurring BoNT/A or a non-naturally occurring BoNT/As thereof, and includes BoNT/A complex comprising the about 150 kDa BoNT/A neurotoxin and associated non-toxin associated proteins (NAPs), as well as the about 150 kDa BoNT/A neurotoxin alone. Non-limiting examples of BoNT/A complexes include, e.g., the 900-kDa BoNT/A complex, the 500-kDa BoNT/A complex, the 300-kDa BoNT/A complex. Non-limiting examples of the about 150 kDa BoNT/A neurotoxin include, e.g., SEQ ID NO: 1, SEQ ID NO: 2, SEQ ID NO: 3, SEQ ID NO: 4.

As used herein, the term "naturally occurring BoNT/A" refers to any BoNT/A produced by a naturally-occurring process, including, without limitation, BoNT/A isoforms produced from a post-translational modification, an alternatively-spliced transcript, or a spontaneous mutation, and BoNT/A subtypes, such as, e.g., a BoNT/A1 subtype, BoNT/A2 subtype, BoNT/A3 subtype, BoNT/A4 subtype, and BoNT/A5 subtype. A naturally occurring BoNT/A includes, without limitation, SEQ ID NO: 1, SEQ ID NO: 2, SEQ ID NO: 3, SEQ ID NO: 4, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 amino acids from SEQ ID NO: 1, SEQ ID NO: 2, SEQ ID NO: 3, or SEQ ID NO: 4. Commercially available pharmaceutical compositions of a naturally-occurring BoNT/A includes, without limitation, BOTOX® (Allergan, Inc., Irvine, Calif.), DYSPORT®/RELOXIN®, (Ipsen Ltd., Slough, England), PURTOX® (Mentor Corp., Santa Barbara, Calif.), XEOMIN® (Merz Pharmaceuticals, GmbH., Frankfurt, Germany), NEURONOX® (Medy-Tox, Inc., Ochang-myeon, South Korea), BTX-A.

As used herein, the term "non-naturally occurring BoNT/A" refers to any BoNT/A whose structure was modified with the aid of human manipulation, including, without limitation, a BoNT/A with an altered amino acid sequence produced by genetic engineering using random mutagenesis or rational design and a BoNT/A produced by in vitro chemical synthesis. Non-limiting examples of non-naturally occurring BoNT/As are described in, e.g., Steward, L. E. et al., Post-translational Modifications and Clostridial Neurotoxins, U.S. Pat. No. 7,223,577; Dolly, J. O. et al., Activatable Clostridial Toxins, U.S. Pat. No. 7,419,676; Steward, L. E. et al., Clostridial Neurotoxin Compositions and Modified Clostridial Neurotoxins, US 2004/0220386; Steward, L. E. et al., Modified Clostridial Toxins With Enhanced Targeting Capabilities For Endogenous Clostridial Toxin Receptor Systems, U.S. Patent Publication No. 2008/0096248; Steward, L. E. et al., Modified Clostridial Toxins With Altered Targeting Capabilities For Clostridial Toxin Target Cells, U.S. Patent Publication No. 2008/0161543; Steward, L. E. et al., Modified Clostridial Toxins With Enhanced Translocation Capabilities and Altered Targeting Activity For Clostridial Toxin Target Cells, U.S. Patent Publication No. 2008/0241881, each of which is hereby incorporated by reference in its entirety.

Thus in an embodiment, the BoNT/A activity being detected is from a naturally occurring BoNT/A. In aspects of this embodiment, the BoNT/A activity being detected is from a BoNT/A isoform or a BoNT/A subtype. In aspects of this embodiment, the BoNT/A activity being detected is from the BoNT/A of SEQ ID NO: 1, SEQ ID NO: 2, SEQ ID NO: 3, or SEQ ID NO: 4. In other aspects of this embodiment, the BoNT/A activity being detected is from a BoNT/A having, e.g., at least 70%, at least 75%, at least 80%, at least 85%, at least 90%, or at least 95% amino acid identity with SEQ ID NO: 1, SEQ ID NO: 2, SEQ ID NO: 3, or SEQ ID NO: 4. In other aspects of this embodiment, the BoNT/A activity being detected is from BOTOX®, DYSPORT®/RELOXIN®, PURTOX®, XEOMIN®, NEURONOX®, or BTX-A.

In another embodiment, the BoNT/A activity being detected is from a non-naturally occurring BoNT/A. In other aspects of this embodiment, the BoNT/A activity being detected is from a non-naturally occurring BoNT/A variant having, e.g., at least 70%, at least 75%, at least 80%, at least 85%, at least 90%, or at least 95% amino acid identity with SEQ ID NO: 1, SEQ ID NO: 2, SEQ ID NO: 3, or SEQ ID NO: 4. In other aspects of this embodiment, the BoNT/A activity being detected is from a non-naturally occurring BoNT/A variant having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 1, SEQ ID NO: 2, SEQ ID NO: 3, or SEQ ID NO: 4. In yet other aspects of this embodiment, the BoNT/A activity being detected is from a non-naturally occurring BoNT/A variant having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 1, SEQ ID NO: 2, SEQ ID NO: 3, or SEQ ID NO: 4.

Aspects of the present disclosure comprise, in part, a SNAP-25. As used herein, the term "SNAP-25" refers to a naturally-occurring SNAP-25 or a non-naturally-occurring SNAP-25 which is preferentially cleaved by a BoNT/A. As used herein, the term "preferentially cleaved" refers to that the cleavage rate of BoNT/A substrate by a BoNT/A is at least one order of magnitude higher than the cleavage rate of any other substrate by BoNT/A. In aspects of this embodiment, the cleavage rate of BoNT/A substrate by a BoNT/A is at least two orders of magnitude higher, at least three orders of magnitude higher, at least four orders of magnitude higher, or at least five orders of magnitude higher than that the cleavage rate of any other substrate by BoNT/A.

As used herein, the term "naturally occurring SNAP-25" refers to any SNAP-25 produced by a naturally-occurring process, including, without limitation, SNAP-25 isoforms produced from a post-translational modification, an alternatively-spliced transcript, or a spontaneous mutation, and SNAP-25 subtypes. A naturally occurring SNAP-25 includes, without limitation, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

As used herein, the term "non-naturally occurring SNAP-25" refers to any SNAP-25 whose structure was modified with the aid of human manipulation, including, without limitation, a SNAP-25 produced by genetic engineering using random mutagenesis or rational design and a SNAP-25 produced by in vitro chemical synthesis. Non-limiting examples of non-naturally occurring SNAP-25s are described in, e.g., Steward, L. E. et al., FRET Protease Assays for Clostridial Toxins, U.S. Pat. No. 7,332,567; Fernandez-Salas et al., Lipophilic Dye-based FRET Assays for Clostridial Toxin Activity, U.S. Patent Publication 2008/0160561, each of which is hereby incorporated by reference in its entirety. A non-naturally occurring SNAP-25 may substitute, delete or add, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

Thus in an embodiment, a SNAP-25 is a naturally occurring SNAP-25. In aspects of this embodiment, the SNAP-25 is a SNAP-25 isoform or a SNAP-25 subtype. In aspects of this embodiment, the naturally occurring SNAP-25 is the naturally occurring SNAP-25 of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In other aspects of this embodiment, the SNAP-25 is a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another embodiment, a SNAP-25 is a non-naturally occurring SNAP-25. In other aspects of this embodiment, the SNAP-25 is a non-naturally occurring SNAP-25 having, e.g., at least 70%, at least 75%, at least 80%, at least 85%, at least 90%, or at least 95% amino acid identity with SEQ ID NO: 1, SEQ ID NO: 2, SEQ ID NO: 3, or SEQ ID NO: 4. In other aspects of this embodiment, the SNAP-25 is a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, the SNAP-25 is a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

A SNAP-25 can be an endogenous SNAP-25 or an exogenous SNAP-25. As used herein, the term "endogenous SNAP-25" refers to a SNAP-25 naturally present in the cell because it is naturally encoded within the cell's genome, such that the cell inherently expresses the SNAP-25 without the need an external source of SNAP-25 or an external source of genetic material encoding a SNAP-25. The expression of an endogenous SNAP-25 may be with or without environmental stimulation such as, e.g., cell differentiation. By definition, an endogenous SNAP-25 can only be a naturally-occurring SNAP-25 or variants thereof. For example, the following established cell lines express an endogenous SNAP-25: BE(2)-M17, Kelly, LA1-55n, N1E-115, N4TG3, N18, Neuro-2a, NG108-15, PC12, SH-SY5Y, SiMa, and SK-N-BE(2)-C.

As used herein, the term "exogenous SNAP-25" refers to a SNAP-25 expressed in a cell through the introduction of an external source of SNAP-25 or an external source of genetic material encoding a SNAP-25 by human manipulation. The expression of an exogenous SNAP-25 may be with or without environmental stimulation such as, e.g., cell differentiation. As a non-limiting example, cells from an established cell line can express an exogenous SNAP-25 by transient or stably transfection of a SNAP-25. As another non-limiting example, cells from an established cell line can express an exogenous SNAP-25 by protein transfection of a SNAP-25. An exogenous SNAP-25 can be a naturally-occurring SNAP-25 or variants thereof, or a non-naturally occurring SNAP-25 or variants thereof.

Thus in an embodiment, cells from an established cell line express an endogenous SNAP-25. In aspects of this embodiment, the endogenous SNAP-25 expressed by cells from an established cell line is a naturally-occurring SNAP-25. In other aspects of this embodiment, the endogenous SNAP-25 expressed by cells from an established cell line is SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet aspects of this embodiment, the endogenous SNAP-25 expressed by cells from an established cell line is a naturally occurring SNAP-25, such as, e.g., a SNAP-25 isoform or a SNAP-25 subtype. In other aspects of this embodiment, the endogenous SNAP-25 expressed by cells from an established cell line is a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another embodiment, cells from an established cell line are transiently or stably engineered to express an exogenous SNAP-25. In an aspect of this embodiment, cells from an established cell line are transiently or stably engineered to express a naturally-occurring SNAP-25. In other aspects of this embodiment, cells from an established cell line are transiently or stably engineered to express the naturally-occurring SNAP-25 of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, cells from an established cell line are transiently or stably engineered to express a naturally occurring SNAP-25, such as, e.g., a SNAP-25 isoform or a SNAP-25 subtype. In still other aspects of this embodiment, cells from an established cell line are transiently or stably engineered to express a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another aspect of the embodiment, cells from an established cell line are transiently or stably engineered to express a non-naturally occurring SNAP-25. In other aspects of this embodiment, cells from an established cell line are transiently or stably engineered to express a non-naturally occurring SNAP-25 having, e.g., at least 70%, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In other aspects of this embodiment, cells from an established cell line are transiently or stably engineered to express a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, cells from an established cell line are transiently or stably engineered to express a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

Assays that detect the cleavage of a BoNT/A substrate after exposure to a BoNT/A can be used to assess whether a cell is expressing an endogenous or exogenous SNAP-25. In these assays, generation of a SNAP-25 cleavage-product would be detected in cells expressing a SNAP-25 after BoNT/A treatment. Non-limiting examples of specific Western blot analysis, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for SNAP-25 cleavage can be useful in identifying cells expressing an endogenous or an exogenous SNAP-25.

As non-limiting examples, Western blot analysis using an antibody that recognizes BoNT/A SNAP-25-cleaved product or both the cleaved and uncleaved forms of SNAP-25 can be used to assay for uptake of BoNT/A. Examples of α-SNAP-25 antibodies useful for these assays include, without limitation, α-SNAP-25 mouse monoclonal antibody SMI-81 (Sternberger Monoclonals Inc., Lutherville, Md.), mouse α-SNAP-25 monoclonal antibody CI 71.1 (Synaptic Systems, Goettingen, Germany), α-SNAP-25 mouse monoclonal antibody CI 71.2 (Synaptic Systems, Goettingen, Germany), α-SNAP-25 mouse monoclonal antibody SP12 (Abcam, Cambridge, Mass.), α-SNAP-25 rabbit polyclonal antiserum (Synaptic Systems, Goettingen, Germany), α-SNAP-25 rabbit polyclonal antiserum (Abcam, Cambridge, Mass.), and α-SNAP-25 rabbit polyclonal antiserum S9684 (Sigma, St Louis, Mo.).

Aspects of the present disclosure comprise, in part, a BoNT/A receptor. As used herein, the term "BoNT/A receptor" refers to either a naturally-occurring BoNT/A receptor or a non-naturally occurring BoNT/A receptor which preferentially interacts with BoNT/A in a manner that elicits a BoNT/A intoxication response. As used herein, the term "preferentially interacts" refers to that the equilibrium dissociation constant (KD) of BoNT/A for a BoNT/A receptor is at least one order of magnitude less than that of BoNT/A for any other receptor at the cell surface. The equilibrium dissociation constant, a specific type of equilibrium constant that measures the propensity of an BoNT/A-BoNT/A receptor complex to separate (dissociate) reversibly into its component molecules, namely the BoNT/A and the BoNT/A receptor, is defined as KD=Ka/Kd at equilibrium. The association constant (Ka) is defined as Ka=[C]/[L][R] and the disassociation constant (Kd) is defined as Kd=[L][R]/[C], where [L] equals the molar concentration of BoNT/A, [R] is the molar concentration of a BoNT/A receptor, and [C] is the molar concentration of the BoNT/A-BoNT/A receptor complex, and where all concentrations are of such components when the system is at equilibrium. The smaller the dissociation constant, the more tightly bound the BoNT/A is to its receptor, or the higher the binding affinity between BoNT/A and BoNT/A receptor. In aspects of this embodiment, the disassociation constant of BoNT/A for a BoNT/A receptor is at least two orders of magnitude less, at least three orders of magnitude less, at least four orders of magnitude less, or at least five orders of magnitude less than that of BoNT/A for any other receptor. In other aspects of this embodiment, the binding affinity of a BoNT/A that preferentially interacts with a BoNT/A receptor can have an equilibrium disassociation constant (KD) of, e.g., of 500 nM or less, 400 nM or less, 300 nM or less, 200 nM, or less 100 nM or less. In other aspects of this embodiment, the binding affinity of a BoNT/A that preferentially interacts with a BoNT/A receptor can have an equilibrium disassociation constant (KD) of, e.g., of 90 nM or less, 80 nM or less, 70 nM or less, 60 nM, 50 nM or less, 40 nM or less, 30 nM or less, 20 nM, or less 10 nM or less. As used herein, the term "elicits a BoNT/A intoxication response" refers to the ability of a BoNT/A receptor to interact with a BoNT/A to form a neurotoxin/receptor complex and the subsequent internalization of that complex into the cell cytoplasm.

As used herein, the term "naturally occurring BoNT/A receptor" refers to any BoNT/A receptor produced by a naturally-occurring process, including, without limitation, BoNT/A receptor isoforms produced from a post-translational modification, an alternatively-spliced transcript, or a spontaneous mutation, and BoNT/A receptor subtypes. A naturally occurring BoNT/A receptor includes, without limitation, a fibroblast growth factor receptor 2 (FGFR2), a fibroblast growth factor receptor 3 (FGFR3), a synaptic vesicle glycoprotein 2 (SV2), and a complex ganglioside like GT1b, such as those described in Ester Fernandez-Salas, et al., Botulinum Toxin Screening Assays, U.S. Patent Publication 2008/0003240; Ester Fernandez-Salas, et al., Botulinum Toxin Screening Assays, U.S. Patent Publication 2008/0182799; Min Dong et al., SV2 is the Protein Receptor for Botulinum Neurotoxin A, Science (2006); S. Mahrhold et al, *The Synaptic Vesicle Protein 2C Mediates the Uptake of Botulinum Neurotoxin A into Phrenic Nerves,* 580(8) FEBS Lett. 2011-2014 (2006), each of which is hereby incorporated by reference in its entirety. A naturally occurring FGFR2 includes, without limitation, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70. A naturally occurring FGFR3 includes, without limitation, SEQ ID NO: 25, SEQ ID NO: 26, and SEQ ID NO: 27, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 25, SEQ ID NO: 26, and SEQ ID NO: 27. A naturally occurring SV2 includes, without limitation, SEQ ID NO: 28, SEQ ID NO: 29, SEQ ID NO: 30, and SEQ ID NO: 31, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 28, SEQ ID NO: 29, SEQ ID NO: 30, and SEQ ID NO: 31.

As used herein, the term "non-naturally occurring BoNT/A receptor variant" refers to any BoNT/A receptor produced with the aid of human manipulation or design, including, without limitation, a BoNT/A receptor produced by genetic engineering using random mutagenesis or rational design and a BoNT/A receptor produced by chemical synthesis. Non-limiting examples of non-naturally occurring BoNT/A variants include, e.g., conservative BoNT/A receptor variants, non-conservative BoNT/A receptor variants, BoNT/A receptor chimeric variants and active BoNT/A receptor fragments.

As used herein, the term "non-naturally occurring BoNT/A receptor" refers to any BoNT/A receptor whose structure was modified with the aid of human manipulation, including, without limitation, a BoNT/A receptor produced by genetic engineering using random mutagenesis or rational design and a BoNT/A receptor produced by in vitro chemical synthesis. Non-limiting examples of non-naturally occurring BoNT/A receptors are described in, e.g., Ester Fernandez-Salas, et al., Botulinum Toxin Screening Assays, U.S. Patent Publication 2008/0003240; Ester Fernandez-Salas, et al., Botulinum Toxin Screening Assays, U.S. Patent Publication 2008/0182799, each of which is hereby incorporated by reference in its entirety. A non-naturally occurring BoNT/A receptor may substitute, delete or add, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

Thus in an embodiment, a BoNT/A receptor is a naturally occurring BoNT/A receptor such as, e.g., FGFR2, FGFR3 or SV2. In aspects of this embodiment, the BoNT/A receptor is a BoNT/A receptor isoform or a BoNT/A receptor subtype. In aspects of this embodiment, the naturally occurring BoNT/A receptor is the naturally occurring BoNT/A receptor of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, the BoNT/A receptor is a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another embodiment, a BoNT/A receptor is a non-naturally occurring BoNT/A receptor, such as, e.g., a genetically-engineered FGFR2, a genetically-engineered FGFR3, or a genetically-engineered SV2. In other aspects of this embodiment, the BoNT/A receptor is a non-naturally occurring BoNT/A receptor having, e.g., at least 70%, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, the BoNT/A receptor is a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, the BoNT/A receptor is a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

A BoNT/A receptor can be an endogenous BoNT/A receptor or an exogenous BoNT/A receptor. As used herein, the term "endogenous BoNT/A receptor" refers to a BoNT/A receptor naturally present in the cell because it is naturally encoded within the cell's genome, such that the cell inherently expresses the BoNT/A receptor without the need for an external source of BoNT/A receptor or an external source of genetic material encoding a BoNT/A receptor. Expression of an endogenous BoNT/A receptor may be with or without environmental stimulation such as e.g., cell differentiation or promoter activation. For example, the following established cell lines express at least one endogenous BoNT/A receptor: BE(2)-M17, Kelly, LA1-55n, N1E-115, N4TG3, N18, Neuro-2a, NG108-15, PC12, SH-SY5Y, SiMa, and SK-N-BE(2)-C. An endogenous BoNT/A receptor can only be a naturally-occurring BoNT/A receptor or naturally-occurring variants thereof.

As used herein, the term "exogenous BoNT/A receptor" refers to a BoNT/A receptor expressed in a cell through the introduction of an external source of BoNT/A receptor or an external source of genetic material encoding a BoNT/A receptor by human manipulation. The expression of an exogenous BoNT/A receptor may be with or without environmental stimulation such as, e.g., cell differentiation or promoter activation. As a non-limiting example, cells from an established cell line can express one or more exogenous BoNT/A receptors by transient or stably transfection of a polynucleotide molecule encoding a BoNT/A receptor, such as, e.g., a FGFR2, a FGFR3, or a SV2. As another non-limiting example, cells from an established cell line can express one or more exogenous BoNT/A receptors by protein transfection of the BoNT/A receptors, such as, e.g., a FGFR2, a FGFR3, or a SV2. An exogenous BoNT/A receptor can be a naturally-occurring BoNT/A receptor or naturally occurring variants thereof, or non-naturally occurring BoNT/A receptor or non-naturally occurring variants thereof.

Thus in an embodiment, cells from an established cell line express an endogenous BoNT/A receptor. In aspects of this embodiment, the endogenous BoNT/A receptor expressed by cells from an established cell line is a naturally-occurring BoNT/A receptor. In other aspects of this embodiment, the endogenous BoNT/A receptor expressed by cells from an established cell line is SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet aspects of this embodiment, the endogenous BoNT/A receptor expressed by cells from an established cell line is a naturally occurring BoNT/A receptor, such as, e.g., a BoNT/A receptor isoform or a BoNT/A receptor subtype. In other aspects of this embodiment, the endogenous BoNT/A receptor expressed by cells from an established cell line is a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another embodiment, cells from an established cell line are transiently or stably engineered to express an exogenous BoNT/A receptor. In an aspect of this embodiment, cells from an established cell line are transiently or stably engineered to express a naturally-occurring BoNT/A receptor. In other aspects of this embodiment, cells from an established cell line are transiently or stably engineered to express the naturally-occurring BoNT/A receptor of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, cells from an established cell line are transiently or stably engineered to express a naturally occurring BoNT/A receptor, such as, e.g., a BoNT/A receptor isoform or a BoNT/A receptor subtype. In still other aspects of this embodiment, cells from an established cell line are transiently or stably engineered to express a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another aspect of the embodiment, cells from an established cell line are transiently or stably engineered to express a non-naturally occurring BoNT/A receptor. In other aspects of this embodiment, cells from an established cell line are transiently or stably engineered to express a non-naturally occurring BoNT/A receptor having, e.g., at least 70%, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, cells from an established cell line are transiently or stably engineered to express a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more noncontiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, cells from an established cell line are transiently or stably engineered to express a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another embodiment, cells from an established cell line are transiently or stably engineered to express an exogenous FGFR2, an exogenous FGFR3, an exogenous SV2, or any combination thereof. In aspects of this embodiment, cells from an established cell line are transiently or stably engineered to express a naturally-occurring FGFR2, a naturally-occurring FGFR3, a naturally-occurring SV2, or any combination thereof. In yet other aspects of this embodiment, cells from an established cell line are transiently or stably engineered to express a non-naturally-occurring FGFR2, a non-naturally-occurring FGFR3, a non-naturally-occurring SV2, or any combination thereof. In still other aspects of this embodiment, cells from an established cell line are transiently or stably engineered to express either a naturally-occurring FGFR2 or a non-naturally-occurring FGFR2, a naturally-occurring FGFR3 or a non-naturally-occurring FGFR3, a naturally-occurring SV2 or a non-naturally-occurring SV2, or any combination thereof.

Cells that express one or more endogenous or exogenous BoNT/A receptors can be identified by routine methods including direct and indirect assays for toxin uptake. Assays that determine BoNT/A binding or uptake properties can be used to assess whether a cell is expressing a BoNT/A receptor. Such assays include, without limitation, cross-linking assays using labeled BoNT/A, such as, e.g., [125I] BoNT/A, [125I], see, e.g., Noriko Yokosawa et al., Binding of *Clostridium botulinum* type C neurotoxin to different neuroblastoma cell lines, 57(1) Infect. Immun. 272-277 (1989); Noriko Yokosawa et al., Binding of botulinum type C1, D and E neurotoxins to neuronal cell lines and synaptosomes, 29(2) Toxicon 261-264 (1991); and Teiichi Nishiki et al., Identification of protein receptor for *Clostridium botulinum* type B neurotoxin in rat brain synaptosomes, 269(14) J. Biol. Chem. 10498-10503 (1994). Other non-limiting assays include immunocytochemical assays that detect BoNT/A binding using labeled or unlabeled antibodies, see, e.g., Atsushi Nishikawa et al., The receptor and transporter for internalization of *Clostridium botulinum* type C progenitor toxin into HT-29 cells, 319(2) Biochem. Biophys. Res. Commun. 327-333 (2004) and immunoprecipitation assays, see, e.g., Yukako Fujinaga et al., Molecular characterization of binding subcomponents of *Clostridium botulinum* type C progenitor toxin for intestinal epithelial cells and erythrocytes, 150(Pt 5) Microbiology 1529-1538 (2004), that detect bound toxin using labeled or unlabeled antibodies. Antibodies useful for these assays include, without limitation, antibodies selected against BoNT/A, antibodies selected against a BoNT/A receptor, such as, e.g., FGFR2, FGFR3, or SV2, and/or antibodies selected against a ganglioside, such as, e.g., GD1a, GD1b, GD3, GQ1b, or GT1b. If the antibody is labeled, the binding of the molecule can be detected by various means, including Western blot analysis, direct microscopic observation of the cellular location of the antibody, measurement of cell or substrate-bound antibody following a wash step, flow cytometry, electrophoresis or capillary electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine BoNT/A uptake properties or characteristics can be useful in identifying cells expressing endogenous or exogenous or BoNT/A receptors.

Assays that monitor the release of a molecule after exposure to BoNT/A can also be used to assess whether a cell is expressing one or more endogenous or exogenous BoNT/A receptors. In these assays, inhibition of the molecule's release would occur in cells expressing a BoNT/A receptor after BoNT/A treatment. Well known assays include methods that measure inhibition of radio-labeled catecholamine release from neurons, such as, e.g., [3H] noradrenaline or [3H] dopamine release, see e.g., A Fassio et al., *Evidence for calcium-dependent vesicular transmitter release insensitive to tetanus toxin and botulinum toxin type F*, 90(3) Neuroscience 893-902 (1999); and Sara Stigliani et al., *The sensitivity of catecholamine release to botulinum toxin Cl and E suggests selective targeting of vesicles set into the readily releasable pool*, 85(2) J. Neurochem. 409-421 (2003), or measures catecholamine release using a fluorometric procedure, see, e.g., Anton de Paiva et al., *A role for the interchain disulfide or its participating thiols in the internalization of botulinum neurotoxin A revealed by a toxin derivative that binds to ecto-acceptors and inhibits transmitter release intracellularly*, 268(28) J. Biol. Chem. 20838-20844 (1993); Gary W. Lawrence et al., *Distinct exocytotic responses of intact and permeabilised chromaffin cells after cleavage of the 25-kDa synaptosomal-associated protein (SNAP-25) or synaptobrevin by botulinum toxin A or B*, 236(3) Eur. J. Biochem. 877-886 (1996); and Patrick Foran et al., *Botulinum neurotoxin Cl cleaves both syntaxin and SNAP-25 in intact and permeabilized chromaffin cells: correlation with its blockade of catecholamine release*, 35(8) Biochemistry 2630-2636 (1996). Other non-limiting examples include assays that measure inhibition of hormone release from endocrine cells, such as, e.g., anterior pituitary cells or ovarian cells. It is understood that these and similar assays for molecule release can be useful in identifying cells expressing endogenous or exogenous or BoNT/A receptors.

Assays that detect the cleavage of a BoNT/A substrate after exposure to a BoNT/A can also be used to assess whether a cell is expressing one or more endogenous or exogenous BoNT/A receptors. In these assays, generation of a BoNT/A substrate cleavage-product, or disappearance of the intact BoNT/A substrate, would be detected in cells expressing a BoNT/A receptor after BoNT/A treatment. Non-limiting examples of specific Western blot analysis, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for BoNT/A substrate cleavage can be useful in identifying cells expressing endogenous or exogenous BoNT/A receptors.

As non-limiting examples, Western blot analysis using an antibody that recognizes BoNT/A SNAP-25-cleaved product or both the cleaved and uncleaved forms of SNAP-25 can be used to assay for uptake of BoNT/A. Examples of α-SNAP-25 antibodies useful for these assays include, without limitation, SMI-81 α-SNAP-25 mouse monoclonal antibody (Sternberger Monoclonals Inc., Lutherville, Md.), CI 71.1 mouse α-SNAP-25 monoclonal antibody (Synaptic Systems, Goettingen, Germany), CI 71.2 α-SNAP-25 mouse monoclonal antibody (Synaptic Systems, Goettingen, Germany), SP12 α-SNAP-25 mouse monoclonal antibody (Abcam, Cambridge, Mass.), α-SNAP-25 rabbit polyclonal antiserum (Synaptic Systems, Goettingen, Germany), α-SNAP-25 rabbit polyclonal antiserum S9684 (Sigma, St. Louis, Mo.), and α-SNAP-25 rabbit polyclonal antiserum (Abcam, Cambridge, Mass.).

Aspects of the present disclosure provide cells that through genetic manipulation or recombinant engineering are made to expresses an exogenous SNAP-25 and/or one or more exogenous BoNT/A receptors. Cells useful to express an exogenous SNAP-25 and/or one or more exogenous BoNT/A receptors through genetic manipulation or recombinant engineering include neuronal cells and non-neuronal cells that may or may not express an endogenous SNAP-25 and/or one or more endogenous BoNT/A receptors. It is further understood that such genetically manipulated or recombinantly engineered cells may express an exogenous SNAP-25 and one or more exogenous BoNT/A receptors under control of a constitutive, tissue-specific, cell-specific or inducible promoter element, enhancer element or both. It is understood that any cell is useful as long as the cell can be genetically manipulated or recombinantly engineered to expresses an exogenous SNAP-25 and/or one or more exogenous BoNT/A receptors and is capable of undergoing BoNT/A intoxication.

Methods useful for introducing into a cell an exogenous polynucleotide molecule encoding a component necessary for the cells to undergo the overall cellular mechanism whereby a BoNT/A proteolytically cleaves a SNAP-25 substrate, such as, e.g., a SNAP-25, a FGFR2, a FGFR3, or a SV2, include, without limitation, chemical-mediated delivery methods, such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated delivery methods, such as, e.g., biolistic particle delivery, microinjection, protoplast fusion and electroporation; and viral-mediated delivery methods, such as, e.g., retroviral-mediated transfection, see e.g., Introducing Cloned Genes into Cultured Mammalian Cells, pp. 16.1-16.62 (Sambrook & Russell, eds., Molecular Cloning A Laboratory Manual, Vol. 3, 3$^{rd}$ ed. 2001); Alessia Colosimo et al., Transfer and Expression of Foreign Genes in Mammalian Cells, 29(2) Biotechniques 314-318, 320-322, 324 (2000); Philip Washbourne & A. Kimberley McAllister, Techniques for Gene Transfer into Neurons, 12(5) Curr. Opin. Neurobiol. 566-573 (2002); and Current Protocols in Molecular Biology, John Wiley and Sons, pp 9.16.4-9.16.11 (2000), each of which is incorporated by reference in its entirety. One skilled in the art understands that selection of a specific method to introduce a polynucleotide molecule into a cell will depend, in part, on whether the cell will transiently or stably contain a component necessary for the cells to undergo the overall cellular mechanism whereby a BoNT/A proteolytically cleaves a SNAP-25 substrate. Non-limiting examples of polynucleotide molecule encoding a component necessary for the cells to undergo the overall cellular mechanism whereby a BoNT/A proteolytically cleaves a SNAP-25 substrate as follows: FGFR2 polynucleotide molecule of SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, or SEQ ID NO: 138; FGFR3 polynucleotide molecule of SEQ ID NO: 139, SEQ ID NO: 140, or SEQ ID NO: 141; SV2 polynucleotide molecule of SEQ ID NO: 142, SEQ ID NO: 143, or SEQ ID NO: 144; and SNAP-25 polynucleotide molecule of SEQ ID NO: 145, or SEQ ID NO: 146.

Chemical-mediated delivery methods are well-known to a person of ordinary skill in the art and are described in, e.g., Martin Jordan & Florian Worm, *Transfection of Adherent and Suspended Cells by Calcium Phosphate*, 33(2) Methods 136-143 (2004); Chun Zhang et al., *Polyethylenimine Strategies for Plasmid Delivery to Brain-Derived Cells*, 33(2) Methods 144-150 (2004), each of which is hereby incorporated by reference in its entirety. Such chemical-mediated delivery methods can be prepared by standard procedures and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

Physical-mediated delivery methods are well-known to a person of ordinary skill in the art and are described in, e.g., Jeike E. Biewenga et al., *Plasmid-Mediated Gene Transfer in Neurons using the Biolistics Technique*, 71(1) J. Neurosci. Methods. 67-75 (1997); John O'Brien & Sarah C. R. Lummis, *Biolistic and Diolistic Transfection: Using the Gene Gun to Deliver DNA and Lipophilic Dyes into Mammalian Cells*, 33(2) Methods 121-125 (2004); M. Golzio et al., *In Vitro and In Vivo Electric Field-Mediated Permeabilization, Gene Transfer, and Expression*, 33(2) Methods 126-135 (2004); and Oliver Gresch et al., *New Non-Viral Method for Gene Transfer into Primary Cells*, 33(2) Methods 151-163 (2004), each of which is hereby incorporated by reference in its entirety.

Viral-mediated delivery methods are well-known to a person of ordinary skill in the art and are described in, e.g., Chooi M. Lai et al., *Adenovirus and Adena-Associated Virus Vectors*, 21 (12) DNA Cell Biol. 895-913 (2002); Ilya Frolov et al., *Alphavirus-Based Expression Vectors: Strategies and Applications*, 93(21) Proc. Natl. Acad. Sci. U.S.A 11371-11377 (1996); Roland Wolkowicź et al., *Lentiviral Vectors for the Delivery of DNA into Mammalian Cells*, 246 Methods Mal. Biol. 391-411 (2004); A. Huser & C. Hofmann, *Baculovirus Vectors: Novel Mammalian Cell Gene-Delivery Vehicles and Their Applications*, 3(1) Am. J. Pharmacogenomics 53-63 (2003); Tiziana Tonini et al., *Transient Production of Retro viral- and Lentiviral-Based Vectors for the Transduction of Mammalian Cells*, 285 Methods Mal. Biol. 141-148 (2004); Manfred Gossen & Hermann Bujard, Tight Control of Gene Expression in Eukaryotic Cells by Tetracycline-Responsive Promoters, U.S. Pat. No. 5,464,758; Hermann Bujard & Manfred Gossen, Methods for Regulating Gene Expression, U.S. Pat. No. 5,814,618; David S. Hogness, Polynucleotides Encoding Insect Steroid Hormone Receptor Polypeptides and Cells Transformed With Same, U.S. Pat. No. 5,514,578; David S. Hogness, Polynucleotide Encoding Insect Ecdysone Receptor, U.S. Pat. No. 6,245,531; Elisabetta Vegeto et al., Progesterone Receptor Having C. Terminal Hormone Binding Domain Truncations, U.S. Pat. No. 5,364,791; Elisabetta Vegeto et al., Mutated Steroid Hormone Receptors, Methods for Their Use and Molecular Switch for Gene Therapy, U.S. Pat. No. 5,874,534, each of which is hereby incorporated by reference in its entirety. Such viral-mediated delivery methods can be prepared by standard procedures and are commercially available, see, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEasy™ Adenoviral Vector System (Stratagene, Inc., La Jolla, Calif.) and AdEasy™ Adenoviral Vector System Instruction Manual 064004f, Stratagene, Inc. Furthermore, such viral delivery systems can be prepared by standard methods and are commercially available, see, e.g., BD™ Tet-Off and Tet-On Gene Expression Systems (BD Biosciences Clontech, Palo Alto, Calif.) and BD™ Tet-Off and Tet-On Gene Expression Systems User Manual, PT3001-1, BD Biosciences Clontech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

Thus, in an embodiment, cells from an established cell line susceptible to BoNT/A intoxication transiently contain a polynucleotide molecule encoding a component necessary for the cells to undergo the overall cellular mechanism whereby a BoNT/A proteolytically cleaves a SNAP-25 substrate. In another embodiment, cells from an established cell line susceptible to BoNT/A intoxication transiently contain a polynucleotide molecule encoding a plurality of components necessary for the cells to undergo the overall cellular mechanism whereby a BoNT/A proteolytically cleaves a SNAP-25 substrate. In aspects of this embodiment, cells from an established cell line susceptible to BoNT/A intoxication transiently contain a polynucleotide molecule encoding FGFR2, FGFR3, SV2 or SNAP-25. In aspects of this embodiment, cells from an established cell line susceptible to BoNT/A intoxication transiently contain the polynucleotide molecule encoding FGFR2 of SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, or SEQ ID NO: 138. In other aspects of this embodiment, cells from an established cell line susceptible to BoNT/A intoxication transiently contain the polynucleotide molecule encoding FGFR3 of SEQ ID NO: 139, SEQ ID NO: 140, or SEQ ID NO: 141. In yet other aspects of this embodiment, cells from an established cell line susceptible to BoNT/A intoxication transiently contain the polynucleotide molecule encoding SV2 of SEQ ID NO: 142, SEQ ID NO: 143, or SEQ ID NO: 144. In yet other aspects of this embodiment, cells from an established cell line susceptible to BoNT/A intoxication transiently contain the polynucleotide molecule encoding SNAP-25 of SEQ ID NO: 145, or SEQ ID NO: 146.

In another embodiment, cells from an established cell line susceptible to BoNT/A intoxication stably contain a polynucleotide molecule encoding a component necessary for the cells to undergo the overall cellular mechanism whereby a BoNT/A proteolytically cleaves a SNAP-25 substrate. In another embodiment, cells from an established cell line susceptible to BoNT/A intoxication stably contain a polynucleotide molecule encoding a plurality of components necessary for the cells to undergo the overall cellular mechanism whereby a BoNT/A proteolytically cleaves a SNAP-25 substrate. In aspects of this embodiment, cells from an established cell line susceptible to BoNT/A intoxication stably contain a polynucleotide molecule encoding FGFR2, FGFR3, SV2 or SNAP-25. In aspects of this embodiment, cells from an established cell line susceptible to BoNT/A intoxication stably contain the polynucleotide molecule encoding FGFR2 of SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, or SEQ ID NO: 138. In other aspects of this embodiment, cells from an established cell line susceptible to BoNT/A intoxication stably contain the polynucleotide molecule encoding FGFR3 of SEQ ID NO: 139, SEQ ID NO: 140, or SEQ ID NO: 141. In yet other aspects of this embodiment, cells from an established cell line susceptible to BoNT/A intoxication stably contain the polynucleotide molecule encoding SV2 of SEQ ID NO: 142, SEQ ID NO: 143, or SEQ ID NO: 144. In yet other aspects of this embodiment, cells from an established cell line susceptible to BoNT/A intoxication stably contain the polynucleotide molecule encoding SNAP-25 of SEQ ID NO: 145, or SEQ ID NO: 146.

As mentioned above, an exogenous component necessary for the cells to undergo the overall cellular mechanism whereby a BoNT/A proteolytically cleaves a SNAP-25 substrate, such as, e.g., a SNAP-25, a FGFR2, a FGFR3, or a SV2 disclosed in the present specification can be introduced into a cell. Any and all methods useful for introducing such an exogenous component with a delivery agent into a cell population can be useful with the proviso that this method transiently introduces the exogenous component disclosed in the present specification in at least 50% of the cells within a given cell population. Thus, aspects of this embodiment can include a cell population in which, e.g., at least 50%, at least 60%, at least 70%, at least 80%, or at least 90% of the given cell population transiently contains an exogenous component necessary for the cells to undergo the overall cellular mechanism whereby a BoNT/A proteolytically cleaves a SNAP-25 substrate, such as, e.g., a SNAP-25, a FGFR2, a FGFR3, or a SV2 disclosed in the present specification. As used herein, the term "delivery agent" refers to any molecule that enables or enhances internalization of a covalently-linked, non-covalently-linked or in any other manner associated with a polypeptide into a cell. Thus, the term "delivery agent" encompasses, without limitation, proteins, peptides, peptidomimetics, small molecules, polynucleotide molecules, liposomes, lipids, viruses, retroviruses and cells that, without limitation, transport a covalently or non-covalently linked molecule to the cell membrane, cell cytoplasm or nucleus. It further is understood that the term "delivery agent" encompasses molecules that are internalized by any mechanism, including delivery agents which function via receptor mediated endocytosis and those which are independent of receptor mediated endocytosis.

A delivery agent can also be an agent that enables or enhances cellular uptake of a covalently linked component, like FGFR2, FGFR3, SV2, or SNAP-25, such as, e.g., by chemical conjugation or by genetically produced fusion proteins. Methods that covalently link delivery agents and methods of using such agents are described in, e.g., Steven F. Dowdy, Protein Transduction System and Methods of Use Thereof, International Publication No WO 00/34308; Gerard Chassaing & Alain Prochiantz, Peptides which can be Used as Vectors for the Intracellular Addressing of Active Molecules, U.S. Pat. No. 6,080,724; Alan Frankel et al., Fusion Protein Comprising TAT-derived Transport Moiety, U.S. Pat. No. 5,674,980; Alan Frankel et al., TAT-derived Transport Polypeptide Conjugates, U.S. Pat. No. 5,747,641; Alan Frankel et al., TAT-derived Transport Polypeptides and Fusion Proteins, U.S. Pat. No. 5,804,604; Peter F. J. O'Hare et al., Use of Transport Proteins, U.S. Pat. No. 6,734,167; Yao-Zhong Lin & Jack J. Hawiger, Method for Importing Biologically Active Molecules into Cells, U.S. Pat. No. 5,807,746; Yao-Zhong Lin & Jack J. Hawiger, Method for Importing Biologically Active Molecules into Cells, U.S. Pat. No. 6,043,339; Yao-Zhong Lin et al., Sequence and Method for Genetic Engineering of Proteins with Cell Membrane Translocating Activity, U.S. Pat. No. 6,248,558; Yao-Zhong Lin et al., Sequence and Method for Genetic Engineering of Proteins with Cell Membrane Translocating Activity, U.S. Pat. No. 6,432,680; Jack J. Hawiger et al., Method for Importing Biologically Active Molecules into Cells, U.S. Pat. No. 6,495,518; Yao-Zhong Lin et al., Sequence and Method for Genetic Engineering of Proteins with Cell Membrane Translocating Activity, U.S. Pat. No. 6,780,843; Jonathan B. Rothbard & Paul A Wender, Method and Composition for Enhancing Transport Across Biological Membranes, U.S. Pat. No. 6,306,993; Jonathan B. Rothbard & Paul A Wender, Method and Composition for Enhancing Transport Across Biological Membranes, U.S. Pat. No. 6,495,663; and Pamela B. Davis et al., Fusion Proteins for Protein Delivery, U.S. Pat. No. 6,287,817, each of which is incorporated by reference in its entirety.

A delivery agent can also be an agent that enables or enhances cellular uptake of a non-covalently associated component, like FGFR2, FGFR3, SV2c, or SNAP-25. Methods that function in the absence of covalent linkage and methods of using such agents are described in, e.g., Gilles Divita et al, Peptide-Mediated Transfection Agents and Methods of Use, U.S. Pat. No. 6,841,535; Philip L Feigner and Olivier Zelphati, Intracellular Protein Delivery Compositions and Methods of Use, U.S. Patent Publication No. 2003/0008813; and Michael Karas, Intracellular Delivery of Small Molecules, Proteins and Nucleic Acids, U.S. Patent Publication 2004/0209797, each of which is incorporated by reference in its entirety. Such peptide delivery agents can be prepared and used by standard methods and are commercially available, see, e.g. the CHARIOT™ Reagent (Active Motif, Carlsbad, Calif.); BIO-PORTER® Reagent (Gene Therapy Systems, Inc., San Diego, Calif.), BIO TREK™ Protein Delivery Reagent (Stratagene, La Jolla, Calif.), and PRO-JECT™ Protein Transfection Reagent (Pierce Biotechnology Inc., Rockford, Ill.).

Aspects of the present disclosure comprise, in part, a sample comprising a BoNT/A. As used herein, the term "sample comprising a BoNT/A" refers to any biological matter that contains or potentially contains an active BoNT/A. A variety of samples can be assayed according to a method disclosed in the present specification including, without limitation, purified, partially purified, or unpurified BoNT/A; recombinant single chain or di-chain toxin with a naturally or non-naturally occurring sequence; recombinant BoNT/A with a modified protease specificity; recombinant BoNT/A with an altered cell specificity; bulk BoNT/A; a formulated BoNT/A product, including, e.g., BOTOX®, DYSPORT®/RELOXIN®, XEOMIN®, PURTOX®, NEURONOX®, BTX-A and; cells or crude, fractionated or partially purified cell lysates from, e.g., bacteria, yeast, insect, or mammalian sources; blood, plasma or serum; raw, partially cooked, cooked, or processed foods; beverages; animal feed; soil samples; water samples; pond sediments; lotions; cosmetics; and clinical formulations. It is understood that the term sample encompasses tissue samples, including, without limitation, mammalian tissue samples, livestock tissue samples such as sheep, cow and pig tissue samples; primate tissue samples; and human tissue samples. Such samples encompass, without limitation, intestinal samples such as infant intestinal samples, and tissue samples obtained from a wound. As non-limiting examples, a method of detecting picomolar amounts of BoNT/A activity can be useful for determining the presence or activity of a BoNT/A in a food or beverage sample; to assay a sample from a human or animal, for example, exposed to a BoNT/A or having one or more symptoms of botulism; to follow activity during production and purification of bulk BoNT/A; to assay a formulated BoNT/A product used in pharmaceutical or cosmetics applications; or to assay a subject's blood serum for the presence or absence of neutralizing α-BoNT/A antibodies.

Thus, in an embodiment, a sample comprising a BoNT/A is a sample comprising any amount of a BoNT/A. In aspects of this embodiment, a sample comprising a BoNT/A comprises about 100 ng or less, about 10 ng or less, about 1 ng or less, about 100 pg or less, about 10 pg or less, or about 1 pg or less of a BoNT/A. In other aspects of this embodiment, a sample comprising a BoNT/A comprises about 1 pM or less, about 100 nM or less, about 10 nM or less, about 1 nM or less, about 100 pM or less, about 10 pM or less, about 1 pM or less, about 100 fM or less, about 10 fM or less, or about 1 fM or less of a BoNT/A.

Aspects of the present disclosure comprise, in part, isolating from the treated cell a SNAP-25 component comprising a SNAP-25 having a carboxyl-terminus at the $P_1$ residue of the BoNT/A cleavage site scissile bond. As used herein, the term "SNAP-25 component comprising a SNAP-25 having a carboxyl-terminus at the $P_1$ residue of the BoNT/A cleavage site scissile bond" refers to a cellular component containing the SNAP-25 cleavage product. It is envisioned that any method suitable for enriching or isolating a SNAP-25 component can be useful, including, without limitation, cell lysing protocols, spin-column purification protocols, immunoprecipitation, affinity purification, and protein chromatography.

Aspects of the present disclosure comprise, in part, an α-SNAP-25 antibody linked to a solid phase support. As used herein, the term "solid-phase support" is synonymous with "solid phase" and refers to any matrix that can be used for immobilizing an α-SNAP-25 antibody disclosed in the present specification. Non-limiting examples of solid phase supports include, e.g., a tube; a plate; a column; pins or "dipsticks"; a magnetic particle, a bead or other spherical or fibrous chromatographic media, such as, e.g., agarose, sepharose, silica and plastic; and sheets or membranes, such as, e.g., nitrocellulose and polyvinylidene fluoride (PVDF). The solid phase support can be constructed using a wide variety of materials such as, e.g., glass, carbon, polystyrene, polyvinylchloride, polypropylene, polyethylene, dextran, nylon, diazocellulose, or starch. The solid phase support selected can have a physical property that renders it readily separable from soluble or unbound material and generally allows unbound materials, such as, e.g., excess reagents, reaction by-products, or solvents, to be separated or otherwise removed (by, e.g., washing, filtration, centrifugation, etc.) from solid phase support-bound assay component. Non-limiting examples of how to make and use a solid phase supports are described in, e.g., Molecular Cloning, A Laboratory Manual, supra, (2001); and Current Protocols in Molecular Biology, supra, (2004), each of which is hereby incorporated by reference in its entirety.

Aspects of the present disclosure comprise, in part, detecting the presence of an antibody-antigen complex comprising an α-SNAP-25 antibody that selectively binds to a SNAP-25 epitope having a carboxyl-terminus at the $P_1$ residue of the BoNT/A cleavage site scissile bond and a SNAP-25 cleavage product having a carboxyl-terminus at the $P_1$ residue of the BoNT/A cleavage site scissile bond. It is envisioned that any detection system can be used to practice aspects of this disclosed immuno-based method, with the provision that the signal to noise ratio can distinguish to a statistically significant degree the signal from the antibody-antigen complex from the background signal. Non-limiting examples of immuno-based detection systems include immunoblot analysis, like Western blotting and dot-blotting, immunoprecipitation analysis, enzyme-linked immunosorbent analysis (ELISA), and sandwich ELISA. The detection of the signal can be achieved using autoradiography with imaging or phosphorimaging (AU), chemiluminescence (CL), electrochemiluminescence (ECL), bioluminescence (BL), fluorescence, resonance energy transfer, plane polarization, colorimetric, or flow cytometry (FC). Descriptions of immuno-based detection systems are disclosed in, e.g., Michael M. Rauhut, Chemiluminescence, In Kirk-Othmer Concise Encyclopedia of Chemical Technology (Ed. Grayson, $3^{rd}$ ed, John Wiley and Sons, 1985); A. W. Knight, A Review of Recent Trends in Analytical Applications of Electrogenerated Chemiluminescence, Trends Anal. Chem. 18(1): 47-62 (1999); K. A. Fahnrich, et al., Recent Applications of Electrogenerated Chemiluminescence in Chemical Analysis, Talanta 54(4): 531-559 (2001); Commonly Used Techniques in Molecular Cloning, pp. A8.1-A8-55 (Sambrook & Russell, eds., Molecular Cloning A Laboratory Manual, Vol. 3, $3^{rd}$ ed. 2001); Detection Systems, pp. A9.1-A9-49 (Sambrook & Russell, eds., Molecular Cloning A Laboratory Manual, Vol. 3, $3^{rd}$ ed. 2001); Electrogenerated Chemiluminescence, (Ed. Allen J. Bard, Marcel Dekker, Inc., 2004), each of which is hereby incorporated by reference in its entirety.

A sandwich ELISA (or sandwich immunoassay) is a method based on two antibodies, which bind to different epitopes on the antigen. A capture antibody having a high binding specificity for the antigen of interest, is bound to a solid surface. The antigen is then added followed by addition of a second antibody referred to as the detection antibody. The detection antibody binds the antigen to a different epitope than the capture antibody. The antigen is therefore 'sandwiched' between the two antibodies. The antibody binding affinity for the antigen is usually the main determinant of immunoassay sensitivity. As the antigen concentration increases the amount of detection antibody increases leading to a higher measured response. To quantify the extent of binding different reporter systems can be used, such as, e.g., an enzyme attached to the secondary antibody and a reporter substrate where the enzymatic reaction forms a readout as the detection signal. The signal generated is proportional to the amount of target antigen present in the sample. The reporter substrate used to measure the binding event determines the detection mode. A spectrophotometric plate reader is used for colorimetric detection. Chemiluminescent and electrochemiluminescence substrates have been developed which further amplify the signal and can be read on a luminescent reader. The reporter can also be a fluorescent readout where the enzyme step of the assay is replaced with a fluorophore and the readout is then measured using a fluorescent reader. Reagents and protocols necessary to perform an ECL sandwich ELISA are commercially available, including, without exception, MSD sandwich ELISA-ECL detection platform (Meso Scale Discovery, Gaithersburg, Md.).

Thus, in an embodiment, detecting the presence of an antibody-antigen complex comprising an α-SNAP-25 antibody that selectively binds to a SNAP-25 epitope having a carboxyl-terminus at the $P_1$ residue of the BoNT/A cleavage site scissile bond and a SNAP-25 cleavage product having a carboxyl-terminus at the $P_1$ residue of the BoNT/A cleavage site scissile bond can be performed using an immuno-blot analysis, an immunoprecipitation analysis, an ELISA, or a sandwich ELISA. In aspects of this embodiment, the detection is performed using a AU, CL, ECL, or BL immuno-blot analysis, a AU, CL, ECL, BL, or FC immunoprecipitation analysis, a AU, CL, ECL, BL, or FC ELISA, or a AU, CL, ECL, BL, or FC sandwich ELISA.

Aspects of the present disclosure can be practiced in a singleplex or multiplex fashion. An immuno-based method of detecting BoNT/A activity practiced in a single-plex fashion is one that only detects the presence of an antibody-antigen complex comprising an α-SNAP-25 antibody and a SNAP-25 cleavage product having a carboxyl-terminus at the $P_1$ residue of the BoNT/A cleavage site scissile bond. An immuno-based method of detecting BoNT/A activity practiced in a multiplex fashion is one that concurrently detects the presence of two or more antibody-antigen complexes; one of which is the antibody-antigen complex comprising an α-SNAP-25 antibody and a SNAP-25 cleavage product having a carboxyl-terminus at the $P_1$ residue of the BoNT/A cleavage site scissile bond; and the other(s) of which is antibody-antigen complex to a second, third, fourth, etc. different protein. A second protein can be used, e.g., as an internal control to minimize sample to sample variability by normalizing the amount of α-SNAP-25/SNAP-25 antibody-antigen complex detected to the amount of antibody-antigen complex detected for the second protein. As such, the second protein is usually one that is consistently expressed by the cell, such as a house-keeping protein. Non-limiting examples of a useful second protein, include, e.g., a Glyceraldehyde-3-Phosphate Dehydrogenase (GAPDH), Syntaxin, cytokines. Methods of performing an immuno-based assay in a multiplex fashion are described in, e.g., U. B. Nielsen and B. H. Geierstanger, *Multiplexed Sandwich Assays in Microarray Format*, J. Immunol. Methods. 290 (1-2): 107-120 2004); R. Barry and M, Soloviev, *Quantitative Protein Profiling using Antibody Arrays*, Proteomics, 4(12): 3717-3726 (2004); M. M. Ling et al., *Multiplexing Molecular Diagnostics and Immunoassays using Emerging Microarray Technologies*, Expert Rev Mol Diagn. 7(1): 87-98 (2007); S. X. Leng et al., *ELISA and Multiplex Technologies for Cytokine Measurement in Inflammation and Aging Research*, J Gerontol A Biol Sci Med Sci. 63(8): 879-884 (2008), each of which is hereby incorporated by reference in its entirety.

Thus, in one embodiment, an immuno-based method of detecting BoNT/A activity practiced in a single-plex fashion by only detecting the presence of an antibody-antigen complex comprising an α-SNAP-25 antibody and a SNAP-25 cleavage product having a carboxyl-terminus at the $P_1$ residue of the BoNT/A cleavage site scissile bond. In another embodiment, immuno-based method of detecting BoNT/A activity practiced in a multiplex fashion by concurrently detecting the presence of an antibody-antigen complex comprising an α-SNAP-25 antibody and a SNAP-25 cleavage product having a carboxyl-terminus at the $P_1$ residue of the BoNT/A cleavage site scissile bond and at least one other antibody-antigen complex to a protein other than SNAP-25, such as, e.g., GAPDH or Syntaxin.

Aspects of the present disclosure provide, in part, a method of determining BoNT/A immunoresistance. As used herein, the term "BoNT/A immunoresistance" means a mammal that does not fully respond to a BoNT/A therapy, or shows a reduced beneficial effect of a BoNT/A therapy because the immune response of that mammal, either directly or indirectly, reduces the efficacy of the therapy. A non-limiting example of reduced efficacy would be the presence in a mammal of at least one neutralizing α-BoNT/A antibody that binds to a BoNT/A toxin in a manner that reduces or prevents the specificity or activity of the toxin. As used herein, the term "BoNT/A therapy" means a treatment, remedy, cure, healing, rehabilitation or any other means of counteracting something undesirable in a mammal requiring neuromodulation using a BoNT/A toxin or administering to a mammal one or more controlled doses of a medication, preparation or mixture of a BoNT/A toxin that has medicinal, therapeutic, curative, cosmetic, remedial or any other beneficial effect. BoNT/A therapy encompasses, without limitation, the use of any naturally occurring or modified fragment thereof, in any formulation, combined with any carrier or active ingredient and administered by any route of administration. An exemplary, well-known BoNT/A therapy is a BOTOX® therapy.

Aspects of the present disclosure provide, in part, a test sample obtained from a mammal being tested for the presence or absence of α-BoNT/A neutralizing antibodies. As used herein, the term "test sample" refers to any biological matter that contains or potentially contains at least one α-BoNT/A antibody. An α-BoNT/A antibody can be a neutralizing anti-BoNT/A antibody or a non-neutralizing anti-BoNT/A antibody. As used herein, the term "neutralizing anti-BoNT/A antibodies" means any α-BoNT/A antibody that will, under physiological conditions, bind to a region of a BoNT/A toxin in such a manner as to reduce or prevent the toxin from exerting its effect in a BoNT/A therapy. As used herein, the term "non-neutralizing α-BoNT/A antibodies" means any α-BoNT/A antibody that will, under physiological conditions, bind to a region of a BoNT/A toxin, but not prevent the toxin from exerting its effect in a BoNT/A therapy. It is envisioned that any and all samples that can contain α-BoNT/A antibodies can be used in this method, including, without limitation, blood, plasma, serum and lymph fluid. In addition, any and all organisms capable of raising α-BoNT/A antibodies against a BoNT/A toxin can serve as a source for a sample including, but not limited to, birds and mammals, including mice, rats, goats, sheep, horses, donkeys, cows, primates and humans. Non-limiting examples of specific protocols for blood collection and serum preparation are described in, e.g., Marjorie Schaub Di Lorenzo & Susan King Strasinger, BLOOD COLLECTION IN HEALTHCARE (F.A. Davis Company, 2001); and Diana Garza & Kathleen Becan-McBride, PHLEBOTOMY HANDBOOK: BLOOD COLLECTION ESSENTIALS (Prentice Hall, 6$^{th}$ ed., 2002). These protocols are routine procedures well within the scope of one skilled in the art and from the teaching herein. A test sample can be obtained from an organism prior to exposure to a BoNT/A toxin, after a single BoNT/A treatment, after multiple BoNT/A toxin treatments, before onset of resistance to a BoNT/A therapy, or after onset of resistance to a BoNT/A therapy.

Aspects of the present disclosure provide, in part, a control sample. As used herein, the term "control sample" means any sample in which the presence or absence of the test sample is known and includes both negative and positive control samples. With respect to neutralizing α-BoNT/A antibodies, a negative control sample can be obtained from an individual who had never been exposed to BoNT/A and may include, without limitation, a sample from the same individual supplying the test sample, but taken before undergoing a BoNT/A therapy; a sample taken from a different individual never been exposed to BoNT/A; a pooled sample taken from a plurality of different individuals never been exposed to BoNT/A. With respect to neutralizing α-BoNT/A antibodies, a positive control sample can be obtained from an individual manifesting BoNT/A immunoresistance and includes, without limitation, individual testing positive in a patient-based testing assays; individual testing positive in an in vivo bioassay; and individual showing hyperimmunity, e.g., a BoNT/A vaccinated individual.

It is further foreseen that α-BoNT/A antibodies can be purified from a sample. Anti-BoNT/A antibodies can be purified from a sample, using a variety of procedures including, without limitation, Protein A/G chromatography and affinity chromatography. Non-limiting examples of specific protocols for purifying antibodies from a sample are described in, e.g., ANTIBODIES: A LABORATORY MANUAL (Edward Harlow & David Lane, eds., Cold Spring Harbor Laboratory Press, $2^{nd}$ ed. 1998); USING ANTIBODIES: A LABORATORY MANUAL: PORTABLE PROTOCOL No. I (Edward Harlow & David Lane, Cold Spring Harbor Laboratory Press, 1998); and MOLECULAR CLONING, A LABORATORY MANUAL, supra, (2001), which are hereby incorporated by reference. In addition, non-limiting examples of antibody purification methods as well as well-characterized reagents, conditions and protocols are readily available from commercial vendors that include, without limitation, Pierce Biotechnology, Inc., Rockford, Ill.; and Zymed Laboratories, Inc., South San Francisco, Calif. These protocols are routine procedures well within the scope of one skilled in the art.

Thus, in an embodiment, a sample comprises blood. In aspect of this embodiment, the sample comprises mouse blood, rat blood, goat blood, sheep blood, horse blood, donkey blood, cow blood, primate blood or human blood. In another embodiment, a sample comprises plasma. In an aspect of this embodiment, a test sample comprises mouse plasma, rat plasma, goat plasma, sheep plasma, horse plasma, donkey plasma, cow plasma, primate plasma or human plasma. In another embodiment, a sample comprises serum. In an aspect of this embodiment, the sample comprises mouse serum, rat serum, goat serum, sheep serum, horse serum, donkey serum, cow serum, primate serum and human serum. In another embodiment, a sample comprises lymph fluid. In aspect of this embodiment, a sample comprises mouse lymph fluid, rat lymph fluid, goat lymph fluid, sheep lymph fluid, horse lymph fluid, donkey lymph fluid, cow lymph fluid, primate lymph fluid or human lymph fluid. In yet another embodiment, a sample is a test sample. In yet another embodiment, a sample is a control sample. In aspects of this embodiment, a control sample is a negative control sample or a positive control sample.

Aspects of the present disclosure provide, in part, comparing the amount of SNAP-25 having a carboxyl-terminus at the $P_1$ residue of the BoNT/A cleavage site scissile bond detected in step (d) to the amount of SNAP-25 having a carboxyl-terminus at the $P_1$ residue of the BoNT/A cleavage site scissile bond detected in step (e). In an embodiment, the amount of SNAP-25 cleavage product in the test sample is higher as compared to the amount of SNAP-25 cleavage product in the control sample. In an aspect of this embodiment, a higher amount of SNAP-25 cleavage product in the test sample as compared to a positive control sample indicates a reduction in or lack of BoNT/A immunoresistance in the mammal. In another aspect of this embodiment, an equivalent amount of SNAP-25 cleavage product in the test sample as compared to a negative control sample indicates a reduction in or lack of BoNT/A immunoresistance in the mammal. In another embodiment, the amount of SNAP-25 cleavage product in the test sample is lower as compared to the amount of SNAP-25 cleavage product in the control sample. In an aspect of this embodiment, a lower or equivalent amount of SNAP-25 cleavage product in the test sample as compared to a positive control sample indicates an increase in or presence of BoNT/A immunoresistance in the mammal. In another aspect of this embodiment, a lower amount of SNAP-25 cleavage product in the test sample as compared to a negative control sample indicates an increase in or presence of BoNT/A immunoresistance in the mammal.

It is envisioned that any and all assay conditions suitable for detecting the present of a neutralizing α-BoNT/A antibody in a sample are useful in the methods disclosed in the present specification, such as, e.g., linear assay conditions and non-linear assay conditions. In an embodiment, the assay conditions are linear. In an aspect of this embodiment, the assay amount of a BoNT/A is in excess. In another aspect of this embodiment, the assay amount of a BoNT/A is rate-limiting. In another aspect of this embodiment, the assay amount of a test sample is rate-limiting.

Aspects of the present disclosure can also be described as follows:

1. A composition comprising a carrier linked to a flexible linker linked to SNAP-25 antigen having a carboxyl-terminus at the $P_1$ residue of the BoNT/A cleavage site scissile bond.

2. The composition of 1, wherein the $P_1$ residue of the BoNT/A cleavage site scissile bond is glutamine or lysine.

3. The composition of 1, wherein the SNAP-25 antigen comprises SEQ ID NO: 147.

4. The composition of 1, wherein the flexible linker and the SNAP-25 antigen amino acid sequence is SEQ ID NO: 38 or SEQ ID NO: 46.

5. An isolated α-SNAP-25 antibody, wherein the isolated α-SNAP-25 antibody binds an epitope comprising a carboxyl-terminus at the $P_1$ residue from the BoNT/A cleavage site scissile bond from a SNAP-25 cleavage product.

6. The isolated α-SNAP-25 antibody of 5, wherein the α-SNAP-25 antibody has an association rate constant for an epitope not comprising a carboxyl-terminus glutamine of the BoNT/A cleavage site scissile bond from a SNAP-25 cleavage product of less than $1\times10^1$ $M^{-1}$ $s^{-1}$; and wherein the α-SNAP-25 antibody has an equilibrium disassociation constant for the epitope of less than 0.450 nM.

7. The isolated α-SNAP-25 antibody of 5, wherein the isolated α-SNAP-25 antibody has a heavy chain variable region comprising the amino acid sequence selected from the group consisting of SEQ ID NO: 72, SEQ ID NO: 74, SEQ ID NO: 76, SEQ ID NO: 80, and SEQ ID NO: 82; and a light chain variable region comprising the amino acid sequence selected from the group consisting of SEQ ID NO: 84, SEQ ID NO: 86, SEQ ID NO: 88, SEQ ID NO: 90, and SEQ ID NO: 92.

8. The isolated α-SNAP-25 antibody of 5, wherein the isolated α-SNAP-25 antibody comprises at least the $V_H$ CDR1 of SEQ ID NO: 93, the $V_H$ CDR1 of SEQ ID NO: 94, the $V_H$ CDR1 of SEQ ID NO: 95, the $V_H$ CDR1 of SEQ ID NO: 118, the $V_H$ CDR1 of SEQ ID NO: 119, or the $V_H$ CDR1 of SEQ ID NO: 120.

9. The isolated α-SNAP-25 antibody of 5, wherein the isolated α-SNAP-25 antibody comprises at least the $V_H$ CDR2 of SEQ ID NO: 96, the $V_H$ CDR2 of SEQ ID NO: 97, the $V_H$ CDR2 of SEQ ID NO: 98, the $V_H$ CDR2 of SEQ ID NO: 99, the V$_H$ CDR2 of SEQ ID NO: 121, the V$_H$ CDR2 of SEQ ID NO: 122, or the V$_H$ CDR2 of SEQ ID NO: 123.

10. The isolated α-SNAP-25 antibody of 5, wherein the isolated α-SNAP-25 antibody comprises at least the V$_H$ CDR3 of SEQ ID NO: 100, the V$_H$ CDR3 of SEQ ID NO: 101, the V$_H$ CDR3 of SEQ ID NO: 102, or the V$_H$ CDR3 of SEQ ID NO: 124.

11. The isolated α-SNAP-25 antibody of 5, wherein the isolated α-SNAP-25 antibody comprises at least the V$_L$ CDR1 of SEQ ID NO: 103, the V$_L$ CDR1 of SEQ ID NO: 104, the V$_L$ CDR1 of SEQ ID NO: 105, the V$_L$ CDR1 of SEQ ID NO: 106, the V$_L$ CDR1 of SEQ ID NO: 107, the V$_L$ CDR1 of SEQ ID NO: 125, the V$_L$ CDR1 of SEQ ID NO: 126, the V$_L$ CDR1 of SEQ ID NO: 127, the V$_L$ CDR1 of SEQ ID NO: 128, or the V$_L$ CDR1 of SEQ ID NO: 129.

12. The isolated α-SNAP-25 antibody of 5, wherein the isolated α-SNAP-25 antibody comprises at least the V$_L$ CDR2 of SEQ ID NO: 108, the V$_L$ CDR2 of SEQ ID NO: 109, the V$_L$ CDR2 of SEQ ID NO: 110, the V$_L$ CDR2 of SEQ ID NO: 111, or the V$_L$ CDR2 of SEQ ID NO: 112.

13. The isolated α-SNAP-25 antibody of 5, wherein the isolated α-SNAP-25 antibody comprises at least the V$_L$ CDR3 of SEQ ID NO: 113, the V$_L$ CDR3 of SEQ ID NO: 114, the V$_L$ CDR3 of SEQ ID NO: 115, the V$_L$ CDR3 of SEQ ID NO: 116, or the V$_L$ CDR3 of SEQ ID NO: 117.

14. The isolated α-SNAP-25 antibody of 5, wherein the isolated α-SNAP-25 antibody comprises a heavy chain variable region comprising SEQ ID NO: 93, SEQ ID NO: 121 and SEQ ID NO: 100; and a light chain variable region comprising SEQ ID NO: 105, SEQ ID NO: 110 and SEQ ID NO: 115.

15. The isolated α-SNAP-25 antibody of 5, wherein the isolated α-SNAP-25 antibody selectively binds the SNAP-25 epitope of SEQ ID NO: 32, SEQ ID NO: 33, SEQ ID NO: 34, SEQ ID NO: 35, SEQ ID NO: 36, SEQ ID NO: 37, SEQ ID NO: 147 or SEQ ID NO: 148.

16. The isolated α-SNAP-25 antibody of 5, wherein the isolated α-SNAP-25 antibody selectively binds the SNAP-25 epitope of SEQ ID NO: 39, SEQ ID NO: 40, SEQ ID NO: 41, SEQ ID NO: 42, SEQ ID NO: 43, or SEQ ID NO: 44.

17. A method of detecting BoNT/A activity, the method comprising the steps of: a) treating a cell from an established cell line with a sample comprising a BoNT/A, wherein the cell from an established cell line is susceptible to BoNT/A intoxication by a BoNT/A; b) isolating from the treated cell a SNAP-25 component comprising a SNAP-25 cleavage product having a carboxyl-terminus at the P$_1$ residue of the BoNT/A cleavage site scissile bond; c) contacting the SNAP-25 component with an α-SNAP-25 antibody, wherein the α-SNAP-25 antibody binds an epitope comprising a carboxyl-terminus at the P$_1$ residue of the BoNT/A cleavage site scissile bond from a SNAP-25 cleavage product; and d) detecting the presence of an antibody-antigen complex comprising the α-SNAP-25 antibody and the SNAP-25 cleavage product; wherein detection by the antibody-antigen complex is indicative of BoNT/A activity.

18. A method of detecting BoNT/A activity, the method comprising the steps of: a) treating a cell from an established cell line with a sample comprising a BoNT/A, wherein the cell from an established cell line is susceptible to BoNT/A intoxication by a BoNT/A; b) isolating from the treated cell a SNAP-25 component comprising a SNAP-25 cleavage product having a carboxyl-terminus at the P$_1$ residue of the BoNT/A cleavage site scissile bond; c) contacting the SNAP-25 component with an α-SNAP-25 antibody linked to a solid phase support, wherein the α-SNAP-25 antibody binds an epitope comprising a carboxyl-terminus at the P$_1$ residue of the BoNT/A cleavage site scissile bond from a SNAP-25 cleavage product; and d) detecting the presence of an antibody-antigen complex comprising the α-SNAP-25 antibody and the SNAP-25 cleavage product; wherein detection by the antibody-antigen complex is indicative of BoNT/A activity.

19. A method of detecting BoNT/A activity, the method comprising the steps of: a) treating a cell from an established cell line with a sample comprising a BoNT/A, wherein the cell from an established cell line is susceptible to BoNT/A intoxication by a BoNT/A; b) isolating from the treated cell a SNAP-25 component comprising a SNAP-25 cleavage product having a carboxyl-terminus at the P$_1$ residue of the BoNT/A cleavage site scissile bond; c) fixing the SNAP-25 component to a solid phase support; d) contacting the SNAP-25 component with an α-SNAP-25 antibody, wherein the α-SNAP-25 antibody binds an epitope comprising a carboxyl-terminus at the P$_1$ residue of the BoNT/A cleavage site scissile bond from a SNAP-25 cleavage product; and e) detecting the presence of an antibody-antigen complex comprising the α-SNAP-25 antibody and the SNAP-25 cleavage product; wherein detection by the antibody-antigen complex is indicative of BoNT/A activity.

20. A method of detecting BoNT/A activity, the method comprising the steps of: a) treating a cell from an established cell line with a sample comprising a BoNT/A, wherein the cell from an established cell line can uptake BoNT/A; b) isolating from the treated cell a SNAP-25 component comprising a SNAP-25 cleavage product having a carboxyl-terminus at the P$_1$ residue of the BoNT/A cleavage site scissile bond; c) contacting the SNAP-25 component with an α-SNAP-25 antibody, wherein the α-SNAP-25 antibody binds an epitope comprising a carboxyl-terminus at the P$_1$ residue of the BoNT/A cleavage site scissile bond from a SNAP-25 cleavage product; and d) detecting the presence of an antibody-antigen complex comprising the α-SNAP-25 antibody and the SNAP-25 cleavage product; wherein detection by the antibody-antigen complex is indicative of BoNT/A activity.

21. A method of detecting BoNT/A activity, the method comprising the steps of: a) treating a cell from an established cell line with a sample comprising a BoNT/A, wherein the cell from an established cell line can uptake BoNT/A; b) isolating from the treated cell a SNAP-25 component comprising a SNAP-25 cleavage product having a carboxyl-terminus at the P$_1$ residue of the BoNT/A cleavage site scissile bond; c) contacting the SNAP-25 component with an α-SNAP-25 antibody linked to a solid phase support, wherein the α-SNAP-25 antibody binds an epitope comprising a carboxyl-terminus at the P$_1$ residue of the BoNT/A cleavage site scissile bond from a SNAP-25 cleavage product; and d) detecting the presence of an antibody-antigen complex comprising the α-SNAP-25 antibody and the SNAP-25 cleavage product; wherein detection by the antibody-antigen complex is indicative of BoNT/A activity.

22. A method of detecting BoNT/A activity, the method comprising the steps of: a) treating a cell from an established cell line with a sample comprising a BoNT/A, wherein the cell from an established cell line can uptake BoNT/A; b) isolating from the treated cell a SNAP-25 component comprising a SNAP-25 cleavage product having a carboxyl-terminus at the P$_1$ residue of the BoNT/A cleavage site scissile bond; c) fixing the SNAP-25 component to a solid phase support; d) contacting the SNAP-25 component with an α-SNAP-25 antibody, wherein the α-SNAP-25 antibody binds an epitope comprising a carboxyl-terminus at the P$_1$ residue of the BoNT/A cleavage site scissile bond from a SNAP-25 cleavage product; and e) detecting the presence of an antibody-antigen complex comprising the α-SNAP-25 antibody and the SNAP-25 cleavage product; wherein detection by the antibody-antigen complex is indicative of BoNT/A activity.

23. A method of determining BoNT/A immunoresistance in a mammal comprising the steps of: a) adding a BoNT/A to a test sample obtained from a mammal being tested for the presence or absence of α-BoNT/A neutralizing antibodies; b) treating a cell from an established cell line with the test sample, wherein the cell from an established cell line is susceptible to BoNT/A intoxication; c) isolating from the treated cells a SNAP-25 component comprising a SNAP-25 cleavage product having a carboxyl-terminus at the $P_1$ residue of the BoNT/A cleavage site scissile bond; d) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; e) detecting the presence of an antibody-antigen complex comprising the α-SNAP-25 antibody and the SNAP-25 cleavage product; f) repeating steps b-e with a negative control sample instead of a test sample, the negative control sample comprising a BoNT/A and a serum known not to contain α-BoNT/A neutralizing antibodies; and g) comparing the amount of antibody-antigen complex detected in step e to the amount of antibody-antigen complex detected in step f, wherein detection of a lower amount of antibody-antigen complex detected in step e relative to the amount of antibody-antigen complex detected in step f is indicative of the presence of a BoNT/A neutralizing antibodies.

24. A method of determining BoNT/A immunoresistance in a mammal comprising the steps of: a) adding a BoNT/A to a test sample obtained from a mammal being tested for the presence or absence of α-BoNT/A neutralizing antibodies; b) treating a cell from an established cell line with the test sample, wherein the cell from an established cell line is susceptible to BoNT/A intoxication; c) isolating from the treated cells a SNAP-25 component comprising a SNAP-25 cleavage product having a carboxyl-terminus at the $P_1$ residue of the BoNT/A cleavage site scissile bond; d) contacting the SNAP-25 component with an α-SNAP-25 antibody linked to a solid phase support, wherein the α-SNAP-25 antibody binds an epitope comprising a carboxyl-terminus at the $P_1$ residue of the BoNT/A cleavage site scissile bond from a SNAP-25 cleavage product; e) detecting the presence of an antibody-antigen complex comprising the α-SNAP-25 antibody and the SNAP-25 cleavage product; f) repeating steps b-e with a negative control sample instead of a test sample, the negative control sample comprising a BoNT/A and a serum known not to contain α-BoNT/A neutralizing antibodies; and g) comparing the amount of antibody-antigen complex detected in step e to the amount of antibody-antigen complex detected in step f, wherein detection of a lower amount of antibody-antigen complex detected in step e relative to the amount of antibody-antigen complex detected in step f is indicative of the presence of α-BoNT/A neutralizing antibodies.

25. A method of determining BoNT/A immunoresistance in a mammal comprising the steps of: a) adding a BoNT/A to a test sample obtained from a mammal being tested for the presence or absence of α-BoNT/A neutralizing antibodies; b) treating a cell from an established cell line with the test sample, wherein the cell from an established cell line is susceptible to BoNT/A intoxication; c) isolating from the treated cells a SNAP-25 component comprising a SNAP-25 cleavage product having a carboxyl-terminus at the $P_1$ residue of the BoNT/A cleavage site scissile bond; d) fixing the SNAP-25 component to a solid phase support; e) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; f) detecting the presence of an antibody-antigen complex comprising the α-SNAP-25 antibody and the SNAP-25 cleavage product; g) repeating steps b-f with a negative control sample instead of a test sample, the negative control sample comprising a BoNT/A and a serum known not to contain α-BoNT/A neutralizing antibodies; and h) comparing the amount of antibody-antigen complex detected in step f to the amount of antibody-antigen complex detected in step g, wherein detection of a lower amount of antibody-antigen complex detected in step f relative to the amount of antibody-antigen complex detected in step g is indicative of the presence of α-BoNT/A neutralizing antibodies.

26. A method of determining BoNT/A immunoresistance in a mammal comprising the steps of: a) adding a BoNT/A to a test sample obtained from a mammal being tested for the presence or absence of α-BoNT/A neutralizing antibodies; b) treating a cell from an established cell line with the test sample, wherein the cell from an established cell line can uptake BoNT/A; c) isolating from the treated cells a SNAP-25 component comprising a SNAP-25 cleavage product having a carboxyl-terminus at the $P_1$ residue of the BoNT/A cleavage site scissile bond; d) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; e) detecting the presence of an antibody-antigen complex comprising the α-SNAP-25 antibody and the SNAP-25 cleavage product; f) repeating steps b-e with a negative control sample instead of a test sample, the negative control sample comprising a BoNT/A and a serum known not to contain α-BoNT/A neutralizing antibodies; and g) comparing the amount of antibody-antigen complex detected in step e to the amount of antibody-antigen complex detected in step f, wherein detection of a lower amount of antibody-antigen complex detected in step e relative to the amount of antibody-antigen complex detected in step f is indicative of the presence of α-BoNT/A neutralizing antibodies.

27. A method of determining BoNT/A immunoresistance in a mammal comprising the steps of: a) adding a BoNT/A to a test sample obtained from a mammal being tested for the presence or absence of α-BoNT/A neutralizing antibodies; b) treating a cell from an established cell line with the test sample, wherein the cell from an established cell line can uptake BoNT/A; c) isolating from the treated cells a SNAP-25 component comprising a SNAP-25 cleavage product having a carboxyl-terminus at the $P_1$ residue of the BoNT/A cleavage site scissile bond; d) contacting the SNAP-25 component with an α-SNAP-25 antibody linked to a solid phase support, wherein the α-SNAP-25 antibody binds an epitope comprising a carboxyl-terminus at the $P_1$ residue of the BoNT/A cleavage site scissile bond from a SNAP-25 cleavage product; e) detecting the presence of an antibody-antigen complex comprising the α-SNAP-25 antibody and the SNAP-25 cleavage product; f) repeating steps b-e with a negative control sample instead of a test sample, the negative control sample comprising a BoNT/A and a serum known not to contain α-BoNT/A neutralizing antibodies; and g) comparing the amount of antibody-antigen complex detected in step e to the amount of antibody-antigen complex detected in step f, wherein detection of a lower amount of antibody-antigen complex detected in step e relative to the amount of antibody-antigen complex detected in step f is indicative of the presence of α-BoNT/A neutralizing antibodies.

28. A method of determining BoNT/A immunoresistance in a mammal comprising the steps of: a) adding a BoNT/A to a test sample obtained from a mammal being tested for the presence or absence of α-BoNT/A neutralizing antibodies; b) treating a cell from an established cell line with the test sample, wherein the cell from an established cell line can uptake BoNT/A; c) isolating from the treated cells a SNAP-25 component comprising a SNAP-25 cleavage product having a carboxyl-terminus at the $P_1$ residue of the BoNT/A cleavage site scissile bond; d) fixing the SNAP-25 component to a solid phase support; e) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; f) detecting the presence of an antibody-antigen complex comprising the α-SNAP-25 antibody and the SNAP-25 cleavage product; g) repeating steps b-f with a negative control sample instead of a test sample, the negative control sample comprising a BoNT/A and a serum known not to contain α-BoNT/A neutralizing antibodies; and h) comparing the amount of antibody-antigen complex detected in step f to the amount of antibody-antigen complex detected in step g, wherein detection of a lower amount of antibody-antigen complex detected in step f relative to the amount of antibody-antigen complex detected in step g is indicative of the presence of α-BoNT/A neutralizing antibodies.

29. The method of 17-22 and 23-25, wherein the cell is susceptible to BoNT/A intoxication by about 500 pM or less, by about 400 pM or less, by about 300 pM or less, by about 200 pM or less, by about 100 pM or less of a BoNT/A.

30. The method of 20-22 and 26-28, wherein the cell can uptake about 500 pM or less, by about 400 pM or less, by about 300 pM or less, by about 200 pM or less, by about 100 pM or less of BoNT/A.

31. The method of 17-22, wherein the sample comprises about 100 ng or less, about 10 ng or less, about 1 ng or less, 100 fg or less, 10fg or less, or 1 fg or less of a BoNT/A.

32. The method of 17-22, wherein the sample comprises about 100 nM or less, about 10 nM or less, about 1 nM or less, about 100 pM or less, about 10 pM or less, about 1 pM or less, about 100 fM or less, about 10 fM or less, or about 1 fM or less of a BoNT/A.

33. The method of 17-28, wherein the α-SNAP-25 antibody is the isolated α-SNAP-25 antibody of 5-16.

34. The method of 17-28, wherein the presence of an antibody-antigen complex is detected by an immuno-blot analysis, an immunoprecipitation analysis, an ELISA, or a sandwich ELISA.

35. The method of 17-28, wherein the immuno-based method has a signal-to-noise ratio for the lower asymptote of at least 3:1, at least 5:1, at least 10:1, at least 20:1, at least 50:1, or at least 100:1.

36. The method of 17-28, wherein the immuno-based method has a signal-to-noise ratio for the higher asymptote of at least 10:1, at least 20:1, at least 50:1, at least 100:1, at least 200:1, at least 300:1, at least 400:1, at least 500:1, or at least 600:1.

37. The method of 17-28, wherein the immuno-based method can detect the $EC_{50}$ activity of, e.g., at least 100 ng, at least 50 ng, at least 10 ng, at least 5 ng, at least 100 pg, at least 50 pg, at least 10 pg, at least 5 pg, at least 100 fg, at least 50 fg, at least 10 fg, or at least 5 fg.

38. The method of 17-28, wherein the immuno-based method can detect the $EC_{50}$ activity of, e.g., at least 10 nM, at least 5 nM, at least 100 pM, at least 50 pM, at least 10 pM, at least 5 pM, at least 100 fM, at least 50 fM, at least 10 fM, at least 5 fM, or at least 1 fM.

39. The method of 17-28, wherein the immuno-based method has an LOO of, e.g., 10 pg or less, 9 pg or less, 8 pg or less, 7 pg or less, 6 pg or less, 5 pg or less, 4 pg or less, 3 pg or less, 2 pg or less, 1 pg or less of a BoNT/A.

40. The method of 17-28, wherein the immuno-based method has an LOD of, e.g., 100 fM or less, 90 fM or less, 80 fM or less, 70 fM or less, 60 fM or less, 50 fM or less, 40 fM or less, 30 fM or less, 20 fM or less, or 10 fM or less of a BoNT/A.

41. The method of 17-28, wherein the immuno-based method has an LOQ of, e.g., 10 pg or less, 9 pg or less, 8 pg or less, 7 pg or less, 6 pg or less, 5 pg or less, 4 pg or less, 3 pg or less, 2 pg or less, 1 pg or less of a BoNT/A.

42. The method of 17-28, wherein the immuno-based method has an LOQ of, e.g., 100 fM or less, 90 fM or less, 80 fM or less, 70 fM or less, 60 fM or less, 50 fM or less, 40 fM or less, 30 fM or less, 20 fM or less, or 10 fM or less of a BoNT/A.

43. The method of 17-28, wherein the immuno-based method can distinguish a fully-active BoNT/A from a partially-active BoNT/A having 70% or less, 60% or less, 50% or less, 40% or less, 30% or less, 20% or less, or 10% or less the activity of a fully-active BoNT/A.

EXAMPLES

Example I

Screening of Candidate Cell Lines

The following example illustrates how to identify established cell lines susceptible to BoNT/A intoxication or have BoNT/A uptake capacity required for a method of detecting BoNT/A activity disclosed in the present specification.

1. Growth of Stock Culture of Candidate Cell Lines.

To grow the cell lines, a suitable density of cells from the cell line being tested were plated in a 162 cm² tissue culture flask containing 30 mL of a suitable growth medium (see Table 1), and grown in a 37° C. incubator under 5% or 10% carbon dioxide until cells reached the desired density.

TABLE 1

Media Used in Cell Line Screening.

| Cell Line | Serum Growth Media Composition |
|---|---|
| Kelly SiMa | RPMI 1640, 10% fetal bovine serum, 1% Penicillin-Streptomycin, 2 mM L-Glutamine |
| NB69 | RPMI 1640, 15% fetal bovine serum, 1% Penicillin-Streptomycin |
| CHP-126 | RPMI 1640, 20% fetal bovine serum, 1% Penicillin-Streptomycin |

TABLE 1-continued

| Media Used in Cell Line Screening. | |
|---|---|
| Cell Line | Serum Growth Media Composition |
| N4TG3 | RPMI 1640, 10% fetal bovine serum, 1% Penicillin-Streptomycin, 100 μM 6-thioguanine |
| MHH-NB-11 | RPMI 1640, 10% fetal bovine serum, 1% Penicillin-Streptomycin, 2 mM L-glutamine, 0.1 mM non-essential amino acids |
| PC12 | RPMI 1640, 5% heat-inactivated fetal bovine serum, 10% equine serum, 2 mM GlutaMAX ™, 10 mM HEPES, 1 mM sodium pyruvate, 1% Penicillin-Streptomycin |
| N18TG2 | DMEM (11885-084, Gibco), 10% fetal bovine serum, 1% Penicillin-Streptomycin, 100 μM 6-thioguanine |
| N1E-115 | 90% DMEM, 10% heat-inactivated fetal bovine serum, 2 mM Glutamine, 2 mM glucose |
| N18 | |
| ND8/34 | |
| NG108-15 | |
| NG115-401L | |
| NS20Y | |
| SK-N-SH | |
| SK-N-DZ | 90% DMEM, 10% heat-inactivated fetal bovine serum, 4 mM Glutamine, 4 mM glucose, |
| SK-N-F1 | 0.1 mM non-essential amino acids, 1.5 g/L $NaHCO_3$ |
| BE(2)-C | EMEM(11090-081, Gibco), Ham's F12 (11765-054, Gibco), 10% heat-inactivated fetal |
| BE(2)-M17 | bovine serum, 2 mM Glutamine, 0.1 mM non-essential amino acids, |
| CHP-212 | |
| LA-1-55n | |
| LA-N-1 | |
| MC-1XC | |
| SK-N-BE(2) | |
| SH-SY5Y | |
| NB4 1A3 | Ham's F10 (12471-017, Gibco), 2.5% heat-inactivated fetal bovine serum, 15% heat-inactivated horse serum, 2 mM Glutamine |
| Neuro-2a | EMEM, 10% heat-inactivated fetal bovine serum, 2 mM Glutamine, 0.1 mM non-essential amino acids, 1.5 g/L $NaHCO_3$, 1 mM Sodium pyruvate |

2. Single-Dose Screening of Candidate Cell Lines Using 1 nM BoNT/A.

One parameter tested to improve the sensitivity of a cell-based assay was to identify suitable cell lines that exhibited a good capacity to uptake a Clostridial neurotoxin and adhere to a substrate surface. Initially, cell lines were tested for their ability to uptake 1 nM BoNT/A and their ability to attach to a surface. To determine whether a cell line was able to uptake 1 nM BoNT/A, a suitable density of cells from a stock culture of the cell line being tested was plated into the wells of 24-well tissue culture plates containing 1 mL of an appropriate serum growth medium (Table 1). The cells were grown in a 37° C. incubator under 5% carbon dioxide until cells reached the desired density (approximately 18 to 24 hours). The growth media was aspirated from each well and replaced with either 1) fresh growth media containing no toxin (untreated cell line) or 2) fresh growth media containing 1 nM of a BoNT/A complex (treated cell line). After an overnight incubation, the cells were washed by aspirating the growth media and rinsing each well with 200 μl of 1×PBS. To harvest the cells, the 1×PBS was aspirated, the cells were lysed by adding 50 μl of 2×SDS Loading Buffer, the lysate was transferred to a clean test tube and the sample was heated to 95° C. for 5 minutes.

To detect for the presence of both uncleaved SNAP-25 substrate and cleaved SNAP-25 products, an aliquot from each harvested sample was analyzed by Western blot. In this analysis, a 12 μl aliquot of the harvested sample was separated by MOPS polyacrylamide gel electrophoresis using NuPAGE® Novex 12% Bis-Tris precast polyacrylamide gels (Invitrogen Inc., Carlsbad, Calif.) under denaturing, reducing conditions. Separated peptides were transferred from the gel onto polyvinylidene fluoride (PVDF) membranes (Invitrogen Inc., Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing Tris-Buffered Saline (TBS) (25 mM 2-amino-2-hydroxymethyl-1,3-propanediol hydrochloric acid (Tris-HCl)(pH 7.4), 137 mM sodium chloride, 2.7 mM potassium chloride), 0.1 TWEEN-20® (polyoxyethylene (20) sorbitan monolaurate), 2% Bovine Serum Albumin (BSA), 5% nonfat dry milk. Blocked membranes were incubated at 4° C. for overnight in TBS, 0.1% TWEEN-20® (polyoxyethylene (20) sorbitan monolaurate), 2% BSA, and 5% nonfat dry milk containing either 1) a 1:5,000 dilution of an α-SNAP-25 mouse monoclonal antibody as the primary antibody (SMI-81; Sternberger Monoclonals Inc., Lutherville, MD); or 2) a 1:5,000 dilution of S9684 α-SNAP-25 rabbit polyclonal antiserum as the primary antibody (Sigma, St. Louis, Mo.). Both α-SNAP-25 mouse monoclonal and rabbit polyclonal antibodies can detect both the uncleaved SNAP-25 substrate and the SNAP-25 cleavage product, allowing for the assessment of overall SNAP-25 expression in each cell line and the percent of SNAP-25 cleaved after BoNT/A treatment as a parameter to assess the amount of BoNT/A uptake. Primary antibody probed blots were washed three times for 15 minutes each time in TBS, TWEEN-20® (polyoxyethylene (20) sorbitan monolaurate). Washed membranes were incubated at room temperature for 2 hours in TBS, 0.1% TWEEN-20® (polyoxyethylene (20) sorbitan monolaurate), 2% BSA, and 5% nonfat dry milk containing either 1) a 1:10,000 dilution of goat polyclonal anti-mouse immunoglobulin G, heavy and light chains (IgG, H+L) antibody conjugated to horseradish peroxidase (Zymed, South San Francisco, Calif.) as a secondary antibody; or 2) a 1:10,000 dilution of goat polyclonal anti-rabbit immunoglobulin G, heavy and light chains (IgG, H+L) antibody conjugated to horseradish peroxidase (Zymed, South San Francisco, Calif.) as a secondary antibody. Secondary antibody-probed blots were washed three times for 15 minutes each time in TBS, 0.1% TWEEN-20® (polyoxyethylene (20) sorbitan monolaurate). Signal detection of the labeled SNAP-25 products were visualized using the ECL Plus™ Western Blot Detection System (GE Healthcare, Amersham Biosciences, Piscataway, N.J.) and the membrane was imaged and the percent of cleaved quantified with a Typhoon 9410 Variable Mode Imager and Imager Analysis software (GE Healthcare, Amersham Biosciences, Piscataway, N.J.). The choice of pixel size (100 to 200 pixels) and PMT voltage settings (350 to 600, normally 400) depended on the individual blot. Table 2 indicates the cell lines where a SNAP-25 cleavage product was detected when treated with 1 nM BoNT/A. The following cell lines exhibited both an uptake of 1 nM BoNT/A and appropriate attachment to a substrate surface: BE(2)-M17, IMR-32, Kelly, LA1-55n, N1E-115, N4TG3, N18, Neuro-2a, NG108-15, PC12, SH-SYSY, SiMa and SK-N-BE(2)-C.

To determine whether a cell line was able to attach to a surface, a suitable density of cells from a stock culture of the cell line being tested was plated into the wells of 24-well tissue culture plates containing 1 mL of an appropriate growth media (Table 1). The cells were grown in a 37° C. incubator under 5% carbon dioxide until cells reach the desired density (approximately 18 to 24 hours). Cell attachment was assessed by the percentage of cells that adhered to the bottom well surface of the tissue plate relative to the total number of cells seeded. Cell lines CHP-126, IMR-32, LA-N-1, MC-IXC, NG115-401L, SK-N-BE(2)-C, SK-N-F1 and SK-N-MC were deemed unsuitable because each cell line exhibited less than 50% attachment (Table 2). All other cells lines tested exhibited suitable cell attachment characteristics (Table 2).

TABLE 2

Single-Dose Screening of Candidate Cell Lines Using 1 nM BoNT/A.

| Cell Line | Description | Source | 1 nM BoNT/A Uptake | Attachment |
|---|---|---|---|---|
| BE(2)-C | Human neuroblastoma | ATCC CRL-2268 | No | >60% |
| BE(2)-M17 | Human neuroblastoma | ATCC CRL-2267 | Yes | >60% |
| CHP-126 | Human neuroblastoma | DSMZ ACC 304 | No | <50% |
| CHP-212 | Human neuroblastoma | ATCC CRL-2273 | No | >60% |
| HCN-1a | Brain cortical neuron | ATCC CRL-10442 | No | >60% |
| HCN-2 | Brain cortical neuron | ATCC CRL-10742 | No | >60% |
| IMR-32 | Human neuroblastoma | ATCC CRL-127 | Yes | <50% |
| Kelly | Human neuroblastoma | ECACC 92110411 | Yes | >60% |
| Kelly | Human neuroblastoma | DSMZ ACC 355 | Yes | >60% |
| LA1-55n | Human neuroblastoma | ECACC 06041203 | Yes | >60% |
| LA-N-1 | Human neuroblastoma | ECACC 06041201 | — | <25% |
| MC-IXC | Human neuroepithelioma | ATCC CRL-2270 | — | <25% |
| MHH-NB-11 | Human neuroblastoma | DSMZ ACC 157 | No | >60% |
| N1E-115 | Mouse neuroblastoma | ATCC CCL-2263 | Yes | >60% |
| N4TG3 | Mouse neuroblastoma | DSMZ ACC 101 | No | >60% |
| N18TG2 | Mouse neuroblastoma | DSMZ ACC 103 | No | >60% |
| NB4 1A3 | Mouse neuroblastoma | ECACC 89121405 | No | >60% |
| ND3 | Mouse neuroblastoma/primary neonatal rat DRG hybrid | ECACC 92090901 | No | >60% |
| ND7/23 | Mouse neuroblastoma/primary rat DRG hybrid | ECACC 92090903 | No | >60% |
| ND8 | Mouse neuroblastoma/primary neonatal rat DRG hybrid | ATCC | No | >60% |
| ND8/34 | Mouse neuroblastoma | ECACC 92090904 | No | >60% |
| ND15 | Mouse neuroblastoma/primary neonatal rat DRG hybrid | ECACC 92090907 | No | >60% |
| ND27 | Mouse neuroblastoma/primary rat DRG hybrid | ECACC 92090912 | No | >60% |
| NB69 | Human neuroblastoma | ECACC 99072802 | No | >60% |
| NDC | Mouse neuroblastoma/primary neonatal rat DRG hybrid | ECACC 92090913 | No | >60% |
| Neuro-2a | Mouse neuroblastoma | ATCC CCL-131 | Yes | >60% |
| NG108-15 | Mouse neuroblastoma/rat glioma hybrid | ECACC 88112302 | Yes | >60% |
| NG115-401L | Mouse neuroblastoma/rat glioma hybrid | ECACC 87032003 | No | <50% |
| NS20Y | Mouse neuroblastoma | DSMZ ACC 94 | No | >60% |
| PC12 | Rat pheochromocytoma | ATCC CRL-1721 | Yes | >60% |
| SH-SY5Y | Human neuroblastoma | ATCC CRL-2266 | Yes | >60% |
| SiMa | Human neuroblastoma | DSMZ ACC 164 | Yes | >60% |
| SK-N-BE(2)-C | Human neuroblastoma | ATCC CRL-2271 | Yes | <50% |
| SK-N-AS | Human neuroblastoma | ATCC CRL-2137 | No | >60% |
| SK-N-DZ | Human neuroblastoma | ATCC CRL-2149 | No | >60% |
| SK-N-F1 | Human neuroblastoma | ATCC CRL-2142 | No | <50% |
| SK-N-MC | Human neuroblastoma | ATCC HTB-10 | — | <25% |
| SK-N-SH | Human neuroblastoma | ECACC 86012802 | No | >60% |
| TE 189.T | Spinal cord | ATCC CRL-7947 | No | >60% |

Example II

Evaluation of Growth Conditions on Neurotoxin Uptake in Candidate Cell Lines The following example illustrates how to determine growth conditions for established cell lines that maximize susceptible to BoNT/A intoxication or have BoNT/A uptake capacity.

26-well Criterion gels (Bio-Rad Laboratories, Hercules, Calif.), and the rabbit polyclonal α-SNAP-25$_{197}$ antibody serum was used as the primary antibody (see Example IV). Table 3 indicates the cell lines that exhibited a SNAP-25 cleavage product when treated with 0.1 nM BoNT/A. Of the cell lines tested, only the SiMa and Neuro-2a cell lines exhibited an uptake of 0.1 nM BoNT/A in the undifferentiated state. However, besides SiMa and Neuro-2a, the cell lines N18, LA1-55n, PC12, and SH-SY5Y all exhibited an uptake of 0.1 nM BoNT/A in the differentiated state.

TABLE 3

Effects of Cell Differentiation on Neurotoxin Uptake of Candidate Cell Lines.

| Cell Line | Description | Source | 0.1 nM BoNT/A Uptake | |
|---|---|---|---|---|
| | | | Undifferentiated | Differentiated |
| BE(2)-M17 | Human neuroblastoma | ATCC CRL-2267 | No | No |
| Kelly | Human neuroblastoma | DSMZ ACC 355 | No | No |
| LA1-55n | Human neuroblastoma | ECACC 06041203 | No | Yes |
| N1E-115 | Mouse neuroblastoma | ATCC CCL-2263 | No | Not Tested |
| N4TG3 | Mouse neuroblastoma | DSMZ ACC 101 | No | Not Tested |
| N18 | Mouse neuroblastoma/rat glioma hybrid | ECACC 88112301 | No | Yes |
| Neuro-2a | Mouse neuroblastoma | ATCC CCL-131 | Yes | Yes |
| NG108-15 | Mouse neuroblastoma/rat glioma hybrid | ECACC 88112302 | No | Not Tested |
| PC12 | Rat pheochromocytoma | ATCC CRL-1721 | No | Yes |
| SH-SY5Y | Human neuroblastoma | ATCC CRL-2266 | No | Yes |
| SiMa | Human neuroblastoma | DSMZ ACC 164 | Yes | Yes |
| SK-N-BE(2)-C | Human neuroblastoma | ATCC CRL-2271 | No | Not Tested |

1. Effects of Cell Differentiation on Neurotoxin Uptake of Candidate Cell Lines.

To determine whether cell differentiation improved neurotoxin uptake, cell lines exhibiting uptake of 1 nM BoNT/A were transferred into serum-free medium to induced differentiation. A suitable density of cells from a stock culture of the cell line being tested was plated into the wells of 24-well tissue culture plates containing 1 mL of a serum-free medium containing Minimum Essential Medium with 2 mM GlutaMAX™ I with Earle's salts, 0.1 mM Non-Essential Amino Acids, 10 mM HEPES, 1 mM Sodium Pyruvate, 100 units/mL Penicillin, and 100 pg/mL Streptomycin. These cells were incubated in a 37° C. incubator under 5% carbon dioxide until the cells differentiated, as assessed by standard and routine morphological criteria, such as growth arrest and neurite extension (approximately 2 to 3 days). As a control, a suitable density of cells from a stock culture of the cell line being tested was plated into the wells of 24-well tissue culture plates containing 1 mL of an appropriate growth medium (Table 1). These undifferentiated control cells were grown in a 37° C. incubator under 5% carbon dioxide until cells reach the desired density (approximately 18 to 24 hours). The media from both differentiated and undifferentiated control cultures was aspirated from each well and replaced with fresh media containing either 0 (untreated sample), 0.1 nM, 0.3 nM, or 1 nM of a BoNT/A complex. After an overnight incubation, the cells were washed and harvested as described in Example I.

To detect for the presence of cleaved SNAP-25 products, an aliquot from each harvested sample was analyzed by Western blot as described in Example I, except that harvested samples are separated by SDS-PAGE using 12% 26-well Criterion gels (Bio-Rad Laboratories, Hercules, Calif.), and the rabbit polyclonal α-SNAP-25$_{197}$ antibody serum was used as the primary antibody (see Example IV).

2. Effects of Ganglioside Treatment on Neurotoxin Uptake of Differentiated Candidate Cell Lines.

To determine whether treatments improving low-affinity binding of neurotoxin could improve neurotoxin uptake, differentiated cell lines exhibiting uptake of 1 nM BoNT/A were treated with ganglioside GT1b. A suitable density of cells from a stock culture of the cell line being tested was plated into the wells of 24-well tissue culture plates containing serum-free medium as described above, with or without 25 pg/mL GT1b (Alexis Biochemicals, San Diego, Calif.). These cells were incubated in a 37° C. incubator under 5% carbon dioxide until the cells differentiated, as assessed by standard and routine morphological criteria as described above. The media was aspirated from each well and replaced with fresh serum-free media containing either 0 (untreated sample), 1.9 pM, 3.7 pM, 7.4 pM, 14.8 pM, 29.7 pM, 59.4 pM, 118.8 pM, 237.5 pM, 574 pM, 950 pM, and 1900 pM of a BoNT/A complex. The cell lines were incubated at two different times, 24 hours and 48 hours. After toxin incubation, the cells were washed and harvested as described in Example I.

To detect for the presence of cleaved SNAP-25 products, an aliquot from each harvested sample was analyzed by Western blot as described in Example I, except that harvested samples are separated by SDS-PAGE using 12% 26-well Criterion gels (Bio-Rad Laboratories, Hercules, Calif.), and the rabbit polyclonal α-SNAP-25$_{197}$ antibody serum was used as the primary antibody (see Example IV). Table 4 indicates the effects of gangliosides treatment on the ability of differentiated cell lines to uptake BoNT/A. These results indicate the lowest concentration of BoNT/A that will produce a detectable band of SNAP-25 cleavage product in the Western blot.

TABLE 4

Effects of GangliosideTreatment on Neurotoxin Uptake of Candidate Cell Lines.

Figures 2A, 2B:
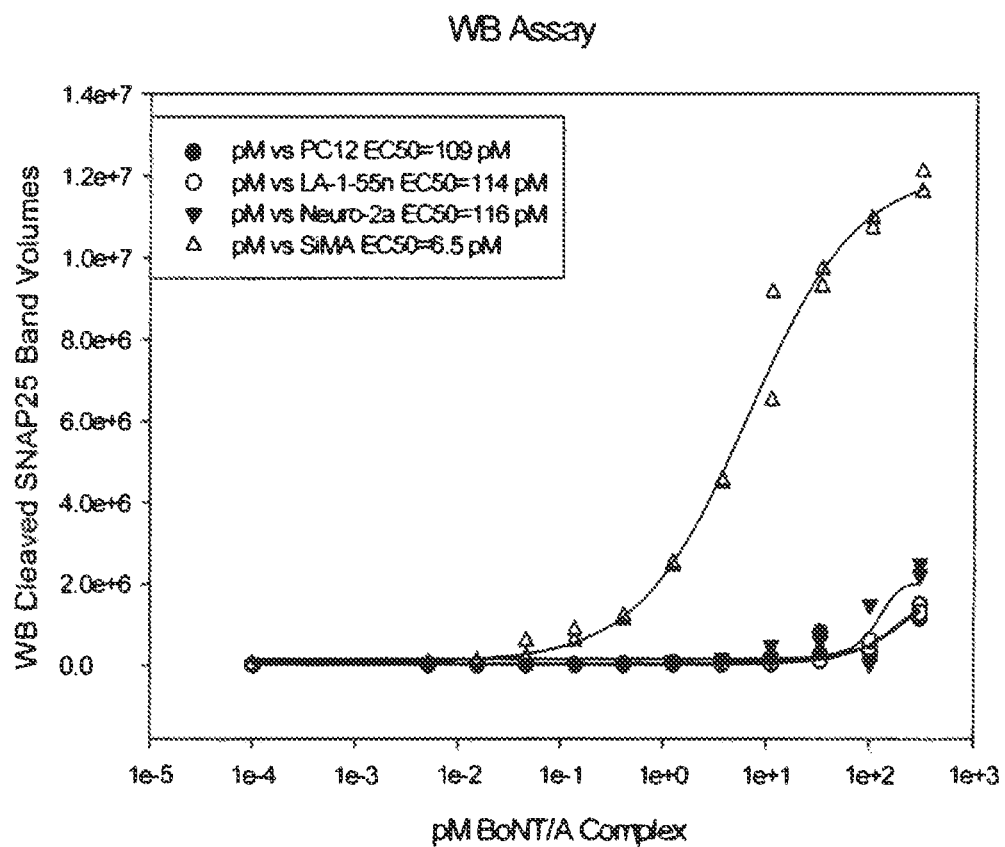
Figure 3:
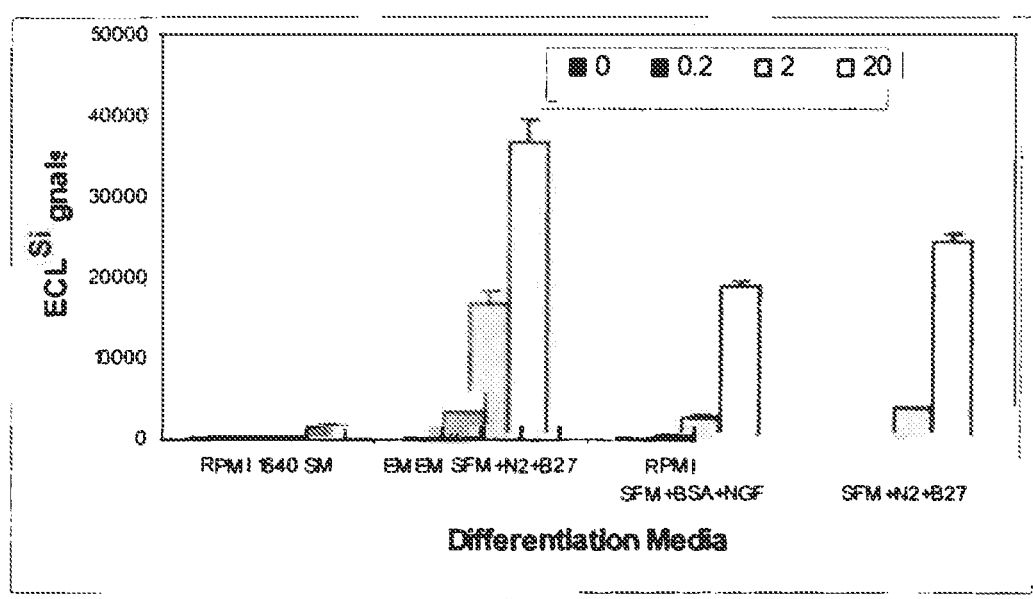
FIG. 3 shows optimization of cell differentiation media for established cell lines useful in an immuno-based method of detecting BoNT/A activity disclosed in the present specification.
Figure 4:
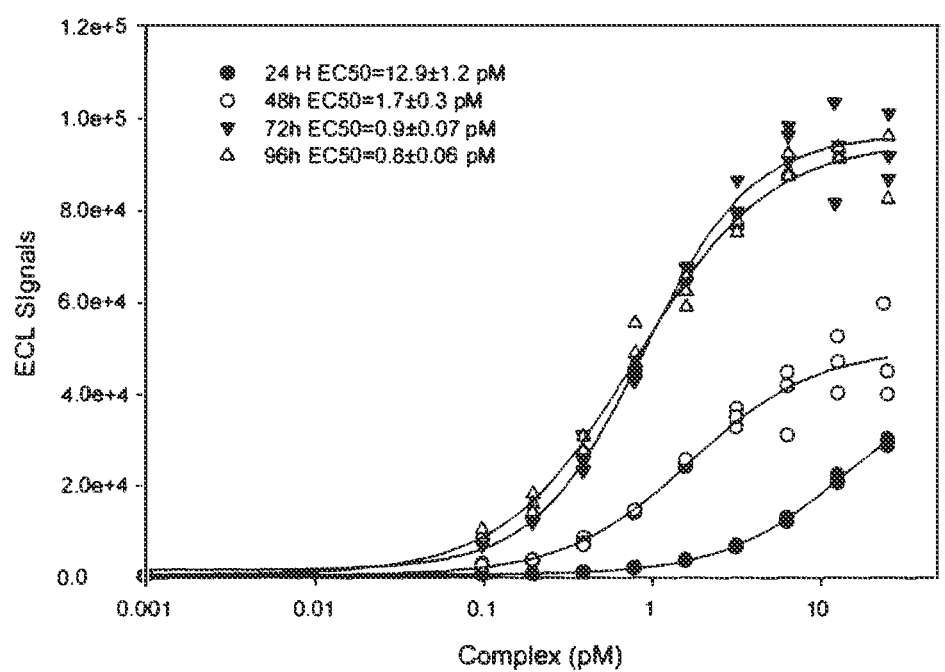
FIG. 4 shows optimization of cell differentiation time for cells comprising an established cell line useful in an immuno-based method of detecting BoNT/A activity disclosed in the present specification.
Figure 6:
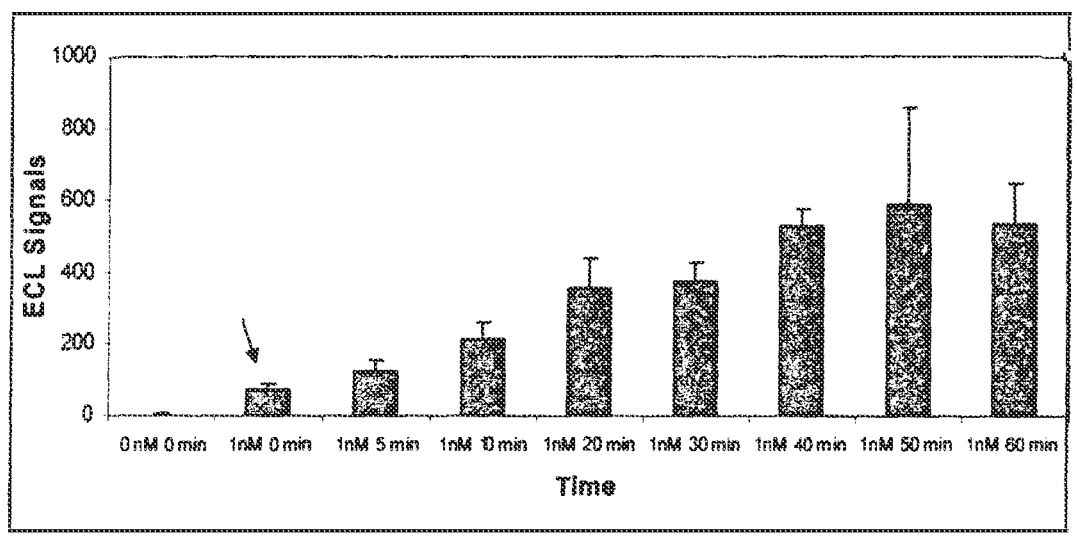
FIG. 6 shows the sensitivity of an immuno-based method of detecting BoNT/A activity disclosed in the present specification. The results indicated that uptake of BoNT/A by the cells took less than one minute before producing significant amounts of SNAP-25 cleavage product over background.

| Cell Line | Description | Source | BoNT/A Uptake | |
|---|---|---|---|---|
| | | | 24 Hour Incubation | 48 Hour Incubation |
| BE(2)-M17 | Human neuroblastoma | ATCC CRL-2267 | 237 ground signal of 0 pM BoNT/A (FIG. 2). In addition, all optimized cell lines provided a signal to noise ratio for the upper asymptote of at least 100:1 when the signal from the 300 pM dose was compared to the background signal of 0 pM BoNT/A (FIG. 2). These results indicate that any of these cell lines could be used to develop an immuno-based method for detecting BoNT/A activity as disclosed in the present specification because the assay was detecting the presence of pM amounts of BoNT/A.

was synthesized and conjugated to Keyhole Limpet Hemocyanin (KLH) to increase immunogenicity. Six Balb/c mice were immunized with this peptide, and after three immunizations in about eight weeks, the mice were bled for testing. The blood was allowed to clot by incubating at 4° C. for 60 minutes. The clotted blood was centrifuged at 10,000×g at 4° C. for 10 minutes to pellet the cellular debris. The resulting serum sample was dispensed into 50 µl aliquots and stored at −20° C. until needed.

TABLE 6

Effects of Optimized Serum-Free Media on Neurotoxin Uptake of Candidate Cell Lines.

| Cell Line | Description | Source | BoNT/A Uptake Control Serum-Free Media | BoNT/A Uptake Optimized Serum-Free Media |
|---|---|---|---|---|
| BE(2)-M17 | Human neuroblastoma | ATCC CRL-2267 | Not Tested | Not Tested |
| Kelly | Human neuroblastoma | DSMZ ACC 355 | Not Tested | Not Tested |
| LA1-55n | Human neuroblastoma | ECACC 06041203 | 7.4 pM | 3.7 pM |
| N1E-115 | Mouse neuroblastoma | ATCC CCL-2263 | Not Tested | Not Tested |
| N4TG3 | Mouse neuroblastoma | DSMZ ACC 101 | Not Tested | Not Tested |
| N18 | Mouse neuroblastoma/rat glioma hybrid | ECACC 88112301 | Not Tested | Not Tested |
| Neuro-2a | Mouse neuroblastoma | ATCC CCL-131 | 3.7 pM | 0.8 pM |
| NG108-15 | Mouse neuroblastoma/rat glioma hybrid | ECACC 88112302 | Not Tested | Not Tested |
| PC12 | Rat pheochromocytoma | ATCC CRL-1721 | 2.0 pM | 0.42 pM |
| SH-SY5Y | Human neuroblastoma | ATCC CRL-2266 | Not Tested | Not Tested |
| SiMa | Human neuroblastoma | DSMZ ACC 164 | 0.23 pM | 0.005 pM |
| SK-N-BE(2)-C | Human neuroblastoma | ATCC CRL-2271 | Not Tested | Not Tested |

Example III

Development of α-SNAP-25 Monoclonal Antibodies that Selectively Bind a SNAP-25 Epitope Having a Free Carboxyl-Terminus at the $P_1$ Residue of the BoNT/A Cleavage Site Scissile Bond The following example illustrates how to make α-SNAP-25 monoclonal antibodies that can selectively bind to a SNAP-25 epitope having a carboxyl-terminus at the $P_1$ residue of the BoNT/A cleavage site scissile bond.
1. Generation of α-SNAP-25 Monoclonal Antibodies.

To develop monoclonal α-SNAP-25 antibodies that bind an epitope comprising a carboxyl-terminus at the $P_1$ residue from the BoNT/A cleavage site scissile bond from a SNAP-25 cleavage product, the 13-residue peptide CDSNKTRID-EANQ$_{COOH}$ (SEQ ID NO: 38) was designed as a SNAP-25 cleavage product antigen. This peptide comprises a flexible linker region and a N-terminal Cysteine residue for conjugation to KLH and amino acids 186-197 of human SNAP-25 (SEQ ID NO: 5) with a carboxylated C-terminal glutamine (SEQ ID NO: 38). The generation of monoclonal antibodies to well-chosen, unique peptide sequences provides control over epitope specificity, allowing the identification of a particular subpopulation of protein among a pool of closely related isoforms. Blast searches revealed that this peptide has high homology only to SNAP-25 and almost no possible cross-reactivity with other proteins in neuronal cells. The sequence was also carefully scrutinized by utilizing computer algorithms to determine hydropathy index, protein surface probability, regions of flexibility, and favorable secondary structure, followed by proper orientation and presentation of the chosen peptide sequence. The peptide A similar strategy based on other SNAP-25 antigens disclosed in the present specification is used to develop α-SNAP-25 monoclonal antibodies that bind an epitope comprising a carboxyl-terminus at the $P_1$ residue from the BoNT/A cleavage site scissile bond from a SNAP-25 cleavage product. For example, the SNAP-25 antigen of SEQ ID NO: 45 can be conjugated to KLH instead of the SNAP-25 antigen of SEQ ID NO: 38. As another example, the amino acids 186-197 of human SNAP-25 from the SNAP-25 antigen of SEQ ID NO: 38 can be replaced with SEQ ID NO: 32, SEQ ID NO: 33, SEQ ID NO: 34, SEQ ID NO: 35, SEQ ID NO: 36, SEQ ID NO: 39, SEQ ID NO: 40, SEQ ID NO: 41, SEQ ID NO: 42, SEQ ID NO: 43, or SEQ ID NO: 44.
2. Screening for the Presence of α-SNAP-25 Monoclonal Antibodies.

To determine the presence of an α-SNAP-25 monoclonal antibody that can selectively bind to a SNAP-25 antigen having a carboxyl-terminus at the $P_1$ residue of the BoNT/A cleavage site scissile bond, comparative ELISA and cell-based cleavage assay were performed using the extracted mouse serum. For comparative ELISA, two fusion proteins were constructed: BirA-HisTag®-SNAP-25$_{134-197}$ of SEQ ID NO: 48 and the BirA-HisTag®-SNAP-25$_{134-206}$ of SEQ ID NO: 49. BirA-HisTag®-SNAP-25$_{134-197}$ comprised a naturally-biotinylated 16 amino acid BirA peptide of SEQ ID NO: 50 amino-terminally linked to a SNAP-25 peptide comprising amino acids 134-197 of SEQ ID NO: 5. BirA-HisTag®-SNAP-25$_{134-206}$ comprised a naturally-biotinylated 16 amino acid BirA peptide of SEQ ID NO: 50 amino-terminally linked to a SNAP-25 peptide comprising amino acids 134-206 of SEQ ID NO: 5. These two substrates were suspended in 1×PBS at a concentration of 10 µg/mL BirA-HisTag®-SNAP-25$_{134-197}$ and the BirA-HisTag®-SNAP-25$_{134-206}$. The BirA-HisTag® SNAP-25$_{134-197}$ and the BirA-HisTag®-SNAP-25$_{134-206}$ were coated onto separate plates by adding approximately 100 µl of the appropriate Substrate Solution and incubating the plates at room temperature for one hour. Washed plates were incubated at 37° C. for one hour in 0.5% BSA in 1×TBS containing a 1:10 to 1:100 dilution of an antibody-containing serum derived from one of the six immunized mice (Mouse 1, Mouse 2, Mouse 3, Mouse 4, Mouse 5, and Mouse 6). Primary antibody probed plates were washed four times for 5 minutes each time in 200 µl TBS, 0.1% TWEEN-20® (polyoxyethylene (20) sorbitan monolaurate). Washed plates were incubated at 37° C. for 1 hour in 1×TBS containing a 1:10,000 dilution of goat polyclonal anti-mouse IgG antibody conjugated to Horseradish peroxidase (Pierce Biotechnology, Rockford, Ill.) as a secondary antibody. Secondary antibody-probed plates were washed four times in 200 µl TBS, 0.1% TWEEN-20® (polyoxyethylene (20) sorbitan monolaurate). Chromogenic detection of the labeled SNAP-25 products were visualized by chromogenic detection using ImmunoPure TMB substrate kit (Pierce Biotechnology, Rockford, Ill.). The development of a yellow color in the BirA-HisTag®-SNAP-25$_{134-197}$ coated plates, but not the BirA-HisTag®-SNAP-25$_{134-206}$ coated plates, indicated that the α-SNAP-25 antibody preferentially recognized the SNAP-25$_{197}$ cleavage product. The resulted indicated that of the six mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

These results were confirmed using an ELISA light chain activity assay. A 96-well Reacti-Bind Streptavidin coated plates (Pierce Biotechnology, Rockford, Ill.) were prepared by adding approximately 100 µl of the following Substrate Solution: Rows A-C were coated with 100 µL of BirA-HisTag®-SNAP-25$_{134-197}$ at twelve different concentrations; Rows D-H were coated with 100 pL of BirA-HisTag®-SNAP-25$_{134-206}$ at 10 µg/mL. The plates were washed by aspirating the Substrate Solution and rinsing each well three times with 200 µl TBS, 0.1% TWEEN-20® (polyoxyethylene (20) sorbitan monolaurate). Dilutions of BoNT/A were pre-reduced at 37° C. for 20 minutes in BoNT/A Incubation Buffer (50 mM HEPES, pH 7.4, 1% fetal bovine serum, 10 µM ZnCl$_2$, 10 mM dithiothreitol) and 100 µl of the pre-reduced BoNT/A was added to the substrate-coated plates and incubated at 37° C. for 90 minutes. BoNT/A treated plates were washed by aspirating the BoNT/A Incubation Buffer and rinsing each plate three times with 200 µl TBS, 0.1% TWEEN-20® (polyoxyethylene (20) sorbitan monolaurate). Washed plates were incubated at 37° C. for one hour in 0.5% BSA in 1×TBS containing a 1:10 to 1:100 dilution of the antibody-containing serum being tested. Primary antibody probed plates were washed four times for 5 minutes each time in 200 µl TBS, 0.1% TWEEN-20® (polyoxyethylene (20) sorbitan monolaurate). Washed plates were incubated at 37° C. for 1 hour in 1×TBS containing a 1:10,000 dilution of goat polyclonal anti-mouse IgG antibody conjugated to Horseradish peroxidase (Pierce Biotechnology, Rockford, Ill.) as a secondary antibody. Secondary antibody-probed plates were washed four times in 200 µl TBS, 0.1% TWEEN-20® (polyoxyethylene (20) sorbitan monolaurate). Chromogenic detection of the labeled SNAP-25 products were visualized by chromogenic detection using ImmunoPure TMB substrate kit (Pierce Biotechnology, Rockford, Ill.). The development of a yellow color, which correlated with the presence of the SNAP-25$_{197}$ cleavage product was detected in BoNT/A treated samples, but not untreated controls, using antibody-containing serum derived from all six immunized mice (Mouse 1, Mouse 2, Mouse 3, Mouse 4, Mouse 5, and Mouse 6). Thus, the comparative ELISA analysis indicated that of the mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

For cell-based cleavage assay, a suitable density of PC12 cells were plated into 60 mm$^2$ tissue culture plates containing 3 mL of an appropriate serum medium (Table 1). The cells were grown in a 37° C. incubator under 5% carbon dioxide until cells reached the appropriate density. A 500 µL transfection solution was prepared by adding 250 µL of OPTI-MEM Reduced Serum Medium containing 15 µL of LipofectAmine 2000 (Invitrogen Inc., Carlsbad, Calif.) incubated at room temperature for 5 minutes to 250 µL of OPTI-MEM Reduced Serum Medium containing 10 pg of a pQBI-25/GFP-BoNT/A-LC expression construct (SEQ ID NO: 51). The pQBI-25/GFP-BoNT/A-LC expression construct comprises a pQBI-25 expression vector (Qbiogene Inc., Carlsbad, Calif.) whose promoter elements are functionally linked to a polynucleotide encoding the GFP-BoNT/A light chain of SEQ ID NO: 52. This transfection mixture was incubated at room temperature for approximately 20 minutes. The media was replaced with fresh unsupplemented media and the 500 µL transfection solution was added to the cells. The cells were then incubated in a 37° C. incubator under 5% carbon dioxide for approximately 6 to 18 hours. The cells were washed and harvested as described in Example II. To detect for the presence of the cleaved SNAP-25$_{197}$ product, an aliquot from each harvested sample was analyzed by Western blot as described in Example II, except that the primary antibody used was a 1:1,000 dilution of the antibody-containing serum and the secondary antibody used was a 1:20,000 of mouse α-IgG Horseradish Peroxidase (Pierce Biotechnology, Rockford, Ill.). A single band corresponding to the SNAP-25$_{197}$ cleavage product was detected in BoNT/A treated samples, but not untreated controls, using antibody-containing serum derived from three mice (Mouse 2, Mouse 3, and Mouse 4). Thus, the cell-based cleavage assay indicated that of the mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

3. Production of Hybridomas.

To make hybridomas producing α-SNAP-25 monoclonal antibodies that can selectively bind to a SNAP-25 antigen having a carboxyl-terminus at the $P_1$ residue of the BoNT/A cleavage site scissile bond, the spleen from Mouse 2 was harvested three days subsequent to a final "booster" immunization and the spleen cells were fused with myeloma cells P3-X63 Ag8.653 using standard hybridoma protocols. These cells were plated into five 96-well plates and hybrids were selected using HAT medium. Within 8-14 days after fusion, the first screening of the approximately 480 parent clones was carried out using comparative ELISA with the BirA-HisTag®-SNAP-25$_{134-197}$ and the BirA-HisTag®-SNAP-25$_{134-206}$ peptides coated in two separate plates. The comparative ELISA provided a quick screen method to identify hybridomas producing antibodies specific for the cleaved SNAP-25$_{197}$. The top 18 clones were subjected to further screening using the cell-based cleavage assay described above and immunostaining of LC/A transfected cells. (Table 7).

TABLE 7

Analysis of Supernatants Containing α-SNAP-25 Monoclonal Antibody

| | Comparative ELISA | | | | Cell-Based Assay | |
|---|---|---|---|---|---|---|
| Clone | OD SNAP-25$_{197}$ | OD SNAP-25$_{206}$ | Ratio$_{197/206}$ | Ratio$_{206/197}$ | SNAP-25$_{197}$ | SNAP-25$_{206}$ |
| 1D3  | 1.805 | 0.225 | 8.02  | 0.13 | +++ | — |
| 1F12 | 0.365 | 0.093 | 3.92  | 0.25 | —   | — |
| 1G10 | 0.590 | 0.137 | 4.31  | 0.23 | ++  | — |
| 1H1  | 0.335 | 0.121 | 2.77  | 0.36 | —   | — |
| 1H8  | 0.310 | 0.302 | 1.03  | 0.97 | +   | — |
| 2C9  | 0.139 | 0.274 | 0.51  | 1.97 | —   | — |
| 2E2  | 0.892 | 0.036 | 24.78 | 0.04 | ++  | — |
| 2E4  | 0.228 | 0.069 | 3.30  | 0.30 | +   | — |
| 2F11 | 1.095 | 1.781 | 0.61  | 1.63 | —   | — |
| 3C1  | 1.268 | 0.053 | 23.92 | 0.04 | ++  | — |
| 3C3  | 0.809 | 0.052 | 15.56 | 0.06 | ++  | — |
| 3E1  | 0.086 | 0.155 | 0.55  | 1.80 | 0   | — |
| 3E8  | 2.048 | 0.053 | 38.64 | 0.03 | +++ | — |
| 3G2  | 0.053 | 0.158 | 0.34  | 2.98 | —   | — |
| 4D1  | 0.106 | 0.218 | 0.49  | 2.06 | —   | — |
| 4G6  | 0.061 | 0.159 | 0.38  | 2.61 | —   | — |
| 5A5  | 0.251 | 0.106 | 2.37  | 0.42 | +   | — |
| 5F11 | 0.243 | 0.061 | 3.98  | 0.25 | —   | — |

Clones 1D3, 1G10, 2E2, 3C1, 3C3, and 3E8 were further cloned by limiting dilution because the conditioned media produced by these clones comprised α-SNAP-25 antibodies with a preferential binding specificity having a ratio$_{197/206}$ of at least 4:1 for the SNAP-25$_{197}$ cleavage product relative to the SNAP-25$_{206}$ uncleaved substrate and detected the SNAP-25$_{197}$-cleavage product using the cell-based cleavage assay and the immunostaining of PC12 cells transfected with GFP-LC/A. Similarly clones 2C9, 2F11, 3G2, 4D1 and 4G6 were further cloned by limiting dilution because the conditioned media produced by these clones comprised α-SNAP-25 antibodies with a preferential binding specificity having a ratio$_{206/197}$ of at least 1.5:1 for the SNAP-25$_{206}$ uncleaved substrate relative to the SNAP-25$_{197}$ cleavage product and detected the SNAP-25$_{206}$-uncleaved substrate using the cell-based cleavage assay. These single-cell derived clones were screened again using comparative ELISA, cell-based cleavage, and immunostaining to confirm their affinity and specificity, and the antibodies were isotyped using standard procedures. Ascites were produced from clones 1D368 (IgM.k), 1G10A12 (IgG3.k), 2C9B10 (IgG3.k), 2E2A6 (IgG3.k), 2F11B6 (IgM.k), 3C1A5 (IgG2a.k), and 3C3E2 (IgG2a.k). Clone 3E8 stopped producing antibodies during the cloning process and could not be further evaluated.

4. Evaluation of Binding Specificity of α-SNAP-25 Monoclonal Antibodies.

To evaluate binding specificity of an α-SNAP-25 monoclonal antibody that can selectively bind to a SNAP-25 antigen having a carboxyl-terminus at the P$_1$ residue of the BoNT/A cleavage site scissile bond, ascites from clones 1D3B8, 1G10A12, 2C9B10, 2E2A6, 2F11B6, 3C1A5, and 3C3E2 were used to detect SNAP-25 cleavage product using the cell-based activity assay, immunocytochemistry and immunoprecipitation.

For the cell-based activity assay, binding specificity was determined by analyzing the ability of α-SNAP-25 antibody-containing ascites to detect the uncleaved SNAP-$25_{206}$ substrate and the cleaved SNAP-$25_{197}$ product by Western blot analysis. A suitable density of PC12 cells were plated into 60 $mm^2$ tissue culture plates containing 3 mL of an appropriate serum medium, grown in a 37° C. incubator under 5% carbon dioxide until an appropriate cell density was reached, and transfected with the either a transfection solution lacking the pQBI-25/GFP-BoNT/A-LC expression construct (untransfected cells) or a transfection solution containing the pQBI-25/GFP-BoNT/A-LC expression construct (transfected cells) as described above. The cells were washed and harvested as described in Example I. To detect for the presence of both the uncleaved SNAP-$25_{206}$ substrate and the cleaved SNAP-$25_{197}$ product, an aliquot from each harvested sample was analyzed by Western blot as described in Example I, except that the primary antibody used was a 1:100 dilution of the α-SNAP-25 monoclonal antibody-containing ascites and the secondary antibody used was a 1:20,000 of α-mouse IgG conjugated to Horseradish Peroxidase (Pierce Biotechnology, Rockford, Ill.). In addition, three commercially available mouse α-SNAP-25 monoclonal antibodies were tested. SMI-81 (Sternberger Monoclonals Inc., Lutherville, Md.), an α-SNAP-25 antibody the manufacturer indicates detects both the uncleaved SNAP-$25_{206}$ substrate and the cleaved SNAP-$25_{197}$ product, was used at a 15,000 dilution according to the manufacturer's recommendations. MC-6050 (Research & Diagnostic Antibodies, Las Vegas, Nev.), an α-SNAP-25 antibody the manufacturer indicates detects both the uncleaved SNAP-$25_{206}$ substrate and the cleaved SNAP-$25_{197}$ product, was used at a 1:100 dilution according to the manufacturer's recommendations. MC-6053 (Research & Diagnostic Antibodies, Las Vegas, Nev.), an α-SNAP-25 antibody the manufacturer indicates detects only the cleaved SNAP-$25_{197}$ product, was used at a 1:100 dilution according to the manufacturer's recommendations.

Table 8 indicates the α-SNAP-25 antibody-containing ascites that detected only the SNAP-$25_{197}$ cleavage product. The cell-based cleavage assay indicated that ascites produced from clones 1D3B8, 2C9B10, 2E2A6, 3C1A5, and 3C3E2 synthesize an α-SNAP-25 monoclonal antibody having high binding specificity for the SNAP-$25_{197}$ cleavage product that allows for the selective recognition of this cleavage product relative to the SNAP-25$_{206}$ uncleaved substrate. Commercial antibody SMI-81 detected the SNAP-25$_{206}$ uncleaved substrate, but only poorly recognized the SNAP-25$_{197}$ cleavage product (Table 8). Surprisingly, commercial antibody MC-6050 only detected the SNAP-25$_{206}$ uncleaved substrate, and failed to recognize the SNAP-25$_{197}$ cleavage product (Table 8). Even more surprisingly, commercial antibody MC-6050 only detected the SNAP-25$_{206}$ uncleaved substrate, and failed to recognize the SNAP-25$_{197}$ cleavage product, even though the manufacturer advertises that this antibody selectively detects the SNAP-25$_{197}$ cleavage product (Table 8). Thus, this analysis indicates that while 1D3B8, 2C9B10, 2E2A6, 3C1A5, and 3C3E2 exhibit suitable selectivity for the SNAP-25$_{197}$ cleavage product, 1G10A12 and 2F11B6 do not. In addition, commercial antibodies SMI-81, MC-6050 and MC-6053 all are unsuitable for the immuno-based methods disclosed in the present application because all failed to selectivity detect the SNAP-25$_{197}$ cleavage product.

For immunocytochemistry analysis, binding specificity was determined by analyzing the ability of α-SNAP-25 antibody-containing ascites to detect the uncleaved SNAP-25$_{206}$ substrate and the cleaved SNAP-25$_{197}$ product by immunostaining. See e.g., Ester Fernandez-Salas et al., *Plasma Membrane Localization Signals in the Light Chain of Botulinum Neurotoxin*, Proc. Natl. Acad. Sci., U.S.A. 101(9): 3208-3213 (2004). A suitable density of PC12 cells were plated, grown, and transfected with either a transfection solution lacking the pQBI-25/GFP-BoNT/A-LC expression construct (untransfected cells) or a transfection solution containing the pQBI-25/GFP-BoNT/A-LC expression construct (transfected cells) as described above. The cells were washed in 1×PBS and fixed in 5 mL of PAF at room temperature for 30 minutes. Fixed cells were washed in phosphate buffered saline, incubated in 5 mL of 0.5% Triton® X-100 (polyethylene glycol octylphenol ether) in 1×PBS, washed in 1×PBS, and permeabilized in 5 mL of methanol at −20° C. for six minutes. Permeabilized cells were blocked in 5 mL of 100 mM glycine at room temperature for 30 minutes, washed in 1×PBS, and blocked in 5 mL of 0.5% BSA in 1×PBS at room temperature for 30 minutes. Blocked cells were washed in 1×PBS and incubated at room temperature for two hours in 0.5% BSA in 1×PBS containing a 1:10 dilution of an ascites from a clonal hybridoma cell line being tested. Primary antibody probed cells were washed three times for 5 minutes each time in 1×PBS. Washed cells were incubated at room temperature for 2 hours in 1×PBS containing a 1:200 dilution of goat polyclonal anti-mouse immunoglobulin G, heavy and light chains (IgG, H+L) antibody conjugated to ALEXA® FLUOR 568 (Invitrogen Inc., Carlsbad, Calif.) as a secondary antibody. Secondary antibody-probed cells were washed three times for 5 minutes each time in 1×PBS. Washed cells were prepared for microscopic examination by mounting in VECTASHIELD® Mounting Media (Vector Laboratories, Burlingame, Calif.) and coverslipped. Images of signal detection were obtained with a Leica confocal microscope using appropriate laser settings. Table 8 indicates that the α-SNAP-25 antibody-containing ascites that specifically detected the SNAP-$25_{197}$-cleavage product. The immunocytochemistry analysis indicated that ascites produced from clones 1 D3B8, 2C9B10, 2E2A6, 3C1A5, and 3C3E2 synthesize an α-SNAP-25 monoclonal antibody having high binding specificity for the SNAP-$25_{197}$ cleavage product that allows for the preferential recognition of this cleavage product relative to the SNAP-$25_{206}$ uncleaved substrate.

For immunoprecipitation analysis, binding specificity was determined by analyzing the ability of Protein A (HiTrap™ Protein A HP Columns, GE Healthcare, Amersham, Piscataway, N.J.), purified α-SNAP-25 monoclonal antibodies to precipitate the uncleaved SNAP-$25_{206}$ substrate and the cleaved SNAP-$25_{197}$ product. See e.g., Chapter 8 *Storing and Purifying Antibodies*, pp. 309-311, Harlow & Lane, supra, 1998a. A suitable density of PC12 cells were plated, grown, and transfected with either a transfection solution containing a pQBI-25/GFP expression construct (control cells; SEQ ID NO: 53) or a transfection solution containing the pQBI-25/GFP-BoNT/A-LC expression construct (experimental cells) as described above. The pQBI-25/GFP expression construct comprises an expression vector whose promoter elements are functionally linked to a polynucleotide encoding GFP of SEQ ID NO: 54. After an overnight incubation, the cells were washed by aspirating the growth media and rinsing each well with 200 μl 1×PBS. To harvest the cells, the PBS was aspirated, the cells were lysed by adding an Immunoprecipitation Lysis Buffer comprising 50 mM HEPES, 150 mM NaCl, 1.5 mM $MgCl_2$, 1 mM EGDT, 10% glycerol, 1% Triton® X-100 (polyethylene glycol octylphenol ether) and a 1× COMPLETE™ Protease inhibitor cocktail (Roche Applied Biosciences, Indianapolis, Ind.) and incubating at 4° C. for one hour. The lysed cells were centrifuged at 3,000×g at 4° C. for 10 minutes to remove cellular debris and the supernatant transferred to a clean tube and diluted to a protein concentration of approximately 1 mg/mL. Approximately 5 μg of purified monoclonal antibody was added to 0.5 mL of diluted supernatant and incubated at 4° C. for two hours. After primary antibody incubation, approximately 50 μl of immobilized Protein G (Pierce Biotechnology, Rockford, Ill.) was added to the diluted supernatant and incubated at 4° C. for one hour. The incubated supernatant was washed three times for 30 minutes each time by adding 0.5 mL of Immunoprecipitation Lysis Buffer, centrifuging at 300×g at 4° C. for one minute to pellet the immobilized Protein G, and decanting the supernatant. After washing, the pellet was resuspended in 30 μl of 1×SDS Loading Buffer and the sample was heated to 95° C. for 5 minutes. To detect for the presence of both the uncleaved SNAP-$25_{206}$ substrate and the cleaved SNAP-$25_{197}$ product, an aliquot from each harvested sample was analyzed by Western blot as described in Example I, except that the primary antibody used was a 1:1,000 dilution of the α-SNAP-25 polyclonal antibody serum (see Example IV) and the secondary antibody used was a 1:20,000 of rabbit α-IgG Horseradish Peroxidase (Pierce Biotechnology, Rockford, Ill.). Table 8 indicates the α-SNAP-25 antibody-containing ascites that specifically pulled down the SNAP-$25_{197}$-cleavage product by immunoprecipitation analysis. The immunoprecipitation analysis indicated that ascites produced from clones 2E2A6 and 3C1A5 synthesize an α-SNAP-25 monoclonal antibody having high binding specificity for the SNAP-$25_{197}$ cleavage product that allows for the preferential recognition of this cleavage product relative to the SNAP-$25_{206}$ uncleaved substrate.

TABLE 8

Analysis of Clone Ascites Containing α-SNAP-25 Monoclonal Antibody

| | Cell-Based Assay | | Immunocytochemistry | | Immunoprecipitation | |
|---|---|---|---|---|---|---|
| Clone | SNAP-25$_{197}$ | SNAP-25$_{206}$ | SNAP-25$_{197}$ | SNAP-25$_{206}$ | SNAP-25$_{197}$ | SNAP-25$_{206}$ |
| 1D3B8 | ++ | — | ++ | – | Not Tested | Not Tested |
| 1G10A12 | ++ | ++ | Not Tested | Not Tested | Not Tested | Not Tested |
| 2C9B10 | ++ | — | ++ | – | Not Tested | Not Tested |
| 2E2A6 | ++ | — | ++ | – | ++ | — |
| 2F11B6 | + | + | + | + | Not Tested | Not Tested |
| 3C1A5 | ++ | — | ++ | — | ++ | — |
| 3C3E2 | + | — | Not Tested | Not Tested | Not Tested | Not Tested |
| MC-6050 | — | + | Not Tested | Not Tested | Not Tested | Not Tested |
| MC-6053 | — | + | Not Tested | Not Tested | Not Tested | Not Tested |
| SMI-81 | –/+ | ++ | Not Tested | Not Tested | Not Tested | Not Tested |

5. Evaluation of Binding Affinity of α-SNAP-25 Monoclonal Antibodies.

To determine the binding affinity of an α-SNAP-25 monoclonal antibody showing high binding specificity for either the SNAP-25$_{197}$ cleavage product or the SNAP-25$_{206}$ uncleaved substrate, binding affinity assays were performed on a BIAcore™ 3000 instrument using carboxymethyl dextran (CM5) sensor chips (BIAcore, Inc., Piscataway, N.J.). Runs were conducted at 25° C. with HBS-EP buffer comprising 10 mM HEPES (pH 7.4), 150 mM sodium chloride, 3 mM EDTA, 0.005% (v/v) surfactant P20 at a flow rate of 10 μl/min. SNAP-25 peptides comprising amino acids 134-197 of SEQ ID NO: 5 (SNAP-25$_{134-197}$) or amino acids 134-206 of SEQ ID NO: 5 (SNAP-25$_{134-206}$) were covalently attached to the surface of the CM5 sensor chips using standard amine coupling. Briefly, the CM5 chips were activated by a 7 minute injection of a mixture of 0.2 M 1-ethyl-3-(3-dimethylaminopropyl) carbodiimide and 0.05 M N-hydroxysuccinimide; the SNAP-25 peptides were then injected in 10 mM sodium acetate (pH 4.0) for 20 min at a flow rate of 10 pL/min; and unreacted succinimide esters were blocked by a 7-min injection of 1 M ethanolamine hydrochloride, pH 8.5. The immobilized amount of SNAP-25$_{134-197}$ or SNAP-25$_{134-206}$ on the chip was reflected by a 100-150 increase in response units (about 0.10-0.15 ng/mm$^2$). Antibody samples comprising either ascites or purified monoclonal antibodies produced from clones 1 D3B8, 2C9B10, 2E2A6, 3C1A5, and 3C3E2, as well as, commercially available α-SNAP-25 antibodies were passed over the surface of the CM5 chips allowing an association time of 10 min and a dissociation time of 20 min. The surfaces were regenerated between runs by a 1 minute injection of 10 mM glycine-HCl (pH 2.5) at a flow rate of 15 μL/min. Sensorgram curves were fitted to a 1:1 kinetic binding model with the BIAevaluation™ 3.0 software.

The results indicate that both 2E2A6 and 3C1A5 were highly specific for cleaved SNAP-25$_{197}$ product over SNAP-25 uncleaved substrate (Table 9). When compared to the binding affinities of MC-6050 and MC-6053, 1D3B6 had an approximately 10-fold higher equilibrium disassociation constant for the SNAP-25 cleavage product relative to these commercial antibodies (Table 9). Interestingly, 2E2A6 had only a slightly lower equilibrium disassociation constant for the SNAP-25 cleavage product relative to these commercial antibodies (0.405 nM versus 0.497 and 0.508) (Table 9). As neither of these commercial α-SNAP-25 antibodies selectively recognized the SNAP-25 cleavage product (Table 8), an equilibrium disassociation constant lower than about 0.5 nM appears, in part, critical to achieve such selectivity. Similarly, when compared to the binding affinities of MC-6050 and MC-6053, 2E2A6 had an about at least one-fold slower off rate/dissociation constant (6.74×10$^{-5}$ versus 8.82×10$^{-4}$ s$^{-1}$ and 1.18×10$^{-3}$ s$^{-1}$) (Table 9). This further suggests that an off rate/dissociation constant lower than about 8.82×10$^{-4}$ appears, in part, critical to achieve selective binding for the SNAP-25 cleavage product. This result is consistent with 1D3B8, which had an off rate/dissociation constant of 5.78×10$^{-5}$ s$^{-1}$ (Table 9).

TABLE 9

Analysis of Binding Affinity α-SNAP-25 Monoclonal Antibodies

| SPR | 1D3B8 | | 2E2A6* | |
|---|---|---|---|---|
| Parameter | SNAP-25$_{197}$ | SNAP-25$_{206}$$^a$ | SNAP-25$_{197}$ | SNAP-25$_{206}$$^b$ |
| Ka (M$^{-1}$ s$^{-1}$) | 1.06 × 10$^6$ | — | 1.70 × 10$^6$ (1.66 × 10$^5$) | — (—) |
| Kd (s$^{-1}$) | 5.78 × 10$^{-5}$ | — | 1.53 × 10$^{-4}$ (6.74 × 10$^{-5}$) | — (—) |
| KD (nM) | 0.050 | — | 0.090 (0.405) | — (—) |

| SPR | 3C1A5 | | 2C9B10 | |
|---|---|---|---|---|
| Parameter | SNAP-25$_{197}$ | SNAP-25$_{206}$$^c$ | SNAP-25$_{197}$ | SNAP-25$_{206}$$^d$ |
| Ka (M$^{-1}$ s$^{-1}$) | 2.17 × 10$^5$ | — | 1.15 × 10$^4$ | — |
| Kd (s$^{-1}$) | 2.88 × 10$^{-4}$ | — | 3.11 × 10$^{-4}$ | — |
| KD (nM) | 1.33 | — | 27.1 | — |

| SPR | MC-6050 | | MC-6053 | |
|---|---|---|---|---|
| Parameter | SNAP-25$_{197}$ | SNAP-25$_{206}$ | SNAP-25$_{197}$ | SNAP-25$_{206}$ |
| Ka (M$^{-1}$ s$^{-1}$) | 1.78 × 10$^6$ | 3.06 × 10$^2$ | 2.32 × 10$^6$ | 1.06 × 10$^2$ |
| Kd (s$^{-1}$) | 8.82 × 10$^{-4}$ | 6.07 × 10$^{-3}$ | 1.18 × 10$^{-3}$ | 2.56 × 10$^{-5}$ |
| KD (nM) | 0.497 | 19,800 | 0.508 | 240 |

*Two independent runs were conducted for this antibody with two different chips.
$^a$No binding was observed when up to 125 nM of α-SNAP-25 monoclonal antibody 1D3B8 was passed over the surface of the CM5 sensor chip after a 10 minute association time.
$^b$No binding was observed when up to 10 μM of α-SNAP-25 monoclonal antibody 2E2A6 was passed over the surface of the CM5 sensor chip after a 10 minute association time.
$^c$No binding was observed when up to 100 nM of α-SNAP-25 monoclonal antibody 3C1A5 was passed over the surface of the CM5 sensor chip after a 10 minute association time.
$^d$No binding was observed when up to 100 nM of α-SNAP-25 monoclonal antibody 2C9B10 was passed over the surface of the CM5 sensor chip after a 10 minute association time.

6. Sequencing of the Epitope from Isolated α-SNAP-25 Monoclonal Antibodies.

To determine the epitope of an isolated α-SNAP-25 monoclonal antibody that can selectively bind to a SNAP-25 antigen having a carboxyl-terminus at the P$_1$ residue of the BoNT/A cleavage site scissile bond, the polynucleotide molecule encoding the variable heavy ($V_H$) and variable light ($V_L$) chains of the α-SNAP-25 monoclonal antibody produced by hybridomas 1D3B8, 2C9B10, 2E2A6, 3C1A5 and 3C3E2 were sequenced. mRNA was extracted and purified from each hybridoma using standard protocols and reversed transcribed into cDNA using either an oligo dT anti-sense primer or a gene-specific (murine IgG1 CH and kappa CL) anti-sense primer. Specific murine and human constant domain primers were used to amplify the cDNA by PCR after cDNA production to determine the isotype of the antibody. Degenerate $V_H$ and $V_L$ primers were used to amplify the variable domains from the cDNA. For 5'RACE, a homopolymeric dCTP tail was added to the 3' end of the cDNA. The heavy and light chains were then amplified with an oligo dG sense primer and a gene specific (CH/KC) anti-sense primer. PCR products included the sequence of the signal peptide, variable domains and constant domains up to the anti-sense primer. The PCR products were gel purified to remove small fragments, and cloned into a blunt or TA vector for sequencing. Five independent clones for each chain were sequenced and alignments of $V_H$ and $V_L$ chains and consensus sequences were determined (Table 10). Methods used to determine the $V_H$ and $V_L$ amino acid sequences are described in, e.g., Roger A. Sabbadini, et al., Novel Bioactive Lipid Derivatives and Methods of Making and Using Same, U.S. Patent Publication 2007/0281320; and Peter Amersdorfer, et al., Molecular Characterization of Murine Humoral Immune Response to Botulinum Neurotoxin Type A Binding Domain as Assessed by Using Phage Antibody Libraries, 65(9) Infect. Immun. 3743-3752, each of which is hereby incorporated by reference in its entirety. In addition, commercial services are available to sequence the variable heavy ($V_H$) and variable light ($V_L$) chains of an antibody and identify the CDR regions, see, e.g., Fusion Antibodies Ltd., Northern Ireland.

The polynucleotide sequence comprising the $V_H$ and $V_L$ chains of the α-SNAP-25 monoclonal antibody produced by the hybridomas disclosed in the present specification is as follows: 1D3B8 $V_H$ (SEQ ID NO: 71), 2C9B10 $V_H$ (SEQ ID NO: 73), 2E2A6 $V_H$ (SEQ ID NO: 75), 3C1A5 $V_H$ variant 1 (SEQ ID NO: 77), 3C1A5 $V_H$ variant 2 (SEQ ID NO: 79), 3C3E2 $V_H$ (SEQ ID NO: 81); 1 D3B8 $V_L$ (SEQ ID NO: 83), 2C9B10 $V_L$ (SEQ ID NO: 85), 2E2A6 $V_L$ (SEQ ID NO: 87), 3C1A5 $V_L$ (SEQ ID NO: 89), and 3C3E2 $V_L$ (SEQ ID NO: 91). The amino acid sequence comprising the $V_H$ and $V_L$ chains of the α-SNAP-25 monoclonal antibody produced by the hybridomas disclosed in the present specification is as follows: 1D3B8 $V_H$ (SEQ ID NO: 72), 2C9B10 $V_H$ (SEQ ID NO: 74), 2E2A6 $V_H$ (SEQ ID NO: 76), 3C1A5 $V_H$ variant 1 (SEQ ID NO: 78), 3C1A5 $V_H$ variant 2 (SEQ ID NO: 80), 3C3E2 $V_H$ (SEQ ID NO: 82); 1D3B8 $V_L$ (SEQ ID NO: 84), 2C9B10 $V_L$ (SEQ ID NO: 86), 2E2A6 $V_L$ (SEQ ID NO: 88), 3C1A5 $V_L$ (SEQ ID NO: 90), and 3C3E2 $V_L$ (SEQ ID NO: 92). The amino acid sequences comprising the $V_H$ and $V_L$ CDR domains of the α-SNAP-25 monoclonal antibody produced by the hybridomas 1 D3B8, 2C9B10, 2E2A6, 3C1A5, and 3C3E2 are given in Table 10.

TABLE 10

CDR Sequences of $V_H$ and $V_L$ domains from α-SNAP-25 Monoclonal Antibodies

| CDR | Sequence | Identified In | SEQ ID NO: |
|---|---|---|---|
| $V_H$ CDR 1 | TFTDHSIH | 2E2A6<br>2C9B10<br>3C1A5 variant 2 | 93 |
| $V_H$ CDR 1 | TFTNYVIH | 3C1A5 variant 1<br>3C3E2 | 94 |
| $V_H$ CDR 1 | IFTDHALH | 1D3B8 | 95 |
| $V_H$ CDR 2 | YIFPGNGNIEYNDKFKG | 2E2A6 | 96 |
| $V_H$ CDR 2 | YLFPGNGNFEYNEKFKG | 2C9B10<br>3C1A5 variant 2 | 97 |
| $V_H$ CDR 2 | YINPYNDGSKYNEKFKG | 3C1A5 variant 1<br>3C3E2 | 98 |
| $V_H$ CDR 2 | YIFPGNGNIEYNEKFKG | 1D3B8 | 99 |
| $V_H$ CDR 3 | KRMGY | 2E2A6<br>3C1A5 variant 2 | 100 |
| $V_H$ CDR 3 | KKMDY | 2C9B10<br>1D3B8 | 101 |
| $V_H$ CDR 3 | ARHLANTYYYFDY | 3C1A5 variant 1<br>3C3E2 | 102 |
| $V_L$ CDR 1 | RSSQSIVHSNGNTYLE | 1D3B8 | 103 |
| $V_L$ CDR 1 | RTTENIYSYFV | 2C9B10 | 104 |
| $V_L$ CDR 1 | RASKSVSTSGYSYMH | 2E2A6 | 105 |
| $V_L$ CDR 1 | KASQDIKSYLS | 3C1A5 | 106 |
| $V_L$ CDR 1 | RASQNIGNYLH | 3C3E2 | 107 |
| $V_L$ CDR 2 | KVSNRFS | 1D3B8 | 108 |

TABLE 10-continued

CDR Sequences of $V_H$ and $V_L$ domains from α-SNAP-25 Monoclonal Antibodies

| CDR | Sequence | Identified In | SEQ ID NO: |
|---|---|---|---|
| $V_L$ CDR 2 | NAKSLAE | 2C9B10 | 109 |
| $V_L$ CDR 2 | LVSNLES | 2E2A6 | 110 |
| $V_L$ CDR 2 | YATSLAD | 3C1A5 | 111 |
| $V_L$ CDR 2 | YASQSIS | 3C3E2 | 112 |
| $V_L$ CDR 3 | FQGSHVPPT | 1D3B8 | 113 |
| $V_L$ CDR 3 | QHHYGTPYT | 2C9B10 | 114 |
| $V_L$ CDR 3 | QHIRELTRS | 2E2A6 | 115 |
| $V_L$ CDR 3 | LQHGESPFT | 3C1A5 | 116 |
| $V_L$ CDR 3 | QQSDTWPLT | 3C3E2 | 117 |

Non-limiting examples of amino acid sequences comprising $V_H$ CDR domain variants of the α-SNAP-25 monoclonal antibody produced by the hybridomas disclosed in the present specification include $V_H$ CDR1 variant SEQ ID NO: 118 for 1D3B8; $V_H$ CDR1 variant SEQ ID NO: 119 for 2C9B10, 2E2A6 and 3C1A5 $V_H$ variant 2; $V_H$ CDR1 variant SEQ ID NO: 120 for 3C1A5 $V_H$ variant 1 and 3C3E2; $V_H$ CDR2 variant SEQ ID NO: 121 for 1D3B8 and 2E2A6; $V_H$ CDR2 variant SEQ ID NO: 122 for 2C9B10 and 3C1A5 $V_H$ variant 2; $V_H$ CDR2 variant SEQ ID NO: 123 for 3C1A5 $V_H$ variant 1, and 3C3E2; $V_H$ CDR3 variant MDY for 1 D3B8 and 2C9B10; $V_H$ CDR3 variant MGY for 2E2A6 and 3C1A5 $V_H$ variant 2; and $V_H$ CDR3 variant SEQ ID NO: 124 for 3C1A5 $V_H$ variant 1 and 3C3E2. Non-limiting examples of amino acid sequences comprising $V_L$ CDR domain variants of the α-SNAP-25 monoclonal antibody produced by the hybridomas disclosed in the present specification include $V_L$ CDR1 variant SEQ ID NO: 125 for 1D3B8; $V_L$ CDR1 variant SEQ ID NO: 126 for 2C9B10; $V_L$ CDR1 variant SEQ ID NO: 127 for 2E2A6; $V_L$ CDR1 variant SEQ ID NO: 128 for 3C1A5; $V_L$ CDR1 variant SEQ ID NO: 129 for 3C3E2; $V_L$ CDR2 variant KVS for 1D3B8; $V_L$ CDR2 variant NAK for 2C9B10; $V_L$ CDR2 variant LVS for 2E2A6; $V_L$ CDR2 variant YAT for 3C1A5; and $V_L$ CDR2 variant YAS for 3C3E2.

Example IV

Development of α-SNAP-25 Polyclonal Antibodies that Selectively Bind a SNAP-25 Epitope Having a Free Carboxyl-Terminus at the $P_1$ Residue of the BoNT/a Cleavage Site Scissile Bond The following example illustrates how to make α-SNAP-25 polyclonal antibodies that can selectively bind to a SNAP-25 epitope having a carboxyl-terminus at the $P_1$ residue of the BoNT/A cleavage site scissile bond.

To develop α-SNAP-25 polyclonal antibodies that bind an epitope comprising a carboxyl-terminus at the $P_1$ residue from the BoNT/A cleavage site scissile bond from a SNAP-25 cleavage product, the 10-residue peptide CGGGRID-EANQ (SEQ ID NO: 46) was designed as a SNAP-25 cleavage product antigen. This peptide comprising a N-terminal Cysteine residue for conjugation to KLH, a G-spacer flexible spacer (GGG) linked to amino acids 191-197 of human SNAP-25 (SEQ ID NO: 5) and has a carboxylated C-terminal glutamine. Blast searches revealed that this peptide has high homology only to SNAP-25 and almost no possible cross-reactivity with other proteins in neuronal cells. The sequence was also carefully scrutinized by utilizing computer algorithms to determine hydropathy index, protein surface probability, regions of flexibility, and favorable secondary structure, followed by proper orientation and presentation of the chosen peptide sequence. The peptide was synthesized and conjugated to Keyhole Limpet Hemocyanin (KLH) to increase immunogenicity. Before the animals were immunized, naïve rabbits were first screened against cell lysates from candidate cell lines in a Western blot in order to identify animals that had no immunoreactivity to the proteins present in the cell lysates. Two pre-screened rabbits were immunized with this peptide, and after three immunizations in about eight weeks, the rabbits were bled for testing. The blood was allowed to clot by incubating at 4° C. for 60 minutes. The clotted blood was centrifuged at 10,000×g at 4° C. for 10 minutes to pellet the cellular debris. The resulting serum sample was dispensed into 50 µL aliquots and stored at −20° C. until needed.

A similar strategy based on other SNAP-25 antigens disclosed in the present specification is used to develop α-SNAP-25 polyclonal antibodies that bind an epitope comprising a carboxyl-terminus at the $P_1$ residue from the BoNT/A cleavage site scissile bond from a SNAP-25 cleavage product. For example, the SNAP-25 antigen of SEQ ID NO: 47 can be conjugated to KLH instead of the SNAP-25 antigen of SEQ ID NO: 46. As another example, the amino acids 191-197 of human SNAP-25 from the SNAP-25 antigen of SEQ ID NO: 38 can be replaced with SEQ ID NO: 33, SEQ ID NO: 34, SEQ ID NO: 35, SEQ ID NO: 36, SEQ ID NO: 37, SEQ ID NO: 39, SEQ ID NO: 40, SEQ ID NO: 41, SEQ ID NO: 42, SEQ ID NO: 43, SEQ ID NO: 44, SEQ ID NO: 147 or SEQ ID NO: 148.

2. Screening for the Presence of α-SNAP-25 Polyclonal Antibodies.

To determine the presence of α-SNAP-25 polyclonal antibodies that can selectively bind to a SNAP-25 antigen having a carboxyl-terminus at the $P_1$ residue of the BoNT/A cleavage site scissile bond, comparative ELISA and cell-based cleavage assays were performed using the extracted rabbit serum as described in Example III. The serum from both rabbits contained α-SNAP-25 polyclonal antibodies that can selectively bind to a SNAP-25 antigen having a carboxyl-terminus at the $P_1$ residue of the BoNT/A cleavage site scissile bond. The α-SNAP-25 rabbit polyclonal antibodies were designated as NTP 22 and NTP 23.

3. Purification of α-SNAP-25 Polyclonal Antibodies.

To purify α-SNAP-25 polyclonal antibodies that can selectively bind to a SNAP-25 antigen having a carboxyl-terminus at the $P_1$ residue of the BoNT/A cleavage site scissile bond, NTP 22 and NTP 23 antibodies from rabbit serum were purified using affinity columns containing the SNAP-25 antigen of SEQ ID NO: 46.

4. Evaluation of Binding Specificity of α-SNAP-25 Polyclonal Antibodies.

To evaluate binding specificity of an α-SNAP-25 polyclonal antibody that can selectively bind to a SNAP-25 antigen having a carboxyl-terminus at the $P_1$ residue of the BoNT/A cleavage site scissile bond, purified NTP 22 and NTP 23 α-SNAP-25 polyclonal antibodies were used to detect cleavage product using the cell-based activity assay, immunocytochemistry and immunoprecipitation as described in Example III. The cell-based cleavage assay, immunocytochemistry analysis and immunoprecipitation analysis all indicated that NTP 22 and NTP 23 α-SNAP-25 polyclonal antibodies did not cross-react with uncleaved SNAP-25. Thus both NTP 22 and NTP 23 have high binding specificity for the SNAP-$25_{197}$ cleavage product that allows for the preferential recognition of this cleavage product relative to the SNAP-$25_{206}$ uncleaved substrate. Affinity for the antigens can be determined using SPR in the BiAcore as described in Example III.

Example V

Component and Condition Preparation for a Sandwich ELISA

The following example illustrates how to identify and prepare the components and conditions necessary to perform a sandwich ELISA useful for conducting immuno-based methods of detecting BoNT/A activity by detecting a SNAP-25 cleavage product using a α-SNAP-25 monoclonal antibody specific for a SNAP-25 having a carboxyl-terminus at the $P_1$ residue of the BoNT/A cleavage site scissile bond.

1. Preparation of Cell Lysates from Cells Treated with BoNT/A.

To obtain a BoNT/A treated cell lysate for analysis, a suitable density of cells from a stock culture of Neuro-2a was seeded into a T175 flask containing 50 mL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES. These cells were incubated in a 37° C. incubator under 5% carbon dioxide until the cells differentiated, as assessed by standard and routine morphological criteria, such as growth arrest and neurite extension (approximately 2 to 3 days). As a control, a suitable density of cells from a stock culture of Neuro-2a was seeded into a T175 flask containing 50 mL of an appropriate growth medium (Table 1). These undifferentiated control cells were grown in a 37° C. incubator under 5% carbon dioxide until 50% confluence was reached (approximately 18 hours). The media from both differentiated and undifferentiated control cultures was aspirated from each well and replaced with fresh media containing either 0 (untreated sample) or 10 nM of a BoNT/A complex. After an overnight incubation, the cells were washed and the cells harvested by lysing in freshly prepared Triton X-100 Lysis Buffer (50 mM HEPES, 150 mM NaCl, 1.5 mM $MgCl_2$, 1 mM EGTA, 1% Triton X-100) at 4° C. for 30 minutes with constant agitation. Lysed cells were centrifuged at 4000 rpm for 20 min at 4° C. to eliminate debris using a bench-top centrifuge. The protein concentrations of cell lysates were measured by Bradford assay.

2. Preparation and Identification of Sandwich ELISA Components.

To identify an appropriate capture antibody-detection antibody pair an ECL sandwich ELISA analysis was conducted on twenty-six different combinations of capture and detection antibody pairs comprising eleven different α-SNAP-25 capture antibodies and seven different α-SNAP-25 detection antibodies (Table 12). The α-SNAP-25 antibodies used were 2E2A6 and 3C1A5 α-SNAP-25 mouse monoclonal antibodies disclosed in the present specification, SMI-81, MC-6050, and MC-6053 α-SNAP-25 mouse monoclonal antibodies disclosed in the present specification, NTP 23 α-SNAP-25 rabbit polyclonal antibodies disclosed in the present specification, S9684 α-SNAP-25 rabbit polyclonal antibodies (Sigma, St. Louis, Mo.), H-50 α-SNAP-25 rabbit polyclonal antibodies (Santa Cruz Biotechnology, Inc., Santa Cruz, Calif.), C-18 α-SNAP-25 goat polyclonal antibodies (Santa Cruz Biotechnology, Inc., Santa Cruz, Calif.), N-19 α-SNAP-25 goat polyclonal antibodies (Santa Cruz Biotechnology, Inc., Santa Cruz, Calif.), and SP12 α-SNAP-25 mouse polyclonal antibodies (Santa Cruz Biotechnology, Inc., Santa Cruz, Calif.).

To prepare the capture antibody solution, the α-SNAP-25 monoclonal antibodies contained in the ascites from hybridoma cell lines 2E2A6 and 3C1A5 as well as the α-SNAP-25 MC-6050 and MC-6053 monoclonal antibodies were purified using a standard Protein A purification protocol. All other α-SNAP-25 antibodies were purchased as purified antibodies.

To prepare the detection antibody solution, the appropriate α-SNAP-25 antibody was conjugated to Ruthenium(II)-tris-bipyridine-(4-methylsulfonate) NHS ester labeling reagent (Meso Scale Discovery, Gaithersburg, Md.) according to the manufacturer's instructions (Meso Scale Discovery, Gaithersburg, Md.). The conjugation reaction was performed by adding 30 pL of distilled water reconstituted MSD SULFO-TAG™ stock solution to 200 pL of 2 mg/mL α-SNAP-25 polyclonal antibodies and incubating the reaction at room temperature for 2 hours in the dark. The labeled antibodies were purified using a standard spin column protocol and the protein concentration determined using a standard colorimetric protein assay. The absorbance of the α-SNAP-25 antibody/MSD SULFO-TAG™ conjugate was measured at 455 nm using a spectrophotometer to determine the concentration in moles per liter. The detection antibody solution was stored at 4° C. until needed.

To prepare the solid phase support comprising the capture antibody that is specific for a SNAP-25 cleavage product, approximately 5 μL of the appropriate α-SNAP-25 monoclonal antibody solution (20 μg/mL in 1×PBS) is added to each well of a 96-well MSD High Bind plate and the solution is allowed to air dry in a biological safety cabinet for 2-3 hours in order to liquid evaporate the solution. The capture antibody-bound wells were then blocked by adding 150 μL of Blocking Buffer comprising 2% Amersham Blocking Reagent (GE Life Sciences, Piscataway, N.J.) and 10% goat serum (VWR, West Chester, Pa.) at room temperature for 2 hours. Blocked plates were sealed and stored at 4° C. until needed.

To detect the presence of a cleaved SNAP-25 cleavage product by ECL sandwich ELISA analysis, the Blocking Buffer from stored plates was aspirated from the wells, 25 pL of a lysate from cells treated with BoNT/A, as described above, was added to each well and the plates were incubated at 4° C. for overnight. Plate wells were washed three times by aspirating the cell lysate and rinsing each well three times with 200 pL 1×PBS, 0.1% TWEEN-20® (polyoxyethylene (20) sorbitan monolaurate). After washing, 25 μl of 5 pg/mL detection antibody solution comprising 2% Amersham Blocking Reagent in 1×PBS, 0.1% TWEEN-20® (polyoxyethylene (20) sorbitan monolaurate) was added to each well, the plate was sealed, and the sealed plate was incubated at room temperature at room temperature for 1 hour with shaking. After detection antibody incubation, the wells were washed three times with 200 μL 1×PBS, 0.1% TWEEN-20® (polyoxyethylene (20) sorbitan monolaurate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). A ratio was calculated by dividing the signal obtained at the 10 nM dose for each antibody-pair by the signal obtained at the 0 nM dose for each antibody-pair (Table 12). These results indicated that among the twenty-six different combinations of antibody pairs tested, only three antibody pairs had signal-to-noise ratios above 10:1 for the higher dose tested: Pair No. 1 (2E2A6 mouse mAb and S9684 rabbit pAb), Pair No. 4 (3C1A5 mouse mAb and S9684 rabbit pAb), and Pair No. 18 (S9684 rabbit pAb and 2E2A6 mouse mAb). Antibody Pair 1 was chosen for further assay development.

Figure 7:
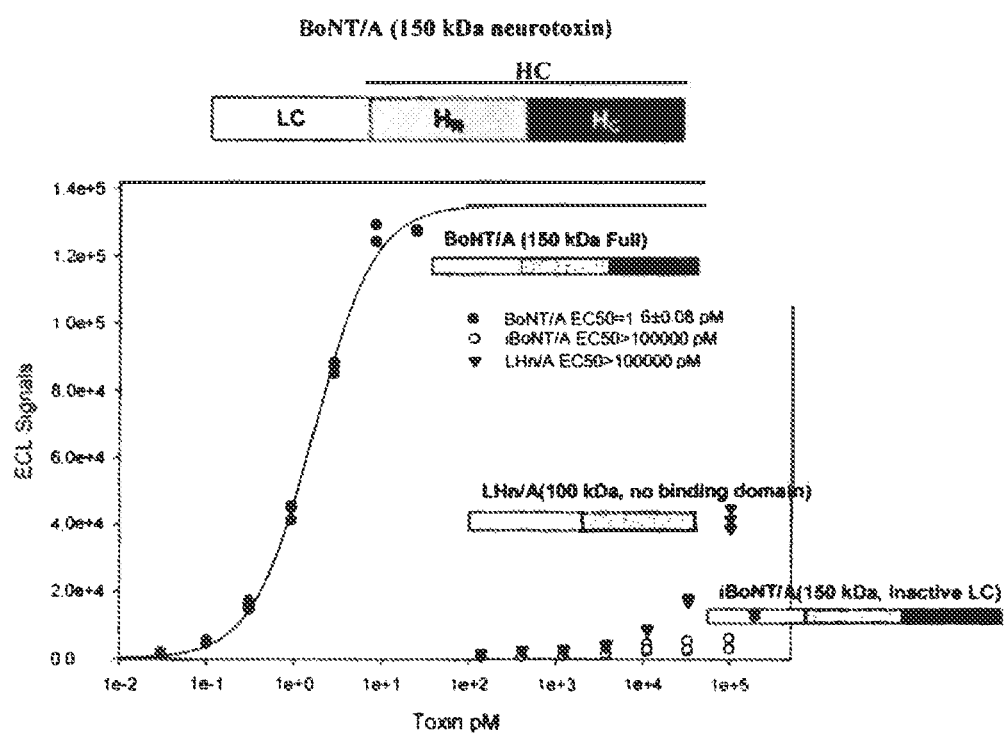
FIG. 7 shows the specificity of an immuno-based method of detecting BoNT/A activity disclosed in the present specification. The results indicate that the immuno-based methods of detecting BoNT/A activity disclosed in the present specification can measure all the steps involved in BoNT/A intoxication.

To determine an optimal differentiation medium, a suitable density of cells from a SiMa cell line was plated into the wells of Collagen IV coated 24-well cell culture plates containing 1 mL of one of the following medias and differentiation supplements: 1) RPMI 1640, 10% fetal bovine serum, 1% Penicillin-Streptomycin, 2 mM L-Glutamine, and 25 μg/mL GT1b); 2) RPMI-1640, 1×B27 supplement, 1×N2 supplement, and 25 μg/mL GT1b; 3) Minimum Essential Medium, 1×B27 supplement, 1×N2 supplement, and 25 μg/mL GT1b; and 4) RPMI-1640, 10% BSA, 1×N2 supplement, 1×NGF supplement, and 25 μg/mL GT1b. Cells were incubated in a 37° C. incubator under 5% carbon dioxide until the cells differentiated, as assessed by standard and routine morphological criteria, such as growth arrest and neurite extension (approximately 3 days). The media was aspirated from each well and replaced with fresh media containing either 0 (untreated sample), 0.2 pM, 2 pM, or 20 pM of a BoNT/A complex. After an overnight treatment, the cells were washed, incubated for an additional two days without toxin to allow for the cleavage of the SNAP-25 substrate, and harvested as described above in Section 1. The protein concentrations of cell lysates were measured by Bradford assay. Detection of the presence of cleaved SNAP-25 product by ECL sandwich ELISA analysis was performed as described above using Antibody Pair 1. As discussed in Example I, undifferentiated cells did not take up toxin as effectively as differentiated cells. The most effective differentiation medium for increasing BoNT/A uptake and consequently SNAP-25 cleavage medium 3 (MEM+N2+B27), followed by medium 2 (RPMI-1640+N2+B27), and medium 4 (RPMI-1640+N2+NGF+BSA) (FIG. 3). Cells cultured in medium 2 resulted in more cleavage of the SNAP-25 as compared to the other media.

TABLE 12

Screening of α-SNAP-25 Antibody Combinations

| Antibody Pair No. | Capture Antibody | Detection Antibody | Detection SNAP-25 cleavage product | Detection SNAP-25 uncleaved substrate | Signal/Noise Ratio (10 nM/0 nM) |
|---|---|---|---|---|---|
| 1 | 2E2A6 mouse mAb | S9684 rabbit pAb | Yes | No | 26.6:1 |
| 2 | 2E2A6 mouse mAb | N-19 goat pAb | Yes | No | 7.3:1 |
| 3 | 2E2A6 mouse mAb | H-50 rabbit pAb | Yes | No | 0.9:1 |
| 4 | 3C1A5 mouse mAb | S9684 rabbit pAb | Yes | No | 12.1:1 |
| 5 | 3C1A5 mouse mAb | N-19 goat pAb | Yes | No | 1.9:1 |
| 6 | 3C1A5 mouse mAb | H-50 rabbit pAb | Yes | No | 0.9:1 |
| 7 | C-18 goat pAb | S9684 rabbit pAb | No | No | 0.8:1 |
| 8 | C-18 goat pAb | N-19 goat pAb | No | No | 0.9:1 |
| 9 | C-18 goat pAb | H-50 rabbit pAb | No | No | 0.9:1 |
| 10 | H-50 rabbit pAb | 2E2A6 mouse mAb | Yes | No | 0.9:1 |
| 11 | H-50 rabbit pAb | C-18 goat pAb | No | No | 1.0:1 |
| 12 | N-19 goat pAb | 2E2A6 mouse mAb | Yes | No | 0.9:1 |
| 13 | N-19 goat pAb | C-18 goat pAb | No | No | 1.1:1 |
| 14 | NTP 23 rabbit pAb | N-19 goat pAb | Yes | No | 1.2:1 |
| 15 | NTP 23 rabbit pAb | C-18 goat pAb | No | No | 1.1:1 |
| 16 | NTP 23 rabbit pAb | SP12 mouse pAb | Yes | No | 1.3:1 |
| 17 | NTP 23 rabbit pAb | H-50 rabbit pAb | Yes | No | 1.1:1 |
| 18 | S9684 rabbit pAb | 2E2A6 mouse mAb | Yes | No | 21.3:1 |
| 19 | S9684 rabbit pAb | C-18 goat pAb | No | No | 0.7:1 |
| 20 | S9684 rabbit pAb | SMI-81mouse mAb | Yes | Yes | 1.2:1 |
| 21 | SMI-81 mouse mAb | S9684 rabbit pAb | Yes | Yes | 1.1:1 |
| 22 | SMI-81 mouse mAb | N-19 goat pAb | Yes | Yes | 1.0:1 |
| 23 | SMI-81 mouse mAb | C-18 goat pAb | No | No | 0.8:1 |
| 24 | SP12 mouse pAb | C-18 goat pAb | No | No | 1.0:1 |
| 25 | MC-6050 mouse mAb | S9684 rabbit pAb | Yes | Yes | 5.0:1 |
| 26 | MC-6053 mouse mAb | S9684 rabbit pAb | Yes | Yes | 7.1:1 |

3. Optimization of Cell Differentiation Conditions.

To determine the optimal differentiation condition for a cell line comprising cells susceptible to BoNT/A intoxication when using a sandwich ELISA detection system, both various cell culture media and length of differentiation time were tested.

To determine an optimal differentiation time, a suitable density of cells from a SiMa cell line was plated into the wells of poly-D-lysine coated 96-well cell culture plates containing 100 µL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES and 25 µg/mL GT1b. Cells were plated at four different days to obtain a differentiation time course testing 6 hrs, 24 h, 48 hrs, and 72 hrs, and were incubated in a 37° C. incubator under 5% carbon dioxide The media was aspirated from each well and replaced with fresh media containing either 0 (untreated sample), 0.1 pM, 0.2 pM, 0.4 pM, 0.8 pM, 1.6 pM, 3.1 pM, 6.25 pM, 12.5 pM, or 25 pM of a BoNT/A complex. After an overnight treatment, the cells were washed, incubated for an additional two days without toxin to allow for the cleavage of the SNAP-25 substrate, and harvested as described above in Section 1. After harvesting, the protein concentrations of cell lysates and detection of the presence of cleaved SNAP-25 product by ECL sandwich ELISA analysis were performed as described above. The raw data obtained from the ECL imager was then transferred to SigmaPlot v. 9.0 and a 4-parameter logistics fit was used to define the dose-response curves. There were no constraints used for the 4-parameter logistic function when plotting the data. Graphical reports were generated using the following analysis: R2 (correlation coefficient), a (Max for data set), b (hillslope), and X0±SE ($EC_{50}$ value±standard error). The results indicated that $EC_{50}$ values of less than 2 pM could be achieved with cells differentiated for 48-72 hrs (FIG. 4). The finding that differentiated cells could be used between 48 hrs to 72 hrs of differentiation, with no significant changes on the performance of the cells, highlights the robustness of the assay. Although differentiation time periods less than 48 hrs may not be suitable for picomolar testing of formulated product, these lesser differentiation times are sensitive enough for bulk drug substance testing.

4. Optimization of BoNT/a Treatment Time.

To determine the optimal length of time cells form a cell line need to be treated with a BoNT/A, various lengths of BoNT/A treatment times were tested. A suitable density of cells from a SiMa cell line was plated into the wells of poly-D-lysine coated 96-well cell culture plates containing 100 μL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES and 25 μg/mL GT1b. Cells were plated and incubated in a 37° C. incubator under 5% carbon dioxide until the cells differentiated, as assessed by standard and routine morphological criteria, such as growth arrest and neurite extension (approximately 3 days). The media was aspirated from each well and replaced with fresh media containing either 0 (untreated sample), 0.1 pM, 0.2 pM, 0.4 pM, 0.8 pM, 1.6 pM, 3.1 pM, 6.3 pM, 12.5 pM, or 25 pM of a BoNT/A complex in RPMI 1640 growth medium in triplicate to generate a full dose-response. Five different BoNT/A treatment length regimens were performed: 1) a 6 hrs BoNT/A treatment, removal and washing of cells, an incubation of cells for 18 hr without BoNT/A, and harvesting of cells as described above in Section 1; 2) a 24 hrs BoNT/A treatment, removal and washing of cells, and harvesting of cells as described above in Section 1; 3) a 24 hrs BoNT/A treatment, removal and washing of cells, an incubation of cells for 24 hr without BoNT/A, and harvesting of cells as described above in Section 1; 4) a 24 hrs BoNT/A incubation, removal and washing of cells, an incubation of cells for 48 hr without BoNT/A, and harvesting of cells as described above in Section 1; and 5) a 24 hrs BoNT/A incubation, removal and washing of cells, an incubation of cells for 72 hr without BoNT/A, and harvesting of cells as described above in Section 1. After harvesting, the protein concentrations of cell lysates, detection of SNAP-25 cleavage product by ECL sandwich ELISA performed, and the $EC_{50}$ calculated as described above. The results indicate that $EC_{50}$ values of less than 2 pM could be achieved with any of the BoNT/A treatments tested (FIG. 5). Interestingly, the 24 hrs+24 hrs, 24 hrs+48 hrs, and 24 hrs+73 hrs BoNT/A treatment regimes generated essentially the same $EC_{50}$ values, 1.0 pM, 1.1, pM and 0.9 pM respectively. The $EC_{50}$ values generated for the 6 hrs+18 hrs and 24 hrs+0 hrs BoNT/A treatment regimes were 1.7 pM and 1.6 pM respectively. Although the amount of signal obtained was lower, these results indicate that BoNT/A treatment times between 6 hrs to 24 hrs plus one day to three days post-treatment incubation can be used to generate an $EC_{50}$ that is adequate for detecting BoNT/A activity and give flexibility in the assay's overall time course.

5. Sensitivity of Immuno-Based Method of Detecting BoNT/a Activity.

To evaluate the sensitivity of the immuno-based methods of detecting BoNT/A activity disclosed in the present specification, the timing of BoNT/A uptake by cells susceptible to BoNT/A intoxication was determined. A suitable density of cells from a SiMa cell line was plated into the wells of poly-D-lysine coated 96-well cell culture plates containing 100 μL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES and 20 μg/mL GT1b. Cells were incubated in a 37° C. incubator under 5% carbon dioxide until the cells differentiated, as assessed by standard and routine morphological criteria, such as growth arrest and neurite extension (approximately 3 days). The media was aspirated from each well, replaced with fresh media containing 1 nM of a BoNT/A complex, and the BoNT/A treated cells were incubated at six different time points of 0 min (neurotoxin added and then immediately removed), 5 min, 10 min, 20 min, 30 min, and 60 min. A negative control of media with no BoNT/A (0 nM) was used. After incubation, the cells were washed and harvested as described above in Section 1. After harvesting, the protein concentrations of cell lysates, detection of SNAP-25 cleavage product by ECL sandwich ELISA performed, and the $EC_{50}$ calculated as described above. The results indicated that uptake of BoNT/A by the cells took less than one minute before producing significant amounts of SNAP-25 cleavage product over background (FIG. 6).

6. Specificity of Immuno-Based Method of Detecting BoNT/a Activity.

To evaluate the specificity of the immuno-based methods of detecting BoNT/A activity disclosed in the present specification, the capacity of cells susceptible to BoNT/A intoxication to accurately distinguish BoNT/A to the exclusion of partially inactivated BoNT/A was determined. A suitable density of cells from a SiMa cell line was plated into the wells of poly-D-lysine coated 96-well cell culture plates containing 100 μL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES and 25 μg/mL GT1b. Cells were incubated in a 37° C. incubator under 5% carbon dioxide until the cells differentiated, as assessed by standard and routine morphological criteria, such as growth arrest and neurite extension (approximately 3 days). The media was aspirated from each well and replaced with fresh media containing either 1) 0 (untreated sample), 0.03 pM, 0.1 pM, 0.31 pM, 0.93 pM, 2.78 pM, 8.33 pM, and 25 pM, of a BoNT/A complex; 2) 0, 0.14 nM, 0.41 nM, 1.23 nM, 3.7 nM, 11.11 nM, 33.33 nM, and 100 nM of an inactive BoNT/A (iBoNT/A); or 3) 0, 0.14 nM, 0.41 nM, 1.23 nM, 3.7 nM, 11.11 nM, 33.33 nM, and 100 nM of an $LH_N/A$ fragment. The iBoNT/A contains a mutation in the zinc binding domain of the light chain that completely inactivates the metalloprotease activity of the neurotoxin, see, e.g., Liqing Zhou, et al., *Expression and Purification of the Light Chain of Botulinum Neurotoxin A: A Single Mutation Abolishes its Cleavage of SNAP-25 and Neurotoxicity after Reconstitution with the Heavy Chain*, Biochemistry 34: 15175-15181 (1995), which is hereby incorporated by reference in its entirety. The $LH_N/A$ fragment lacks the binding domain, but contains an intact translocation domain and light chain, see, e.g., Clifford C. Shone, et al., Recombinant Toxin Fragments, U.S. Pat. No. 6,461,617, which is hereby incorporated by reference in its entirety. After 24 hrs treatment, the cells were washed, incubated for an additional two days without toxin to allow for the cleavage of SNAP-25 substrate, and harvested as described above in Section 1. After harvesting, the protein concentrations of cell lysates, detection of SNAP-25 cleavage product by ECL sandwich ELISA performed, and the $EC_{50}$ calculated as described above. The results indicate that the binding affinity of cells for iBoNT/A and $LH_N/A$ ($EC_{50}$>100 nM) are at least 60,000 lower than the binding affinity for BoNT/A ($EC_{50}$=1.6 pM) (FIG. 7). No SNAP-25 cleavage product was detected in cells treated with iBoNT/A at all concentrations tested. Although a low amount of SNAP-25 cleavage product was detected in cells treated with the highest dose of the $LH_N/A$ fragment, this activity is due to non-specific uptake of this fragment due to the activity of the translocation domain. Thus, the results indicate that the immuno-based methods of detecting BoNT/A activity disclosed in the present specification can measure all the steps involved in the intoxication process whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25.

Example VI

Immuno-Based Method of Detecting BoNT/a Activity Using ECL Sandwich ELISA

The following example illustrates immuno-based methods of detecting BoNT/A activity by detecting a SNAP-25 cleavage product using a α-SNAP-25 monoclonal antibody specific for a SNAP-25 cleavage product having a carboxyl-terminus at the $P_1$ residue of the BoNT/A cleavage site scissile bond using ECL sandwich ELISA.

To prepare a lysate from cells treated with a BoNT/A, a suitable density of cells from an established cell line was plated into the wells of 96-well tissue culture plates containing 100 μL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES and 25 μg/mL GT1b (see Examples I and II). These cells were incubated in a 37° C. incubator under 5% carbon dioxide until the cells differentiated, as assessed by standard and routine morphological criteria, such as growth arrest and neurite extension (approximately 3 days). The media from the differentiated cells was aspirated from each well and replaced with fresh media containing either 0 (untreated sample), 0.03 pM, 0.1 pM, 0.3 pM, 0.9 pM, 2.8 pM, 8.3 pM, and 25 pM of a BoNT/A complex. After a 24 hr treatment, the cells were washed, and incubated for an additional two days without toxin. To cells were harvested as described in Example V.

To prepare the α-SNAP-25 capture antibody solution, the α-SNAP-25 monoclonal antibody contained in the ascites from hybridoma cell line 2E2A6 was purified using a standard Protein A purification protocol. To prepare the α-SNAP-25 detection antibody solution, α-SNAP-25 rabbit polyclonal antibody S9684 (Sigma, St. Louis, Mo.) was conjugated to Ruthenium(II)-tris-bipyridine-(4-methylsulfonate) NHS ester labeling reagent (Meso Scale Discovery, Gaithersburg, Md.) according to the manufacturer's instructions (Meso Scale Discovery, Gaithersburg, Md.). The conjugation reaction, purification of labeled α-SNAP-25 antibody, concentration determination and storage were as described in Example V.

To prepare the solid phase support comprising the capture antibody that is specific for a SNAP-25 cleaved product, approximately 5 μL of α-SNAP-25 monoclonal antibody 2E2A6 solution (20 μg/mL in 1×PBS) was added to each well of a 96-well MSD High Bind plate and the solution is allowed to air dry in a biological safety cabinet for 2-3 hours in order to liquid evaporate the solution. The capture antibody-bound wells were then blocked and used directly to detect BoNT/A activity.

Figure 8:
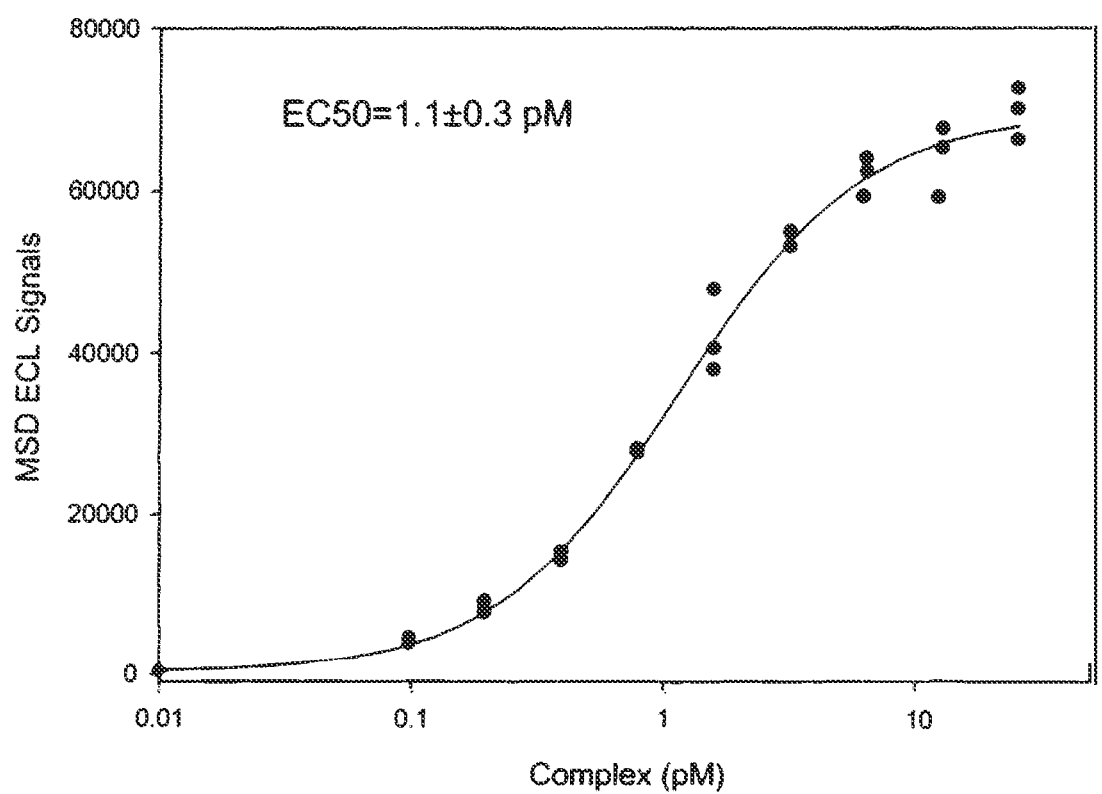
FIG. 8 shows a dose response curve of differentiated SiMa cells treated with a BoNT/A complex using an immuno-based method of detecting BoNT/A activity disclosed in the present specification.
Figure 9:
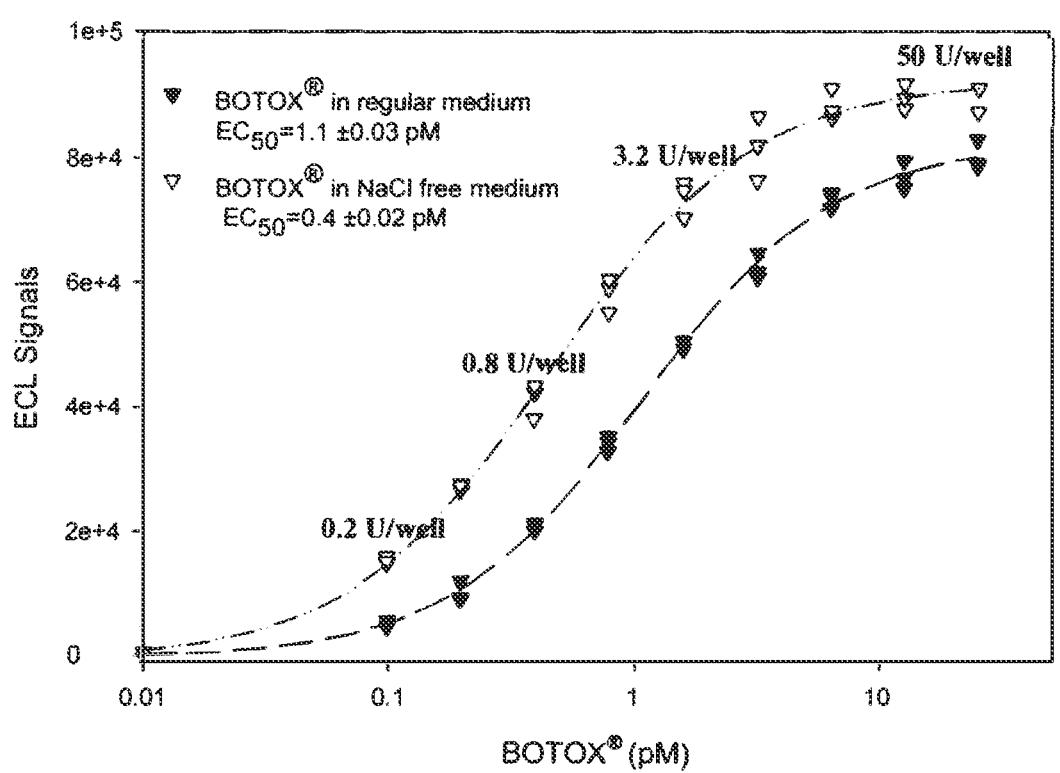
FIG. 9 shows the results of an immuno-based BoNT/A activity assay for a formulated BoNT/A pharmaceutical product using an immuno-based method of detecting BoNT/A activity disclosed in the present specification.
Figures 10A, 10B:
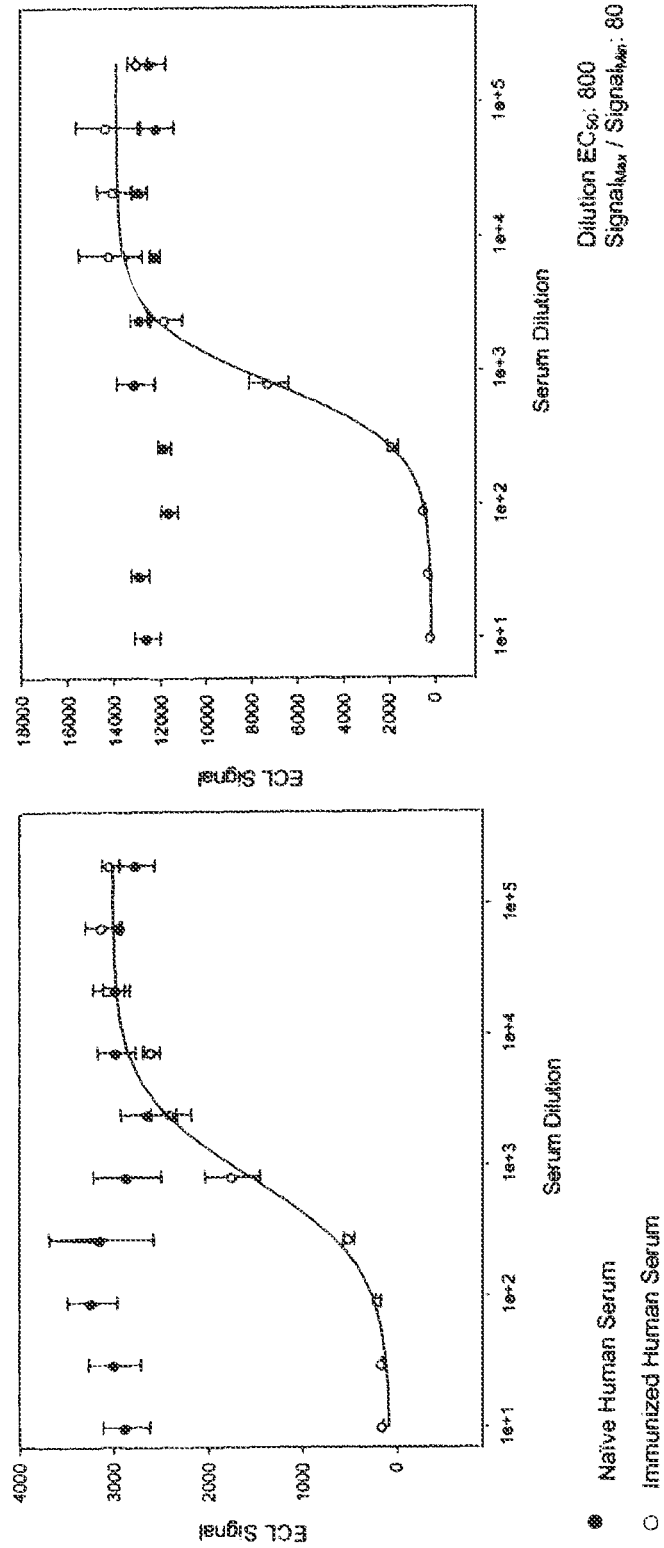
FIGS. 10A-10B show the detection of neutralizing α-BoNT/A antibodies in human serum using an immuno-based method of detecting BoNT/A activity disclosed in the present specification.

To detect the presence of a cleaved SNAP-25 product by ECL sandwich ELISA analysis, the Blocking Buffer from stored plates was aspirated from the wells, 25 μL of a lysate from cells treated with BoNT/A was added to each well and the plates were incubated at 4° C. for overnight. Plate wells were washed three times by aspirating the cell lysate and rinsing each well three times with 200 μL 1×PBS, 0.1% TWEEN-20® (polyoxyethylene (20) sorbitan monolaurate). After washing, 25 μl of 5 μg/mL detection antibody solution comprising 2% Amersham Blocking Reagent in 1×PBS, 0.1% TWEEN-20® (polyoxyethylene (20) sorbitan monolaurate) was added to each well, the plate was sealed, and the sealed plate was incubated at room temperature at room temperature for 1 hour with shaking. After detection antibody incubation, the wells were washed three times with 200 μL 1×PBS, 0.1% TWEEN-20® (polyoxyethylene (20) sorbitan monolaurate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). The collected data was analyzed and the $EC_{50}$ calculated as described in Example V. A representative result is shown in FIG. 8. These results indicated that on average 1.0 pM of BoNT/A at the $EC_{50}$ was detected (a range of about 0.3 pM to about 2.0 pM) with a signal-to-noise ratio for the lower asymptote of about 15:1 to about 20:1 and a signal-to-noise ratio for the upper asymptote of about 20:1 to about 500:1.

Example VII

Immuno-Based Method of Detecting BoNT/a Activity Using CL Sandwich ELISA

The following example illustrates immuno-based methods of detecting BoNT/A activity by detecting a SNAP-25 cleavage product using a α-SNAP-25 monoclonal antibody specific for a SNAP-25 having a carboxyl-terminus at the $P_1$ residue of the BoNT/A cleavage site scissile bond by CL sandwich ELISA.

Lysate from cells treated with a BoNT/A and the α-SNAP-25 capture antibody solution were prepared as described in Example VI.

To prepare the α-SNAP-25 detection antibody solution, α-SNAP-25 polyclonal antibody S9684 (Sigma, St. Louis, Mo.) was conjugated to Horseradish peroxidase (HRP) according to the manufacturer's instructions (Pierce Biotechnology, Inc., Rockford, Ill.). The conjugation reaction was performed by adding to 500 μL of 1 mg/mL α-SNAP-25 polyclonal antibodies to a vial containing lyophilized activated peroxidase, mixing the components, and then adding 10 μL of sodium cyanoborohydride. This reaction mixture was incubated at room temperature for 1 hour in a fume hood. After quenching the reaction, the labeled antibodies were purified using a standard spin column protocol and the protein concentration determined using a standard colorimetric protein assay. The absorbance of the α-SNAP-25 polyclonal antibody/HRP conjugate was measured at 455 nm using a spectrophotometer to determine the concentration in moles per liter. The α-SNAP-25 detection antibody solution was stored at 4° C. until needed.

To prepare the solid phase support comprising the α-SNAP-25 capture antibody that is specific for the SNAP-25 cleaved product, approximately 100 μL of α-SNAP-25 monoclonal antibody 2E2A6 solution (1 mg/mL in 1×PBS) was added to each well of a 96-well Greiner white plate and the plates were incubated at 4° C. overnight, and then any excess antibody solution was discarded. The capture antibody-bound wells were then blocked by adding 150 μl of Blocking Buffer comprising 2% Amersham Blocking Reagent (GE Life Sciences, Piscataway, N.J.) and 10% goat serum (VWR, West Chester, Pa.) at room temperature for 1 hour. The blocking buffer was discarded and the plates were blotted dry on paper towels by inverting and tapping. The capture antibody-bound wells were then blocked and used directly to detect BoNT/A activity.

To detect the presence of a cleaved SNAP-25 product by CL sandwich ELISA analysis, 50 μL of a lysate from cells treated with BoNT/A was added to each well, the plate was sealed, and the sealed plate was incubated on a shaker rotating at 500 rpm at 4° C. for 2-4 hours to overnight. Plate wells were washed three times by aspirating the cell lysate and rinsing each well three times with 200 μl 1×PBS, 0.05% TWEEN-20® (polyoxyethylene (20) sorbitan monolaurate). After washing, 100 μL of 1 mg/mL α-SNAP-25 polyclonal antibody/HRP detection antibody solution comprising 2% Amersham Blocking Reagent in 1×PBS, 0.1% TWEEN-20® (polyoxyethylene (20) sorbitan monolaurate) was added to each well, the plate was sealed, and the sealed plate was incubated on a shaker rotating at 650 rpm at room temperature for 1 hour. After detection antibody incubation, the wells were washed three times with 200 μl 1×PBS, 0.05% TWEEN-20® (polyoxyethylene (20) sorbitan monolaurate). After washing 100 μl of SuperSignal ELISA Pico 1:1 mixture (Pierce Biotechnology, Inc., Rockford, Ill.) was added to each well and the plates were read using a luminometer (Molecular Devices, Sunnyvale, Calif.) at 395 nm. The collected data was analyzed and the $EC_{50}$ calculated as described in Example V. These results indicated that on average 1.0 pM of BoNT/A at the $EC_{50}$ was detected (a range of about 0.3 pM to about 2.0 pM) with a signal-to-noise ratio for the lower asymptote of about 15:1 to about 20:1 and a signal-to-noise ratio for the upper asymptote of about 20:1 to about 500:1.

Example VIII

Immuno-Based Method of Detecting BoNT/a Activity Using Multiplex ECL Sandwich ELISA The following example illustrates multiplex immuno-based methods of detecting BoNT/A activity by detecting a SNAP-25 cleavage product using a α-SNAP-25 monoclonal antibody specific for a SNAP-25 cleavage product and a second antibody pair for a different protein.

1. Preparation and Identification of Capture Antibody-Detection Antibody Pair for a Second Protein.

To obtain an untreated cell lysate for analysis, a suitable density of cells from a stock culture of SiMa cells were seeded into a T175 flask containing 40 mL of a growth medium containing 1×RPMI 1640, 10% FBS, 0.1 mM Non-Essential Amino Acids, 10 mM HEPES, 1 mM sodium pyruvate, and 100 U/100 μg of penicillin-streptomycin. These cells were incubated in a 37° C. incubator under 5% carbon dioxide until the cells were approximately 70-90% confluent. The cells were washed and harvested by lysing in freshly prepared Triton X-100 Lysis Buffer (20 mM Tris pH 7.5, 150 mM sodium chloride, 0.001M EDTA, 1 mM EGTA, and 1% Triton-X-100) at 4° C. for approximately 30 minutes with constant agitation. Lysed cells were centrifuged at approximately 3300-3330×g for 40 minutes at 8° C. to eliminate debris using a bench-top centrifuge.

To identify an appropriate capture antibody-detection antibody pair for a second protein, an ECL sandwich ELISA analysis was conducted on 21 different combinations of capture and detection antibody pairs comprising of five different proteins (Table 13). The antibodies used were α-Syntaxin 1A-HPC mouse monoclonal antibody S0664 (Sigma, St. Louis, Mo.), α-GAPDH mouse monoclonal antibody MAB374 (Chemicon, Temecula, Calif.), α-Syntaxin 1 rabbit polyclonal antibody S1172-1 (Sigma, St. Louis, Mo.), α-GAPDH rabbit polyclonal antibody 2275-PC-1 (R & D Systems, Minneapolis, Minn.), α-Syntaxin 2 rabbit polyclonal antibody S5687 (Sigma, St. Louis, Mo.), α-human syntaxin 2 mouse monoclonal antibody MAB2936 (R & D Systems, Minneapolis, Minn.), α-mouse syntaxin 2 goat polyclonal antibody AF2568 (Sigma, St. Louis, Mo.), α-Syntaxin 2 rabbit polyclonal antibody AB5596 (Sigma, St. Louis, Mo.), α-Syntaxin 1 rabbit polyclonal antibody S1172-2 (Sigma, St. Louis, Mo.), α-h, m, r actin sheep polyclonal antibody AF4000 (R & D Systems, Minneapolis, Minn.), α-beta actin mouse monoclonal antibody A1978 (Sigma, St. Louis, Mo.), α-beta mouse polyclonal antibody actin A2228 (Sigma, St. Louis, Mo.), mouse α-GAPDH mouse monoclonal antibody G8795 (Sigma, St. Louis, Mo.), α-GAPDH rabbit polyclonal antibody G9595 (Sigma, St. Louis, Mo.).

To prepare the second protein capture antibody solution, the monoclonal antibodies were purchased as purified antibodies. To prepare the second protein detection antibody solution, the appropriate antibody was conjugated to Ruthenium(II)-tris-bipyridine-(4-methylsulfonate) NHS ester labeling reagent (Meso Scale Discovery, Gaithersburg, Md.) according to the manufacturer's instructions (Meso Scale Discovery, Gaithersburg, Md.). The conjugation reaction was performed by adding 30 μL of distilled water reconstituted MSD SULFO-TAG™ stock solution to 200 μL of 2 mg/mL polyclonal antibodies and incubating the reaction at room temperature for 2 hours in the dark. The labeled antibodies were purified using a standard spin column protocol and the protein concentration determined using a standard colorimetric protein assay. The absorbance of the antibody/MSD SULFO-TAG™ conjugate was measured at 455 nm using a spectrophotometer to determine the concentration in moles per liter. The detection antibody solution was stored at 4° C. until needed.

To prepare the solid phase support comprising the capture antibody that is specific for a SNAP-25 cleaved product, approximately 5 μL of α-SNAP-25 monoclonal antibody 2E2A6 solution (20 μg/mL in 1×PBS) was added to each well of a 96-well MSD High Bind plate and the solution is allowed to air dry in a biological safety cabinet for 2-3 hours in order to liquid evaporate the solution, and then the plates were sealed and stored at 4° C. until needed. The dried capture antibody-bound wells were then blocked by adding 150 μL of Blocking Buffer comprising of 3% BSA (Pierce, Rockford, Ill.) 10% goat serum (Rockland Immunochemicals, Gilbertsville, Pa.), and Difco 1% skim milk (BD BioSciences Franklin Lakes, N.J.) in 0.05% Tween-20 PBS at room temperature for 1-2 hours.

To detect the presence of protein by ECL sandwich ELISA analysis, the Blocking Buffer from stored plates was aspirated from the wells, 25 μL of a lysate from cells treated with BoNT/A, as described above, was added to each well and the plates were incubated at 4° C. for overnight. Plate wells were washed three times by aspirating the cell lysate and rinsing each well three times with 200 μL 1×PBS, 0.1% TWEEN-20® (polyoxyethylene (20) sorbitan monolaurate). After washing, 25 μL of 5 μg/mL the appropriate second protein detection antibody solution, resuspended in the blocking buffer as described above, was added to each well, the plate was sealed, and the sealed plate was incubated at room temperature for about 1 hour with shaking. After detection antibody incubation, the wells were washed three times with 250 μL 1×PBS, 0.1% TWEEN-20® (polyoxyethylene (20) sorbitan monolaurate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). A ratio was calculated by dividing the signal obtained from the untreated cell lysates for each antibody-pair by the signal obtained for the lysis buffer control (0 nM dose) for each antibody-pair (Table 13).

These results indicated that among the twenty-one different combinations of antibody pairs tested, only two antibody pairs had signal-to-noise ratios above 10:1 for the higher dose tested: Pair No. 16 α-GAPDH mouse monoclonal antibody MAB374 and α-GAPDH rabbit polyclonal antibody RDS2275-PC-1; and Pair 21: α-GAPDH mouse monoclonal antibody MAB374 and α-GAPDH rabbit polyclonal antibody G9545. The α-GAPDH mouse monoclonal antibody MAB374 and α-GAPDH rabbit polyclonal antibody G9545 pair was selected as the second protein capture antibody-detection antibody pair for the multiplex ECL sandwich ELISA.

TABLE 13

Screening of Second Protein Antibody Combinations

| Antibody Pair No. | Capture Antibody | Detection Antibody | Detection of Protein | Signal/Noise Ratio (lysate/buffer) |
|---|---|---|---|---|
| 1 | α-syntaxin 2 S5687 pAb | α-syntaxin 2 MAB2936 mAb | No | 0.92 |
| 2 | α-syntaxin 2 AF2568 pAb | α-syntaxin 2 AB5596 pAb | No | 1.1 |
| 3 | α-syntaxin 2 AF2568 | α-syntaxin 2 S5687 pAb | No | 1.11 |
| 4 | α-syntaxin 2 AF2936 pAb | α-syntaxin 2 AB5596 pAb | Yes | 1.63 |
| 5 | α-syntaxin 2 AF2936 pAb | α-syntaxin 2 S5687 pAb | Yes | 1.6 |
| 6 | α-syntaxin 2 AB5596 pAb | α-syntaxin 2 S5687 pAb | No | 0.82 |
| 7 | α-syntaxin 2 AB5596 pAb | α-syntaxin 2 MAB2936 mAb | No | 0.87 |
| 8 | α-syntaxin 2 MAB2936 mAb | α-syntaxin 2 AB5596 pAb | Yes | 1.2 |
| 9 | α-syntaxin 2 MAB2936 mAb | α-syntaxin 2 S5687 pAb | No | 1.07 |
| 10 | α-syntaxin S0664 mAb | α-syntaxin 1 S1172-1 pAb | Yes | 4.23 |
| 11 | α-syntaxin S0664 mAb | α-syntaxin 1 S1172-2 pAb | No | 1.21 |
| 12 | α-syntaxin 1 S1172-1 pAb | α-syntaxin S0664 mAb | Yes | 5.5 |
| 13 | α-syntaxin 1 S1172-2 pAb | α-syntaxin S0664 mAb | Yes | 2.5 |
| 14 | α-h, m, r actin AF4000 pAb | α-beta actin A1978 mAb | No | 1.04 |
| 15 | α-h, m, r actin AF4000 pAb | α-beta actin A2228 mAb | No | 1.08 |
| 16 | α-GAPDH MAB374 mAb | α-GAPDH 2275-PC-1 pAb | Yes | 20.04 |
| 17 | α-GAPDH MAB374 mAb | α-GAPDH G8795 mAb | No | 0.89 |
| 18 | α-GAPDH 2275-PC-1 pAb | α-GAPDH MAB374 mAb | No | 1.08 |
| 19 | α-GAPDH 2275-PC-1 pAb | α-GAPDH G8795 mAb | Yes | 1.27 |
| 20 | α-GAPDH G8795 mAb | α-GAPDH 2275-PC-1 pAb | Yes | 2.74 |
| 21 | α-GAPDH MAB374 mAb | α-GAPDH G9545 pAb | Yes | ≥100 |

2. Immuno-Based Method of Detecting BoNT/a Activity Using Multiplex ECL Sandwich ELISA.

To obtain a BoNT/A treated cell lysate for analysis, a suitable density of cells from a stock culture of a SiMa cell line were seeded into a poly-D-lysine 96-well plate containing a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES. These cells were incubated in a 37° C. incubator under 5% carbon dioxide until the cells differentiated, as assessed by standard and routine morphological criteria, such as growth arrest and neurite extension (approximately 3 days). The media was aspirated from each well and replaced with fresh media containing either 0 (untreated sample), 0.67 U/mL, 2.35 U/mL, 8.23 U/mL, 28.82 U/mL, 101 U/mL, 353 U/mL of a BoNT/A complex. After a 24 hr treatment, the cells were washed, incubated for an additional two days without toxin. The cells were washed, harvested, and processed as described above in Section 1.

The α-SNAP-25 capture antibody solution and the α-SNAP-25 detection antibody solution, were prepared as described in Example VII. To prepare the α-GAPDH capture antibody solution, the α-GAPDH monoclonal antibody mouse MAB374 (Chemicon, Temecula, Calif.) was prepared as described in Section 1 above. To prepare the α-GAPDH detection antibody solution, α-GAPDH rabbit polyclonal antibody G9545 (Sigma, St. Louis, Mo.) was conjugated to Ruthenium(II)-tris-bipyridine-(4-methylsulfonate) NHS ester labeling reagent (Meso Scale Discovery, Gaithersburg, Md.) according to the manufacturer's instructions (Meso Scale Discovery, Gaithersburg, Md.). The conjugation reaction, purification of labeled α-SNAP-25 antibody, concentration determination and storage were as described in Section 1 above.

To prepare the solid phase support comprising the a α-SNAP-25 capture antibody and the α-GAPDH capture antibody, approximately 2.5 nL of the α-SNAP-25 capture antibody solution (45 µg/mL in 1×PBS) and 2.5 nL of the α-GAPDH capture antibody solution (120 µg/mL in 1×PBS) were added to each well of a 96-well MSD High Bind plate in a multiplex format using a robotic system. The solution is allowed to air dry in a biological safety cabinet for at least 2-3 hours in order to liquid evaporate the solution. The capture antibody-bound wells were then blocked and used directly to detect BoNT/A activity and the GAPDH protein.

To detect the presence of SNAP-25 cleavage product by multiplex ECL sandwich ELISA analysis, the Blocking Buffer from stored plates was aspirated from the wells, 25 µL of a lysate from cells treated with BoNT/A, as described above, was added to each well and the plates were incubated at 4° C. for overnight. Plate wells were washed three times by aspirating the cell lysate and rinsing each well three times with 200 µL 1×PBS, 0.1% TWEEN-20® (polyoxyethylene (20) sorbitan monolaurate). After washing, 25 µL of 5 µg/mL the α-SNAP-25 detection antibody solution and 25 µL of 5 µg/mL the α-GAPDH detection antibody solution, as described above, was added to each well, the plate was sealed, and the sealed plate was incubated at room temperature for about 1 hour with shaking. After detection antibody incubation, the wells were washed three times with 250 µL 1×PBS, 0.1% TWEEN-20® (polyoxyethylene (20) sorbitan monolaurate). After washing 150 µL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). The collected data was analyzed and the relative potency from the normalized data is calculated as described in Example V, except that PLA 2.0 software (Stegmann Systems, GmbH, Germany) was used.

As a comparison, the detection of SNAP-25 cleavage product was also performed using the singleplex ECL sandwich ELISA as described in Example VI.

The results indicated that the SNAP-25 data obtained from the singleplex ECL sandwich ELISA, or from the non-normalized SNAP-25 data obtained from the multiplex ECL sandwich ELISA, revealed one outlier sample dose that did not fit into the dose-response curve. However, normalization of the SNAP-25 data against the GAPDH data gave a better curve fit and the potency was closer to the expected value.

Example IX

Immuno-Based Method of Detecting BoNT/a Activity Using Multiplex EC Sandwich ELISA The following example illustrates multiplex immuno-based methods of detecting BoNT/A activity by detecting a SNAP-25 cleavage product using a α-SNAP-25 monoclonal antibody specific for a SNAP-25 cleavage product and a second antibody pair for a different protein.

The lysate from cells treated with a BoNT/A was prepared as described in Example VI. The α-SNAP-25 capture antibody solution, the α-SNAP-25 detection antibody solution, and the α-SNAP-25 solid phase support were prepared as described in Example VII.

To prepare α-GAPDH capture antibody solution, α-GAPDH monoclonal antibody MAB374 (Millipore, Billerica, Mass.) was purchased as a purified antibody. To prepare the α-GAPDH detection antibody solution, an α-GAPDH polyclonal antibody G9545 (Sigma, St. Louis, Mo.) was conjugated to Horseradish peroxidase (HRP) according to the manufacturer's instructions (Pierce Biotechnology, Inc., Rockford, Ill.). The conjugation reaction, concentration determination and storage were as described in Example VII.

To prepare the solid phase support comprising a second capture antibody specific for the second protein, approximately 100 µL of monoclonal antibody solution comprising 1 µg/mL α-GAPDH monoclonal antibody MAB374 was added to each well of a 96-well Greiner white plate and the plates were incubated at 4° C. overnight, and then any excess antibody solution was discarded. The α-GAPDH capture antibody-bound wells were then blocked by adding 150 µl of Blocking Buffer comprising 2% Amersham Blocking Reagent (GE Life Sciences, Piscataway, N.J.) and 10% goat serum (VWR, West Chester, Pa.) at room temperature for 1 hour. The blocking buffer was discarded and the plates were blotted dry on paper towels by inverting and tapping. The capture antibody-bound wells were then blocked and used directly to detect BoNT/A activity.

To detect the presence of a cleaved SNAP-25 product by multiplex CL sandwich ELISA analysis, 50 µL of cell lysates from cells treated with BoNT/A was added to each well of the α-SNAP-25 capture antibody solid phase support and the α-GAPDH capture antibody solid phase support, the plate was sealed, and the sealed plate was incubated on a shaker rotating at 500 rpm at 4° C. for 2-4 hours to overnight. Plate wells were washed three times by aspirating the cell lysate and rinsing each well three times with 200 µl 1×PBS, 0.05% TWEEN-20® (polyoxyethylene (20) sorbitan monolaurate). After washing, 100 µL of a detection antibody solution comprising 2% Amersham Blocking Reagent in 1×PBS, 0.1% TWEEN-20® (polyoxyethylene (20) sorbitan monolaurate), and 1 mg/mL α-SNAP-25 polyclonal antibody/HRP was added to each well of the α-SNAP-25 capture antibody solid phase support, the plate was sealed, and the sealed plate was incubated on a shaker rotating at 650 rpm at room temperature for 1 hour. Similarly, 100 µL of a detection antibody solution comprising 2% Amersham Blocking Reagent in 1×PBS, 0.1% TWEEN-20® (polyoxyethylene (20) sorbitan monolaurate), and 0.25 mg/mL α-GAPDH G9545 polyclonal antibody/HRP (Sigma Co., St Louis, Mo.) was added to each well of the α-GAPDH capture antibody solid phase support, the plate was sealed, and the sealed plate was placed on a shaker rotating at 650 rpm at room temperature for 1 hour. After detection antibody incubation, the wells were washed three times with 200 µl 1×PBS, 0.05% TWEEN-20® (polyoxyethylene (20) sorbitan monolaurate). After washing 100 µl of SuperSignal ELISA Pico 1:1 mixture (Pierce Biotechnology, Inc., Rockford, Ill.) was added to each well and the plates were read using a luminometer (Molecular Devices, Sunnyvale, Calif.) at 395 nm. The collected data was analyzed and the $EC_{50}$ calculated as described in Example V. The results indicated that the data points collected for the amounts of α-SNAP-25 antibody-antigen complex detected were a better fit after normalization to the amounts of α-GAPDH antibody-antigen complex detected, thereby producing a more accurate reading. These results indicated that on average 1.0 pM of BoNT/A at the $EC_{50}$ was detected (a range of about 0.3 pM to about 2.0 pM) with a signal-to-noise ratio for the lower asymptote of about 15:1 to about 20:1 and a signal-to-noise ratio for the upper asymptote of about 20:1 to about 500:1.

A similar design can be used for multiplex immuno-based methods of detecting BoNT/A activity by detecting a SNAP-25 cleavage product using a α-SNAP-25 monoclonal antibody specific for a SNAP-25 cleavage product having a carboxyl-terminus at the $P_1$ residue of the BoNT/A cleavage site scissile bond using ECL sandwich ELISA with the same α-GAPDH antibody pair.

Example X

Immuno-Based Method to Detect Picomolar Amounts of BoNT/A

The following example illustrates how to perform immuno-based methods of detecting BoNT/A activity that can detect picomolar amounts of the BoNT/A pharmaceutical product, such as, e.g., BOTOX® DYSPORT®/RELOXIN®, PURTOX®, XEOMIN®, NEURONOX®, or BTX-A.

1. Immuno-Based Method of Detecting BoNT/a Using ECL Sandwich ELISA.

To prepare a lysate from cells treated with a BoNT/A, approximately 50,000 to 150,000 cells from an established cell line were plated into the wells of 96-well tissue culture poly-D-lysine plates containing 100 μL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES and 25 μg/mL GT1b (see Examples I and II). These cells were incubated in a 37° C. incubator under 5% carbon dioxide until the cells differentiated, as assessed by standard and routine morphological criteria, such as growth arrest and neurite extension (approximately 2 to 3 days). The media from the differentiated cells was aspirated from each well and replaced with fresh media containing either 0 (untreated sample), 0.03 pM, 0.1 pM, 0.3 pM, 0.9 pM, 2.8 pM, 8.3 pM, or 25 pM of a BoNT/A pharmaceutical product reconstituted in a sodium chloride free solution; or 0 (untreated sample), 0.7 U/mL, 2.1 U/mL, 6.2 U/mL, 18.5 U/mL, 55.6 U/mL, 166.7 U/mL or 500 U/mL of a BoNT/A pharmaceutical product reconstituted in a sodium chloride free medium. Because the BoNT/A pharmaceutical product contains sodium chloride, its addition to the culture medium resulted in a hypertonic media that was detrimental to cell viability. To circumvent the hypertonicity issue, 200 μL of MEM media made without sodium chloride was used to reconstitute the BoNT/A pharmaceutical product giving a final concentration of 25 pM BoNT/A (500 U/mL). The matrix was kept constant for all concentrations along the dose-response curve by adding sodium chloride in the media used to make the dilutions match the amount of excipients present at the highest concentration used (25 pM or 500 U/mL). After a 24 hr treatment, the cells were washed, and incubated for an additional two days without toxin. To harvest the cells, the medium was aspirated, washed with 1×PBS, and lysed by adding 30 μl of Lysis Buffer comprising 50 mM HEPES, 150 mM NaCl, 1.5 mM $MgCl_2$, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris and the supernatant was transferred to a capture antibody coated 96-well plate to perform the detection step.

The α-SNAP-25 capture antibody solution, the α-SNAP-25 detection antibody solution, and the solid phase support comprising the capture antibody that is specific for a SNAP-25 cleaved product were prepared as described in Example VI.

To detect the presence of a cleaved SNAP-25 product by ECL sandwich ELISA analysis, the Blocking Buffer from stored plates was aspirated, 25 μL of a lysate from cells treated with BoNT/A was added to each well and the plates were incubated at 4° C. for either 2 hrs or 24 hrs. Plate wells were washed three times by aspirating the cell lysate and rinsing each well three times with 200 μL 1×PBS, 0.1% TWEEN-20® (polyoxyethylene (20) sorbitan monolaurate). After washing, 25 μl of 5 μg/mL α-SNAP-25 detection antibody solution comprising 2% Amersham Blocking Reagent in 1×PBS, 0.1% TWEEN-20® (polyoxyethylene (20) sorbitan monolaurate) was added to each well, the plate was sealed, and the sealed plate was incubated at room temperature for 1 hour with shaking. After α-SNAP-25 detection antibody incubation, the wells were washed three times with 200 μL 1×PBS, 0.1% TWEEN-20® (polyoxyethylene (20) sorbitan monolaurate). After washing, the plates were processed, collected data was analyzed, and the $EC_{50}$ calculated as described in Example V. These results indicated that on average 1.0 pM of BoNT/A at the $EC_{50}$ was detected (a range of about 0.3 pM to about 2.0 pM) with a signal-to-noise ratio for the lower asymptote of about 15:1 to about 20:1 and a signal-to-noise ratio for the upper asymptote of about 20:1 to about 500:1 (FIG. 9). This method can also be performed in a multiplex fashion as described in Example VIII.

2. Immuno-Based Method of Detecting BoNT/A Using CL Sandwich ELISA.

Lysate from cells treated with a BoNT/A and the α-SNAP-25 capture antibody solution will be prepared as described in Example VI. The α-SNAP-25 detection antibody solution and solid phase support comprising the capture antibody that is specific for a SNAP-25 cleaved product will be prepared as described in Example VII.

To detect the presence of a cleaved SNAP-25 product by CL sandwich ELISA analysis, 25 μL of a lysate from cells treated with BoNT/A will be added to each well, the plate was sealed, and the sealed plate was incubated on a shaker rotating at 500 rpm at 4° C. for either 2 hrs or 24 hrs. Plate wells will be washed three times by aspirating the cell lysate and rinsing each well three times with 200 μl 1×PBS, 0.05% TWEEN-20® (polyoxyethylene (20) sorbitan monolaurate). After washing, 100 μL of 1 mg/mL α-SNAP-25 polyclonal antibody/HRP detection antibody solution comprising 2% Amersham Blocking Reagent in 1×PBS, 0.1% TWEEN-20® (polyoxyethylene (20) sorbitan monolaurate) will be added to each well, the plate was sealed, and the sealed plate was incubated on a shaker rotating at 650 rpm at room temperature for 1 hour. After detection antibody incubation, the wells will be washed three times with 200 μl 1×PBS, 0.05% TWEEN-20® (polyoxyethylene (20) sorbitan monolaurate). After washing 100 μl of SuperSignal ELISA Pico 1:1 mixture (Pierce Biotechnology, Inc., Rockford, Ill.) will be added to each well and the plates will be read using a luminometer (Molecular Devices, Sunnyvale, Calif.) at 395 nm. The collected data will be analyzed and the $EC_{50}$ will be calculated as described in Example V. This method can also be performed in a multiplex fashion as described in Example VIII.

Example XI

Immuno-Based Method to Detect Neutralizing α-BoNT/a Antibodies

The following example illustrates how to perform an immuno-based method that can detect the presence of neutralizing α-BoNT/A antibodies.

BoNT/A, is currently used for a wide range of medical indications including muscle hyperactivity, ophthalmologic, gastrointestinal, urologic, and cosmetic. With repeated long-term treatment of BoNT/A, a patient may develop neutralizing α-BoNT/A antibodies to the toxin leading to immunoresistance. Neutralizing α-BoNT/A antibodies inhibit BoNT/A activity by stopping the toxin's uptake into neuronal cells by binding to the binding domain ($H_C$) and/or the translocation domain ($H_N$) of BoNT/A. Some studies have suggested that up to 5-10% of patients repeatedly treated for dystonia with formulations of BoNT/A have immunoresistance due to the development of neutralizing α-BoNT/A antibodies. The established assay to determine the presence of the neutralizing α-BoNT/A antibodies in patient's blood is the mouse protection assay (MPA). Currently, BoNT/A is incubated with a patient's serum prior to injection into mice. The presence of antibodies is manifested by a decreased response to the neurotoxin in the animal. Since the MPA is an in vivo based assay, it would be more cost and time efficient if it was replaced with a cell-based assay.

To detect the presence or absence of neutralizing α-BoNT/A antibodies, the immuno-based methods of determining BoNT/A activity disclosed in the present specification can be used. One way is to determine the amount of SNAP-25 cleavage product present after treatment with various concentrations of BoNT/A using a Western blot detection method, the other way was to use an ECL sandwich ELISA detection method.

To prepare a sample comprising neutralizing α-BoNT/A antibodies and a negative control sample known to lack α-BoNT/A neutralizing antibodies, serum was isolated from blood of different individuals. Individuals declining immunizations were referred to as naïve individuals. Individuals accepting immunization were referred to as immunized individuals. The blood was drawn into a serum tube with a clot activator (BD Biosciences, Bedford, Mass.). Serum was obtained by centrifugation of the blood at 1000×g for 10 minutes at 4° C. The serum of two donors was obtained: one individual was immunized to BoNT/A while the other was not.

To prepare a lysate from cells treated with a sample comprising BoNT/A, SiMa cells were seeded in a poly-D-lysine 96-well plate and differentiated as described in Example VI. The human serums were serially diluted 1:100-1:152,000 by 2.5 fold increments using serum-free media. The BoNT/A was suspended in 0.5 mL SiMa culture media at a concentration of 10 pM. The media containing BoNT/A and α-BoNT/A antibodies were mixed and incubated for 15 min or 1 hr at room temperature. The cells were treated with BoNT/A with human serum for 2 hr followed by a 15 hr incubation in fresh growth media. The cells were also treated for 15 hr with no additional incubation time.

To detect the presence of a cleaved SNAP-25 product by Western blot analysis, the media was aspirated from each well, the cells suspended in 50 µL of SDS-PAGE loading buffer, and then heated to 95° C. for 5 minutes. An aliquot from each harvested sample was analyzed by Western blot as described in Example I, except that harvested samples are separated by SDS-PAGE using 12% 26-well Criterion gels (Bio-Rad Laboratories, Hercules, Calif.), and the rabbit polyclonal α-SNAP-25$_{197}$ antibody serum was used as the primary antibody (see Example IV). The results indicate that test samples resulted in reduced cleavage of SNAP-25 when compared to the negative control sample, demonstrating that the serum from the immunized individual contained neutralizing α-BoNT/A antibodies.

To detect the presence of a cleaved SNAP-25 product by ECL Sandwich ELISA, the media was removed from each well and the cells were lysed as described in Example V. The α-SNAP-25 capture antibody solution, the α-SNAP-25 detection antibody solution, and the α-SNAP-25 solid phase support were prepared as described in Example VII. Supernatants were transferred to the α-SNAP-25 solid phase support and an ECL sandwich ELISA assay was performed as detailed in Example V. The collected data was analyzed and the $EC_{50}$ calculated as described in Example V, except that the $EC_{50}$ is the serum dilution needed to inhibit the activity of the BoNT/A to ½ its maximum and the ratio of maximal signal (Signal$_{Max}$) to minimum signal (Signal$_{Min}$) was obtained by dividing the SNAP-25 cleavage product signal obtained with the highest dilution of serum by the signal obtained with the lowest serum dilution.

The results indicate that the presence of neutralizing α-BoNT/A in human serum could be detected. The activity of the BoNT/A complex incubated in serum from the immunized individual decreased as the serum dilution decreased, whereas, the presence of naïve serum had no impact on the assay at every dilution tested. This assay can be performed using a formulated BoNT/A pharmaceutical product, a bulk BoNT/A complex, or a purified neurotoxin.

Example XII

Immuno-Based Method to Detect BoNT/a Activity Using Engineered Cells

The following example illustrates how to introduce a polynucleotide molecule encoding a BoNT/A receptor into cells from an established cell line to further improve susceptibility to BoNT/A intoxication or improve BoNT/A uptake capacity.

To introduce an exogenous BoNT/A receptor into cells comprising an established cell line, an expression construct comprising a polynucleotide molecule of SEQ ID NO: 130 encoding the FGFR2 of SEQ ID NO: 59, or a polynucleotide molecule of SEQ ID NO: 139 encoding the FGFR3 of SEQ ID NO: 25, was transfected into cells from an established cell line by a cationic lipid method. A suitable density (about 5×10$^6$ cells) of cells from an established cell line are plated in a 100 mm tissue culture dish containing 5 mL of complete culture media and grown in a 37° C. incubator under 5% carbon dioxide until the cells reached a density appropriate for transfection. A 3 mL transfection solution is prepared by adding 1.5 mL of OPTI-MEM Reduced Serum Medium containing 60 µL of LipofectAmine 2000 (Invitrogen, Carlsbad, Calif.) incubated at room temperature for 5 minutes to 1.5 mL of OPTI-MEM Reduced Serum Medium containing 24 µg of an expression construct encoding a FGFR2 or a FGFR3, or a control expression construct encoding a green fluorescent protein (GFP). This transfection mixture was incubated at room temperature for approximately 30 minutes. The complete media is replaced with the 3 mL transfection solution and the cells are incubated in a 37° C. incubator under 5% carbon dioxide for approximately 8 hours. Transfection media is replaced with 3 mL of fresh complete culture media and the cells are incubated in a 37°

C. incubator under 5% carbon dioxide for approximately 24 hours. Media is replaced with 3 mL of fresh complete culture media containing approximately 1 mM G418 (Invitrogen, Carlsbad, Calif.). Cells are incubated in a 37° C. incubator under 5% carbon dioxide for approximately 1 week, the old media is replaced with fresh complete culture media containing 0.5 mM G418. Once antibiotic-resistant colonies are established, resistant clones are replated to new 100 mm culture plates containing fresh complete culture media, supplemented with approximately 0.5 mM G418 until these cells reached a density of 6 to 20×10$^5$ cells/mL.

To determine if the overexpression of BoNT/A receptors improved cell susceptibility to BoNT/A intoxication or improved BoNT/A uptake capacity, a dose-response curve was generated using cells treated with different doses of a BoNT/A complex. To prepare a lysate from cells treated with a BoNT/A, a suitable density of cells from an established transfected cell line was plated into the wells of 96-well tissue culture plates containing 100 μL of an appropriate serum-free medium (Table 5). These cells were incubated in a 37° C. incubator under 5% carbon dioxide until the cells differentiated, as assessed by standard and routine morphological criteria, such as growth arrest and neurite extension (approximately 3 days). The media from the differentiated cells was aspirated from each well and replaced with fresh media containing either 0 (untreated sample), 0.01 nM, 0.04 nM, 0.12 nM, 0.37 nM, 1.1 nM, 3.3 nM, and 10 nM of a BoNT/A complex for cells comprising a SiMa or a PC12 transfected cell line; and 0 (untreated sample), 0.14 nM, 0.40 nM, 1.2 nM, 3.7 nM, 11 nM, 33 nM, and 100 nM of a BoNT/A complex for cells comprising a Neuro-2a transfected cell line. The cells were treated with BoNT/A containing media for 6 hrs followed by incubation with fresh media for 15 hrs and harvested by adding 40 μL of 2×SDS-PAGE loading buffer and heating the plate to 95° C. for 5 min.

To detect for the presence of SNAP-25 cleavage product, an aliquot from each harvested sample was analyzed by Western blot as described in Example I, except that harvested samples are separated by SDS-PAGE using 12% 26-well Criterion gels (Bio-Rad Laboratories, Hercules, Calif.), and the following primary antibodies were used a 1:1,000 dilution of rabbit polyclonal α-SNAP-25 antibody serum (Example IV) (AGN, polyclonal antibody), a 1:500 dilution of α-FGFR2 rabbit polyclonal C-17 (Santa Cruz Biotechnology, Santa Cruz, Calif.), or a 1:500 dilution of α-FGFR3 rabbit polyclonal C-15 (Santa Cruz Biotechnology, Santa Cruz, Calif.). The intensity of the protein of interest from each sample was calculated using Image Quant (GE Healthcare, Piscataway, N.J.) and the EC$_{50}$ for each of the cells lines was estimated using SigmaPlot software.

The results indicate that cells transfected with FGFR2 or FGFR3 were more sensitive to BoNT/A than cells transfected with GFP and also showed a higher level of SNAP-25 cleavage (Table 14). The EC$_{50}$ values for cells over-expressing FGFR2 or FGFR3 were lower than the EC$_{50}$ values exhibited by cells over-expressing GFP, indicating that introduction of FGFR2 or FGFR3 improved cell susceptibility to BoNT/A intoxication or improved BoNT/A uptake capacity.

TABLE 14

Effects of Introducing Exogenous BoNT/A Receptors on Cell Susceptibilty to BoNT/A Intoxication or BoNT/A Uptake

| Cells | Transfected Gene | EC$_{50}$ (nM) | Max Signal |
|---|---|---|---|
| SiMa | GFP | 0.0812 ± 0.010 | 22,733,787 |
| SiMa | FGFR2 | 0.0459 ± 0.003 | 26,136,578 |
| SiMa | FGFR3 | 0.0377 ± 0.006 | 24,326,271 |
| PC-12 | GFP | 3.3362 ± 1.881 | 26,956,063 |
| PC-12 | FGFR2 | 0.3429 ± 0.059 | 25,376,114 |
| PC-12 | FGFR3 | 0.2634 ± 0.026 | 24,102,459 |
| Neuro-2a | GFP | 61.80 ± 9.710 | 4,605,974 |
| Neuro-2a | FGFR2 | 31.59 ± 8.800 | 23,279,765 |
| Neuro-2a | FGFR3 | 11.55 ± 5.240 | 28,347,413 |

Detection for the presence of SNAP-25 cleavage product can also be performed using sandwich ELISA as described in Examples VI-X.

SEQUENCE LISTING

```
<160> NUMBER OF SEQ ID NOS: 148

<210> SEQ ID NO 1
<211> LENGTH: 1296
<212> TYPE: PRT
<213> ORGANISM: Clostridium botulinum

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
```

```
            100                 105                 110
Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
            130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
            165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
            210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
            450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525
```

```
Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
    755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
    835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
    915                 920                 925

Lys Asn Ala Ile Val Tyr Asn Ser Met Tyr Glu Asn Phe Ser Thr Ser
930                 935                 940
```

```
Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 2
<211> LENGTH: 1296
<212> TYPE: PRT
<213> ORGANISM: Clostridium botulinum

<400> SEQUENCE: 2

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30
```

-continued

```
Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
 50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
                115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
        210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
        275                 280                 285

Lys Phe Lys Asp Val Ala Ser Thr Leu Asn Lys Ala Lys Ser Ile Ile
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Asn Phe Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
370                 375                 380

Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
                405                 410                 415

Lys Asn Phe Thr Gly Leu Phe Glu Phe Tyr Lys Leu Leu Cys Val Arg
                420                 425                 430

Gly Ile Ile Pro Phe Lys Thr Lys Ser Leu Asp Glu Gly Tyr Asn Lys
                435                 440                 445
```

```
Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asp Lys Val Glu Glu
465                 470                 475                 480

Ile Thr Ala Asp Thr Asn Ile Glu Ala Ala Glu Glu Asn Ile Ser Leu
            485                 490                 495

Asp Leu Ile Gln Gln Tyr Tyr Leu Thr Phe Asp Phe Asp Asn Glu Pro
        500                 505                 510

Glu Asn Ile Ser Ile Glu Asn Leu Ser Ser Asp Ile Ile Gly Gln Leu
        515                 520                 525

Glu Pro Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Asp Ser Arg Ile Ile Leu Thr Asn Ser Ala Glu Glu Ala Leu
                565                 570                 575

Leu Lys Pro Asn Val Ala Tyr Thr Phe Phe Ser Ser Lys Tyr Val Lys
            580                 585                 590

Lys Ile Asn Lys Ala Val Glu Ala Phe Met Phe Leu Asn Trp Ala Glu
        595                 600                 605

Glu Leu Val Tyr Asp Phe Thr Asp Glu Thr Asn Glu Val Thr Thr Met
610                 615                 620

Asp Lys Ile Ala Asp Ile Thr Ile Ile Val Pro Tyr Ile Gly Pro Ala
625                 630                 635                 640

Leu Asn Ile Gly Asn Met Leu Ser Lys Gly Glu Phe Val Glu Ala Ile
                645                 650                 655

Ile Phe Thr Gly Val Val Ala Met Leu Glu Phe Ile Pro Glu Tyr Ala
            660                 665                 670

Leu Pro Val Phe Gly Thr Phe Ala Ile Val Ser Tyr Ile Ala Asn Lys
        675                 680                 685

Val Leu Thr Val Gln Thr Ile Asn Asn Ala Leu Ser Lys Arg Asn Glu
690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Val Leu
            820                 825                 830

Gln Val Asp Arg Leu Lys Asp Glu Val Asn Asn Thr Leu Ser Ala Asp
        835                 840                 845

Ile Pro Phe Gln Leu Ser Lys Tyr Val Asp Asn Lys Lys Leu Leu Ser
850                 855                 860

Thr Phe Thr Glu Tyr Ile Lys Asn Ile Val Asn Thr Ser Ile Leu Ser
```

-continued

```
                865                 870                 875                 880
        Ile Val Tyr Lys Lys Asp Asp Leu Ile Asp Leu Ser Arg Tyr Gly Ala
                        885                 890                 895
        Lys Ile Asn Ile Gly Asp Arg Val Tyr Tyr Asp Ser Ile Asp Lys Asn
                        900                 905                 910
        Gln Ile Lys Leu Ile Asn Leu Glu Ser Ser Thr Ile Glu Val Ile Leu
                        915                 920                 925
        Lys Asn Ala Ile Val Tyr Asn Ser Met Tyr Glu Asn Phe Ser Thr Ser
                        930                 935                 940
        Phe Trp Ile Lys Ile Pro Lys Tyr Phe Ser Lys Ile Asn Leu Asn Asn
        945                 950                 955                 960
        Glu Tyr Thr Ile Ile Asn Cys Ile Glu Asn Asn Ser Gly Trp Lys Val
                        965                 970                 975
        Ser Leu Asn Tyr Gly Glu Ile Ile Trp Thr Leu Gln Asp Asn Lys Gln
                        980                 985                 990
        Asn Ile Gln Arg Val Val Phe Lys Tyr Ser Gln Met Val Asn Ile Ser
                        995                 1000                1005
        Asp Tyr Ile Asn Arg Trp Ile Phe Val Thr Ile Thr Asn Asn Arg Leu
                        1010                1015                1020
        Thr Lys Ser Lys Ile Tyr Ile Asn Gly Arg Leu Ile Asp Gln Lys Pro
        1025                1030                1035                1040
        Ile Ser Asn Leu Gly Asn Ile His Ala Ser Asn Lys Ile Met Phe Lys
                        1045                1050                1055
        Leu Asp Gly Cys Arg Asp Pro Arg Arg Tyr Ile Met Ile Lys Tyr Phe
                        1060                1065                1070
        Asn Leu Phe Asp Lys Glu Leu Asn Glu Lys Glu Ile Lys Asp Leu Tyr
                        1075                1080                1085
        Asp Ser Gln Ser Asn Ser Gly Ile Leu Lys Asp Phe Trp Gly Asn Tyr
                        1090                1095                1100
        Leu Gln Tyr Asp Lys Pro Tyr Tyr Met Leu Asn Leu Phe Asp Pro Asn
        1105                1110                1115                1120
        Lys Tyr Val Asp Val Asn Asn Ile Gly Ile Arg Gly Tyr Met Tyr Leu
                        1125                1130                1135
        Lys Gly Pro Arg Gly Ser Val Val Thr Thr Asn Ile Tyr Leu Asn Ser
                        1140                1145                1150
        Thr Leu Tyr Glu Gly Thr Lys Phe Ile Ile Lys Lys Tyr Ala Ser Gly
                        1155                1160                1165
        Asn Glu Asp Asn Ile Val Arg Asn Asn Asp Arg Val Tyr Ile Asn Val
                        1170                1175                1180
        Val Val Lys Asn Lys Glu Tyr Arg Leu Ala Thr Asn Ala Ser Gln Ala
        1185                1190                1195                1200
        Gly Val Glu Lys Ile Leu Ser Ala Leu Glu Ile Pro Asp Val Gly Asn
                        1205                1210                1215
        Leu Ser Gln Val Val Val Met Lys Ser Lys Asp Asp Gln Gly Ile Arg
                        1220                1225                1230
        Asn Lys Cys Lys Met Asn Leu Gln Asp Asn Asn Gly Asn Asp Ile Gly
                        1235                1240                1245
        Phe Ile Gly Phe His Leu Tyr Asp Asn Ile Ala Lys Leu Val Ala Ser
                        1250                1255                1260
        Asn Trp Tyr Asn Arg Gln Val Gly Lys Ala Ser Arg Thr Phe Gly Cys
        1265                1270                1275                1280
        Ser Trp Glu Phe Ile Pro Val Asp Asp Gly Trp Gly Glu Ser Ser Leu
                        1285                1290                1295
```

<210> SEQ ID NO 3
<211> LENGTH: 1292
<212> TYPE: PRT
<213> ORGANISM: Clostridium botulinum

<400> SEQUENCE: 3

```
Met Pro Phe Val Asn Lys Pro Phe Asn Tyr Arg Asp Pro Gly Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Glu Gly Val Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Ile Lys Leu Phe Asp
                85                  90                  95

Arg Ile Tyr Ser Thr Gly Leu Gly Arg Met Leu Leu Ser Phe Ile Val
            100                 105                 110

Lys Gly Ile Pro Phe Trp Gly Gly Ser Thr Ile Asp Thr Glu Leu Lys
        115                 120                 125

Val Ile Asp Thr Asn Cys Ile Asn Val Ile Glu Pro Gly Gly Ser Tyr
    130                 135                 140

Arg Ser Glu Glu Leu Asn Leu Val Ile Thr Gly Pro Ser Ala Asp Ile
145                 150                 155                 160

Ile Gln Phe Glu Cys Lys Ser Phe Gly His Asp Val Phe Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Thr Phe Ala Thr Asp Pro Ala Val Thr Leu Ala His Glu
    210                 215                 220

Leu Ile His Ala Ala His Arg Leu Tyr Gly Ile Ala Ile Asn Pro Asn
225                 230                 235                 240

Arg Val Leu Lys Val Lys Thr Asn Ala Tyr Tyr Glu Met Ser Gly Leu
                245                 250                 255

Glu Val Ser Phe Glu Glu Leu Arg Thr Phe Gly Gly Asn Asp Thr Asn
            260                 265                 270

Phe Ile Asp Ser Leu Trp Gln Lys Lys Phe Ser Arg Asp Ala Tyr Asp
        275                 280                 285

Asn Leu Gln Asn Ile Ala Arg Ile Leu Asn Glu Ala Lys Thr Ile Val
    290                 295                 300

Gly Thr Thr Thr Pro Leu Gln Tyr Met Lys Asn Ile Phe Ile Arg Lys
305                 310                 315                 320

Tyr Phe Leu Ser Glu Asp Ala Ser Gly Lys Ile Ser Val Asn Lys Ala
                325                 330                 335

Ala Phe Lys Glu Phe Tyr Arg Val Leu Thr Arg Gly Phe Thr Glu Leu
            340                 345                 350

Glu Phe Val Asn Pro Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
```

```
            370                 375                 380
Thr Ile Asn Glu Gly Phe Asn Leu Glu Gly Ala Asn Ser Asn Gly Gln
385                 390                 395                 400

Asn Thr Glu Ile Asn Ser Arg Asn Phe Thr Arg Leu Lys Asn Phe Thr
                405                 410                 415

Gly Leu Phe Glu Phe Tyr Lys Leu Leu Cys Val Arg Gly Ile Ile Pro
                420                 425                 430

Phe Lys Thr Lys Ser Leu Asp Glu Gly Tyr Asn Lys Ala Leu Asn Tyr
            435                 440                 445

Leu Cys Ile Lys Val Asn Asn Trp Asp Leu Phe Phe Ser Pro Ser Glu
        450                 455                 460

Asp Asn Phe Thr Asn Asp Leu Asp Lys Val Glu Glu Ile Thr Ala Asp
465                 470                 475                 480

Thr Asn Ile Glu Ala Ala Glu Glu Asn Ile Ser Ser Asp Leu Ile Gln
                485                 490                 495

Gln Tyr Tyr Leu Thr Phe Asp Phe Asp Asn Glu Pro Glu Asn Ile Ser
                500                 505                 510

Ile Glu Asn Leu Ser Ser Asp Ile Ile Gly Gln Leu Glu Pro Met Pro
            515                 520                 525

Asn Ile Glu Arg Phe Pro Asn Gly Lys Lys Tyr Glu Leu Asp Lys Tyr
        530                 535                 540

Thr Met Phe His Tyr Leu Arg Ala Gln Glu Phe Glu His Gly Asp Ser
545                 550                 555                 560

Arg Ile Ile Leu Thr Asn Ser Ala Glu Glu Ala Leu Leu Lys Pro Asn
                565                 570                 575

Val Ala Tyr Thr Phe Phe Ser Ser Lys Tyr Val Lys Lys Ile Asn Lys
                580                 585                 590

Ala Val Glu Ala Val Ile Phe Leu Ser Trp Ala Glu Gly Leu Val Tyr
            595                 600                 605

Asp Phe Thr Asp Glu Thr Asn Glu Val Thr Thr Met Asp Lys Ile Ala
        610                 615                 620

Asp Ile Thr Ile Ile Val Pro Tyr Ile Gly Pro Ala Leu Asn Ile Gly
625                 630                 635                 640

Asn Met Val Ser Lys Gly Glu Phe Val Glu Ala Ile Leu Phe Thr Gly
                645                 650                 655

Val Val Ala Leu Leu Glu Phe Ile Pro Glu Tyr Ser Leu Pro Val Phe
                660                 665                 670

Gly Thr Phe Ala Ile Val Ser Tyr Ile Ala Asn Lys Val Leu Thr Val
            675                 680                 685

Gln Thr Ile Asn Asn Ala Leu Ser Lys Arg Asn Glu Lys Trp Asp Glu
        690                 695                 700

Val Tyr Lys Tyr Thr Val Thr Asn Trp Leu Ala Lys Val Asn Thr Gln
705                 710                 715                 720

Ile Asp Leu Ile Arg Glu Lys Met Lys Lys Ala Leu Glu Asn Gln Ala
                725                 730                 735

Glu Ala Thr Arg Ala Ile Ile Asn Tyr Gln Tyr Asn Gln Tyr Thr Glu
                740                 745                 750

Glu Glu Lys Asn Asn Ile Asn Phe Asn Ile Asp Asp Leu Ser Ser Lys
            755                 760                 765

Leu Asn Arg Ser Ile Asn Arg Ala Met Ile Asn Ile Asn Lys Phe Leu
        770                 775                 780

Asp Gln Cys Ser Val Ser Tyr Leu Met Asn Ser Met Ile Pro Tyr Ala
785                 790                 795                 800
```

```
Val Lys Arg Leu Lys Asp Phe Asp Ala Ser Val Arg Asp Val Leu Leu
                805                 810                 815

Lys Tyr Ile Tyr Asp Asn Arg Gly Thr Leu Ile Leu Gln Val Asp Arg
            820                 825                 830

Leu Lys Asp Glu Val Asn Asn Thr Leu Ser Ala Asp Ile Pro Phe Gln
        835                 840                 845

Leu Ser Lys Tyr Val Asn Asp Lys Lys Leu Leu Ser Thr Phe Thr Glu
    850                 855                 860

Tyr Ile Lys Asn Ile Val Asn Thr Ser Ile Leu Ser Ile Val Tyr Lys
865                 870                 875                 880

Lys Asp Asp Leu Ile Asp Leu Ser Arg Tyr Gly Ala Lys Ile Asn Ile
                885                 890                 895

Gly Asp Arg Val Tyr Tyr Asp Ser Ile Asp Lys Asn Gln Ile Lys Leu
            900                 905                 910

Ile Asn Leu Glu Ser Ser Thr Ile Glu Val Ile Leu Lys Asn Ala Ile
        915                 920                 925

Val Tyr Asn Ser Met Tyr Glu Asn Phe Ser Thr Ser Phe Trp Ile Lys
    930                 935                 940

Ile Pro Lys Tyr Phe Ser Lys Ile Asn Leu Asn Asn Glu Tyr Thr Ile
945                 950                 955                 960

Ile Asn Cys Ile Glu Asn Asn Ser Gly Trp Lys Val Ser Leu Asn Tyr
                965                 970                 975

Gly Glu Ile Ile Trp Thr Leu Gln Asp Asn Lys Gln Asn Ile Gln Arg
            980                 985                 990

Val Val Phe Lys Tyr Ser Gln Met Val Asn Ile Ser Asp Tyr Ile Asn
        995                 1000                1005

Arg Trp Met Phe Val Thr Ile Thr Asn Asn Arg Leu Thr Lys Ser Lys
    1010                1015                1020

Ile Tyr Ile Asn Gly Arg Leu Ile Asp Gln Lys Pro Ile Ser Asn Leu
1025                1030                1035                1040

Gly Asn Ile His Ala Ser Asn Lys Ile Met Phe Lys Leu Asp Gly Cys
                1045                1050                1055

Arg Asp Pro Arg Arg Tyr Ile Met Ile Lys Tyr Phe Asn Leu Phe Asp
            1060                1065                1070

Lys Glu Leu Asn Glu Lys Glu Ile Lys Asp Leu Tyr Asp Ser Gln Ser
        1075                1080                1085

Asn Pro Gly Ile Leu Lys Asp Phe Trp Gly Asn Tyr Leu Gln Tyr Asp
    1090                1095                1100

Lys Pro Tyr Tyr Met Leu Asn Leu Phe Asp Pro Asn Lys Tyr Val Asp
1105                1110                1115                1120

Val Asn Asn Ile Gly Ile Arg Gly Tyr Met Tyr Leu Lys Gly Pro Arg
                1125                1130                1135

Gly Ser Val Met Thr Thr Asn Ile Tyr Leu Asn Ser Thr Leu Tyr Met
            1140                1145                1150

Gly Thr Lys Phe Ile Ile Lys Lys Tyr Ala Ser Gly Asn Glu Asp Asn
        1155                1160                1165

Ile Val Arg Asn Asn Asp Arg Val Tyr Ile Asn Val Val Val Lys Asn
    1170                1175                1180

Lys Glu Tyr Arg Leu Ala Thr Asn Ala Ser Gln Ala Gly Val Glu Lys
1185                1190                1195                1200

Ile Leu Ser Ala Leu Glu Ile Pro Asp Val Gly Asn Leu Ser Gln Val
                1205                1210                1215
```

```
Val Val Met Lys Ser Lys Asp Asp Gln Gly Ile Arg Asn Lys Cys Lys
            1220                1225                1230

Met Asn Leu Gln Asp Asn Asn Gly Asn Asp Ile Gly Phe Val Gly Phe
        1235                1240                1245

His Leu Tyr Asp Asn Ile Ala Lys Leu Val Ala Ser Asn Trp Tyr Asn
    1250                1255                1260

Arg Gln Val Gly Lys Ala Ser Arg Thr Phe Gly Cys Ser Trp Glu Phe
1265            1270                1275                1280

Ile Pro Val Asp Asp Gly Trp Gly Glu Ser Ser Leu
                1285                1290

<210> SEQ ID NO 4
<211> LENGTH: 1296
<212> TYPE: PRT
<213> ORGANISM: Clostridium botulinum

<400> SEQUENCE: 4

Met Pro Leu Val Asn Gln Gln Ile Asn Tyr Tyr Asp Pro Val Asn Gly
1               5                   10                  15

Val Asp Ile Ala Tyr Ile Lys Ile Pro Asn Ala Gly Lys Met Gln Pro
            20                  25                  30

Val Lys Ala Phe Lys Ile His Asn Lys Val Trp Val Ile Pro Glu Arg
        35                  40                  45

Asp Ile Phe Thr Asn Pro Glu Glu Val Asp Leu Asn Pro Pro Glu
    50                  55                  60

Ala Lys Gln Val Pro Ile Ser Tyr Tyr Asp Ser Ala Tyr Leu Ser Thr
65                  70                  75                  80

Asp Asn Glu Lys Asp Asn Tyr Leu Lys Gly Val Ile Lys Leu Phe Glu
                85                  90                  95

Arg Ile Tyr Ser Thr Asp Leu Gly Arg Met Leu Leu Ile Ser Ile Val
            100                 105                 110

Arg Gly Ile Pro Phe Trp Gly Gly Lys Ile Asp Thr Glu Leu Lys
        115                 120                 125

Val Ile Asp Thr Asn Cys Ile Asn Ile Ile Gln Leu Asp Asp Ser Tyr
    130                 135                 140

Arg Ser Glu Glu Leu Asn Leu Ala Ile Ile Gly Pro Ser Ala Asn Ile
145                 150                 155                 160

Ile Glu Ser Gln Cys Ser Ser Phe Arg Asp Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Val Gly Phe Glu Glu Ser Leu Glu Val Asp Thr Asn Pro Leu Leu
        195                 200                 205

Gly Ala Gly Lys Phe Ala Gln Asp Pro Ala Val Ala Leu Ala His Glu
    210                 215                 220

Leu Ile His Ala Glu His Arg Leu Tyr Gly Ile Ala Ile Asn Thr Asn
225                 230                 235                 240

Arg Val Phe Lys Val Asn Thr Asn Ala Tyr Tyr Glu Met Ala Gly Leu
                245                 250                 255

Glu Val Ser Leu Glu Leu Ile Thr Phe Gly Gly Asn Asp Ala Lys
            260                 265                 270

Phe Ile Asp Ser Leu Gln Lys Lys Glu Phe Ser Leu Tyr Tyr Tyr Asn
        275                 280                 285

Lys Phe Lys Asp Ile Ala Ser Thr Leu Asn Lys Ala Lys Ser Ile Val
    290                 295                 300
```

```
Gly Thr Thr Ala Ser Leu Gln Tyr Met Lys Asn Val Phe Lys Glu Lys
305                 310                 315                 320

Tyr Leu Leu Ser Glu Asp Ala Thr Gly Lys Phe Leu Val Asp Arg Leu
                325                 330                 335

Lys Phe Asp Glu Leu Tyr Lys Leu Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Asp Val Asn Tyr
            370                 375                 380

Thr Ile His Asp Gly Phe Asn Leu Arg Asn Thr Asn Leu Ala Ala Asn
385                 390                 395                 400

Phe Asn Gly Gln Asn Ile Glu Ile Asn Asn Lys Asn Phe Asp Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Glu Gly Tyr Asn Lys
                435                 440                 445

Ala Leu Asn Glu Leu Cys Ile Lys Val Asn Asn Trp Asp Leu Phe Phe
            450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Asn Ile Ser Leu
                485                 490                 495

Asp Leu Ile Gln Gln Tyr Tyr Leu Asn Phe Asn Phe Asp Asn Glu Pro
            500                 505                 510

Glu Asn Thr Ser Ile Glu Asn Leu Ser Ser Asp Ile Ile Gly Gln Leu
                515                 520                 525

Glu Pro Met Pro Asn Ile Glu Arg Phe Pro Asn Gly Lys Lys Tyr Glu
            530                 535                 540

Leu Asn Lys Tyr Thr Met Phe His Tyr Leu Arg Ala Gln Glu Phe Lys
545                 550                 555                 560

His Ser Asn Ser Arg Ile Ile Leu Thr Asn Ser Ala Lys Glu Ala Leu
                565                 570                 575

Leu Lys Pro Asn Ile Val Tyr Thr Phe Phe Ser Ser Lys Tyr Ile Lys
            580                 585                 590

Ala Ile Asn Lys Ala Val Glu Ala Val Thr Phe Val Asn Trp Ile Glu
            595                 600                 605

Asn Leu Val Tyr Asp Phe Thr Asp Glu Thr Asn Glu Val Ser Thr Met
            610                 615                 620

Asp Lys Ile Ala Asp Ile Thr Ile Val Ile Pro Tyr Ile Gly Pro Ala
625                 630                 635                 640

Leu Asn Ile Gly Asn Met Ile Tyr Lys Gly Glu Phe Val Glu Ala Ile
                645                 650                 655

Ile Phe Ser Gly Ala Val Ile Leu Leu Glu Ile Val Pro Glu Ile Ala
                660                 665                 670

Leu Pro Val Leu Gly Thr Phe Ala Leu Val Ser Tyr Val Ser Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Ile
705                 710                 715                 720
```

```
Val Asn Thr Gln Ile Asn Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
    770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Ile Gly
            820                 825                 830

Gln Val Asn Arg Leu Lys Asp Lys Val Asn Asn Thr Leu Ser Ala Asp
        835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Thr Asn Ala Ser Ile Leu Ser
865                 870                 875                 880

Ile Val Tyr Lys Asp Asp Leu Ile Asp Leu Ser Arg Tyr Gly Ala
                885                 890                 895

Glu Ile Tyr Asn Gly Asp Lys Val Tyr Tyr Asn Ser Ile Asp Lys Asn
            900                 905                 910

Gln Ile Arg Leu Ile Asn Leu Glu Ser Ser Thr Ile Glu Val Ile Leu
        915                 920                 925

Lys Lys Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Phe Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Ile
    1010                1015                1020

Thr Lys Ser Lys Ile Tyr Ile Asn Gly Arg Leu Ile Asp Gln Lys Pro
1025                1030                1035                1040

Ile Ser Asn Leu Gly Asn Ile His Ala Ser Asn Lys Ile Met Phe Lys
                1045                1050                1055

Leu Asp Gly Cys Arg Asp Pro His Arg Tyr Ile Val Ile Lys Tyr Phe
            1060                1065                1070

Asn Leu Phe Asp Lys Glu Leu Ser Glu Lys Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Ser Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Asp Asn Val Met Thr Thr Asn Ile Tyr Leu Asn Ser
```

```
                    1140                1145                1150
Ser Leu Tyr Met Gly Thr Lys Phe Ile Ile Lys Lys Tyr Ala Ser Gly
            1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
            1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Arg Glu Arg Pro Leu
                1285                1290                1295

<210> SEQ ID NO 5
<211> LENGTH: 206
<212> TYPE: PRT
<213> ORGANISM: Homo sapiens

<400> SEQUENCE: 5

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 6
<211> LENGTH: 206
```

<212> TYPE: PRT
<213> ORGANISM: Homo sapiens

<400> SEQUENCE: 6

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 7
<211> LENGTH: 206
<212> TYPE: PRT
<213> ORGANISM: Macaca mulatta

<400> SEQUENCE: 7

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140
```

```
Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 8
<211> LENGTH: 206
<212> TYPE: PRT
<213> ORGANISM: Rattus norvegicus

<400> SEQUENCE: 8

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 9
<211> LENGTH: 206
<212> TYPE: PRT
<213> ORGANISM: Rattus norvegicus

<400> SEQUENCE: 9

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60
```

```
Asp Gln Ile Asn Lys Asp Met Lys Glu Ala Glu Lys Asn Leu Thr Asp
 65                  70                  75                  80

Leu Gly Lys Phe Cys Gly Leu Cys Val Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 10
<211> LENGTH: 206
<212> TYPE: PRT
<213> ORGANISM: Mus musculus

<400> SEQUENCE: 10

Met Ala Glu Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
                 20                  25                  30

Leu Gln Leu Val Glu Glu Ser Lys Asp Ala Gly Ile Arg Thr Leu Val
             35                  40                  45

Met Leu Asp Glu Gln Gly Glu Gln Leu Glu Arg Ile Glu Glu Gly Met
         50                  55                  60

Asp Gln Ile Asn Lys Asp Met Lys Glu Ala Glu Lys Asn Leu Thr Asp
 65                  70                  75                  80

Leu Gly Lys Phe Cys Gly Leu Cys Val Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 11
<211> LENGTH: 206
<212> TYPE: PRT
<213> ORGANISM: Gallus gallus
```

<400> SEQUENCE: 11

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 12
<211> LENGTH: 204
<212> TYPE: PRT
<213> ORGANISM: Carassius auratus

<400> SEQUENCE: 12

```
Met Ala Glu Asp Ala Asp Met Arg Asn Glu Leu Ser Asp Met Gln Gln
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Lys Asn Leu Asn Asp
65                  70                  75                  80

Leu Gly Lys Phe Cys Gly Leu Cys Ser Cys Pro Cys Asn Lys Met Lys
                85                  90                  95

Ser Gly Gly Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Asp Ala Arg Glu Asn Glu Met
    130                 135                 140

Asp Glu Asn Leu Glu Gln Val Gly Gly Ile Ile Gly Asn Leu Arg His
145                 150                 155                 160
```

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200

<210> SEQ ID NO 13
<211> LENGTH: 203
<212> TYPE: PRT
<213> ORGANISM: Carassius auratus

<400> SEQUENCE: 13

Met Ala Asp Glu Ala Asp Met Arg Asn Glu Leu Thr Asp Met Gln Ala
1               5                   10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200

<210> SEQ ID NO 14
<211> LENGTH: 204
<212> TYPE: PRT
<213> ORGANISM: Danio rerio

<400> SEQUENCE: 14

Met Ala Glu Asp Ser Asp Met Arg Asn Glu Leu Ala Asp Met Gln Gln
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Glu Lys Asn Leu Asn Asp
65                  70                  75                  80

```
Leu Gly Lys Phe Cys Gly Leu Cys Ser Cys Pro Cys Asn Lys Met Lys
                85                  90                  95

Ser Gly Ala Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Asp Ala Arg Glu Asn Glu Met
    130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200
```

<210> SEQ ID NO 15
<211> LENGTH: 203
<212> TYPE: PRT
<213> ORGANISM: Danio rerio

<400> SEQUENCE: 15

```
Met Ala Asp Glu Ser Asp Met Arg Asn Glu Leu Asn Asp Met Gln Ala
1               5                   10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200
```

<210> SEQ ID NO 16
<211> LENGTH: 210
<212> TYPE: PRT
<213> ORGANISM: Torpedo marmorata

<400> SEQUENCE: 16

```
Met Glu Asn Ser Val Glu Asn Ser Met Asp Pro Arg Ser Glu Gln Glu
1               5                   10                  15

Glu Met Gln Arg Cys Ala Asp Gln Ile Thr Asp Glu Ser Leu Glu Ser
            20                  25                  30

Thr Arg Arg Met Leu Gln Leu Val Glu Glu Ser Lys Asp Ala Gly Ile
        35                  40                  45

Arg Thr Leu Val Met Leu Asp Glu Gln Gly Glu Gln Leu Glu Arg Ile
    50                  55                  60

Glu Glu Gly Met Asp Gln Ile Asn Lys Asp Met Lys Glu Ala Glu Lys
65                  70                  75                  80

Asn Leu Ser Asp Leu Gly Lys Cys Cys Gly Leu Cys Ser Cys Pro Cys
                85                  90                  95

Asn Lys Leu Lys Asn Phe Glu Ala Gly Gly Ala Tyr Lys Lys Val Trp
            100                 105                 110

Gly Asn Asn Gln Asp Gly Val Val Ala Ser Gln Pro Ala Arg Val Met
        115                 120                 125

Asp Asp Arg Glu Gln Met Ala Met Ser Gly Gly Tyr Ile Arg Arg Ile
    130                 135                 140

Thr Asp Asp Ala Arg Glu Asn Glu Met Glu Glu Asn Leu Asp Gln Val
145                 150                 155                 160

Gly Ser Ile Ile Gly Asn Leu Arg His Met Ala Leu Asp Met Ser Asn
                165                 170                 175

Glu Ile Gly Ser Gln Asn Ala Gln Ile Asp Arg Ile Val Val Lys Gly
            180                 185                 190

Asp Met Asn Lys Ala Arg Ile Asp Glu Ala Asn Lys His Ala Thr Lys
        195                 200                 205

Met Leu
    210

<210> SEQ ID NO 17
<211> LENGTH: 206
<212> TYPE: PRT
<213> ORGANISM: Xenopus laevis

<400> SEQUENCE: 17

Met Ala Asp Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Gly Ala Tyr Asn Lys Ala Trp Gly Asn Asn Gln Asp Gly Val
            100                 105                 110

Val Ala Ser Gln Pro Ala Arg Val Asp Glu Arg Glu Gln Met Ala
        115                 120                 125

Ile Ser Gly Gly Phe Val Arg Arg Val Thr Asn Asp Ala Arg Glu Thr
    130                 135                 140

Glu Met Asp Glu Asn Leu Glu Gln Val Gly Gly Ile Ile Gly Asn Leu
```

```
                145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
                180                 185                 190

Asp Glu Ala Asn Lys His Ala Thr Lys Met Leu Gly Ser Gly
                195                 200                 205

<210> SEQ ID NO 18
<211> LENGTH: 206
<212> TYPE: PRT
<213> ORGANISM: Xenopus laevis

<400> SEQUENCE: 18

Met Ala Asp Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Tyr Val Glu Gly Ser Lys Asp Ala Gly Ile Arg Thr Leu Val
                35                  40                  45

Met Leu Asp Glu Gln Gly Glu Gln Leu Glu Arg Ile Glu Glu Gly Met
            50                  55                  60

Glu Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
                115                 120                 125

Ile Ser Gly Gly Phe Val Arg Arg Val Thr Asn Asp Ala Arg Glu Thr
            130                 135                 140

Glu Met Asp Glu Asn Leu Glu Gln Val Gly Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
                180                 185                 190

Asp Glu Ala Asn Lys His Ala Thr Lys Met Leu Gly Ser Gly
                195                 200                 205

<210> SEQ ID NO 19
<211> LENGTH: 212
<212> TYPE: PRT
<213> ORGANISM: Strongylocentrotus purpuratus

<400> SEQUENCE: 19

Met Glu Asp Gln Asn Asp Met Asn Met Arg Ser Glu Leu Glu Glu Ile
1               5                   10                  15

Gln Met Gln Ser Asn Met Gln Thr Asp Glu Ser Leu Glu Ser Thr Arg
                20                  25                  30

Arg Met Leu Gln Met Ala Glu Ser Gln Asp Met Gly Ile Lys Thr
                35                  40                  45

Leu Val Met Leu Asp Glu Gln Gly Glu Gln Leu Asp Arg Ile Glu Glu
            50                  55                  60

Gly Met Asp Gln Ile Asn Thr Asp Met Arg Glu Ala Glu Lys Asn Leu
```

```
                65                  70                  75                  80
Thr Gly Leu Glu Lys Cys Cys Gly Ile Cys Val Cys Pro Trp Lys Lys
                    85                  90                  95

Leu Gly Asn Phe Glu Lys Gly Asp Asp Tyr Lys Lys Thr Trp Lys Gly
                    100                 105                 110

Asn Asp Asp Gly Lys Val Asn Ser His Gln Pro Met Arg Met Glu Asp
                    115                 120                 125

Asp Arg Asp Gly Cys Gly Gly Asn Ala Ser Met Ile Thr Arg Ile Thr
                130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                    165                 170                 175

Ile Gly Ala Gln Asn Ser Gln Val Gly Arg Ile Thr Ser Lys Ala Glu
                    180                 185                 190

Ser Asn Glu Gly Arg Ile Asn Ser Ala Asp Lys Arg Ala Lys Asn Ile
                    195                 200                 205

Leu Arg Asn Lys
    210

<210> SEQ ID NO 20
<211> LENGTH: 212
<212> TYPE: PRT
<213> ORGANISM: Drosophila melanogaster

<400> SEQUENCE: 20

Met Pro Ala Asp Pro Ser Glu Glu Val Ala Pro Gln Val Pro Lys Thr
1               5                   10                  15

Glu Leu Glu Glu Leu Gln Ile Asn Ala Gln Gly Val Ala Asp Glu Ser
                    20                  25                  30

Leu Glu Ser Thr Arg Arg Met Leu Ala Leu Cys Glu Glu Ser Lys Glu
                35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80

Ala Glu Lys Asn Leu Ser Gly Met Glu Lys Cys Cys Gly Ile Cys Val
                    85                  90                  95

Leu Pro Cys Asn Lys Ser Gln Ser Phe Lys Glu Asp Asp Gly Thr Trp
                    100                 105                 110

Lys Gly Asn Asp Asp Gly Lys Val Val Asn Asn Gln Pro Gln Arg Val
                    115                 120                 125

Met Asp Asp Arg Asn Gly Met Met Ala Gln Ala Gly Tyr Ile Gly Arg
                130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                    165                 170                 175

Ser Glu Leu Glu Asn Gln Asn Arg Gln Ile Asp Arg Ile Asn Arg Lys
                    180                 185                 190

Gly Glu Ser Asn Glu Ala Arg Ile Ala Val Ala Asn Gln Arg Ala His
                    195                 200                 205

Gln Leu Leu Lys
    210
```

```
<210> SEQ ID NO 21
<211> LENGTH: 212
<212> TYPE: PRT
<213> ORGANISM: Hirudo medicinalis

<400> SEQUENCE: 21

Met Ala Lys Asp Ile Lys Pro Lys Pro Ala Asn Gly Arg Asp Ser Pro
1               5                   10                  15

Thr Asp Leu Gln Glu Ile Gln Leu Gln Met Asn Ala Ile Thr Asp Asp
            20                  25                  30

Ser Leu Glu Ser Thr Arg Arg Met Leu Ala Met Cys Glu Glu Ser Lys
        35                  40                  45

Asp Ala Gly Ile Arg Thr Leu Val Met Leu Asp Glu Gln Gly Glu Gln
    50                  55                  60

Leu Asp Arg Ile Glu Glu Gly Met Asp Gln Ile Asn Gln Asp Met Arg
65                  70                  75                  80

Asp Ala Glu Lys Asn Leu Glu Gly Met Glu Lys Cys Cys Gly Leu Cys
                85                  90                  95

Ile Leu Pro Trp Lys Arg Thr Lys Asn Phe Asp Lys Gly Ala Glu Trp
            100                 105                 110

Asn Lys Gly Asp Glu Gly Lys Val Asn Thr Asp Gly Pro Arg Leu Val
        115                 120                 125

Val Gly Asp Gly Asn Met Gly Pro Ser Gly Phe Ile Thr Lys Ile
    130                 135                 140

Thr Asn Asp Ala Arg Glu Glu Met Glu Gln Asn Met Gly Glu Val
145                 150                 155                 160

Ser Asn Met Ile Ser Asn Leu Arg Asn Met Ala Val Asp Met Gly Ser
                165                 170                 175

Glu Ile Asp Ser Gln Asn Arg Gln Val Asp Arg Ile Asn Asn Lys Met
            180                 185                 190

Thr Ser Asn Gln Leu Arg Ile Ser Asp Ala Asn Lys Arg Ala Ser Lys
        195                 200                 205

Leu Leu Lys Glu
    210

<210> SEQ ID NO 22
<211> LENGTH: 212
<212> TYPE: PRT
<213> ORGANISM: Loligo pealei

<400> SEQUENCE: 22

Met Ser Ala Asn Gly Glu Val Glu Val Pro Lys Thr Glu Leu Glu Glu
1               5                   10                  15

Ile Gln Gln Gln Cys Asn Gln Val Thr Asp Asp Ser Leu Glu Ser Thr
            20                  25                  30

Arg Arg Met Leu Asn Met Cys Glu Glu Ser Lys Glu Ala Gly Ile Arg
        35                  40                  45

Thr Leu Val Met Leu Asp Glu Gln Gly Glu Gln Leu Asp Arg Ile Glu
    50                  55                  60

Glu Gly Leu Asp Gln Ile Asn Gln Asp Met Lys Asp Ala Glu Lys Asn
65                  70                  75                  80

Leu Glu Gly Met Glu Lys Cys Cys Gly Leu Cys Val Leu Pro Trp Lys
                85                  90                  95

Arg Gly Lys Ser Phe Glu Lys Ser Gly Asp Tyr Ala Asn Thr Trp Lys
            100                 105                 110
```

```
Lys Asp Asp Asp Gly Pro Thr Asn Thr Asn Gly Pro Arg Val Thr Val
            115                 120                 125

Gly Asp Gln Asn Gly Met Gly Pro Ser Ser Gly Tyr Val Thr Arg Ile
    130                 135                 140

Thr Asn Asp Ala Arg Glu Asp Met Glu Asn Asn Met Lys Glu Val
145                 150                 155                 160

Ser Ser Met Ile Gly Asn Leu Arg Asn Met Ala Ile Asp Met Gly Asn
                165                 170                 175

Glu Ile Gly Ser Gln Asn Arg Gln Val Asp Arg Ile Gln Gln Lys Ala
            180                 185                 190

Glu Ser Asn Glu Ser Arg Ile Asp Glu Ala Asn Lys Lys Ala Thr Lys
        195                 200                 205

Leu Leu Lys Asn
    210

<210> SEQ ID NO 23
<211> LENGTH: 220
<212> TYPE: PRT
<213> ORGANISM: Lymnaea stagnalis

<400> SEQUENCE: 23

Met Thr Thr Asn Gly Glu Ile Leu Pro Val Gly Glu Glu Glu Glu
1               5                   10                  15

Glu Leu Gly Glu Asp Ala Leu Leu Arg Lys Gln Ile Asp Cys Asn Thr
            20                  25                  30

Asn Glu Ser Leu Glu Ser Thr Arg Arg Met Leu Ser Leu Cys Glu Glu
        35                  40                  45

Ser Lys Glu Ala Gly Ile Lys Thr Leu Val Met Leu Asp Glu Gln Gly
    50                  55                  60

Glu Gln Leu Asp Arg Ile Glu Glu Gly Met Gly Gln Ile Asn Gln Asp
65                  70                  75                  80

Met Arg Asp Ala Glu Lys Asn Leu Glu Gly Leu Glu Lys Cys Cys Gly
                85                  90                  95

Leu Cys Val Leu Pro Trp Lys Arg Ser Lys Asn Phe Glu Lys Gly Ser
            100                 105                 110

Asp Tyr Asn Lys Thr Trp Lys Ala Ser Glu Asp Gly Lys Ile Asn Thr
        115                 120                 125

Asn Gly Pro Arg Leu Val Val Asp Gln Gly Asn Gly Ser Gly Pro Thr
    130                 135                 140

Gly Gly Tyr Ile Thr Arg Ile Thr Asn Asp Ala Arg Glu Asp Glu Met
145                 150                 155                 160

Glu Gln Asn Ile Gly Glu Val Ala Gly Met Val Ser Asn Leu Arg Asn
                165                 170                 175

Met Ala Val Asp Met Gly Asn Glu Ile Glu Ser Gln Asn Lys Gln Leu
            180                 185                 190

Asp Arg Ile Asn Gln Lys Gly Gly Ser Leu Asn Val Arg Val Asp Glu
        195                 200                 205

Ala Asn Lys Arg Ala Asn Arg Ile Leu Arg Lys Gln
    210                 215                 220

<210> SEQ ID NO 24
<211> LENGTH: 207
<212> TYPE: PRT
<213> ORGANISM: Caenorhabditis elegans

<400> SEQUENCE: 24
```

-continued

Met Ser Gly Asp Asp Asp Ile Pro Glu Gly Leu Glu Ala Ile Asn Leu
1               5                   10                  15

Lys Met Asn Ala Thr Thr Asp Ser Leu Glu Ser Thr Arg Arg Met
        20                  25                  30

Leu Ala Leu Cys Glu Glu Ser Lys Glu Ala Gly Ile Lys Thr Leu Val
            35                  40                  45

Met Leu Asp Asp Gln Gly Glu Gln Leu Glu Arg Cys Glu Gly Ala Leu
50                  55                  60

Asp Thr Ile Asn Gln Asp Met Lys Glu Ala Glu Asp His Leu Lys Gly
65                  70                  75                  80

Met Glu Lys Cys Cys Gly Leu Cys Val Leu Pro Trp Asn Lys Thr Asp
                85                  90                  95

Asp Phe Glu Lys Thr Glu Phe Ala Lys Ala Trp Lys Lys Asp Asp Asp
            100                 105                 110

Gly Gly Val Ile Ser Asp Gln Pro Arg Ile Thr Val Gly Asp Ser Ser
                115                 120                 125

Met Gly Pro Gln Gly Gly Tyr Ile Thr Lys Ile Thr Asn Asp Ala Arg
130                 135                 140

Glu Asp Glu Met Asp Glu Asn Val Gln Gln Val Ser Thr Met Val Gly
145                 150                 155                 160

Asn Leu Arg Asn Met Ala Ile Asp Met Ser Thr Glu Val Ser Asn Gln
                165                 170                 175

Asn Arg Gln Leu Asp Arg Ile His Asp Lys Ala Gln Ser Asn Glu Val
            180                 185                 190

Arg Val Glu Ser Ala Asn Lys Arg Ala Lys Asn Leu Ile Thr Lys
        195                 200                 205

<210> SEQ ID NO 25
<211> LENGTH: 808
<212> TYPE: PRT
<213> ORGANISM: Homo sapiens

<400> SEQUENCE: 25

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
        20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

```
Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
                340                 345                 350

Leu Ser Val His Gly Pro Arg Ala Ala Glu Glu Leu Val Glu Ala
                355                 360                 365

Asp Glu Ala Gly Ser Val Tyr Ala Gly Ile Leu Ser Tyr Gly Val Gly
        370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
                420                 425                 430

Met Ser Ser Asn Thr Pro Leu Val Arg Ile Ala Arg Leu Ser Ser Gly
            435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
            515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590
```

```
Phe Lys Asp Leu Val Ser Cys Ala Tyr Gln Val Ala Arg Gly Met Glu
            595                 600                 605

Tyr Leu Ala Ser Gln Lys Cys Ile His Arg Asp Leu Ala Ala Arg Asn
610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805

<210> SEQ ID NO 26
<211> LENGTH: 806
<212> TYPE: PRT
<213> ORGANISM: Homo sapiens

<400> SEQUENCE: 26

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Lys Asp Gly Thr Gly Leu
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160
```

```
Lys Lys Leu Leu Ala Val Pro Ala Ala Asn Thr Val Arg Phe Arg Cys
            165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Ile Lys Leu Arg His
        195                 200                 205

Gln Gln Trp Ser Leu Val Met Glu Ser Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
        290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
        370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
                420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
        450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575
```

```
Tyr Ser Phe Asp Thr Cys Lys Pro Pro Glu Glu Gln Leu Thr Phe Lys
                580                 585                 590

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
        610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gln Asp Thr Pro Ser Ser Ser Ser Ser Ser Gly
770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 27
<211> LENGTH: 694
<212> TYPE: PRT
<213> ORGANISM: Homo sapiens

<400> SEQUENCE: 27

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140
```

```
Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Val Ser Leu Glu Ser Asn Ala Ser Met Ser
305                 310                 315                 320

Ser Asn Thr Pro Leu Val Arg Ile Ala Arg Leu Ser Ser Gly Glu Gly
                325                 330                 335

Pro Thr Leu Ala Asn Val Ser Glu Leu Glu Leu Pro Ala Asp Pro Lys
            340                 345                 350

Trp Glu Leu Ser Arg Ala Arg Leu Thr Leu Gly Lys Pro Leu Gly Glu
        355                 360                 365

Gly Cys Phe Gly Gln Val Val Met Ala Glu Ala Ile Gly Ile Asp Lys
    370                 375                 380

Asp Arg Ala Ala Lys Pro Val Thr Val Ala Val Lys Met Leu Lys Asp
385                 390                 395                 400

Asp Ala Thr Asp Lys Asp Leu Ser Asp Leu Val Ser Glu Met Glu Met
                405                 410                 415

Met Lys Met Ile Gly Lys His Lys Asn Ile Ile Asn Leu Leu Gly Ala
            420                 425                 430

Cys Thr Gln Gly Gly Pro Leu Tyr Val Leu Val Glu Tyr Ala Ala Lys
        435                 440                 445

Gly Asn Leu Arg Glu Phe Leu Arg Ala Arg Arg Pro Pro Gly Leu Asp
    450                 455                 460

Tyr Ser Phe Asp Thr Cys Lys Pro Pro Glu Glu Gln Leu Thr Phe Lys
465                 470                 475                 480

Asp Leu Val Ser Cys Ala Tyr Gln Val Ala Arg Gly Met Glu Tyr Leu
                485                 490                 495

Ala Ser Gln Lys Cys Ile His Arg Asp Leu Ala Ala Arg Asn Val Leu
            500                 505                 510

Val Thr Glu Asp Asn Val Met Lys Ile Ala Asp Phe Gly Leu Ala Arg
        515                 520                 525

Asp Val His Asn Leu Asp Tyr Tyr Lys Lys Thr Thr Asn Gly Arg Leu
    530                 535                 540

Pro Val Lys Trp Met Ala Pro Glu Ala Leu Phe Asp Arg Val Tyr Thr
545                 550                 555                 560
```

His Gln Ser Asp Val Trp Ser Phe Gly Val Leu Leu Trp Glu Ile Phe
                565                 570                 575

Thr Leu Gly Gly Ser Pro Tyr Pro Gly Ile Pro Val Glu Glu Leu Phe
            580                 585                 590

Lys Leu Leu Lys Glu Gly His Arg Met Asp Lys Pro Ala Asn Cys Thr
        595                 600                 605

His Asp Leu Tyr Met Ile Met Arg Glu Cys Trp His Ala Ala Pro Ser
    610                 615                 620

Gln Arg Pro Thr Phe Lys Gln Leu Val Glu Asp Leu Asp Arg Val Leu
625                 630                 635                 640

Thr Val Thr Ser Thr Asp Glu Tyr Leu Asp Leu Ser Ala Pro Phe Glu
                645                 650                 655

Gln Tyr Ser Pro Gly Gly Gln Asp Thr Pro Ser Ser Ser Ser Ser Gly
            660                 665                 670

Asp Asp Ser Val Phe Ala His Asp Leu Leu Pro Pro Ala Pro Pro Ser
        675                 680                 685

Ser Gly Gly Ser Arg Thr
    690

<210> SEQ ID NO 28
<211> LENGTH: 604
<212> TYPE: PRT
<213> ORGANISM: Homo sapiens

<400> SEQUENCE: 28

Ala Gln Arg Arg Lys Glu Arg Glu Leu Ala Gln Gln Tyr Glu Ala
1               5                   10                  15

Ile Leu Arg Glu Cys Gly His Gly Arg Phe Gln Trp Thr Leu Tyr Phe
                20                  25                  30

Val Leu Gly Leu Ala Leu Met Ala Asp Gly Val Glu Val Phe Val Val
            35                  40                  45

Gly Phe Val Leu Pro Ser Ala Glu Lys Asp Met Cys Leu Ser Asp Ser
        50                  55                  60

Asn Lys Gly Met Leu Gly Leu Ile Val Tyr Leu Gly Met Met Val Gly
65                  70                  75                  80

Ala Phe Leu Trp Gly Gly Leu Ala Asp Arg Leu Gly Arg Arg Gln Cys
                85                  90                  95

Leu Leu Ile Ser Leu Ser Val Asn Ser Val Phe Ala Phe Phe Ser Ser
            100                 105                 110

Phe Val Gln Gly Tyr Gly Thr Phe Leu Phe Cys Arg Leu Leu Ser Gly
        115                 120                 125

Val Gly Ile Gly Gly Ser Ile Pro Ile Val Phe Ser Tyr Phe Ser Glu
130                 135                 140

Phe Leu Ala Gln Glu Lys Arg Gly Glu His Leu Ser Trp Leu Cys Met
145                 150                 155                 160

Phe Trp Met Ile Gly Gly Val Tyr Ala Ala Met Ala Trp Ala Ile
                165                 170                 175

Ile Pro His Tyr Gly Trp Ser Phe Gln Met Gly Ser Ala Tyr Gln Phe
            180                 185                 190

His Ser Trp Arg Val Phe Val Leu Val Cys Ala Phe Pro Ser Val Phe
        195                 200                 205

Ala Ile Gly Ala Leu Thr Thr Gln Pro Glu Ser Pro Arg Phe Phe Leu
    210                 215                 220

Glu Asn Gly Lys His Asp Glu Ala Trp Met Val Leu Lys Gln Val His
225                 230                 235                 240

Asp Thr Asn Met Arg Ala Lys Gly His Pro Glu Arg Val Phe Ser Val
            245                 250                 255

Thr His Ile Lys Thr Ile His Gln Glu Asp Glu Leu Ile Glu Ile Gln
            260                 265                 270

Ser Asp Thr Gly Thr Trp Tyr Gln Arg Trp Gly Val Arg Ala Leu Ser
            275                 280                 285

Leu Gly Gly Gln Val Trp Gly Asn Phe Leu Ser Cys Phe Gly Pro Glu
            290                 295                 300

Tyr Arg Arg Ile Thr Leu Met Met Met Gly Val Trp Phe Thr Met Ser
305                 310                 315                 320

Phe Ser Tyr Tyr Gly Leu Thr Val Trp Phe Pro Asp Met Ile Arg His
                325                 330                 335

Leu Gln Ala Val Asp Tyr Ala Ser Arg Thr Lys Val Phe Pro Gly Glu
            340                 345                 350

Arg Val Glu His Val Thr Phe Asn Phe Thr Leu Glu Asn Gln Ile His
            355                 360                 365

Arg Gly Gly Gln Tyr Phe Asn Asp Lys Phe Ile Gly Leu Arg Leu Lys
            370                 375                 380

Ser Val Ser Phe Glu Asp Ser Leu Phe Glu Glu Cys Tyr Phe Glu Asp
385                 390                 395                 400

Val Thr Ser Ser Asn Thr Phe Phe Arg Asn Cys Thr Phe Ile Asn Thr
                405                 410                 415

Val Phe Tyr Asn Thr Asp Leu Phe Glu Tyr Lys Phe Val Asn Ser Arg
            420                 425                 430

Leu Ile Asn Ser Thr Phe Leu His Asn Lys Glu Gly Cys Pro Leu Asp
            435                 440                 445

Val Thr Gly Thr Gly Glu Gly Ala Tyr Met Val Tyr Phe Val Ser Phe
            450                 455                 460

Leu Gly Thr Leu Ala Val Leu Pro Gly Asn Ile Val Ser Ala Leu Leu
465                 470                 475                 480

Met Asp Lys Ile Gly Arg Leu Arg Met Leu Ala Gly Ser Ser Val Met
                485                 490                 495

Ser Cys Val Ser Cys Phe Phe Leu Ser Phe Gly Asn Ser Glu Ser Ala
            500                 505                 510

Met Ile Ala Leu Leu Cys Leu Phe Gly Gly Val Ser Ile Ala Ser Trp
            515                 520                 525

Asn Ala Leu Asp Val Leu Thr Val Glu Leu Tyr Pro Ser Asp Lys Arg
            530                 535                 540

Thr Thr Ala Phe Gly Phe Leu Asn Ala Leu Cys Lys Leu Ala Ala Val
545                 550                 555                 560

Leu Gly Ile Ser Ile Phe Thr Ser Phe Val Gly Ile Thr Lys Ala Ala
                565                 570                 575

Pro Ile Leu Phe Ala Ser Ala Ala Leu Ala Leu Gly Ser Ser Leu Ala
            580                 585                 590

Leu Lys Leu Pro Glu Thr Arg Gly Gln Val Leu Gln
            595                 600

<210> SEQ ID NO 29
<211> LENGTH: 683
<212> TYPE: PRT
<213> ORGANISM: Homo sapiens

<400> SEQUENCE: 29

Met Asp Asp Tyr Lys Tyr Gln Asp Asn Tyr Gly Gly Tyr Ala Pro Ser

-continued

```
1               5                   10                  15
Asp Gly Tyr Tyr Arg Gly Asn Glu Ser Asn Pro Glu Glu Asp Ala Gln
                20                  25                  30

Ser Asp Val Thr Glu Gly His Asp Glu Glu Asp Glu Ile Tyr Glu Gly
                35                  40                  45

Glu Tyr Gln Gly Ile Pro His Pro Asp Asp Val Lys Ala Lys Gln Ala
            50                  55                  60

Lys Met Ala Pro Ser Arg Met Asp Ser Leu Arg Gly Gln Thr Asp Leu
65                  70                  75                  80

Met Ala Glu Arg Leu Glu Asp Glu Gln Leu Ala His Gln Tyr Glu
                    85                  90                  95

Thr Ile Met Asp Glu Cys Gly His Gly Arg Phe Gln Trp Ile Leu Phe
                100                 105                 110

Phe Val Leu Gly Leu Ala Leu Met Ala Asp Gly Val Glu Val Phe Val
                115                 120                 125

Val Ser Phe Ala Leu Pro Ser Ala Glu Lys Asp Met Cys Leu Ser Ser
            130                 135                 140

Ser Lys Lys Gly Met Leu Gly Met Ile Val Tyr Leu Gly Met Met Ala
145                 150                 155                 160

Gly Ala Phe Ile Leu Gly Gly Leu Ala Asp Lys Leu Gly Arg Lys Arg
                165                 170                 175

Val Leu Ser Met Ser Leu Ala Val Asn Ala Ser Phe Ala Ser Leu Ser
                180                 185                 190

Ser Phe Val Gln Gly Tyr Gly Ala Phe Leu Phe Cys Arg Leu Ile Ser
                195                 200                 205

Gly Ile Gly Ile Gly Gly Ala Leu Pro Ile Val Phe Ala Tyr Phe Ser
            210                 215                 220

Glu Phe Leu Ser Arg Glu Lys Arg Gly Glu His Leu Ser Trp Leu Gly
225                 230                 235                 240

Ile Phe Trp Met Thr Gly Gly Leu Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Val Ile Val Cys Ala Leu Pro Cys Thr
                275                 280                 285

Val Ser Met Val Ala Leu Lys Phe Met Pro Glu Ser Pro Arg Phe Leu
            290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser Asn Ile Lys Thr Pro Lys Gln Met Asp Glu Phe Ile Glu Ile
                340                 345                 350

Gln Ser Ser Thr Gly Thr Trp Tyr Gln Arg Trp Leu Val Arg Phe Lys
            355                 360                 365

Thr Ile Phe Lys Gln Val Trp Asp Asn Ala Leu Tyr Cys Val Met Gly
370                 375                 380

Pro Tyr Arg Met Asn Thr Leu Ile Leu Ala Val Val Trp Phe Ala Met
385                 390                 395                 400

Ala Phe Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
                420                 425                 430
```

-continued

```
Glu His Val Tyr Gly Ala Thr Ile Asn Phe Thr Met Glu Asn Gln Ile
            435                 440                 445

His Gln His Gly Lys Leu Val Asn Asp Lys Phe Thr Arg Met Tyr Phe
    450                 455                 460

Lys His Val Leu Phe Glu Asp Thr Phe Phe Asp Glu Cys Tyr Phe Glu
465                 470                 475                 480

Asp Val Thr Ser Thr Asp Thr Tyr Phe Lys Asn Cys Thr Ile Glu Ser
                485                 490                 495

Thr Ile Phe Tyr Asn Thr Asp Leu Tyr Glu His Lys Phe Ile Asn Cys
            500                 505                 510

Arg Phe Ile Asn Ser Thr Phe Leu Glu Gln Lys Glu Gly Cys His Met
    515                 520                 525

Asp Leu Glu Gln Asp Asn Asp Phe Leu Ile Tyr Leu Val Ser Phe Leu
530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Ser Met Leu Ile Ser
                565                 570                 575

Ala Val Cys Cys Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
    595                 600                 605

Ala Leu Asp Val Ile Thr Val Glu Leu Tyr Pro Thr Asn Gln Arg Ala
610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Leu Ile Ala Leu
            660                 665                 670

Arg Leu Pro Glu Thr Arg Glu Gln Val Leu Ile
    675                 680

<210> SEQ ID NO 30
<211> LENGTH: 727
<212> TYPE: PRT
<213> ORGANISM: Homo sapiens

<400> SEQUENCE: 30

Met Glu Asp Ser Tyr Lys Asp Arg Thr Ser Leu Met Lys Gly Ala Lys
1               5                   10                  15

Asp Ile Ala Arg Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Glu Asp Asp Asp Tyr Tyr Pro Ala Gly Glu Thr
    50                  55                  60

Tyr Asn Gly Glu Ala Asn Asp Asp Glu Gly Ser Ser Glu Ala Thr Glu
65                  70                  75                  80

Gly His Asp Glu Asp Asp Glu Ile Tyr Glu Gly Glu Tyr Gln Gly Ile
                85                  90                  95

Pro Ser Met Asn Gln Ala Lys Asp Ser Ile Val Ser Val Gly Gln Pro
            100                 105                 110

Lys Gly Asp Glu Tyr Lys Asp Arg Arg Glu Leu Glu Ser Glu Arg Arg
```

-continued

```
            115                 120                 125
Ala Asp Glu Glu Glu Leu Ala Gln Gln Tyr Glu Leu Ile Ile Gln Glu
130                 135                 140

Cys Gly His Gly Arg Phe Gln Trp Ala Leu Phe Val Leu Gly Met
145                 150                 155                 160

Ala Leu Met Ala Asp Gly Val Glu Val Phe Val Gly Phe Val Leu
                165                 170                 175

Pro Ser Ala Glu Thr Asp Leu Cys Ile Pro Asn Ser Gly Ser Gly Trp
                180                 185                 190

Leu Gly Ser Ile Val Tyr Leu Gly Met Met Val Gly Ala Phe Phe Trp
            195                 200                 205

Gly Gly Leu Ala Asp Lys Val Gly Arg Lys Gln Ser Leu Leu Ile Cys
            210                 215                 220

Met Ser Val Asn Gly Phe Ala Phe Leu Ser Ser Phe Val Gln Gly
225                 230                 235                 240

Tyr Gly Phe Phe Leu Phe Cys Arg Leu Leu Ser Gly Phe Gly Ile Gly
                245                 250                 255

Gly Ala Ile Pro Thr Val Phe Ser Tyr Phe Ala Glu Val Leu Ala Arg
                260                 265                 270

Glu Lys Arg Gly Glu His Leu Ser Trp Leu Cys Met Phe Trp Met Ile
            275                 280                 285

Gly Gly Ile Tyr Ala Ser Ala Met Ala Trp Ala Ile Ile Pro His Tyr
            290                 295                 300

Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
                340                 345                 350

His Asp Glu Ala Trp Met Ile Leu Lys Leu Ile His Asp Thr Asn Met
            355                 360                 365

Arg Ala Arg Gly Gln Pro Glu Lys Val Phe Thr Val Asn Lys Ile Lys
370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Asp Asn
                420                 425                 430

Thr Ile Lys Leu Thr Ile Val Trp Phe Thr Leu Ser Phe Gly Tyr Tyr
            435                 440                 445

Gly Leu Ser Val Trp Phe Pro Asp Val Ile Lys Pro Leu Gln Ser Asp
            450                 455                 460

Glu Tyr Ala Leu Leu Thr Arg Asn Val Glu Arg Asp Lys Tyr Ala Asn
465                 470                 475                 480

Phe Thr Ile Asn Phe Thr Met Glu Asn Gln Ile His Thr Gly Met Glu
                485                 490                 495

Tyr Asp Asn Gly Arg Phe Ile Gly Val Lys Phe Lys Ser Val Thr Phe
                500                 505                 510

Lys Asp Ser Val Phe Lys Ser Cys Thr Phe Glu Asp Val Thr Ser Val
            515                 520                 525

Asn Thr Tyr Phe Lys Asn Cys Thr Phe Ile Asp Thr Val Phe Asp Asn
            530                 535                 540
```

Thr Asp Phe Glu Pro Tyr Lys Phe Ile Asp Ser Glu Phe Lys Asn Cys
545                 550                 555                 560

Ser Phe Phe His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
            580                 585                 590

Val Leu Pro Gly Asn Ile Val Ser Ala Leu Leu Met Asp Arg Ile Gly
        595                 600                 605

Arg Leu Thr Met Leu Gly Gly Ser Met Val Leu Ser Gly Ile Ser Cys
    610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
            660                 665                 670

Phe Leu Asn Ala Leu Cys Lys Ala Ala Ala Val Leu Gly Asn Leu Ile
        675                 680                 685

Phe Gly Ser Leu Val Ser Ile Thr Lys Ser Ile Pro Ile Leu Leu Ala
    690                 695                 700

Ser Thr Val Leu Val Cys Gly Gly Leu Val Gly Leu Cys Leu Pro Asp
705                 710                 715                 720

Thr Arg Thr Gln Val Leu Met
                725

<210> SEQ ID NO 31
<211> LENGTH: 742
<212> TYPE: PRT
<213> ORGANISM: Homo sapiens

<400> SEQUENCE: 31

Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45

Phe Glu Glu Glu Asp Asp Asp Phe Pro Ala Pro Ser Asp Gly
    50                  55                  60          Gly
                                                        Tyr Tyr Arg Gly Glu Gly Thr Gln Asp Glu Glu Gly Gly Ala Ser
65                  70                  75                  80

Ser Asp Ala Thr Glu Gly His Asp Glu Asp Asp Glu Ile Tyr Glu Gly
            85                  90                  95

Glu Tyr Gln Asp Ile Pro Arg Ala Glu Ser Gly Gly Lys Gly Glu Arg
        100                 105                 110

Met Ala Asp Gly Ala Pro Leu Ala Gly Val Arg Gly Gly Leu Ser Asp
    115                 120                 125

Gly Glu Gly Pro Pro Gly Gly Arg Gly Glu Ala Gln Arg Arg Lys Glu
130                 135                 140

Arg Glu Glu Leu Ala Gln Gln Tyr Glu Ala Ile Leu Arg Glu Cys Gly
145                 150                 155                 160

His Gly Arg Phe Gln Trp Thr Leu Tyr Phe Val Leu Gly Leu Ala Leu
                165                 170                 175

Met Ala Asp Gly Val Glu Val Phe Val Val Gly Phe Val Leu Pro Ser

```
            180                 185                 190
Ala Glu Lys Asp Met Cys Leu Ser Asp Ser Asn Lys Gly Met Leu Gly
            195                 200                 205
Leu Ile Val Tyr Leu Gly Met Met Val Gly Ala Phe Leu Trp Gly Gly
            210                 215                 220
Leu Ala Asp Arg Leu Gly Arg Arg Gln Cys Leu Leu Ile Ser Leu Ser
225                 230                 235                 240
Val Asn Ser Val Phe Ala Phe Phe Ser Ser Phe Val Gln Gly Tyr Gly
                245                 250                 255
Thr Phe Leu Phe Cys Arg Leu Leu Ser Gly Val Gly Ile Gly Gly Ser
                260                 265                 270
Ile Pro Ile Val Phe Ser Tyr Phe Ser Glu Phe Leu Ala Gln Glu Lys
                275                 280                 285
Arg Gly Glu His Leu Ser Trp Leu Cys Met Phe Trp Met Ile Gly Gly
            290                 295                 300
Val Tyr Ala Ala Ala Met Ala Trp Ala Ile Ile Pro His Tyr Gly Trp
305                 310                 315                 320
Ser Phe Gln Met Gly Ser Ala Tyr Gln Phe His Ser Trp Arg Val Phe
                325                 330                 335
Val Leu Val Cys Ala Phe Pro Ser Val Phe Ala Ile Gly Ala Leu Thr
                340                 345                 350
Thr Gln Pro Glu Ser Pro Arg Phe Phe Leu Glu Asn Gly Lys His Asp
                355                 360                 365
Glu Ala Trp Met Val Leu Lys Gln Val His Asp Thr Asn Met Arg Ala
            370                 375                 380
Lys Gly His Pro Glu Arg Val Phe Ser Val Thr His Ile Lys Thr Ile
385                 390                 395                 400
His Gln Glu Asp Glu Leu Ile Glu Ile Gln Ser Asp Thr Gly Thr Trp
                405                 410                 415
Tyr Gln Arg Trp Gly Val Arg Ala Leu Ser Leu Gly Gly Gln Val Trp
                420                 425                 430
Gly Asn Phe Leu Ser Cys Phe Gly Pro Glu Tyr Arg Arg Ile Thr Leu
            435                 440                 445
Met Met Met Gly Val Trp Phe Thr Met Ser Phe Ser Tyr Tyr Gly Leu
            450                 455                 460
Thr Val Trp Phe Pro Asp Met Ile Arg His Leu Gln Ala Val Asp Tyr
465                 470                 475                 480
Ala Ser Arg Thr Lys Val Phe Pro Gly Glu Arg Val Gly His Val Thr
                485                 490                 495
Phe Asn Phe Thr Leu Glu Asn Gln Ile His Arg Gly Gly Gln Tyr Phe
                500                 505                 510
Asn Asp Lys Phe Ile Gly Leu Arg Leu Lys Ser Val Ser Phe Glu Asp
            515                 520                 525
Ser Leu Phe Glu Glu Cys Tyr Phe Glu Asp Val Thr Ser Ser Asn Thr
            530                 535                 540
Phe Phe Arg Asn Cys Thr Phe Ile Asn Thr Val Phe Tyr Asn Thr Asp
545                 550                 555                 560
Leu Phe Glu Tyr Lys Phe Val Asn Ser Arg Leu Ile Asn Ser Thr Phe
                565                 570                 575
Leu His Asn Lys Glu Gly Cys Pro Leu Asp Val Thr Gly Thr Gly Glu
                580                 585                 590
Gly Ala Tyr Met Val Tyr Phe Val Ser Phe Leu Gly Thr Leu Ala Val
                595                 600                 605
```

```
Leu Pro Gly Asn Ile Val Ser Ala Leu Leu Met Asp Lys Ile Gly Arg
            610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
            690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740

<210> SEQ ID NO 32
<211> LENGTH: 7
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 32

Arg Ile Asp Glu Ala Asn Gln
1               5

<210> SEQ ID NO 33
<211> LENGTH: 8
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 33

Thr Arg Ile Asp Glu Ala Asn Gln
1               5

<210> SEQ ID NO 34
<211> LENGTH: 9
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 34

Lys Thr Arg Ile Asp Glu Ala Asn Gln
1               5

<210> SEQ ID NO 35
<211> LENGTH: 10
<212> TYPE: PRT
<213> ORGANISM: Artificial Sequence
<220> FEATURE:
```

```
<223> OTHER INFORMATION: SNAP-25 antigen having a free carboxyl-terminus
      at the P1 residue of the scissile bond of the BoNT/A
      cleavage site

<400> SEQUENCE: 35

Asn Lys Thr Arg Ile Asp Glu Ala Asn Gln
1               5                   10

<210> SEQ ID NO 36
<211> LENGTH: 11
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 36

Ser Asn Lys Thr Arg Ile Asp Glu Ala Asn Gln
1               5                   10

<210> SEQ ID NO 37
<211> LENGTH: 12
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 37

Asp Ser Asn Lys Thr Arg Ile Asp Glu Ala Asn Gln
1               5                   10

<210> SEQ ID NO 38
<211> LENGTH: 13
<212> TYPE: PRT
<213> ORGANISM: Artificial Sequence
<220> FEATURE:
<223> OTHER INFORMATION: SNAP-25 antigen having a free carboxylated
      carboxyl-terminus at the P1 residue of the
      scissile bond of the BoNT/A cleavage site
<221> NAME/KEY: SITE
<222> LOCATION: (13)...(13)
<223> OTHER INFORMATION: carboxylated glutamine

<400> SEQUENCE: 38

Cys Asp Ser Asn Lys Thr Arg Ile Asp Glu Ala Asn Gln
1               5                   10

<210> SEQ ID NO 39
<211> LENGTH: 7
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 39

Arg Ile Asp Glu Ala Asn Lys
1               5

<210> SEQ ID NO 40
<211> LENGTH: 8
<212> TYPE: PRT
<213> ORGANISM: Artificial Sequence
<220> FEATURE:
<223> OTHER INFORMATION: SNAP-25 antigen having a free carboxyl-terminus
``` at the P1 residue of the scissile bond of the BoNT/A
      cleavage site

<400> SEQUENCE: 40

Ala Arg Ile Asp Glu Ala Asn Lys
1               5

<210> SEQ ID NO 41
<211> LENGTH: 9
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 41

Lys Ala Arg Ile Asp Glu Ala Asn Lys
1               5

<210> SEQ ID NO 42
<211> LENGTH: 10
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 42

Asn Lys Ala Arg Ile Asp Glu Ala Asn Lys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 43

Met Asn Lys Ala Arg Ile Asp Glu Ala Asn Lys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 44

Asp Met Asn Lys Ala Arg Ile Asp Glu Ala Asn Lys
1               5                   10

<210> SEQ ID NO 45
<211> LENGTH: 13
<212> TYPE: PRT
<213> ORGANISM: Artificial Sequence
<220> FEATURE:
<223> OTHER INFORMATION: SNAP-25 antigen having a free carboxylated
      carboxyl-terminus at the P1 residue of the
      scissile bond of the BoNT/A cleavage site
<221> NAME/KEY: SITE
<222> LOCATION: (13)...(13)

<223> OTHER INFORMATION: Carboxylated lysine

<400> SEQUENCE: 45

Cys Asp Met Asn Lys Ala Arg Ile Asp Glu Ala Asn Lys
1               5                   10

<210> SEQ ID NO 46
<211> LENGTH: 11
<212> TYPE: PRT
<213> ORGANISM: Artificial Sequence
<220> FEATURE:
<223> OTHER INFORMATION: SNAP-25 antigen

<400> SEQUENCE: 46

Cys Gly Gly Gly Arg Ile Asp Glu Ala Asn Gln
1               5                   10

<210> SEQ ID NO 47
<211> LENGTH: 11
<212> TYPE: PRT
<213> ORGANISM: Artificial Sequence
<220> FEATURE:
<223> OTHER INFORMATION: SNAP-25 antigen

<400> SEQUENCE: 47

Cys Gly Gly Gly Arg Ile Asp Glu Ala Asn Lys
1               5                   10

<210> SEQ ID NO 48
<211> LENGTH: 88
<212> TYPE: PRT
<213> ORGANISM: Artificial Sequence
<220> FEATURE:
<223> OTHER INFORMATION: BirA-HisTag?-SNAP-25-134-197

<400> SEQUENCE: 48

Met Gly Gly Gly Leu Asn Asp Ile Phe Glu Ala Gln Lys Ile Glu Trp
1               5                   10                  15

His His His His His His His His Ile Arg Arg Val Thr Asn Asp Ala
                20                  25                  30

Arg Glu Asn Glu Met Asp Glu Asn Leu Glu Gln Val Ser Gly Ile Ile
            35                  40                  45

Gly Asn Leu Arg His Met Ala Leu Asp Met Gly Asn Glu Ile Asp Thr
        50                  55                  60

Gln Asn Arg Gln Ile Asp Arg Ile Met Glu Lys Ala Asp Ser Asn Lys
65                  70                  75                  80

Thr Arg Ile Asp Glu Ala Asn Gln
                85

<210> SEQ ID NO 49
<211> LENGTH: 97
<212> TYPE: PRT
<213> ORGANISM: Artificial Sequence
<220> FEATURE:
<223> OTHER INFORMATION: BirA-HisTag?-SNAP-25-134-206

<400> SEQUENCE: 49

Met Gly Gly Gly Leu Asn Asp Ile Phe Glu Ala Gln Lys Ile Glu Trp
1               5                   10                  15

His His His His His His His His Ile Arg Arg Val Thr Asn Asp Ala
                20                  25                  30

Arg Glu Asn Glu Met Asp Glu Asn Leu Glu Gln Val Ser Gly Ile Ile
            35                  40                  45

Gly Asn Leu Arg His Met Ala Leu Asp Met Gly Asn Glu Ile Asp Thr
    50                  55                  60

Gln Asn Arg Gln Ile Asp Arg Ile Met Glu Lys Ala Asp Ser Asn Lys
65                  70                  75                  80

Thr Arg Ile Asp Glu Ala Asn Gln Arg Ala Thr Lys Met Leu Gly Ser
                85                  90                  95

Gly

<210> SEQ ID NO 50
<211> LENGTH: 16
<212> TYPE: PRT
<213> ORGANISM: Artificial Sequence
<220> FEATURE:
<223> OTHER INFORMATION: BirA peptide

<400> SEQUENCE: 50

Gly Gly Gly Leu Asn Asp Ile Phe Glu Ala Gln Lys Ile Glu Trp His
1               5                   10                  15

<210> SEQ ID NO 51
<211> LENGTH: 7570
<212> TYPE: DNA
<213> ORGANISM: Artificial Sequence
<220> FEATURE:
<223> OTHER INFORMATION: pQBI-25/GFP-BoNT/A-LC expression construct.

<400> SEQUENCE: 51
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcc tcgaggcctg gccattgcat acgttgtatc 240
catatcataa tatgtacatt tatattggct catgtccaac attaccgcca tgttgacatt 300
gattattgac tagttattaa tagtaatcaa ttacggggtc attagttcat agcccatata 360
tggagttccg cgttacataa cttacggtaa atggcccgcc tggctgaccg cccaacgacc 420
cccgcccatt gacgtcaata atgacgtatg ttcccatagt aacgccaata gggactttcc 480
attgacgtca atgggtggag tatttacggt aaactgccca cttggcagta catcaagtgt 540
atcatatgcc aagtacgccc cctattgacg tcaatgacgg taaatggccc gcctggcatt 600
atgcccagta catgacctta tgggactttc ctacttggca gtacatctac gtattagtca 660
tcgctattac catggtgatg cggttttggc agtacatcaa tgggcgtgga tagcggtttg 720
actcacgggg atttccaagt ctccacccca ttgacgtcaa tgggagtttg ttttggcacc 780
aaaatcaacg ggactttcca aaatgtcgta acaactccgc cccattgacg caaatgggcg 840
gtaggcgtgt acggtgggag gtctatataa gcagagctcg tttagtgaac cgtcagatcg 900
cctggagacg ccatccacgc tgttttgacc tccatagaag acaccgggac cgatccagcc 960
tccgcgggcc accatggagg gcccggttac cggtaccgga tccagatatc tgggcggccg 1020
ctcagcaagc ttcgcgaatt cgggaggcgg aggtggagct agcaaaggag aagaactctt 1080
cactggagtt gtcccaattc ttgttgaatt agatggtgat gttaacggcc acaagttctc 1140
tgtcagtgga gagggtgaag gtgatgcaac atacggaaaa cttaccctga agttcatctg 1200
cactactggc aaactgcctg ttccatggcc aacactagtc actactctgt gctatggtgt 1260
tcaatgcttt tcaagatacc cggatcatat gaaacggcat gactttttca agagtgccat 1320

```
gcccgaaggt tatgtacagg aaaggaccat cttcttcaaa gatgacggca actacaagac   1380
acgtgctgaa gtcaagtttg aaggtgatac ccttgttaat agaatcgagt taaaaggtat   1440
tgacttcaag gaagatggca acattctggg acacaaattg aatacaact ataactcaca    1500 caatgtatac atcatggcag acaaacaaaa gaatggaatc aaagtgaact tcaagacccg   1560
ccacaacatt gaagatggaa gcgttcaact agcagaccat tatcaacaaa atactccaat   1620
tggcgatggc cctgtccttt taccagacaa ccattacctg tccacacaat ctgcccttc    1680 gaaagatccc aacgaaaaga gagaccacat ggtccttctt gagtttgtaa cagctgctgg   1740
gattacacat ggcatggatg aactgtacaa catcgatgga ggcggaggtg gaccttttgt   1800
taataaacaa tttaattata agatcctgt aaatggtgtt gatattgctt atataaaaat    1860
tccaaatgca ggacaaatgc aaccagtaaa agcttttaaa attcataata aaatatgggt   1920
tattccagaa agagatacat ttacaaatcc tgaagaagga gatttaaatc caccaccaga   1980
agcaaaacaa gttccagttt catattatga ttcaacatat ttaagtacag ataatgaaaa   2040
agataattat ttaaagggag ttacaaaatt atttgagaga atttattcaa ctgatcttgg   2100
aagaatgttg ttaacatcaa tagtaagggg aataccattt tggggtggaa gtacaataga   2160
tacagaatta aaagttattg atactaattg tattaatgtg atacaaccag atggtagtta   2220
tagatcagaa gaacttaatc tagtaataat aggaccctca gctgatatta tacagtttga   2280
atgtaaaagc tttggacatg aagttttgaa tcttacgcga aatggttatg gctctactca   2340
atacattaga tttagcccag attttacatt tggttttgag gagtcacttg aagttgatac   2400
aaatcctctt ttaggtgcag gcaaatttgc tacagatcca gcagtaacat tagcacatga   2460
acttatacat gctggacata gattatatgg aatagcaatt aatccaaata gggttttaa    2520 agtaaatact aatgcctatt atgaaatgag tgggttagaa gtaagctttg aggaacttag   2580
aacatttggg ggacatgatg caaagtttat agatagttta caggaaaacg aatttcgtct   2640
atattattat aataagttta aagatatagc aagtacactt aataaagcta atcaatagt    2700 aggtactact gcttcattac agtatatgaa aaatgttttt aaagagaaat atctcctatc   2760
tgaagataca tctggaaaat tttcggtaga taaattaaaa tttgataagt tatacaaaat   2820
gttaacagag atttacacag aggataattt tgttaagttt tttaaagtac ttaacagaaa   2880
aacatatttg aattttgata aagccgtatt taagataaat atagtaccta aggtaaatta   2940
cacaatatat gatggattta atttaagaaa tacaaattta gcagcaaact ttaatggtca   3000
aaatacagaa attaataata tgaatttac taaactaaaa aatttactg gattgtttga    3060 atttttataag ttgctatgtg taagagggat aatcacttcg aaatgaacgc gttggcccta   3120
ttctatagtg tcacctaaat gctagagctc gctgatcagc ctcgactgtg ccttctagtt   3180
gccagccatc tgttgtttgc ccctcccccg tgccttcctt gaccctggaa ggtgccactc   3240
ccactgtcct ttcctaataa aatgaggaaa ttgcatcgca ttgtctgagt aggtgtcatt   3300
ctattctggg gggtgggtg gggcaggaca gcaaggggga ggattgggaa gacaatagca    3360
ggcatgctgg ggatgcggtg ggctctatgg cttctgaggc ggaaagaacc agctggggct   3420
ctagggggta tccccacgcg ccctgtagcg gcgcattaag cgcggcgggt gtggtggtta   3480
cgcgcagcgt gaccgctaca cttgccagcg ccctagcgcc cgctcctttc gctttcttcc   3540
cttcctttct cgccacgttc gccggctttc cccgtcaagc tctaaatcgg ggcatccctt   3600
tagggttccg atttagtgct ttacggcacc tcgaccccaa aaaacttgat tagggtgatg   3660
gttcacgtag tgggccatcg ccctgataga cggttttcg ccctttgacg ttggagtcca   3720
```

```
cgttctttaa tagtggactc ttgttccaaa ctggaacaac actcaaccct atctcggtct   3780
attcttttga tttataaggg attttgggga tttcggccta ttggttaaaa aatgagctga   3840
tttaacaaaa atttaacgcg aattaattct gtggaatgtg tgtcagttag ggtgtggaaa   3900
gtccccaggc tccccaggca ggcagaagta tgcaaagcat gcatctcaat tagtcagcaa   3960
ccaggtgtgg aaagtcccca ggctccccag caggcagaag tatgcaaagc atgcatctca   4020
attagtcagc aaccatagtc ccgcccctaa ctccgcccat cccgcccta actccgccca    4080
gttccgccca ttctccgccc catggctgac taatttttt tatttatgca gaggccgagg    4140
ccgcctctgc ctctgagcta ttccagaagt agtgaggagg cttttttgga ggcctaggct   4200
tttgcaaaaa gctcccggga gcttgtatat ccattttcgg atctgatcaa gagacaggat   4260
gaggatcgtt tcgcatgatt gaacaagatg gattgcacgc aggttctccg gccgcttggg   4320
tggagaggct attcggctat gactgggcac aacagacaat cggctgctct gatgccgccg   4380
tgttccggct gtcagcgcag gggcgcccgg ttctttttgt caagaccgac ctgtccggtg   4440
ccctgaatga actgcaggac gaggcagcgc ggctatcgtg gctggccacg acgggcgttc   4500
cttgcgcagc tgtgctcgac gttgtcactg aagcgggaag ggactggctg ctattgggcg   4560
aagtgccggg gcaggatctc ctgtcatctc accttgctcc tgccgagaaa gtatccatca   4620
tggctgatgc aatgcggcgg ctgcatacgc ttgatccggc tacctgccca ttcgaccacc   4680
aagcgaaaca tcgcatcgag cgagcacgta ctcggatgga agccggtctt gtcgatcagg   4740
atgatctgga cgaagagcat caggggctcg cgccagccga actgttcgcc aggctcaagg   4800
cgcgcatgcc cgacggcgag gatctcgtcg tgacccatgg cgatgcctgc ttgccgaata   4860
tcatggtgga aaatggccgc ttttctggat tcatcgactg tggccggctg ggtgtggcgg   4920
accgctatca ggacatagcg ttggctaccc gtgatattgc tgaagagctt ggcggcgaat   4980
gggctgaccg cttcctcgtg ctttacggta tcgccgctcc cgattcgcag cgcatcgcct   5040
tctatcgcct tcttgacgag ttcttctgag cgggactctg gggttcgaaa tgaccgacca   5100
agcgacgccc aacctgccat cacgagattt cgattccacc gccgccttct atgaaaggtt   5160
gggcttcgga atcgttttcc gggacgccgg ctggatgatc ctccagcgcg ggatctcat    5220
gctggagttc ttcgcccacc ccaacttgtt tattgcagct tataatggtt acaaataaag   5280
caatagcatc acaaatttca caaataaagc atttttttca ctgcattcta gttgtggttt   5340
gtccaaactc atcaatgtat cttatcatgt ctgtataccg tcgacctcta gctagagctt   5400
ggcgtaatca tggtcatagc tgtttcctgt gtgaaattgt tatccgctca caattccaca   5460
caacatacga gccggaagca taaagtgtaa agcctggggt gcctaatgag tgagctaact   5520
cacattaatt gcgttgcgct cactgcccgc tttccagtcg ggaaacctgt cgtgccagct   5580
gcattaatga atcggccaac gcgcgggag aggcggtttg cgtattgggc gctcttccgc    5640
ttcctcgctc actgactcgc tgcgctcggt cgttcggctg cggcgagcgg tatcagctca   5700
ctcaaaggcg gtaatacggt tatccacaga atcagggat aacgcaggaa agaacatgtg    5760
agcaaaaggc cagcaaaagg ccaggaaccg taaaaaggcc gcgttgctgg cgttttccca   5820
taggctccgc cccctgacg agcatcacaa aaatcgacgc tcaagtcaga ggtggcgaaa    5880
cccgacagga ctataaagat accaggcgtt tcccctgga agctccctcg tgcgctctcc    5940
tgttccgacc ctgccgctta ccggatacct gtccgccttt ctcccttcgg gaagcgtggc   6000
gctttctcaa tgctcacgct gtaggtatct cagttcggtg taggtcgttc gctccaagct   6060
```

-continued

```
gggctgtgtg cacgaacccc ccgttcagcc cgaccgctgc gccttatccg gtaactatcg   6120
tcttgagtcc aacccggtaa gacacgactt atcgccactg gcagcagcca ctggtaacag   6180
gattagcaga gcgaggtatg taggcggtgc tacagagttc ttgaagtggt ggcctaacta   6240
cggctacact agaaggacag tatttggtat ctgcgctctg ctgaagccag ttaccttcgg   6300
aaaaagagtt ggtagctctt gatccggcaa acaaaccacc gctggtagcg gtggtttttt   6360
tgtttgcaag cagcagatta cgcgcagaaa aaaaggatct caagaagatc ctttgatctt   6420
ttctacgggg tctgacgctc agtggaacga aaactcacgt taagggattt tggtcatgag   6480
attatcaaaa aggatcttca cctagatcct tttaaattaa aaatgaagtt ttaaatcaat   6540
ctaaagtata tatgagtaaa cttggtctga cagttaccaa tgcttaatca gtgaggcacc   6600
tatctcagcg atctgtctat ttcgttcatc catagttgcc tgactccccg tcgtgtagat   6660
aactacgata cgggagggct taccatctgg ccccagtgct gcaatgatac cgcgagaccc   6720
acgctcaccg gctccagatt tatcagcaat aaaccagcca gccggaaggg ccgagcgcag   6780
aagtggtcct gcaactttat ccgcctccat ccagtctatt aattgttgcc gggaagctag   6840
agtaagtagt tcgccagtta atagtttgcg caacgttgtt gccattgcta caggcatcgt   6900
ggtgtcacgc tcgtcgtttg gtatggcttc attcagctcc ggttcccaac gatcaaggcg   6960
agttacatga tcccccatgt tgtgcaaaaa agcggttagc tccttcggtc ctccgatcgt   7020
tgtcagaagt aagttggccg cagtgttatc actcatggtt atggcagcac tgcataattc   7080
tcttactgtc atgccatccg taagatgctt ttctgtgact ggtgagtact caaccaagtc   7140
attctgagaa tagtgtatgc ggcgaccgag ttgctcttgc ccggcgtcaa tacgggataa   7200
taccgcgcca catagcagaa ctttaaaagt gctcatcatt ggaaaacgtt cttcggggcg   7260
aaaactctca aggatcttac cgctgttgag atccagttcg atgtaaccca ctcgtgcacc   7320
caactgatct tcagcatctt ttactttcac cagcgtttct gggtgagcaa aaacaggaag   7380
gcaaaatgcc gcaaaaaagg gaataagggc gacacggaaa tgttgaatac tcatactctt   7440
cctttttcaa tattattgaa gcatttatca gggttattgt ctcatgagcg gatacatatt   7500
tgaatgtatt tagaaaaata aacaaatagg ggttccgcgc acatttcccc gaaaagtgcc   7560
acctgacgtc                                                          7570
```

<210> SEQ ID NO 52
<211> LENGTH: 682
<212> TYPE: PRT
<213> ORGANISM: Artificial Sequence
<220> FEATURE:
<223> OTHER INFORMATION: GFP-BoNT/A light chain amino acid sequence.

<400> SEQUENCE: 52

```
Ala Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Cys Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95
```

```
Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Thr Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Asn Ile Asp
225                 230                 235                 240

Gly Gly Gly Gly Gly Pro Phe Val Asn Lys Gln Phe Asn Tyr Lys Asp
                245                 250                 255

Pro Val Asn Gly Val Asp Ile Ala Tyr Ile Lys Ile Pro Asn Ala Gly
            260                 265                 270

Gln Met Gln Pro Val Lys Ala Phe Lys Ile His Asn Lys Ile Trp Val
        275                 280                 285

Ile Pro Glu Arg Asp Thr Phe Thr Asn Pro Glu Glu Gly Asp Leu Asn
    290                 295                 300

Pro Pro Pro Glu Ala Lys Gln Val Pro Val Ser Tyr Tyr Asp Ser Thr
305                 310                 315                 320

Tyr Leu Ser Thr Asp Asn Glu Lys Asp Asn Tyr Leu Lys Gly Val Thr
                325                 330                 335

Lys Leu Phe Glu Arg Ile Tyr Ser Thr Asp Leu Gly Arg Met Leu Leu
            340                 345                 350

Thr Ser Ile Val Arg Gly Ile Pro Phe Trp Gly Gly Ser Thr Ile Asp
        355                 360                 365

Thr Glu Leu Lys Val Ile Asp Thr Asn Cys Ile Asn Val Ile Gln Pro
    370                 375                 380

Asp Gly Ser Tyr Arg Ser Glu Glu Leu Asn Leu Val Ile Ile Gly Pro
385                 390                 395                 400

Ser Ala Asp Ile Ile Gln Phe Glu Cys Lys Ser Phe Gly His Glu Val
                405                 410                 415

Leu Asn Leu Thr Arg Asn Gly Tyr Gly Ser Thr Gln Tyr Ile Arg Phe
            420                 425                 430

Ser Pro Asp Phe Thr Phe Gly Phe Glu Glu Ser Leu Glu Val Asp Thr
        435                 440                 445

Asn Pro Leu Leu Gly Ala Gly Lys Phe Ala Thr Asp Pro Ala Val Thr
    450                 455                 460

Leu Ala His Glu Leu Ile His Ala Gly His Arg Leu Tyr Gly Ile Ala
465                 470                 475                 480

Ile Asn Pro Asn Arg Val Phe Lys Val Asn Thr Asn Ala Tyr Tyr Glu
                485                 490                 495

Met Ser Gly Leu Glu Val Ser Phe Glu Glu Leu Arg Thr Phe Gly Gly
            500                 505                 510
```

His Asp Ala Lys Phe Ile Asp Ser Leu Gln Glu Asn Glu Phe Arg Leu
            515                 520                 525

Tyr Tyr Tyr Asn Lys Phe Lys Asp Ile Ala Ser Thr Leu Asn Lys Ala
        530                 535                 540

Lys Ser Ile Val Gly Thr Thr Ala Ser Leu Gln Tyr Met Lys Asn Val
545                 550                 555                 560

Phe Lys Glu Lys Tyr Leu Leu Ser Glu Asp Thr Ser Gly Lys Phe Ser
                565                 570                 575

Val Asp Lys Leu Lys Phe Asp Lys Leu Tyr Lys Met Leu Thr Glu Ile
            580                 585                 590

Tyr Thr Glu Asp Asn Phe Val Lys Phe Phe Lys Val Leu Asn Arg Lys
        595                 600                 605

Thr Tyr Leu Asn Phe Asp Lys Ala Val Phe Lys Ile Asn Ile Val Pro
    610                 615                 620

Lys Val Asn Tyr Thr Ile Tyr Asp Gly Phe Asn Leu Arg Asn Thr Asn
625                 630                 635                 640

Leu Ala Ala Asn Phe Asn Gly Gln Asn Thr Glu Ile Asn Asn Met Asn
                645                 650                 655

Phe Thr Lys Leu Lys Asn Phe Thr Gly Leu Phe Glu Phe Tyr Lys Leu
            660                 665                 670

Leu Cys Val Arg Gly Ile Ile Thr Ser Lys
        675                 680

<210> SEQ ID NO 53
<211> LENGTH: 6259
<212> TYPE: DNA
<213> ORGANISM: Artificial Sequence
<220> FEATURE:
<223> OTHER INFORMATION: pQBI-25/GFP expression construct.

<400> SEQUENCE: 53
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcc tcgaggcctg gccattgcat acgttgtatc     240
catatcataa tatgtacatt tatattggct catgtccaac attaccgcca tgttgacatt     300
gattattgac tagttattaa tagtaatcaa ttacggggtc attagttcat agcccatata     360
tggagttccg cgttacataa cttacggtaa atggcccgcc tggctgaccg cccaacgacc     420
cccgcccatt gacgtcaata atgacgtatg ttcccatagt aacgccaata gggactttcc     480
attgacgtca atgggtggag tatttacggt aaactgccca cttggcagta catcaagtgt     540
atcatatgcc aagtacgccc cctattgacg tcaatgacgg taaatggccc gcctggcatt     600
atgcccagta catgacctta tgggactttc ctacttggca gtacatctac gtattagtca     660
tcgctattac catggtgatg cggttttggc agtacatcaa tgggcgtgga tagcggtttg     720
actcacgggg atttccaagt ctccacccca ttgacgtcaa tgggagtttg ttttggcacc     780
aaaatcaacg ggactttcca aaatgtcgta caactccgc cccattgacg caaatgggcg     840
gtaggcgtgt acggtgggag gtctatataa gcagagctcg tttagtgaac cgtcagatcg     900
cctggagacg ccatccacgc tgttttgacc tccatagaag acaccgggac cgatccagcc     960
tccgcgggcc accatggagg cccggttac cggtaccgga tccagatatc tgggcggcc    1020 ctcagcaagc ttcgcgaatt cgggaggcgg aggtggagct agcaaggag aagaactctt    1080

```
cactggagtt gtcccaattc ttgttgaatt agatggtgat gttaacggcc acaagttctc    1140
tgtcagtgga gagggtgaag gtgatgcaac atacggaaaa cttaccctga agttcatctg    1200
cactactggc aaactgcctg ttccatggcc aacactagtc actactctgt gctatggtgt    1260
tcaatgcttt tcaagatacc cggatcatat gaaacggcat gacttttca agagtgccat     1320 gcccgaaggt tatgtacagg aaaggaccat cttcttcaaa gatgacggca actacaagac    1380
acgtgctgaa gtcaagtttg aaggtgatac ccttgttaat agaatcgagt taaaaggtat    1440
tgacttcaag gaagatggca acattctggg acacaaattg gaatacaact ataactcaca    1500
caatgtatac atcatggcag acaaacaaaa gaatggaatc aaagtgaact tcaagacccg    1560
ccacaacatt gaagatggaa gcgttcaact agcagaccat tatcaacaaa atactccaat    1620
tggcgatggc cctgtccttt taccagacaa ccattacctg tccacacaat ctgcccttc     1680 gaaagatccc aacgaaaaga gagaccacat ggtccttctt gagtttgtaa cagctgctgg    1740
gattacacat ggcatggatg aactgtacaa catcgatgga gcggaggtg atgaacgcg      1800 ttggccctat tctatagtgt cacctaaatg ctagagctcg ctgatcagcc tcgactgtgc    1860
cttctagttg ccagccatct gttgtttgcc cctccccgt gccttccttg accctggaag     1920
gtgccactcc cactgtcctt tcctaataaa atgaggaaat tgcatcgcat tgtctgagta    1980
ggtgtcattc tattctgggg ggtggggtgg ggcaggacag caaggggag gattgggaag     2040 acaatagcag gcatgctggg gatgcggtgg gctctatggc ttctgaggcg aaagaacca    2100 gctggggctc tagggggtat ccccacgcgc cctgtagcgg cgcattaagc gcggcgggtg    2160
tggtggttac gcgcagcgtg accgctacac ttgccagcgc cctagcgccc gctcctttcg    2220
ctttcttccc ttcctttctc gccacgttcg ccggctttcc ccgtcaagct ctaaatcggg    2280
gcatcccttt agggttccga tttagtgctt tacggcacct cgaccccaaa aaacttgatt    2340
agggtgatgg ttcacgtagt gggccatcgc cctgatagac ggtttttcgc cctttgacgt    2400
tggagtccac gttctttaat agtggactct tgttccaaac tggaacaaca ctcaacccta    2460
tctcggtcta ttcttttgat ttataaggga ttttggggat ttcggcctat tggttaaaaa    2520
atgagctgat ttaacaaaaa tttaacgcga attaattctg tggaatgtgt gtcagttagg    2580
gtgtggaaag tccccaggct ccccaggcag gcagaagtat gcaaagcatg catctcaatt    2640
agtcagcaac caggtgtgga aagtccccag gctccccagc aggcagaagt atgcaaagca    2700
tgcatctcaa ttagtcagca accatagtcc cgcccctaac tccgcccatc ccgcccctaa    2760
ctccgcccag ttccgcccat tctccgcccc atggctgact aatttttttt atttatgcag    2820
aggccgaggc cgcctctgcc tctgagctat tccagaagta gtgaggaggc ttttttggag    2880
gcctaggctt ttgcaaaaag ctcccgggag cttgtatatc cattttcgga tctgatcaag    2940
agacaggatg aggatcgttt cgcatgattg aacaagatgg attgcacgca ggttctccgg    3000
ccgcttgggt ggagaggcta ttcggctatg actgggcaca acagacaatc ggctgctctg    3060
atgccgccgt gttccggctg tcagcgcagg ggcgcccggt tctttttgtc aagaccgacc    3120
tgtccggtgc cctgaatgaa ctgcaggacg aggcagcgcg gctatcgtgg ctggccacga    3180
cgggcgttcc ttgcgcagct gtgctcgacg ttgtcactga agcgggaagg gactggctgc    3240
tattgggcga agtgccgggg caggatctcc tgtcatctca ccttgctcct gccgagaaag    3300
tatccatcat ggctgatgca atgcggcggc tgcatacgct tgatccggct acctgcccat    3360
tcgaccacca agcgaaacat cgcatcgagc gagcacgtac tcggatgaa gccggtcttg     3420 tcgatcagga tgatctggac gaagagcatc aggggctcgc gccagccgaa ctgttcgcca    3480
```

```
ggctcaaggc gcgcatgccc gacggcgagg atctcgtcgt gacccatggc gatgcctgct    3540
tgccgaatat catggtggaa aatggccgct tttctggatt catcgactgt ggccggctgg    3600
gtgtggcgga ccgctatcag gacatagcgt tggctacccg tgatattgct gaagagcttg    3660
gcggcgaatg ggctgaccgc ttcctcgtgc tttacggtat cgccgctccc gattcgcagc    3720
gcatcgcctt ctatcgcctt cttgacgagt tcttctgagc gggactctgg ggttcgaaat    3780
gaccgaccaa gcgacgccca acctgccatc acgagatttc gattccaccg ccgcttcta    3840 tgaaaggttg ggcttcggaa tcgttttccg ggacgccggc tggatgatcc tccagcgcgg    3900
ggatctcatg ctggagttct tcgcccaccc caacttgttt attgcagctt ataatggtta    3960
caaataaagc aatagcatca caaatttcac aaataaagca ttttttttcac tgcattctag    4020 ttgtggtttg tccaaactca tcaatgtatc ttatcatgtc tgtataccgt cgacctctag    4080
ctagagcttg gcgtaatcat ggtcatagct gtttcctgtg tgaaattgtt atccgctcac    4140
aattccacac aacatacgag ccggaagcat aaagtgtaaa gcctggggtg cctaatgagt    4200
gagctaactc acattaattg cgttgcgctc actgcccgct ttccagtcgg gaaacctgtc    4260
gtgccagctg cattaatgaa tcggccaacg cgcggggaga ggcggtttgc gtattgggcg    4320
ctcttccgct tcctcgctca ctgactcgct gcgctcggtc gttcggctgc ggcgagcggt    4380
atcagctcac tcaaaggcgg taatacggtt atccacagaa tcaggggata acgcaggaaa    4440
gaacatgtga gcaaaaggcc agcaaaaggc caggaaccgt aaaaaggccg cgttgctggc    4500
gtttttccat aggctccgcc cccctgacga gcatcacaaa aatcgacgct caagtcagag    4560
gtggcgaaac ccgacaggac tataaagata ccaggcgttt ccccctggaa gctccctcgt    4620
gcgctctcct gttccgaccc tgccgcttac cggatacctg tccgcctttc tcccttcggg    4680
aagcgtggcg ctttctcaat gctcacgctg taggtatctc agttcggtgt aggtcgttcg    4740
ctccaagctg ggctgtgtgc acgaaccccc cgttcagccc gaccgctgcg ccttatccgg    4800
taactatcgt cttgagtcca acccggtaag acacgactta tcgccactgg cagcagccac    4860
tggtaacagg attagcagag cgaggtatgt aggcggtgct acagagttct tgaagtggtg    4920
gcctaactac ggctacacta aaggacagt atttggtatc tgcgctctgc tgaagccagt    4980
taccttcgga aaaagagttg gtagctcttg atccggcaaa caaaccaccg ctggtagcgg    5040 tggtttttttt gtttgcaagc agcagattac gcgcagaaaa aaaggatctc aagaagatcc    5100
tttgatcttt tctacggggt ctgacgctca gtggaacgaa aactcacgtt aagggatttt    5160
ggtcatgaga ttatcaaaaa ggatcttcac ctagatcctt ttaaattaaa aatgaagttt    5220
taaatcaatc taaagtatat atgagtaaac ttggtctgac agttaccaat gcttaatcag    5280
tgaggcacct atctcagcga tctgtctatt tcgttcatcc atagttgcct gactccccgt    5340
cgtgtagata actacgatac gggagggctt accatctggc cccagtgctg caatgatacc    5400
gcgagaccca cgctcaccgg ctccagattt atcagcaata aaccagccag ccggaagggc    5460
cgagcgcaga gtggtcctg caactttatc cgcctccatc cagtctatta attgttgccg    5520
ggaagctaga gtaagtagtt cgccagttaa tagtttgcgc aacgttgttg ccattgctac    5580
aggcatcgtg gtgtcacgct cgtcgtttgg tatggcttca ttcagctccg gttcccaacg    5640
atcaaggcga gttacatgat cccccatgtt gtgcaaaaaa gcggttagct ccttcggtcc    5700
tccgatcgtt gtcagaagta agttggccgc agtgttatca ctcatggtta tggcagcact    5760
gcataattct cttactgtca tgccatccgt aagatgcttt tctgtgactg gtgagtactc    5820
```

```
aaccaagtca ttctgagaat agtgtatgcg gcgaccgagt tgctcttgcc cggcgtcaat    5880
acgggataat accgcgccac atagcagaac tttaaaagtg ctcatcattg gaaaacgttc    5940 ttcgggcga aaactctcaa ggatcttacc gctgttgaga tccagttcga tgtaacccac     6000
tcgtgcaccc aactgatctt cagcatcttt tactttcacc agcgtttctg ggtgagcaaa    6060
aacaggaagg caaatgccg caaaaaggg aataagggcg cacggaaat gttgaatact       6120 catactcttc ctttttcaat attattgaag catttatcag ggttattgtc tcatgagcgg    6180
atacatattt gaatgtattt agaaaaataa acaaataggg gttccgcgca catttccccg    6240
aaaagtgcca cctgacgtc                                                 6259
```

<210> SEQ ID NO 54
<211> LENGTH: 245
<212> TYPE: PRT
<213> ORGANISM: Artificial Sequence
<220> FEATURE:
<223> OTHER INFORMATION: GFP amino acid sequence.

<400> SEQUENCE: 54

```
Ala Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Cys Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Thr Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Asn Ile Asp
225                 230                 235                 240

Gly Gly Gly Gly Gly
                245
```

<210> SEQ ID NO 55
<211> LENGTH: 4
<212> TYPE: PRT
<213> ORGANISM: Artificial Sequence

```
<220> FEATURE:
<223> OTHER INFORMATION: G-spacer flexible spacer

<400> SEQUENCE: 55

Gly Gly Gly Gly
1

<210> SEQ ID NO 56
<211> LENGTH: 5
<212> TYPE: PRT
<213> ORGANISM: Artificial Sequence
<220> FEATURE:
<223> OTHER INFORMATION: G-spacer flexible spacer

<400> SEQUENCE: 56

Gly Gly Gly Gly Ser
1               5

<210> SEQ ID NO 57
<211> LENGTH: 4
<212> TYPE: PRT
<213> ORGANISM: Artificial Sequence
<220> FEATURE:
<223> OTHER INFORMATION: A-spacer flexible spacer

<400> SEQUENCE: 57

Ala Ala Ala Ala
1

<210> SEQ ID NO 58
<211> LENGTH: 5
<212> TYPE: PRT
<213> ORGANISM: Artificial Sequence
<220> FEATURE:
<223> OTHER INFORMATION: A-spacer flexible spacer

<400> SEQUENCE: 58

Ala Ala Ala Ala Val
1               5

<210> SEQ ID NO 59
<211> LENGTH: 821
<212> TYPE: PRT
<213> ORGANISM: Homo sapiens

<400> SEQUENCE: 59

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125
```

```
Ser Ser Gly Asp Asp Glu Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
                180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
                340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
    435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
    515                 520                 525

Ser Asp Leu Val Ser Glu Met Glu Met Met Lys Met Ile Gly Lys His
    530                 535                 540

Lys Asn Ile Ile Asn Leu Leu Gly Ala Cys Thr Gln Asp Gly Pro Leu
```

Tyr Val Ile Val Glu Tyr Ala Ser Lys Gly Asn Leu Arg Glu Tyr Leu
545                 550                 555                 560
                565                 570                 575

Arg Ala Arg Arg Pro Gly Met Glu Tyr Ser Tyr Asp Ile Asn Arg
                580                 585                 590

Val Pro Glu Glu Gln Met Thr Phe Lys Asp Leu Val Ser Cys Thr Tyr
                595                 600                 605

Gln Leu Ala Arg Gly Met Glu Tyr Leu Ala Ser Gln Lys Cys Ile His
                610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
                660                 665                 670

Glu Ala Leu Phe Asp Arg Val Tyr Thr His Gln Ser Asp Val Trp Ser
                675                 680                 685

Phe Gly Val Leu Met Trp Glu Ile Phe Thr Leu Gly Gly Ser Pro Tyr
                690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
                740                 745                 750

Leu Val Glu Asp Leu Asp Arg Ile Leu Thr Leu Thr Thr Asn Glu Glu
                755                 760                 765

Tyr Leu Asp Leu Ser Gln Pro Leu Glu Gln Tyr Ser Pro Ser Tyr Pro
                770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
                820

<210> SEQ ID NO 60
<211> LENGTH: 822
<212> TYPE: PRT
<213> ORGANISM: Homo sapiens

<400> SEQUENCE: 60

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
                35                  40                  45

Val Tyr Val Ala Ala Pro Gly Glu Ser Leu Glu Val Arg Cys Leu Leu
                50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

```
Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
        210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
```

515                 520                 525
Leu Ser Asp Leu Val Ser Glu Met Glu Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820

<210> SEQ ID NO 61
<211> LENGTH: 769
<212> TYPE: PRT
<213> ORGANISM: Homo sapiens

<400> SEQUENCE: 61

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

-continued

```
Lys Asp Ala Ala Val Ile Ser Trp Thr Lys Asp Gly Val His Leu Gly
 65                  70                  75                  80

Pro Asn Asn Arg Thr Val Leu Ile Gly Glu Tyr Leu Gln Ile Lys Gly
                 85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
```

```
                    485                 490                 495
Val Met Ala Glu Ala Val Gly Ile Asp Lys Asp Lys Pro Lys Glu Ala
                500                 505                 510

Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
        530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Ile

<210> SEQ ID NO 62
<211> LENGTH: 709
<212> TYPE: PRT
<213> ORGANISM: Homo sapiens

<400> SEQUENCE: 62

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
```

-continued

```
                85                  90                  95
Ala Thr Pro Arg Asp Ser Gly Leu Tyr Ala Cys Thr Ala Ser Arg Thr
            100                 105                 110
Val Asp Ser Glu Thr Trp Tyr Phe Met Val Asn Val Thr Asp Ala Ile
        115                 120                 125
Ser Ser Gly Asp Asp Glu Asp Thr Asp Gly Ala Glu Asp Phe Val
    130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
        195                 200                 205
Val Arg Asn Gln His Trp Ser Leu Ile Met Glu Ser Val Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Ala Pro Gly Arg Glu Lys Glu
                245                 250                 255
Ile Thr Ala Ser Pro Asp Tyr Leu Glu Ile Ala Ile Tyr Cys Ile Gly
            260                 265                 270
Val Phe Leu Ile Ala Cys Met Val Val Thr Val Ile Leu Cys Arg Met
        275                 280                 285
Lys Asn Thr Thr Lys Lys Pro Asp Phe Ser Ser Gln Pro Ala Val His
    290                 295                 300
Lys Leu Thr Lys Arg Ile Pro Leu Arg Arg Gln Val Thr Val Ser Ala
305                 310                 315                 320
Glu Ser Ser Ser Ser Met Asn Ser Asn Thr Pro Leu Val Arg Ile Thr
                325                 330                 335
Thr Arg Leu Ser Ser Thr Ala Asp Thr Pro Met Leu Ala Gly Val Ser
            340                 345                 350
Glu Tyr Glu Leu Pro Glu Asp Pro Lys Trp Glu Phe Pro Arg Asp Lys
        355                 360                 365
Leu Thr Leu Gly Lys Pro Leu Gly Glu Gly Cys Phe Gly Gln Val Val
    370                 375                 380
Met Ala Glu Ala Val Gly Ile Asp Lys Asp Lys Pro Lys Glu Ala Val
385                 390                 395                 400
Thr Val Ala Val Lys Met Leu Lys Asp Asp Ala Thr Glu Lys Asp Leu
                405                 410                 415
Ser Asp Leu Val Ser Glu Met Glu Met Met Lys Met Ile Gly Lys His
            420                 425                 430
Lys Asn Ile Ile Asn Leu Leu Gly Ala Cys Thr Gln Asp Gly Pro Leu
        435                 440                 445
Tyr Val Ile Val Glu Tyr Ala Ser Lys Gly Asn Leu Arg Glu Tyr Leu
    450                 455                 460
Arg Ala Arg Arg Pro Pro Gly Met Glu Tyr Ser Tyr Asp Ile Asn Arg
465                 470                 475                 480
Val Pro Glu Glu Gln Met Thr Phe Lys Asp Leu Val Ser Cys Thr Tyr
                485                 490                 495
Gln Leu Ala Arg Gly Met Glu Tyr Leu Ala Ser Gln Lys Cys Ile His
            500                 505                 510
```

-continued

Arg Asp Leu Ala Ala Arg Asn Val Leu Val Thr Glu Asn Asn Val Met
        515                 520                 525

Lys Ile Ala Asp Phe Gly Leu Ala Arg Asp Ile Asn Asn Ile Asp Tyr
    530                 535                 540

Tyr Lys Lys Thr Thr Asn Gly Arg Leu Pro Val Lys Trp Met Ala Pro
545                 550                 555                 560

Glu Ala Leu Phe Asp Arg Val Tyr Thr His Gln Ser Asp Val Trp Ser
                565                 570                 575

Phe Gly Val Leu Met Trp Glu Ile Phe Thr Leu Gly Gly Ser Pro Tyr
            580                 585                 590

Pro Gly Ile Pro Val Glu Glu Leu Phe Lys Leu Lys Glu Gly His
        595                 600                 605

Arg Met Asp Lys Pro Ala Asn Cys Thr Asn Glu Leu Tyr Met Met Met
    610                 615                 620

Arg Asp Cys Trp His Ala Val Pro Ser Gln Arg Pro Thr Phe Lys Gln
625                 630                 635                 640

Leu Val Glu Asp Leu Asp Arg Ile Leu Thr Leu Thr Asn Glu Glu
                645                 650                 655

Tyr Leu Asp Leu Ser Gln Pro Leu Glu Gln Tyr Ser Pro Ser Tyr Pro
            660                 665                 670

Asp Thr Arg Ser Ser Cys Ser Ser Gly Asp Asp Ser Val Phe Ser Pro
        675                 680                 685

Asp Pro Met Pro Tyr Glu Pro Cys Leu Pro Gln Tyr Pro His Ile Asn
    690                 695                 700

Gly Ser Val Lys Thr
705

<210> SEQ ID NO 63
<211> LENGTH: 707
<212> TYPE: PRT
<213> ORGANISM: Homo sapiens

<400> SEQUENCE: 63

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Thr
        35                  40                  45

Asp Gly Ala Glu Asp Phe Val Ser Glu Asn Ser Asn Asn Lys Arg Ala
    50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn

```
                        165                 170                 175
Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
            195                 200                 205

Gly Ser Lys Tyr Gly Pro Asp Gly Leu Pro Tyr Leu Lys Val Leu Lys
            210                 215                 220

Ala Ala Gly Val Asn Thr Thr Asp Lys Glu Ile Glu Val Leu Tyr Ile
225                 230                 235                 240

Arg Asn Val Thr Phe Glu Asp Ala Gly Glu Tyr Thr Cys Leu Ala Gly
                245                 250                 255

Asn Ser Ile Gly Ile Ser Phe His Ser Ala Trp Leu Thr Val Leu Pro
                260                 265                 270

Ala Pro Gly Arg Glu Lys Glu Ile Thr Ala Ser Pro Asp Tyr Leu Glu
                275                 280                 285

Ile Ala Ile Tyr Cys Ile Gly Val Phe Leu Ile Ala Cys Met Val Val
                290                 295                 300

Thr Val Ile Leu Cys Arg Met Lys Asn Thr Thr Lys Lys Pro Asp Phe
305                 310                 315                 320

Ser Ser Gln Pro Ala Val His Lys Leu Thr Lys Arg Ile Pro Leu Arg
                325                 330                 335

Arg Gln Val Thr Val Ser Ala Glu Ser Ser Ser Ser Met Asn Ser Asn
                340                 345                 350

Thr Pro Leu Val Arg Ile Thr Thr Arg Leu Ser Ser Thr Ala Asp Thr
                355                 360                 365

Pro Met Leu Ala Gly Val Ser Glu Tyr Glu Leu Pro Glu Asp Pro Lys
            370                 375                 380

Trp Glu Phe Pro Arg Asp Lys Leu Thr Leu Gly Lys Pro Leu Gly Glu
385                 390                 395                 400

Gly Cys Phe Gly Gln Val Val Met Ala Glu Ala Val Gly Ile Asp Lys
                405                 410                 415

Asp Lys Pro Lys Glu Ala Val Thr Val Ala Val Lys Met Leu Lys Asp
                420                 425                 430

Asp Ala Thr Glu Lys Asp Leu Ser Asp Leu Val Ser Glu Met Glu Met
            435                 440                 445

Met Lys Met Ile Gly Lys His Lys Asn Ile Ile Asn Leu Leu Gly Ala
            450                 455                 460

Cys Thr Gln Asp Gly Pro Leu Tyr Val Ile Val Glu Tyr Ala Ser Lys
465                 470                 475                 480

Gly Asn Leu Arg Glu Tyr Leu Arg Ala Arg Arg Pro Pro Gly Met Glu
                485                 490                 495

Tyr Ser Tyr Asp Ile Asn Arg Val Pro Glu Glu Gln Met Thr Phe Lys
                500                 505                 510

Asp Leu Val Ser Cys Thr Tyr Gln Leu Ala Arg Gly Met Glu Tyr Leu
                515                 520                 525

Ala Ser Gln Lys Cys Ile His Arg Asp Leu Ala Ala Arg Asn Val Leu
            530                 535                 540

Val Thr Glu Asn Asn Val Met Lys Ile Ala Asp Phe Gly Leu Ala Arg
545                 550                 555                 560

Asp Ile Asn Asn Ile Asp Tyr Tyr Lys Lys Thr Thr Asn Gly Arg Leu
                565                 570                 575

Pro Val Lys Trp Met Ala Pro Glu Ala Leu Phe Asp Arg Val Tyr Thr
                580                 585                 590
```

His Gln Ser Asp Val Trp Ser Phe Gly Val Leu Met Trp Glu Ile Phe
    595                 600                 605

Thr Leu Gly Gly Ser Pro Tyr Pro Gly Ile Pro Val Glu Glu Leu Phe
    610                 615                 620

Lys Leu Lys Glu Gly His Arg Met Asp Lys Pro Ala Asn Cys Thr
625                 630                 635                 640

Asn Glu Leu Tyr Met Met Met Arg Asp Cys Trp His Ala Val Pro Ser
                645                 650                 655

Gln Arg Pro Thr Phe Lys Gln Leu Val Glu Asp Leu Asp Arg Ile Leu
                660                 665                 670

Thr Leu Thr Thr Asn Glu Glu Lys Lys Val Ser Gly Ala Val Asp
    675                 680                 685

Cys His Lys Pro Pro Cys Asn Pro Ser His Leu Pro Cys Val Leu Ala
    690                 695                 700

Val Asp Gln
705

<210> SEQ ID NO 64
<211> LENGTH: 706
<212> TYPE: PRT
<213> ORGANISM: Homo sapiens

<400> SEQUENCE: 64

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
            35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys Ala Ala Gly Val Asn Thr Thr Asp Lys Glu
        195                 200                 205

Ile Glu Val Leu Tyr Ile Arg Asn Val Thr Phe Glu Asp Ala Gly Glu
    210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala

```
                    245                 250                 255
Ser Pro Asp Tyr Leu Glu Ile Ala Ile Tyr Cys Ile Gly Val Phe Leu
                260                 265                 270
Ile Ala Cys Met Val Val Thr Val Ile Leu Cys Arg Met Lys Asn Thr
                275                 280                 285
Thr Lys Lys Pro Asp Phe Ser Ser Gln Pro Ala Val His Lys Leu Thr
            290                 295                 300
Lys Arg Ile Pro Leu Arg Arg Gln Val Thr Val Ser Ala Glu Ser Ser
305                 310                 315                 320
Ser Ser Met Asn Ser Asn Thr Pro Leu Val Arg Ile Thr Thr Arg Leu
                325                 330                 335
Ser Ser Thr Ala Asp Thr Pro Met Leu Ala Gly Val Ser Glu Tyr Glu
                340                 345                 350
Leu Pro Glu Asp Pro Lys Trp Glu Phe Pro Arg Asp Lys Leu Thr Leu
                355                 360                 365
Gly Lys Pro Leu Gly Glu Gly Cys Phe Gly Gln Val Val Met Ala Glu
            370                 375                 380
Ala Val Gly Ile Asp Lys Asp Lys Pro Lys Glu Ala Val Thr Val Ala
385                 390                 395                 400
Val Lys Met Leu Lys Asp Asp Ala Thr Glu Lys Asp Leu Ser Asp Leu
                405                 410                 415
Val Ser Glu Met Glu Met Met Lys Met Ile Gly Lys His Lys Asn Ile
                420                 425                 430
Ile Asn Leu Leu Gly Ala Cys Thr Gln Asp Gly Pro Leu Tyr Val Ile
                435                 440                 445
Val Glu Tyr Ala Ser Lys Gly Asn Leu Arg Glu Tyr Leu Arg Ala Arg
            450                 455                 460
Arg Pro Pro Gly Met Glu Tyr Ser Tyr Asp Ile Asn Arg Val Pro Glu
465                 470                 475                 480
Glu Gln Met Thr Phe Lys Asp Leu Val Ser Cys Thr Tyr Gln Leu Ala
                485                 490                 495
Arg Gly Met Glu Tyr Leu Ala Ser Gln Lys Cys Ile His Arg Asp Leu
                500                 505                 510
Ala Ala Arg Asn Val Leu Val Thr Glu Asn Asn Val Met Lys Ile Ala
            515                 520                 525
Asp Phe Gly Leu Ala Arg Asp Ile Asn Asn Ile Asp Tyr Tyr Lys Lys
            530                 535                 540
Thr Thr Asn Gly Arg Leu Pro Val Lys Trp Met Ala Pro Glu Ala Leu
545                 550                 555                 560
Phe Asp Arg Val Tyr Thr His Gln Ser Asp Val Trp Ser Phe Gly Val
                565                 570                 575
Leu Met Trp Glu Ile Phe Thr Leu Gly Gly Ser Pro Tyr Pro Gly Ile
                580                 585                 590
Pro Val Glu Glu Leu Phe Lys Leu Leu Lys Glu Gly His Arg Met Asp
                595                 600                 605
Lys Pro Ala Asn Cys Thr Asn Glu Leu Tyr Met Met Met Arg Asp Cys
            610                 615                 620
Trp His Ala Val Pro Ser Gln Arg Pro Thr Phe Lys Gln Leu Val Glu
625                 630                 635                 640
Asp Leu Asp Arg Ile Leu Thr Leu Thr Thr Asn Glu Glu Tyr Leu Asp
                645                 650                 655
Leu Ser Gln Pro Leu Glu Gln Tyr Ser Pro Ser Tyr Pro Asp Thr Arg
                660                 665                 670
```

Ser Ser Cys Ser Ser Gly Asp Asp Ser Val Phe Ser Pro Asp Pro Met
            675                 680                 685

Pro Tyr Glu Pro Cys Leu Pro Gln Tyr Pro His Ile Asn Gly Ser Val
        690                 695                 700

Lys Thr
705

<210> SEQ ID NO 65
<211> LENGTH: 705
<212> TYPE: PRT
<213> ORGANISM: Homo sapiens

<400> SEQUENCE: 65

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Ser Ala Glu Ser Ser Ser
305                 310                 315                 320

Ser Met Asn Ser Asn Thr Pro Leu Val Arg Ile Thr Thr Arg Leu Ser

```
            325                 330                 335
Ser Thr Ala Asp Thr Pro Met Leu Ala Gly Val Ser Glu Tyr Glu Leu
            340                 345                 350
Pro Glu Asp Pro Lys Trp Glu Phe Pro Arg Asp Lys Leu Thr Leu Gly
            355                 360                 365
Lys Pro Leu Gly Glu Gly Cys Phe Gly Gln Val Val Met Ala Glu Ala
            370                 375                 380
Val Gly Ile Asp Lys Asp Lys Pro Lys Glu Ala Val Thr Val Ala Val
385                 390                 395                 400
Lys Met Leu Lys Asp Asp Ala Thr Glu Lys Asp Leu Ser Asp Leu Val
            405                 410                 415
Ser Glu Met Glu Met Met Lys Met Ile Gly Lys His Lys Asn Ile Ile
            420                 425                 430
Asn Leu Leu Gly Ala Cys Thr Gln Asp Gly Pro Leu Tyr Val Ile Val
            435                 440                 445
Glu Tyr Ala Ser Lys Gly Asn Leu Arg Glu Tyr Leu Arg Ala Arg Arg
            450                 455                 460
Pro Pro Gly Met Glu Tyr Ser Tyr Asp Ile Asn Arg Val Pro Glu Glu
465                 470                 475                 480
Gln Met Thr Phe Lys Asp Leu Val Ser Cys Thr Tyr Gln Leu Ala Arg
            485                 490                 495
Gly Met Glu Tyr Leu Ala Ser Gln Lys Cys Ile His Arg Asp Leu Ala
            500                 505                 510
Ala Arg Asn Val Leu Val Thr Glu Asn Asn Val Met Lys Ile Ala Asp
            515                 520                 525
Phe Gly Leu Ala Arg Asp Ile Asn Asn Ile Asp Tyr Tyr Lys Lys Thr
            530                 535                 540
Thr Asn Gly Arg Leu Pro Val Lys Trp Met Ala Pro Glu Ala Leu Phe
545                 550                 555                 560
Asp Arg Val Tyr Thr His Gln Ser Asp Val Trp Ser Phe Gly Val Leu
            565                 570                 575
Met Trp Glu Ile Phe Thr Leu Gly Gly Ser Pro Tyr Pro Gly Ile Pro
            580                 585                 590
Val Glu Glu Leu Phe Lys Leu Leu Lys Glu Gly His Arg Met Asp Lys
            595                 600                 605
Pro Ala Asn Cys Thr Asn Glu Leu Tyr Met Met Met Arg Asp Cys Trp
            610                 615                 620
His Ala Val Pro Ser Gln Arg Pro Thr Phe Lys Gln Leu Val Glu Asp
625                 630                 635                 640
Leu Asp Arg Ile Leu Thr Leu Thr Thr Asn Glu Glu Tyr Leu Asp Leu
            645                 650                 655
Ser Gln Pro Leu Glu Gln Tyr Ser Pro Ser Tyr Pro Asp Thr Arg Ser
            660                 665                 670
Ser Cys Ser Ser Gly Asp Asp Ser Val Phe Ser Pro Asp Pro Met Pro
            675                 680                 685
Tyr Glu Pro Cys Leu Pro Gln Tyr Pro His Ile Asn Gly Ser Val Lys
            690                 695                 700
Thr
705

<210> SEQ ID NO 66
<211> LENGTH: 704
<212> TYPE: PRT
<213> ORGANISM: Homo sapiens
```

<400> SEQUENCE: 66

| | | | | | | | | | | | | | | |
|---|---|---|---|---|---|---|---|---|---|---|---|---|---|---|
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
            85                  90                  95

Gln His Trp Ser Leu Ile Met Glu Ser Val Val Pro Ser Asp Lys Gly
        100                 105                 110

Asn Tyr Thr Cys Val Val Glu Asn Glu Tyr Gly Ser Ile Asn His Thr
    115                 120                 125

Tyr His Leu Asp Val Val Glu Arg Ser Pro His Arg Pro Ile Leu Gln
130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
            165                 170                 175

Lys His Val Glu Lys Asn Gly Ser Lys Tyr Gly Pro Asp Gly Leu Pro
        180                 185                 190

Tyr Leu Lys Val Leu Lys Ala Ala Gly Val Asn Thr Thr Asp Lys Glu
    195                 200                 205

Ile Glu Val Leu Tyr Ile Arg Asn Val Thr Phe Glu Asp Ala Gly Glu
210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
            245                 250                 255

Ser Pro Asp Tyr Leu Glu Ile Ala Ile Tyr Cys Ile Gly Val Phe Leu
        260                 265                 270

Ile Ala Cys Met Val Val Thr Val Ile Leu Cys Arg Met Lys Asn Thr
    275                 280                 285

Thr Lys Lys Pro Asp Phe Ser Ser Gln Pro Ala Val His Lys Leu Thr
290                 295                 300

Lys Arg Ile Pro Leu Arg Arg Gln Val Ser Ala Glu Ser Ser Ser Ser
305                 310                 315                 320

Met Asn Ser Asn Thr Pro Leu Val Arg Ile Thr Thr Arg Leu Ser Ser
            325                 330                 335

Thr Ala Asp Thr Pro Met Leu Ala Gly Val Ser Glu Tyr Glu Leu Pro
        340                 345                 350

Glu Asp Pro Lys Trp Glu Phe Pro Arg Asp Lys Leu Thr Leu Gly Lys
    355                 360                 365

Pro Leu Gly Glu Gly Cys Phe Gly Gln Val Val Met Ala Glu Ala Val
370                 375                 380

Gly Ile Asp Lys Asp Lys Pro Lys Glu Ala Val Thr Val Ala Val Lys
385                 390                 395                 400

Met Leu Lys Asp Asp Ala Thr Glu Lys Asp Leu Ser Asp Leu Val Ser 405                 410                 415
Glu Met Glu Met Met Lys Met Ile Gly Lys His Lys Asn Ile Ile Asn
                420                 425                 430
Leu Leu Gly Ala Cys Thr Gln Asp Gly Pro Leu Tyr Val Ile Val Glu
            435                 440                 445
Tyr Ala Ser Lys Gly Asn Leu Arg Glu Tyr Leu Arg Ala Arg Arg Pro
        450                 455                 460
Pro Gly Met Glu Tyr Ser Tyr Asp Ile Asn Arg Val Pro Glu Glu Gln
465                 470                 475                 480
Met Thr Phe Lys Asp Leu Val Ser Cys Thr Tyr Gln Leu Ala Arg Gly
                485                 490                 495
Met Glu Tyr Leu Ala Ser Gln Lys Cys Ile His Arg Asp Leu Ala Ala
                500                 505                 510
Arg Asn Val Leu Val Thr Glu Asn Asn Val Met Lys Ile Ala Asp Phe
            515                 520                 525
Gly Leu Ala Arg Asp Ile Asn Asn Ile Asp Tyr Tyr Lys Lys Thr Thr
        530                 535                 540
Asn Gly Arg Leu Pro Val Lys Trp Met Ala Pro Glu Ala Leu Phe Asp
545                 550                 555                 560
Arg Val Tyr Thr His Gln Ser Asp Val Trp Ser Phe Gly Val Leu Met
                565                 570                 575
Trp Glu Ile Phe Thr Leu Gly Gly Ser Pro Tyr Pro Gly Ile Pro Val
                580                 585                 590
Glu Glu Leu Phe Lys Leu Leu Lys Glu Gly His Arg Met Asp Lys Pro
            595                 600                 605
Ala Asn Cys Thr Asn Glu Leu Tyr Met Met Met Arg Asp Cys Trp His
        610                 615                 620
Ala Val Pro Ser Gln Arg Pro Thr Phe Lys Gln Leu Val Glu Asp Leu
625                 630                 635                 640
Asp Arg Ile Leu Thr Leu Thr Thr Asn Glu Glu Tyr Leu Asp Leu Ser
                645                 650                 655
Gln Pro Leu Glu Gln Tyr Ser Pro Ser Tyr Pro Asp Thr Arg Ser Ser
                660                 665                 670
Cys Ser Ser Gly Asp Asp Ser Val Phe Ser Pro Asp Pro Met Pro Tyr
            675                 680                 685
Glu Pro Cys Leu Pro Gln Tyr Pro His Ile Asn Gly Ser Val Lys Thr
        690                 695                 700

<210> SEQ ID NO 67
<211> LENGTH: 680
<212> TYPE: PRT
<213> ORGANISM: Homo sapiens

<400> SEQUENCE: 67

Met Val Ser Trp Gly Arg Phe Ile Cys Leu Val Val Val Thr Met Ala
1               5                   10                  15
Thr Leu Ser Leu Ala Arg Pro Ser Phe Ser Leu Val Glu Asp Thr Thr
                20                  25                  30
Leu Glu Pro Glu Asp Ala Ile Ser Ser Gly Asp Asp Glu Asp Asp Thr
            35                  40                  45
Asp Gly Ala Glu Asp Phe Val Ser Glu Asn Ser Asn Asn Lys Arg Ala
        50                  55                  60
Pro Tyr Trp Thr Asn Thr Glu Lys Met Glu Lys Arg Leu His Ala Val
65                  70                  75                  80

```
Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
        195                 200                 205

Gly Ser Lys Tyr Gly Pro Asp Gly Leu Pro Tyr Leu Lys Val Leu Lys
    210                 215                 220

His Ser Gly Ile Asn Ser Ser Asn Ala Glu Val Leu Ala Leu Phe Asn
225                 230                 235                 240

Val Thr Glu Ala Asp Ala Gly Glu Tyr Ile Cys Lys Val Ser Asn Tyr
                245                 250                 255

Ile Gly Gln Ala Asn Gln Ser Ala Trp Leu Thr Val Leu Pro Lys Gln
            260                 265                 270

Gln Ala Pro Gly Arg Glu Lys Glu Ile Thr Ala Ser Pro Asp Tyr Leu
        275                 280                 285

Glu Ile Ala Ile Tyr Cys Ile Gly Val Phe Leu Ile Ala Cys Met Val
    290                 295                 300

Val Thr Val Ile Leu Cys Arg Met Lys Asn Thr Thr Lys Lys Pro Asp
305                 310                 315                 320

Phe Ser Ser Gln Pro Ala Val His Lys Leu Thr Lys Arg Ile Pro Leu
                325                 330                 335

Arg Arg Gln Val Thr Val Ser Ala Glu Ser Ser Ser Ser Met Asn Ser
            340                 345                 350

Asn Thr Pro Leu Val Arg Ile Thr Thr Arg Leu Ser Ser Thr Ala Asp
        355                 360                 365

Thr Pro Met Leu Ala Gly Val Ser Glu Tyr Glu Leu Pro Glu Asp Pro
    370                 375                 380

Lys Trp Glu Phe Pro Arg Asp Lys Leu Thr Leu Gly Lys Pro Leu Gly
385                 390                 395                 400

Glu Gly Cys Phe Gly Gln Val Val Met Ala Glu Ala Val Gly Ile Asp
                405                 410                 415

Lys Asp Lys Pro Lys Glu Ala Val Thr Val Ala Val Lys Met Leu Lys
            420                 425                 430

Asp Asp Ala Thr Glu Lys Asp Leu Ser Asp Leu Val Ser Glu Met Glu
        435                 440                 445

Met Met Lys Met Ile Gly Lys His Lys Asn Ile Ile Asn Leu Leu Gly
    450                 455                 460

Ala Cys Thr Gln Asp Gly Pro Leu Tyr Val Ile Val Glu Tyr Ala Ser
465                 470                 475                 480

Lys Gly Asn Leu Arg Glu Tyr Leu Arg Ala Arg Arg Pro Pro Gly Met
                485                 490                 495

Glu Tyr Ser Tyr Asp Ile Asn Arg Val Pro Glu Glu Gln Met Thr Phe
```

```
                500             505             510
Lys Asp Leu Val Ser Cys Thr Tyr Gln Leu Ala Arg Gly Met Glu Tyr
        515                 520                 525

Leu Ala Ser Gln Lys Cys Ile His Arg Asp Leu Ala Ala Arg Asn Val
        530                 535                 540

Leu Val Thr Glu Asn Asn Val Met Lys Ile Ala Asp Phe Gly Leu Ala
545                 550                 555                 560

Arg Asp Ile Asn Asn Ile Asp Tyr Tyr Lys Lys Thr Thr Asn Gly Arg
                565                 570                 575

Leu Pro Val Lys Trp Met Ala Pro Glu Ala Leu Phe Asp Arg Val Tyr
                580                 585                 590

Thr His Gln Ser Asp Val Trp Ser Phe Gly Val Leu Met Trp Glu Ile
        595                 600                 605

Phe Thr Leu Gly Gly Ser Pro Tyr Pro Gly Ile Pro Val Glu Glu Leu
        610                 615                 620

Phe Lys Leu Leu Lys Glu Gly His Arg Met Asp Lys Pro Ala Asn Cys
625                 630                 635                 640

Thr Asn Glu Leu Tyr Met Met Met Arg Asp Cys Trp His Ala Val Pro
                645                 650                 655

Ser Gln Arg Pro Thr Phe Lys Gln Leu Val Glu Asp Leu Asp Arg Ile
                660                 665                 670

Leu Thr Leu Thr Thr Asn Glu Ile
        675                 680

<210> SEQ ID NO 68
<211> LENGTH: 396
<212> TYPE: PRT
<213> ORGANISM: Homo sapiens

<400> SEQUENCE: 68

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Thr Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190
```

```
Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Gly Ile Tyr Cys Ser Phe Ser
            355                 360                 365

Leu Gly Phe Phe Pro Phe Ser Trp Leu Thr Ala Ile Lys Leu Thr Gln
            370                 375                 380

Leu Leu Leu Ser Glu Met Ala Pro Phe Ile Leu Ala
385                 390                 395

<210> SEQ ID NO 69
<211> LENGTH: 317
<212> TYPE: PRT
<213> ORGANISM: Homo sapiens

<400> SEQUENCE: 69

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175
```

```
Phe Arg Cys Pro Ala Gly Gly Asn Pro Met Pro Thr Met Arg Trp Leu
                180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
        210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
        290                 295                 300

Gly Leu Pro Tyr Leu Lys Val Leu Lys Val Arg Thr Phe
305                 310                 315

<210> SEQ ID NO 70
<211> LENGTH: 266
<212> TYPE: PRT
<213> ORGANISM: Homo sapiens

<400> SEQUENCE: 70

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
```

Asn His Thr Tyr His Leu Asp Val Val Gly Glu Ser Ala Ser Pro Arg
225                 230                 235                 240

Val Ala Ala Ala Tyr Gln Pro Ile Leu Ala
            245                 250                 255

<210> SEQ ID NO 71
<211> LENGTH: 336
<212> TYPE: DNA
<213> ORGANISM: Mus musculus

<400> SEQUENCE: 71
caggtgaagc tgcaggagtc tggcgctgag ttggtgaaac ctggggcttc agtgaagata        60
tcctgcaagg cttctggcta catcttcact gaccatgctc ttcactgggt gaggcagaag       120
cctgaacagg gcctggaatg gattgggtat attttttccg aaatggtaa tattgagtac        180 aatgagaagt tcaagggcaa ggccacactg actgcagaca atcctccag tactgcctac        240 atgcagctca acagcctgac atctgaggat tctgcaatgt atttctgtaa aaagatggac       300
tactggggcc aagggaccac ggtcaccgtc tcctca                                  336

<210> SEQ ID NO 72
<211> LENGTH: 111
<212> TYPE: PRT
<213> ORGANISM: Mus musculus

<400> SEQUENCE: 72

Val Lys Leu Gln Glu Ser Gly Ala Glu Leu Val Lys Pro Gly Ala Ser
1               5                   10                  15

Val Lys Ile Ser Cys Lys Ala Ser Gly Tyr Ile Phe Thr Asp His Ala
            20                  25                  30

Leu His Trp Val Arg Gln Lys Pro Glu Gln Gly Leu Glu Trp Ile Gly
        35                  40                  45

Tyr Ile Phe Pro Gly Asn Gly Asn Ile Glu Tyr Asn Glu Lys Phe Lys
    50                  55                  60

Gly Lys Ala Thr Leu Thr Ala Asp Lys Ser Ser Ser Thr Ala Tyr Met
65                  70                  75                  80

Gln Leu Asn Ser Leu Thr Ser Gly Asp Ser Ala Met Tyr Phe Cys Lys
                85                  90                  95

Lys Met Asp Tyr Trp Gly Gln Gly Thr Thr Val Thr Val Ser Ser
            100                 105                 110

<210> SEQ ID NO 73
<211> LENGTH: 336
<212> TYPE: DNA
<213> ORGANISM: Mus musculus

<400> SEQUENCE: 73
caggtgaagc tgcaggagtc tggcgctgag ttggtgaaac ctggggcttc agtgaagatc        60
tcctgcaagg cttctggtta caccttcact gaccattcta ttcactgggt gaagcagaag       120
cctggacagg gcctagaatg gattggatat ctttttcccg aaatggtaa tttgaatat         180 aatgagaaat tcaagggcaa ggccacactg actgcagaca atcctccag cactgcctac        240 atgcacctca acagcctgac atctgaggat tctgcagtgt atttctgtaa aaagatggac       300
tactggggcc aagggaccac ggtcaccgtc tcctca                                  336

<210> SEQ ID NO 74

<211> LENGTH: 111
<212> TYPE: PRT
<213> ORGANISM: Mus musculus

<400> SEQUENCE: 74

```
Val Lys Leu Gln Glu Ser Gly Ala Glu Leu Val Lys Pro Gly Ala Ser
1               5                   10                  15

Val Lys Ile Ser Cys Lys Ala Ser Gly Tyr Thr Phe Thr Asp His Ser
            20                  25                  30

Ile His Trp Val Lys Gln Lys Pro Gly Gln Gly Leu Glu Trp Ile Gly
        35                  40                  45

Tyr Leu Phe Pro Gly Asn Gly Asn Phe Glu Tyr Asn Glu Lys Phe Lys
    50                  55                  60

Gly Lys Ala Thr Leu Thr Ala Asp Lys Ser Ser Thr Ala Tyr Met
65                  70                  75                  80

His Leu Asn Ser Leu Thr Ser Glu Asp Ser Ala Val Tyr Phe Cys Lys
                85                  90                  95

Lys Met Asp Tyr Trp Gly Gln Gly Thr Thr Val Thr Val Ser Ser
            100                 105                 110
```

<210> SEQ ID NO 75
<211> LENGTH: 336
<212> TYPE: DNA
<213> ORGANISM: Mus musculus

<400> SEQUENCE: 75

```
caggttcagc tgcagcagtc cgacgctgag ttggtgaaac ctggggcttc agtgaagata      60
tcctgcaggg cttctggcta caccttcact gaccattcta ttcactgggt gaagcagcag     120
cctggccagg gcctggaatg gatcggatat attttcccg gaaatggaaa tattgaatac      180
aatgacaaat tcaagggcaa ggccacactg actcagaca aatcctccgg cactgcctac      240
atgcagctca acagcctgac atctgaggat tctgcagtgt atttctgtaa aaggatgggg     300
tactggggtc aaggaacctc agtcaccgtc tcctca                              336
```

<210> SEQ ID NO 76
<211> LENGTH: 111
<212> TYPE: PRT
<213> ORGANISM: Mus musculus

<400> SEQUENCE: 76

```
Val Gln Leu Gln Gln Ser Asp Ala Glu Leu Val Lys Pro Gly Ala Ser
1               5                   10                  15

Val Lys Ile Ser Cys Arg Ala Ser Gly Tyr Thr Phe Thr Asp His Ser
            20                  25                  30

Ile His Trp Val Lys Gln Gln Pro Gly Gln Gly Leu Glu Trp Ile Gly
        35                  40                  45

Tyr Ile Phe Pro Gly Asn Gly Asn Ile Glu Tyr Asn Asp Lys Phe Lys
    50                  55                  60

Gly Lys Ala Thr Leu Thr Ala Asp Lys Ser Ser Gly Thr Ala Tyr Met
65                  70                  75                  80

Gln Leu Asn Ser Leu Thr Ser Glu Asp Ser Ala Val Tyr Phe Cys Lys
                85                  90                  95

Arg Met Gly Tyr Trp Gly Gln Gly Thr Ser Val Thr Val Ser Ser
            100                 105                 110
```

<210> SEQ ID NO 77
<211> LENGTH: 360

```
<212> TYPE: DNA
<213> ORGANISM: Mus musculus

<400> SEQUENCE: 77
caggtcaagc tgcaggagtc tggacctgaa ctggtaaagc ctggggcttc agtgaagatg      60
tcctgcaagg cttctggata cacattcact aactatgtta tacactgggt gaagcaaaag     120
cctgggcagg gccttgagtg gattggatat attaatcctt acaatgatgg ctctaagtac     180
aatgagaagt tcaaaggcaa ggcctcactg acttcagaca atcctccag cacagcctac      240 atggagctca gcagcctgac ctctgaggac tctgcggtct attactgtgc aagacatctc     300
gctaatacct actactactt tgactactgg ggccaaggga ccacggtcac cgtctcctca     360

<210> SEQ ID NO 78
<211> LENGTH: 119
<212> TYPE: PRT
<213> ORGANISM: Mus musculus

<400> SEQUENCE: 78

Val Lys Leu Gln Glu Ser Gly Pro Glu Leu Val Lys Pro Gly Ala Ser
1               5                   10                  15

Val Lys Met Ser Cys Lys Ala Ser Gly Tyr Thr Phe Thr Asn Tyr Val
            20                  25                  30

Ile His Trp Val Lys Gln Lys Pro Gly Gln Gly Leu Glu Trp Ile Gly
        35                  40                  45

Tyr Ile Asn Pro Tyr Asn Asp Gly Ser Lys Tyr Asn Glu Lys Phe Lys
    50                  55                  60

Gly Lys Ala Ser Leu Thr Ser Asp Lys Ser Ser Thr Ala Tyr Met
65                  70                  75                  80

Glu Leu Ser Ser Leu Thr Ser Glu Asp Ser Ala Val Tyr Tyr Cys Ala
                85                  90                  95

Arg His Leu Ala Asn Thr Tyr Tyr Tyr Phe Asp Tyr Trp Gly Gln Gly
            100                 105                 110

Thr Thr Val Thr Val Ser Ser
        115

<210> SEQ ID NO 79
<211> LENGTH: 336
<212> TYPE: DNA
<213> ORGANISM: Mus musculus

<400> SEQUENCE: 79
caggtcaagc tgcaggagtc tggcgctgag ttggtgaaac ctggggcttc agtgaagatc      60
tcctgcaagg cttctggcta caccttcact gaccattcta ttcactgggt gaagcagaag     120
cctggacagg gcctagaatg gattggatat cttttccccg gaaatggtaa ttttgagtac     180
aatgaaaaat tcaagggcaa ggccacactg actgcagaca atcctccag cactgtctac      240 atgtacctca cagcctgac atctgaggat tctgcagtgt atttctgtaa aaggatgggg      300
tactggggcc aagggaccac ggtcaccgtc tcctca                                336

<210> SEQ ID NO 80
<211> LENGTH: 111
<212> TYPE: PRT
<213> ORGANISM: Mus musculus

<400> SEQUENCE: 80

Val Lys Leu Gln Glu Ser Gly Ala Glu Leu Val Lys Pro Gly Ala Ser
1               5                   10                  15
```

Val Lys Ile Ser Cys Lys Ala Ser Gly Tyr Thr Phe Thr Asp His Ser
            20                  25                  30

Ile His Trp Val Lys Gln Lys Pro Gly Gln Gly Leu Glu Trp Ile Gly
        35                  40                  45

Tyr Leu Phe Pro Gly Asn Gly Asn Phe Glu Tyr Asn Glu Lys Phe Lys
    50                  55                  60

Gly Lys Ala Thr Leu Thr Ala Asp Lys Ser Ser Thr Val Tyr Met
65                  70                  75                  80

Tyr Leu Asn Ser Leu Thr Ser Glu Asp Ser Ala Val Tyr Phe Cys Lys
                85                  90                  95

Arg Met Gly Tyr Trp Gly Gln Gly Thr Thr Val Thr Val Ser Ser
            100                 105                 110

<210> SEQ ID NO 81
<211> LENGTH: 357
<212> TYPE: DNA
<213> ORGANISM: Mus musculus

<400> SEQUENCE: 81
gtgaagctgc aggagtctgg acctgaactg gtaaagcctg ggcttcagt gaagatgtcc      60 tgcaaggctt ctggatacac attcactaac tatgttatac actgggtgaa gcaaaagcct     120
gggcagggcc ttgagtggat tggatatatt aatccttaca atgatggctc taagtacaat     180
gagaagttca aggcaaggc ctcactgact tcagacaaat cctccagcac agcctacatg      240
gagctcagca gcctgacctc tgaggactct gcggtctatt actgtgcaag acatctcgct    300
aatacctact actactttga ctactggggc caaggcacca ctctcacagt ctcctca       357

<210> SEQ ID NO 82
<211> LENGTH: 120
<212> TYPE: PRT
<213> ORGANISM: Mus musculus

<400> SEQUENCE: 82

Gln Val Gln Leu Gln Glu Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ser Lys Tyr Asn Glu Lys Phe
    50                  55                  60

Lys Gly Lys Ala Ser Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg His Leu Ala Asn Thr Tyr Tyr Tyr Phe Asp Tyr Trp Gly Gln
            100                 105                 110

Gly Thr Thr Leu Thr Val Ser Ser
        115                 120

<210> SEQ ID NO 83
<211> LENGTH: 342
<212> TYPE: DNA
<213> ORGANISM: Mus musculus

<400> SEQUENCE: 83

```
gatgttttga tgacccaaac tccactctcc ctgcctgtca gtcttggaga tcaagcctcc    60
atctcttgca gatctagtca gagcattgta catagtaatg aaacaccta  tttagaatgg   120 tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcct   300
cctacgttcg gtgctgggac caagctggag ctgaaacggg ct                      342
```

<210> SEQ ID NO 84
<211> LENGTH: 113
<212> TYPE: PRT
<213> ORGANISM: Mus musculus

<400> SEQUENCE: 84

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Ala Gly Thr Lys Leu Glu Leu Lys
            100                 105                 110

Arg

<210> SEQ ID NO 85
<211> LENGTH: 324
<212> TYPE: DNA
<213> ORGANISM: Mus musculus

<400> SEQUENCE: 85

```
gacatccaga tgactcagtc tccagcctcc ctatctgcat ctgtgggaga aactgtcacc    60
atcacatgtc gaacaactga aaatatttac agttatttg  tatggtctca gcagagacag   120
ggaaaatctc ctcagctccg ggtctataat gcaaaatcct tagcagaagg tgtgccatca   180
agtttcaatg tcagtgtatc aggcacacag ttttctctga agatcaatag cctgcagcct   240
gaagattttg ggacttatca ctgtcaacac cattatggta ctccgtacac gttcggaggg   300
gggaccaggc tggaaataag acgg                                          324
```

<210> SEQ ID NO 86
<211> LENGTH: 108
<212> TYPE: PRT
<213> ORGANISM: Mus musculus

<400> SEQUENCE: 86

Asp Ile Gln Met Thr Gln Ser Pro Ala Ser Leu Ser Ala Ser Val Gly
1               5                   10                  15

Glu Thr Val Thr Ile Thr Cys Arg Thr Thr Glu Asn Ile Tyr Ser Tyr
            20                  25                  30

Phe Val Trp Ser Gln Gln Arg Gln Gly Lys Ser Pro Gln Leu Arg Val
        35                  40                  45

```
Tyr Asn Ala Lys Ser Leu Ala Glu Gly Val Pro Ser Ser Phe Asn Val
         50                  55                  60

Ser Val Ser Gly Thr Gln Phe Ser Leu Lys Ile Asn Ser Leu Gln Pro
 65                  70                  75                  80

Glu Asp Phe Gly Thr Tyr His Cys Gln His Tyr Gly Thr Pro Tyr
                 85                  90                  95

Thr Phe Gly Gly Gly Thr Arg Leu Glu Ile Arg Arg
            100                 105
```

<210> SEQ ID NO 87
<211> LENGTH: 336
<212> TYPE: DNA
<213> ORGANISM: Mus musculus

<400> SEQUENCE: 87

```
gacattgtgc tgacacagtc tcctgcttcc ttagctgtat ctctgggca gagggccacc      60
atctcgtaca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240
cctgtggagg aggaggatgc tgcaacctat tactgtcagc acattaggga gcttacacgt   300
tcggaggggg gcaccaagct ggaaatcaaa cggaga                             336
```

<210> SEQ ID NO 88
<211> LENGTH: 112
<212> TYPE: PRT
<213> ORGANISM: Mus musculus

<400> SEQUENCE: 88

```
Asp Ile Val Leu Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
                 20                  25                  30

Gly Tyr Ser Tyr Met His Trp Asn Gln Gln Lys Pro Gly Gln Pro Pro
             35                  40                  45

Arg Leu Leu Ile Tyr Leu Val Ser Asn Leu Glu Ser Gly Val Pro Ala
         50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Thr Lys Leu Glu Ile Lys Arg Arg
                100                 105                 110
```

<210> SEQ ID NO 89
<211> LENGTH: 327
<212> TYPE: DNA
<213> ORGANISM: Mus musculus

<400> SEQUENCE: 89

```
gacatcaaga tgacccagtc tccatcctcc atgtatgcat cgctgggaga gagagtcact      60
atcacttgca aggcgagtca ggacattaaa agctatttaa gctggtacca gcagaaacca   120
tggaaatctc ctaagaccct gatctattat gcaacaagct ggcagatgg ggtcccatca   180
agattcagtg gcagtggatc tgggcaagat tattctctaa ccatcagcag cctggagtct   240
gacgatacag caacttatta ctgtctacag catggtgaga gcccgtacac gttcggaggg   300
```

```
gggaccaagc tggaaataaa acgggct                                         327
```

<210> SEQ ID NO 90
<211> LENGTH: 108
<212> TYPE: PRT
<213> ORGANISM: Mus musculus

<400> SEQUENCE: 90

```
Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys Arg
            100                 105
```

<210> SEQ ID NO 91
<211> LENGTH: 327
<212> TYPE: DNA
<213> ORGANISM: Mus musculus

<400> SEQUENCE: 91

```
gatgttgtgc taactcagtc tcctgccacc ctgtctgtga ctccaggaga tagagtcagt    60
ctttcctgca gggccagcca aaatattggc aactacctac actggtatca acagaaatca   120
catgagtctc caaggcttct catcaagtat gcttcccagt ccatctctgg gatcccctcc   180
aggttcagtg gcagtggatc agtcacagat ttcactctca atatcaacag tgtggagact   240
gaagattttg gaatgtattt ctgtcaacag agtgacacct ggcctctcac gttcggtgct   300
gggaccaagc tggagctgaa acgggct                                       327
```

<210> SEQ ID NO 92
<211> LENGTH: 108
<212> TYPE: PRT
<213> ORGANISM: Mus musculus

<400> SEQUENCE: 92

```
Asp Val Val Leu Thr Gln Ser Pro Ala Thr Leu Ser Val Thr Pro Gly
 1               5                  10                  15

Asp Arg Val Ser Leu Ser Cys Arg Ala Ser Gln Asn Ile Gly Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Val Thr Asp Phe Thr Leu Asn Ile Asn Ser Val Glu Thr
65                  70                  75                  80

Glu Asp Phe Gly Met Tyr Phe Cys Gln Gln Ser Asp Thr Trp Pro Leu
                85                  90                  95

Thr Phe Gly Ala Gly Thr Lys Leu Glu Leu Lys Arg
            100                 105
```

```
               100             105

<210> SEQ ID NO 93
<211> LENGTH: 8
<212> TYPE: PRT
<213> ORGANISM: Mus musculus

<400> SEQUENCE: 93

Thr Phe Thr Asp His Ser Ile His
1               5

<210> SEQ ID NO 94
<211> LENGTH: 8
<212> TYPE: PRT
<213> ORGANISM: Mus musculus

<400> SEQUENCE: 94

Thr Phe Thr Asn Tyr Val Ile His
1               5

<210> SEQ ID NO 95
<211> LENGTH: 8
<212> TYPE: PRT
<213> ORGANISM: Mus musculus

<400> SEQUENCE: 95

Ile Phe Thr Asp His Ala Leu His
1               5

<210> SEQ ID NO 96
<211> LENGTH: 17
<212> TYPE: PRT
<213> ORGANISM: Mus musculus

<400> SEQUENCE: 96

Tyr Ile Phe Pro Gly Asn Gly Asn Ile Glu Tyr Asn Asp Lys Phe Lys
1               5                   10                  15

Gly

<210> SEQ ID NO 97
<211> LENGTH: 17
<212> TYPE: PRT
<213> ORGANISM: Mus musculus

<400> SEQUENCE: 97

Tyr Leu Phe Pro Gly Asn Gly Asn Phe Glu Tyr Asn Glu Lys Phe Lys
1               5                   10                  15

Gly

<210> SEQ ID NO 98
<211> LENGTH: 17
<212> TYPE: PRT
<213> ORGANISM: Mus musculus

<400> SEQUENCE: 98

Tyr Ile Asn Pro Tyr Asn Asp Gly Ser Lys Tyr Asn Glu Lys Phe Lys
1               5                   10                  15

Gly

<210> SEQ ID NO 99
<211> LENGTH: 17
<212> TYPE: PRT
<213> ORGANISM: Mus musculus
```

```
<400> SEQUENCE: 99

Tyr Ile Phe Pro Gly Asn Gly Asn Ile Glu Tyr Asn Glu Lys Phe Lys
1               5                   10                  15

Gly

<210> SEQ ID NO 100
<211> LENGTH: 5
<212> TYPE: PRT
<213> ORGANISM: Mus musculus

<400> SEQUENCE: 100

Lys Arg Met Gly Tyr
1               5

<210> SEQ ID NO 101
<211> LENGTH: 5
<212> TYPE: PRT
<213> ORGANISM: Mus musculus

<400> SEQUENCE: 101

Lys Lys Met Asp Tyr
1               5

<210> SEQ ID NO 102
<211> LENGTH: 13
<212> TYPE: PRT
<213> ORGANISM: Mus musculus

<400> SEQUENCE: 102

Ala Arg His Leu Ala Asn Thr Tyr Tyr Tyr Phe Asp Tyr
1               5                   10

<210> SEQ ID NO 103
<211> LENGTH: 16
<212> TYPE: PRT
<213> ORGANISM: Mus musculus

<400> SEQUENCE: 103

Arg Ser Ser Gln Ser Ile Val His Ser Asn Gly Asn Thr Tyr Leu Glu
1               5                   10                  15

<210> SEQ ID NO 104
<211> LENGTH: 11
<212> TYPE: PRT
<213> ORGANISM: Mus musculus

<400> SEQUENCE: 104

Arg Thr Thr Glu Asn Ile Tyr Ser Tyr Phe Val
1               5                   10

<210> SEQ ID NO 105
<211> LENGTH: 15
<212> TYPE: PRT
<213> ORGANISM: Mus musculus

<400> SEQUENCE: 105

Arg Ala Ser Lys Ser Val Ser Thr Ser Gly Tyr Ser Tyr Met His
1               5                   10                  15

<210> SEQ ID NO 106
<211> LENGTH: 11
<212> TYPE: PRT
<213> ORGANISM: Mus musculus
```

```
<400> SEQUENCE: 106

Lys Ala Ser Gln Asp Ile Lys Ser Tyr Leu Ser
1               5                   10

<210> SEQ ID NO 107
<211> LENGTH: 11
<212> TYPE: PRT
<213> ORGANISM: Mus musculus

<400> SEQUENCE: 107

Arg Ala Ser Gln Asn Ile Gly Asn Tyr Leu His
1               5                   10

<210> SEQ ID NO 108
<211> LENGTH: 7
<212> TYPE: PRT
<213> ORGANISM: Mus musculus

<400> SEQUENCE: 108

Lys Val Ser Asn Arg Phe Ser
1               5

<210> SEQ ID NO 109
<211> LENGTH: 7
<212> TYPE: PRT
<213> ORGANISM: Mus musculus

<400> SEQUENCE: 109

Asn Ala Lys Ser Leu Ala Glu
1               5

<210> SEQ ID NO 110
<211> LENGTH: 7
<212> TYPE: PRT
<213> ORGANISM: Mus musculus

<400> SEQUENCE: 110

Leu Val Ser Asn Leu Glu Ser
1               5

<210> SEQ ID NO 111
<211> LENGTH: 7
<212> TYPE: PRT
<213> ORGANISM: Mus musculus

<400> SEQUENCE: 111

Tyr Ala Thr Ser Leu Ala Asp
1               5

<210> SEQ ID NO 112
<211> LENGTH: 7
<212> TYPE: PRT
<213> ORGANISM: Mus musculus

<400> SEQUENCE: 112

Tyr Ala Ser Gln Ser Ile Ser
1               5

<210> SEQ ID NO 113
<211> LENGTH: 9
<212> TYPE: PRT
<213> ORGANISM: Mus musculus

<400> SEQUENCE: 113
```

```
Phe Gln Gly Ser His Val Pro Pro Thr
1               5

<210> SEQ ID NO 114
<211> LENGTH: 9
<212> TYPE: PRT
<213> ORGANISM: Mus musculus

<400> SEQUENCE: 114

Gln His His Tyr Gly Thr Pro Tyr Thr
1               5

<210> SEQ ID NO 115
<211> LENGTH: 9
<212> TYPE: PRT
<213> ORGANISM: Mus musculus

<400> SEQUENCE: 115

Gln His Ile Arg Glu Leu Thr Arg Ser
1               5

<210> SEQ ID NO 116
<211> LENGTH: 9
<212> TYPE: PRT
<213> ORGANISM: Mus musculus

<400> SEQUENCE: 116

Leu Gln His Gly Glu Ser Pro Phe Thr
1               5

<210> SEQ ID NO 117
<211> LENGTH: 9
<212> TYPE: PRT
<213> ORGANISM: Mus musculus

<400> SEQUENCE: 117

Gln Gln Ser Asp Thr Trp Pro Leu Thr
1               5

<210> SEQ ID NO 118
<211> LENGTH: 5
<212> TYPE: PRT
<213> ORGANISM: Mus musculus

<400> SEQUENCE: 118

Asp His Ala Leu His
1               5

<210> SEQ ID NO 119
<211> LENGTH: 5
<212> TYPE: PRT
<213> ORGANISM: Mus musculus

<400> SEQUENCE: 119

Asp His Ser Ile His
1               5

<210> SEQ ID NO 120
<211> LENGTH: 5
<212> TYPE: PRT
<213> ORGANISM: Mus musculus

<400> SEQUENCE: 120

Asn Tyr Val Ile His
```

```
<210> SEQ ID NO 121
<211> LENGTH: 9
<212> TYPE: PRT
<213> ORGANISM: Mus musculus

<400> SEQUENCE: 121

Ile Phe Pro Gly Asn Gly Asn Ile Glu
1               5

<210> SEQ ID NO 122
<211> LENGTH: 9
<212> TYPE: PRT
<213> ORGANISM: Mus musculus

<400> SEQUENCE: 122

Leu Phe Pro Gly Asn Gly Asn Phe Glu
1               5

<210> SEQ ID NO 123
<211> LENGTH: 9
<212> TYPE: PRT
<213> ORGANISM: Mus musculus

<400> SEQUENCE: 123

Ile Asn Pro Tyr Asn Asp Gly Ser Lys
1               5

<210> SEQ ID NO 124
<211> LENGTH: 11
<212> TYPE: PRT
<213> ORGANISM: Mus musculus

<400> SEQUENCE: 124

His Leu Ala Asn Thr Tyr Tyr Tyr Phe Asp Tyr
1               5                   10

<210> SEQ ID NO 125
<211> LENGTH: 5
<212> TYPE: PRT
<213> ORGANISM: Mus musculus

<400> SEQUENCE: 125

Ser Asn Gly Asn Thr
1               5

<210> SEQ ID NO 126
<211> LENGTH: 5
<212> TYPE: PRT
<213> ORGANISM: Mus musculus

<400> SEQUENCE: 126

Glu Asn Ile Tyr Ser
1               5

<210> SEQ ID NO 127
<211> LENGTH: 5
<212> TYPE: PRT
<213> ORGANISM: Mus musculus

<400> SEQUENCE: 127

Thr Ser Gly Tyr Ser
1               5
```

<210> SEQ ID NO 128
<211> LENGTH: 5
<212> TYPE: PRT
<213> ORGANISM: Mus musculus

<400> SEQUENCE: 128

Gln Asp Ile Lys Ser
1               5

<210> SEQ ID NO 129
<211> LENGTH: 5
<212> TYPE: PRT
<213> ORGANISM: Mus musculus

<400> SEQUENCE: 129

Gln Asn Ile Gly Asn
1               5

<210> SEQ ID NO 130
<211> LENGTH: 4654
<212> TYPE: DNA
<213> ORGANISM: Homo sapiens

<400> SEQUENCE: 130

| | | | | | |
|---|---|---|---|---|---|
| ggcggcggct | ggaggagagc | gcggtggaga | gccgagcggg | cgggcggcgg | gtgcggagcg | 60 |
| ggcgagggag | cgcgcgcggc | cgccacaaag | ctcgggcgcc | gcggggctgc | atgcggcgta | 120 |
| cctggcccgg | cgcggcgact | gctctccggg | ctggcggggg | ccggccgcga | gccccggggg | 180 |
| ccccgaggcc | gcagcttgcc | tgcgcgctct | gagccttcgc | aactcgcgag | caaagtttgg | 240 |
| tggaggcaac | gccaagcctg | agtccttttct | tcctctcgtt | ccccaaatcc | gagggcagcc | 300 |
| cgcgggcgtc | atgcccgcgc | tcctccgcag | cctggggtac | gcgtgaagcc | cgggaggctt | 360 |
| ggcgccggcg | aagacccaag | gaccactctt | ctgcgtttgg | agttgctccc | cgcaaccccg | 420 |
| ggctcgtcgc | tttctccatc | ccgacccacg | cggggcgcgg | ggacaacaca | ggtcgcggag | 480 |
| gagcgttgcc | attcaagtga | ctgcagcagc | agcggcagcg | cctcggttcc | tgagcccacc | 540 |
| gcaggctgaa | ggcattgcgc | gtagtccatg | cccgtagagg | aagtgtgcag | atgggattaa | 600 |
| cgtccacatg | gagatatgga | agaggaccgg | ggattggtac | cgtaaccatg | gtcagctggg | 660 |
| gtcgtttcat | ctgcctggtc | gtggtcacca | tggcaacctt | gtccctggcc | cggccctcct | 720 |
| tcagtttagt | tgaggatacc | acattagagc | cagaagagcc | accaaccaaa | taccaaatct | 780 |
| ctcaaccaga | agtgtacgtg | gctgcgccag | gggagtcgct | agaggtgcgc | tgcctgttga | 840 |
| aagatgccgc | cgtgatcagt | tggactaagg | atggggtgca | cttggggccc | aacaatagga | 900 |
| cagtgcttat | tggggagtac | ttgcagataa | agggcgccac | gcctagagac | tccggcctct | 960 |
| atgcttgtac | tgccagtagg | actgtagaca | gtgaaacttg | gtacttcatg | gtgaatgtca | 1020 |
| cagatgccat | ctcatccgga | gatgatgagg | atgacaccga | tggtgcggaa | gattttgtca | 1080 |
| gtgagaacag | taacaacaag | agagcaccat | actggaccaa | cacagaaaag | atggaaaagc | 1140 |
| ggctccatgc | tgtgcctgcg | gccaacactg | tcaagtttcg | ctgcccagcc | gggggggaacc | 1200 |
| caatgccaac | catgcggtgg | ctgaaaaacg | ggaaggagtt | taagcaggag | catcgcattg | 1260 |
| gaggctacaa | ggtacgaaac | cagcactgga | gcctcattat | ggaaagtgtg | gtcccatctg | 1320 |
| acaagggaaa | ttatacctgt | gtagtggaga | atgaatacgg | gtccatcaat | cacacgtacc | 1380 |
| acctggatgt | tgtggagcga | tcgcctcacc | ggcccatcct | ccaagccgga | ctgccggcaa | 1440 |
| atgcctccac | agtggtcgga | ggagacgtag | agtttgtctg | caaggtttac | agtgatgccc | 1500 |

```
agccccacat ccagtggatc aagcacgtgg aaaagaacgg cagtaaatac gggcccgacg    1560
ggctgcccta cctcaaggtt ctcaaggccg ccggtgttaa caccacggac aaagagattg    1620
aggttctcta tattcggaat gtaacttttg aggacgctgg ggaatatacg tgcttggcgg    1680
gtaattctat tgggatatcc tttcactctg catggttgac agttctgcca gcgcctggaa    1740
gagaaaagga gattacagct tccccagact acctggagat agccatttac tgcatagggg    1800
tcttcttaat cgcctgtatg gtggtaacag tcatcctgtg ccgaatgaag aacacgacca    1860
agaagccaga cttcagcagc cagccggctg tgcacaagct gaccaaacgt atcccctgc     1920 ggagacaggt aacagtttcg gctgagtcca gctcctccat gaactccaac ccccgctgg     1980 tgaggataac aacacgcctc tcttcaacgg cagacacccc catgctggca ggggtctccg    2040
agtatgaact tccagaggac ccaaaatggg agtttccaag agataagctg acactgggca    2100
agcccctggg agaaggttgc tttgggcaag tggtcatggc ggaagcagtg ggaattgaca    2160 aagcaagcc caaggaggcg gtcaccgtgg ccgtgaagat gttgaaagat gatgccacag     2220
agaaagacct ttctgatctg gtgtcagaga tggagatgat gaagatgatt gggaaacaca    2280
agaatatcat aaatcttctt ggagcctgca cacaggatgg gcctctctat gtcatagttg    2340
agtatgcctc taaaggcaac ctccgagaat acctccgagc ccggaggcca cccgggatgg    2400
agtactccta tgacattaac cgtgttcctg aggagcagat gaccttcaag gacttggtgt    2460
catgcaccta ccagctggcc agaggcatgg agtacttggc ttcccaaaaa tgtattcatc    2520
gagatttagc agccagaaat gttttggtaa cagaaaacaa tgtgatgaaa atagcagact    2580
ttggactcgc cagagatatc aacaatatag actattacaa aaagaccacc aatgggcggc    2640
ttccagtcaa gtggatggct ccagaagccc tgtttgatag agtatacact catcagagtg    2700
atgtctggtc cttcggggtg ttaatgtggg agatcttcac tttagggggc tcgccctacc    2760
cagggattcc cgtggaggaa cttttttaagc tgctgaagga aggacacaga atggataagc    2820
cagccaactg caccaacgaa ctgtacatga tgatgaggga ctgttggcat gcagtgccct    2880
cccagagacc aacgttcaag cagttggtag aagacttgga tcgaattctc actctcacaa    2940
ccaatgagga atacttggac ctcagccaac ctctcgaaca gtattcacct agttaccctg    3000
acacaagaag ttcttgttct tcaggagatg attctgtttt ttctccagac cccatgcctt    3060
acgaaccatg ccttcctcag tatccacaca taaacggcag tgttaaaaca tgaatgactg    3120
tgtctgcctg tccccaaaca ggacagcact gggaacctag ctacactgag cagggagacc    3180
atgcctccca gagcttgttg tctccacttg tatatatgga tcagaggagt aaataattgg    3240
aaaagtaatc agcatatgtg taaagattta tacagttgaa aacttgtaat cttccccagg    3300
aggagaagaa ggtttctgga gcagtggact gccacaagcc accatgtaac ccctctcacc    3360
tgccgtgcgt actggctgtg gaccagtagg actcaaggtg gacgtgcgtt ctgccttcct    3420
tgttaatttt gtaataattg gagaagattt atgtcagcac acacttacag agcacaaatg    3480
cagtatatag gtgctggatg tatgtaaata tattcaaatt atgtataaat atatattata    3540
tatttacaag gagttatttt ttgtattgat tttaaatgga tgtcccaatg cacctagaaa    3600
attggtctct cttttttttaa tagctatttg ctaaatgctg ttcttacaca taatttctta    3660
attttcaccg agcagaggtg gaaaaatact tttgctttca gggaaaatgg tataacgtta    3720
atttattaat aaaattggtaa tatacaaaac aattaatcat ttatagtttt ttttgtaatt    3780
taagtggcat ttctatgcag gcagcacagc agactagtta atctattgct tggacttaac    3840
```

| | |
|---|---|
| tagttatcag atcctttgaa aagagaatat ttacaatata tgactaattt ggggaaaatg | 3900 |
| aagtttttgat ttatttgtgt ttaaatgctg ctgtcagacg attgttctta gacctcctaa | 3960 |
| atgccccata ttaaaagaac tcattcatag gaaggtgttt cattttggtg tgcaaccctg | 4020 |
| tcattacgtc aacgcaacgt ctaactggac ttcccaagat aaatggtacc agcgtcctct | 4080 |
| taaaagatgc cttaatccat tccttgagga cagaccttag ttgaaatgat agcagaatgt | 4140 |
| gcttctctct ggcagctggc cttctgcttc tgagttgcac attaatcaga ttagcctgta | 4200 |
| ttctcttcag tgaattttga taatggcttc cagactcttt ggcgttggag acgcctgtta | 4260 |
| ggatcttcaa gtcccatcat agaaaattga acacagagt tgttctgctg atagttttgg | 4320 |
| ggatacgtcc atcttttaa gggattgctt tcatctaatt ctggcaggac ctcaccaaaa | 4380 |
| gatccagcct catacctaca tcagacaaaa tatcgccgtt gttccttctg tactaaagta | 4440 |
| ttgtgttttg ctttggaaac acccactcac tttgcaatag ccgtgcaaga tgaatgcaga | 4500 |
| ttacactgat cttatgtgtt acaaaattgg agaaagtatt taataaaacc tgttaatttt | 4560 |
| tatactgaca ataaaaatgt ttctacagat attaatgtta acaagacaaa ataaatgtca | 4620 |
| cgcaacttat ttttttaata aaaaaaaaaa aaaa | 4654 |

<210> SEQ ID NO 131
<211> LENGTH: 4657
<212> TYPE: DNA
<213> ORGANISM: Homo sapiens

<400> SEQUENCE: 131

| | |
|---|---|
| ggcggcggct ggaggagagc gcggtggaga gccgagcggg cgggcggcgg gtgcggagcg | 60 |
| ggcgagggag cgcgcgcggc cgccacaaag ctcgggcgcc gcggggctgc atgcggcgta | 120 |
| cctggcccgg cgcggcgact gctctccggg ctggcggggg ccggccgcga gccccggggg | 180 |
| ccccgaggcc gcagcttgcc tgcgcgctct gagccttcgc aactcgcgag caaagtttgg | 240 |
| tggaggcaac gccaagcctg agtcctttct tcctctcgtt ccccaaatcc gagggcagcc | 300 |
| cgcgggcgtc atgcccgcgc tcctccgcag cctggggtac gcgtgaagcc cgggaggctt | 360 |
| ggcgccggcg aagacccaag gaccactctt ctgcgtttgg agttgctccc cgcaaccccg | 420 |
| ggctcgtcgc tttctccatc ccgacccacg cggggcgcgg gacaacaca ggtcgcggag | 480 |
| gagcgttgcc attcaagtga ctgcagcagc agcggcagcg cctcggttcc tgagcccacc | 540 |
| gcaggctgaa ggcattgcgc gtagtccatg cccgtagagg aagtgtgcag atgggattaa | 600 |
| cgtccacatg gagatatgga agaggaccgg ggattggtac cgtaaccatg gtcagctggg | 660 |
| gtcgtttcat ctgcctggtc gtggtcacca tgcaaccctt gtccctggcc cggccctcct | 720 |
| tcagtttagt tgaggatacc acattagagc cagaagagcc accaaccaaa taccaaatct | 780 |
| ctcaaccaga agtgtacgtg gctgcgccag gggagtcgct agaggtgcgc tgcctgttga | 840 |
| aagatgccgc cgtgatcagt tggactaagg atggggtgca cttggggccc aacaatagga | 900 |
| cagtgcttat tgggggagtac ttgcagataa agggcgccac gcctagagac tccggcctct | 960 |
| atgcttgtac tgccagtagg actgtagaca gtgaaacttg gtacttcatg gtgaatgtca | 1020 |
| cagatgccat ctcatccgga gatgatgagg atgacaccga tggtgcggaa gattttgtca | 1080 |
| gtgagaacag taacaacaag agagcaccat actggaccaa cacagaaaag atggaaaagc | 1140 |
| ggctccatgc tgtgcctgcg gccaacactg tcaagtttcg ctgcccagcc gggggggaacc | 1200 |
| caatgccaac catgcggtgg ctgaaaaacg ggaaggagtt taagcaggag catcgcattg | 1260 |
| gaggctacaa ggtacgaaac cagcactgga gcctcattat ggaaagtgtg gtcccatctg | 1320 |

```
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaagcact cggggataaa tagttccaat gcagaagtgc   1620
tggctctgtt caatgtgacc gaggcggatg ctggggaata tatatgtaag gtctccaatt   1680
atatagggca ggccaaccag tctgcctggc tcactgtcct gccaaaacag caagcgcctg   1740
gaagagaaaa ggagattaca gcttccccag actacctgga gatagccatt tactgcatag   1800
gggtcttctt aatcgcctgt atggtggtaa cagtcatcct gtgccgaatg aagaacacga   1860
ccaagaagcc agacttcagc agccagccgg ctgtgcacaa gctgaccaaa cgtatccccc   1920
tgcggagaca ggtaacagtt tcggctgagt ccagctcctc catgaactcc aacacccgc    1980 tggtgaggat aacaacacgc ctctcttcaa cggcagacac ccccatgctg cagggggtct   2040
ccgagtatga acttccagag gacccaaaat gggagtttcc aagagataag ctgacactgg   2100
gcaagcccct gggagaaggt tgctttgggc aagtggtcat ggcggaagca gtgggaattg   2160
acaaagacaa gcccaaggag gcggtcaccg tggccgtgaa gatgttgaaa gatgatgcca   2220
cagagaaaga cctttctgat ctggtgtcag agatggagat gatgaagatg attgggaaac   2280
acaagaatat cataaatctt cttggagcct gcacacagga tgggcctctc tatgtcatag   2340
ttgagtatgc ctctaaaggc aacctccgag aatacctccg agcccggagg ccacccggga   2400
tggagtactc ctatgacatt aaccgtgttc ctgaggagca gatgaccttc aaggacttgg   2460
tgtcatgcac ctaccagctg gccagaggca tggagtactt ggcttcccaa aaatgtattc   2520
atcgagattt agcagccaga aatgttttgg taacagaaaa caatgtgatg aaaatagcag   2580
actttggact cgccagagat atcaacaata tagactatta caaaaagacc accaatgggc   2640
ggcttccagt caagtggatg gctccagaag ccctgtttga tagagtatac actcatcaga   2700
gtgatgtctg gtccttcggg gtgttaatgt gggagatctt cactttaggg ggctcgccct   2760
acccagggat tcccgtggag gaacttttta agctgctgaa ggaaggacac agaatggata   2820
agccagccaa ctgcaccaac gaactgtaca tgatgatgag ggactgttgg catgcagtgc   2880
cctcccagag accaacgttc aagcagttgg tagaagactt ggatcgaatt ctcactctca   2940
caaccaatga ggaatacttg gacctcagcc aacctctcga acagtattca cctagttacc   3000
ctgacacaag aagttcttgt tcttcaggag atgattctgt tttttctcca gaccccatgc   3060
cttacgaacc atgccttcct cagtatccac acataaacgg cagtgttaaa acatgaatga   3120
ctgtgtctgc ctgtccccaa acaggacagc actgggaacc tagctacact gagcagggag   3180
accatgcctc ccagagcttg ttgtctccac ttgtatatat ggatcagagg agtaaataat   3240
tggaaaagta atcagcatat gtgtaaagat ttatacagtt gaaaacttgt aatcttcccc   3300
aggaggagaa gaaggtttct ggagcagtgg actgccacaa gccaccatgt aaccccctctc  3360 acctgccgtg cgtactggct gtggaccagt aggactcaag gtggacgtgc gttctgcctt   3420
ccttgttaat tttgtaataa ttggagaaga tttatgtcag cacacactta cagagcacaa   3480
atgcagtata taggtgctgg atgtatgtaa atatattcaa attatgtata aatatatatt   3540
atatatttac aaggagttat tttttgtatt gattttaaat ggatgtccca atgcacctag   3600
aaaattggtc tctctttttt taatagctat ttgctaaatg ctgttcttac acataaatttc  3660
```

```
ttaattttca ccgagcagag gtggaaaaat acttttgctt tcagggaaaa tggtataacg      3720
ttaatttatt aataaattgg taatatacaa aacaattaat catttatagt tttttttgta      3780
atttaagtgg catttctatg caggcagcac agcagactag ttaatctatt gcttggactt      3840
aactagttat cagatccttt gaaaagagaa tatttacaat atatgactaa tttggggaaa      3900
atgaagtttt gatttatttg tgtttaaatg ctgctgtcag acgattgttc ttagacctcc      3960
taaatgcccc atattaaaag aactcattca taggaaggtg tttcattttg gtgtgcaacc      4020
ctgtcattac gtcaacgcaa cgtctaactg gacttcccaa gataaatggt accagcgtcc      4080
tcttaaaaga tgccttaatc cattccttga ggacagacct tagttgaaat gatagcagaa      4140
tgtgcttctc tctggcagct ggccttctgc ttctgagttg cacattaatc agattagcct      4200
gtattctctt cagtgaattt tgataatggc ttccagactc tttggcgttg gagacgcctg      4260
ttaggatctt caagtcccat catagaaaat tgaaacacag agttgttctg ctgatagttt      4320
tggggatacg tccatctttt taagggattg ctttcatcta attctggcag gacctcacca      4380
aaagatccag cctcatacct acatcagaca aaatatcgcc gttgttcctt ctgtactaaa      4440
gtattgtgtt ttgctttgga aacacccact cactttgcaa tagccgtgca agatgaatgc      4500
agattacact gatcttatgt gttacaaaat tggagaaagt atttaataaa acctgttaat      4560
ttttatactg acaataaaaa tgtttctaca gatattaatg ttaacaagac aaaataaatg      4620
tcacgcaact tattttttta ataaaaaaaa aaaaaaa                              4657

<210> SEQ ID NO 132
<211> LENGTH: 2781
<212> TYPE: DNA
<213> ORGANISM: Homo sapiens

<400> SEQUENCE: 132
tgactgcagc agcagcggca gcgcctcggt tcctgagccc accgcaggct gaaggcattg        60
cgcgtagtcc atgcccgtag aggaagtgtg cagatgggat taacgtccac atggagatat       120
ggaagaggac cggggattgg taccgtaacc atggtcagct ggggtcgttt catctgcctg       180
gtcgtggtca ccatggcaac cttgtccctg gccggccct ccttcagttt agttgaggat        240
accacattag agccagaaga gccaccaacc aaataccaaa tctctcaacc agaagtgtac       300
gtggctgcgc caggggagtc gctagaggtg cgctgcctgt tgaaagatgc cgccgtgatc       360
agttggacta aggatggggt gcacttgggg cccaacaata ggacagtgct tattggggag       420
tacttgcaga taaagggcgc cacgcctaga gactccggcc tctatgcttg tactgccagt       480
aggactgtag acagtgaaac ttggtacttc atggtgaatg tcacagatgc catctcatcc       540
ggagatgatg aggatgacac cgatggtgcg gaagattttg tcagtgagaa cagtaacaac       600
aagagagcac catactggac caacacagaa agatggaaa agcggctcca tgctgtgcct       660
gcggccaaca ctgtcaagtt cgctgcccca gccggggga acccaatgcc aaccatgcgg       720
tggctgaaaa acgggaagga gtttaagcag gagcatcgca ttggaggcta caaggtacga       780
aaccagcact ggagcctcat tatggaaagt gtggtcccat ctgacaaggg aaattatacc       840
tgtgtagtgg agaatgaata cggtccatc aatcacacgt accacctgga tgttgtggag       900
cgatcgcctc accggcccat cctccaagcc ggactgccgg caaatgcctc cacagtggtc       960
ggaggagacg tagagtttgt ctgcaaggtt tacagtgatg cccagcccca catccagtgg      1020
atcaagcacg tggaaaagaa cggcagtaaa tacgggcccg acgggctgcc ctacctcaag      1080
gttctcaagc actcggggat aaatagttcc aatgcagaag tgctggctct gttcaatgtg      1140
```

```
accgaggcgg atgctgggga atatatatgt aaggtctcca attatatagg gcaggccaac    1200
cagtctgcct ggctcactgt cctgccaaaa cagcaagcgc ctggaagaga aaaggagatt    1260
acagcttccc cagactacct ggagatagcc atttactgca tagggtgtct cttaatcgcc    1320
tgtatggtgg taacagtcat cctgtgccga atgaagaaca cgaccaagaa gccagacttc    1380
agcagccagc cggctgtgca caagctgacc aaacgtatcc ccctgcggag acaggtaaca    1440
gtttcggctg agtccagctc ctccatgaac tccaacaccc cgctggtgag gataacaaca    1500
cgcctctctt caacggcaga caccccatg ctggcagggg tctccgagta tgaacttcca    1560
gaggacccaa aatgggagtt tccaagagat aagctgacac tgggcaagcc cctgggagaa    1620
ggttgctttg gcaagtggt catggcggaa gcagtgggaa ttgacaaaga caagcccaag    1680
gaggcggtca ccgtggccgt gaagatgttg aaagatgatg ccacagagaa agacctttct    1740
gatctggtgt cagagatgga gatgatgaag atgattggga aacacaagaa tatcataaat    1800
cttcttggag cctgcacaca ggatgggcct ctctatgtca tagttgagta tgcctctaaa    1860
ggcaacctcc gagaatacct ccgagcccgg aggccacccg ggatggagta ctcctatgac    1920
attaaccgtg ttcctgagga gcagatgacc ttcaaggact tggtgtcatg cacctaccag    1980
ctggccagag gcatggagta cttggcttcc caaaaatgta ttcatcgaga tttagcagcc    2040
agaaatgttt tggtaacaga aaacaatgtg atgaaaatag cagactttgg actcgccaga    2100
gatatcaaca atatagacta ttacaaaaag accaccaatg gcggcttcc agtcaagtgg    2160 atggctccag aagccctgtt tgatagagta tacactcatc agagtgatgt ctggtccttc    2220
ggggtgttaa tgtgggagat cttcacttta ggggctcgc cctacccagg gattcccgtg    2280
gaggaacttt ttaagctgct gaaggaagga cacagaatgg ataagccagc caactgcacc    2340
aacgaactgt acatgatgat gagggactgt tggcatgcag tgccctccca gagaccaacg    2400
ttcaagcagt tggtagaaga cttggatcga attctcactc tcacaaccaa tgagatctga    2460
aagtttatgg cttcattgag aaactgggaa aagttggtca ggcgcagtgg ctcatgcctg    2520
taatcccagc actttgggag gccgaggcag gcggatcatg aggtcaggag ttccagacca    2580
gcctggccaa catggtgaaa ccctgtctct actaaagata caaaaaatta gccgggcgtg    2640
ttggtgtgca cctgtaatcc cagctactcc gggaggctga ggcaggagag tcacttgaac    2700
cggggaggcg gaggttgcag tgagccgaga tcatgccatt gcattccagc cttggcgaca    2760
gagcgagact ccgtctcaaa a                                              2781
```

<210> SEQ ID NO 133
<211> LENGTH: 3821
<212> TYPE: DNA
<213> ORGANISM: Homo sapiens

<400> SEQUENCE: 133

```
tgactgcagc agcagcggca gcgcctcggt tcctgagccc accgcaggct gaaggcattg      60
cgcgtagtcc atgcccgtag aggaagtgtg cagatgggat taacgtccac atggagatat     120
ggaagaggac cggggattgg taccgtaacc atggtcagct ggggtcgttt catctgcctg     180
gtcgtggtca ccatggcaac cttgtccctg gcccggccct ccttcagttt agttgaggat     240
accacattag agccagaaga gccaccaacc aaataccaaa tctctcaacc agaagtgtac     300
gtggctgcgc caggggagtc gctagaggtg cgctgcctgt tgaaagatgc cgccgtgatc     360
agttggacta aggatggggt gcacttgggg cccaacaata ggacagtgct tattggggag     420
```

```
tacttgcaga taaagggcgc cacgcctaga gactccggcc tctatgcttg tactgccagt    480
aggactgtag acagtgaaac ttggtacttc atggtgaatg tcacagatgc catctcatcc    540
ggagatgatg aggatgacac cgatggtgcg gaagattttg tcagtgagaa cagtaacaac    600
aagagagcac catactggac caacacagaa aagatggaaa agcggctcca tgctgtgcct    660
gcggccaaca ctgtcaagtt tcgctgccca gccgggggga acccaatgcc aaccatgcgg    720
tggctgaaaa acgggaagga gtttaagcag gagcatcgca ttggaggcta caaggtacga    780
aaccagcact ggagcctcat tatggaaagt gtggtcccat ctgacaaggg aaattatacc    840
tgtgtagtgg agaatgaata cgggtccatc aatcacacgt accacctgga tgttgtggcg    900
cctggaagag aaaaggagat tacagcttcc ccagactacc tggagatagc catttactgc    960
ataggggtct tcttaatcgc ctgtatggtg gtaacagtca tcctgtgccg aatgaagaac   1020
acgaccaaga agccagactt cagcagccag ccggctgtgc acaagctgac caaacgtatc   1080
cccctgcgga gacaggtaac agtttcggct gagtccagct cctccatgaa ctccaacacc   1140
ccgctggtga ggataacaac acgcctctct tcaacggcag acaccccat gctggcaggg   1200
gtctccgagt atgaacttcc agaggaccca aaatgggagt ttccaagaga taagctgaca   1260
ctgggcaagc cctgggagga aggttgcttt gggcaagtgg tcatggcgga agcagtggga   1320
attgacaaag acaagcccaa ggaggcggtc accgtggccg tgaagatgtt gaaagatgat   1380
gccacagaga aagacctttc tgatctggtg tcagagatgg agatgatgaa gatgattggg   1440
aaacacaaga atatcataaa tcttcttgga gcctgcacac aggatgggcc tctctatgtc   1500
atagttgagt atgcctctaa aggcaacctc cgagaatacc tccgagcccg gaggccaccc   1560
gggatggagt actcctatga cattaaccgt gttcctgagg agcagatgac cttcaaggac   1620
ttggtgtcat gcacctacca gctggccaga ggcatggagt acttggcttc ccaaaaatgt   1680
attcatcgag atttagcagc cagaaatgtt ttggtaacag aaaacaatgt gatgaaaata   1740
gcagactttg gactcgccag agatatcaac aatatagact attacaaaaa gaccaccaat   1800
gggcggcttc cagtcaagtg gatggctcca gaagccctgt ttgatagagt atacactcat   1860
cagagtgatg tctggtcctt cggggtgtta atgtgggaga tcttcacttt aggggggctcg   1920
ccctacccag ggattcccgt ggaggaactt tttaagctgc tgaaggaagg acacagaatg   1980
gataagccag ccaactgcac caacgaactg tacatgatga tgagggactg ttggcatgca   2040
gtgccctccc agagaccaac gttcaagcag ttggtagaag acttggatcg aattctcact   2100
ctcacaacca atgaggaata cttggacctc agccaacctc tcgaacagta ttcacctagt   2160
taccctgaca caagaagttc ttgttcttca ggagatgatt ctgttttttc tccagacccc   2220
atgccttacg aaccatgcct tcctcagtat ccacacataa acggcagtgt taaaacatga   2280
atgactgtgt ctgcctgtcc ccaaacagga cagcactggg aacctagcta cactgagcag   2340
ggagaccatg cctcccagag cttgttgtct ccacttgtat atatggatca gaggagtaaa   2400
taattggaaa agtaatcagc atatgtgtaa agatttatac agttgaaaac ttgtaatctt   2460
ccccaggagg agaagaaggt ttctggagca gtggactgcc acaagccacc atgtaacccc   2520
tctcacctgc cgtgcgtact ggctgtggac cagtaggact caaggtggac gtgcgttctg   2580
ccttccttgt taattttgta ataattggag aagatttatg tcagcacaca cttacagagc   2640
acaaatgcag tatataggtg ctggatgtat gtaaatatat tcaaattatg tataaatata   2700
tattatatat ttcaaggag ttattttttg tattgatttt aaatggatgt cccaatgcac   2760
ctagaaaatt ggtctctctt tttttaatag ctatttgcta aatgctgttc ttacacataa   2820
```

| | |
|---|---|
| tttcttaatt ttcaccgagc agaggtggaa aaatacttt gctttcaggg aaaatggtat | 2880 |
| aacgttaatt tattaataaa ttggtaatat acaaaacaat taatcattta tagttttttt | 2940 |
| tgtaatttaa gtggcattc tatgcaggca gcacagcaga ctagttaatc tattgcttgg | 3000 |
| acttaactag ttatcagatc ctttgaaaag agaatattta caatatatga ctaatttggg | 3060 |
| gaaaatgaag ttttgattta tttgtgttta aatgctgctg tcagacgatt gttcttagac | 3120 |
| ctcctaaatg ccccatatta aaagaactca ttcataggaa ggtgtttcat tttggtgtgc | 3180 |
| aaccctgtca ttacgtcaac gcaacgtcta actggactc ccaagataaa tggtaccagc | 3240 |
| gtcctcttaa aagatgcctt aatccattcc ttgaggacag accttagttg aaatgatagc | 3300 |
| agaatgtgct tctctctggc agctggcctt ctgcttctga gttgcacatt aatcagatta | 3360 |
| gcctgtattc tcttcagtga atttgataa tggcttccag actctttggc gttggagacg | 3420 |
| cctgttagga tcttcaagtc ccatcataga aaattgaaac acagagttgt tctgctgata | 3480 |
| gttttgggga tacgtccatc tttttaaggg attgctttca tctaattctg gcaggacctc | 3540 |
| accaaaagat ccagcctcat acctacatca gacaaaatat cgccgttgtt ccttctgtac | 3600 |
| taaagtattg tgttttgctt tggaaacacc cactcacttt gcaatagccg tgcaagatga | 3660 |
| atgcagatta cactgatctt atgtgttaca aaattggaga agtatttaa taaaacctgt | 3720 |
| taattttat actgacaata aaaatgtttc tacagatatt aatgttaaca agacaaaata | 3780 |
| aatgtcacgc aacttatttt tttaataaaa aaaaaaaaa a | 3821 |

<210> SEQ ID NO 134
<211> LENGTH: 3708
<212> TYPE: DNA
<213> ORGANISM: Homo sapiens

<400> SEQUENCE: 134

| | |
|---|---|
| aatttgttga ggaatttccc cctagccttg acccctgac agctcccgct cctactcagt | 60 |
| gctggggaga agtagggagg ccttaagcga agagatgggt ctgcactttg gaggagccgg | 120 |
| acactgttga ctttcctgat gtgaaatcta cccaggaaca aaacaccagt gactgcagca | 180 |
| gcagcggcag cgcctcggtt cctgagccca ccgcaggctg aaggcattgc gcgtagtcca | 240 |
| tgcccgtaga ggaagtgtgc agatgggatt aacgtccaca tggagatatg aagaggacc | 300 |
| ggggattggt accgtaacca tggtcagctg gggtcgtttc atctgcctgg tcgtggtcac | 360 |
| catggcaacc ttgtccctgg cccggccctc cttcagttta gttgaggata ccacattaga | 420 |
| gccagaagat gccatctcat ccggagatga tgaggatgac accgatggtg cggaagattt | 480 |
| tgtcagtgag aacagtaaca acaagagagc accatactgg accaacacag aaaagatgga | 540 |
| aaagcggctc catgctgtgc ctgcggccaa cactgtcaag tttcgctgcc cagccggggg | 600 |
| gaacccaatg ccaaccatgc ggtggctgaa aaacgggaag agtttaagc aggagcatcg | 660 |
| cattggaggc tacaaggtac gaaaccagca ctggagcctc attatggaaa gtgtggtccc | 720 |
| atctgacaag ggaaattata cctgtgtagt ggagaatgaa tacgggtcca tcaatcacac | 780 |
| gtaccacctg gatgttgtgg agcgatcgc tcaccggccc atcctccaag ccggactgcc | 840 |
| ggcaaatgcc tccacagtgg tcggaggaga cgtagagttt gtctgcaagg tttacagtga | 900 |
| tgcccagccc cacatccagt ggatcaagca cgtggaaaag aacggcagta aatacgggcc | 960 |
| cgacgggctg ccctacctca aggttctcaa ggccgccggt gttaacacca cggacaaaga | 1020 |
| gattgaggtt ctctatattc ggaatgtaac ttttgaggac gctggggaat atacgtgctt | 1080 |

```
ggcgggtaat tctattggga tatcctttca ctctgcatgg ttgacagttc tgccagcgcc    1140
tggaagagaa aaggagatta cagcttcccc agactacctg gagatagcca tttactgcat    1200
aggggtcttc ttaatcgcct gtatggtggt aacagtcatc ctgtgccgaa tgaagaacac    1260
gaccaagaag ccagacttca gcagccagcc ggctgtgcac aagctgacca aacgtatccc    1320
cctgcggaga caggtaacag tttcggctga gtccagctcc tccatgaact ccaacacccc    1380
gctggtgagg ataacaacac gcctctcttc aacggcagac accccatgc tggcaggggt     1440 ctccgagtat gaacttccag aggacccaaa atgggagttt ccaagagata agctgacact    1500
gggcaagccc ctgggagaag gttgctttgg gcaagtggtc atggcggaag cagtgggaat    1560
tgacaaagac aagcccaagg aggcggtcac cgtggccgtg aagatgttga agatgatgc     1620 cacagagaaa gaccttctg atctggtgtc agagatggag atgatgaaga tgattgggaa     1680
acacaagaat atcataaatc ttcttggagc ctgcacacag gatgggcctc tctatgtcat    1740
agttgagtat gcctctaaag gcaacctccg agaatacctc cgagcccgga ggccacccgg    1800
gatggagtac tcctatgaca ttaaccgtgt tcctgaggag cagatgacct tcaaggactt    1860
ggtgtcatgc acctaccagc tggccagagg catggagtac ttggcttccc aaaaatgtat    1920
tcatcgagat ttagcagcca gaaatgtttt ggtaacagaa aacaatgtga tgaaaatagc    1980
agactttgga ctcgccagag atatcaacaa tatagactat tacaaaaaga ccaccaatgg    2040
gcggcttcca gtcaagtgga tggctccaga agccctgttt gatagagtat acactcatca    2100
gagtgatgtc tggtccttcg gggtgttaat gtgggagatc ttcactttag ggggctcgcc    2160
ctacccaggg attcccgtgg aggaactttt taagctgctg aaggaaggac acagaatgga    2220
taagccagcc aactgcacca acgaactgta catgatgatg agggactgtt ggcatgcagt    2280
gccctcccag agaccaacgt tcaagcagtt ggtagaagac ttggatcgaa ttctcactct    2340
cacaaccaat gaggaggaga agaaggtttc tggagcagtg gactgccaca agccaccatg    2400
taacccctct cacctgccgt gcgtactggc tgtggaccag taggactcaa ggtgacgtg     2460 cgttctgcct tccttgttaa ttttgtaata attggagaag atttatgtca gcacacactt    2520
acagagcaca aatgcagtat ataggtgctg gatgtatgta aatatattca aattatgtat    2580
aaatatatat tatatattta caaggagtta tttttttgtat tgattttaaa tggatgtccc    2640
aatgcaccta gaaaattggt ctctcttttt ttaatagcta tttgctaaat gctgttctta    2700
cacataattt cttaattttc accgagcaga ggtggaaaaa tacttttgct ttcagggaaa    2760
atggtataac gttaatttat taataaattg gtaatataca aaacaattaa tcatttatag    2820 tttttttttgt aatttaagtg gcatttctat gcaggcagca cagcagacta gttaatctat    2880
tgcttggact taactagtta tcagatcctt tgaaaagaga atatttacaa tatatgacta    2940
atttggggaa aatgaagttt tgatttattt gtgtttaaat gctgctgtca gacgattgtt    3000
cttagacctc ctaaatgccc catattaaaa gaactcattc ataggaaggt gtttcattt      3060 ggtgtgcaac cctgtcatta cgtcaacgca acgtctaact ggacttccca agataaatgg    3120
taccagcgtc ctcttaaaag atgccttaat ccattccttg aggacagacc ttagttgaaa    3180
tgatagcaga atgtgcttct ctctggcagc tggccttctg cttctgagtt gcacattaat    3240
cagattagcc tgtattctct tcagtgaatt ttgataatgg cttccagact ctttggcgtt    3300
ggagacgcct gttaggatct tcaagtccca tcatagaaaa ttgaaacaca gagttgttct    3360
gctgatagtt ttggggatac gtccatcttt ttaagggatt gctttcatct aattctggca    3420
ggacctcacc aaaagatcca gcctcatacc tacatcagac aaaatatcgc cgttgttcct    3480
```

| | |
|---|---|
| tctgtactaa agtattgtgt tttgctttgg aaacacccac tcactttgca atagccgtgc | 3540 |
| aagatgaatg cagattacac tgatcttatg tgttacaaaa ttggagaaag tatttaataa | 3600 |
| aacctgttaa tttttatact gacaataaaa atgtttctac agatattaat gttaacaaga | 3660 |
| caaaataaat gtcacgcaac ttattttttt aataaaaaaa aaaaaaaa | 3708 |

<210> SEQ ID NO 135
<211> LENGTH: 4103
<212> TYPE: DNA
<213> ORGANISM: Homo sapiens

<400> SEQUENCE: 135

| | |
|---|---|
| gagcacacat tgcctcactg aagtggctgc acgtatctga gtcctgtagc tactgtttta | 60 |
| tctctgtttc ttaaaagtat gcttttaaaa agattagcct cacacatttc tgtggaccgg | 120 |
| tctggtggta tcacctggga ctctgaggtg aggatggaag gatttagcag ataatgaaaa | 180 |
| agaactctgt ttgcgcacat ttgagaggct gaaaatggt tttatcccac ttgggctgga | 240 |
| gtgatttggc attggggaag attccctgac tcgccaatct cttccttta gtgactgcag | 300 |
| cagcagcgga agcgcctcgg ttcctgagcc accgcaggc tgaaggcatt gcgcgtagtc | 360 |
| catgcccgta gaggaagtgt gcagatggga ttaacgtcca catggagata tggaagagga | 420 |
| ccggggattg gtaccgtaac catggtcagc tggggtcgtt tcatctgcct ggtcgtggtc | 480 |
| accatggcaa ccttgtccct ggcccggccc tccttcagtt tagttgagga taccacatta | 540 |
| gagccagaag gagcaccata ctggaccaac acagaaaaga tggaaaagcg gctccatgct | 600 |
| gtgcctgcgg ccaacactgt caagtttcgc tgcccagccg gggggaaccc aatgccaacc | 660 |
| atgcggtggc tgaaaaacgg gaaggagttt aagcaggagc atcgcattgg aggctacaag | 720 |
| gtacgaaacc agcactggag cctcattatg gaaagtgtgg tcccatctga caagggaaat | 780 |
| tatacctgtg tagtggagaa tgaatacggg tccatcaatc acgtacca cctggatgtt | 840 |
| gtggagcgat cgcctcaccg gcccatcctc caagccggac tgccggcaaa tgcctccaca | 900 |
| gtggtcggag gagacgtaga gtttgtctgc aaggtttaca gtgatgccca gccccacatc | 960 |
| cagtggatca agcacgtgga aaagaacggc agtaaatacg ggcccgacgg gctgccctac | 1020 |
| ctcaaggttc tcaaggccgc cggtgttaac accacggaca agagattga ggttctctat | 1080 |
| attcggaatg taacttttga ggacgctggg gaatatacgt gcttggcggg taattctatt | 1140 |
| gggatatcct ttcactctgc atggttgaca gttctgccag cgcctggaag agaaaaggag | 1200 |
| attacagctt ccccagacta cctggagata gccatttact gcataggggt cttcttaatc | 1260 |
| gcctgtatgg tggtaacagt catcctgtgc cgaatgaaga acacgaccaa gaagccagac | 1320 |
| ttcagcagcc agccggctgt gcacaagctg accaaacgta tcccccctgcg agacaggta | 1380 |
| acagtttcgg ctgagtccag ctcctccatg aactccaaca ccccgctggt gaggataaca | 1440 |
| acacgcctct cttcaacggc agacacccc atgctggcag gggtctccga gtatgaactt | 1500 |
| ccagaggacc caaaatggga gtttccaaga gataagctga cactgggcaa gccccctggga | 1560 |
| gaaggttgct ttgggcaagt ggtcatggcg gaagcagtgg gaattgacaa agacaagccc | 1620 |
| aaggaggcgg tcaccgtggc cgtgaagatg ttgaaagatg atgccacaga gaaagacctt | 1680 |
| tctgatctgg tgtcagagat ggagatgatg aagatgattg ggaaacacaa gaatatcata | 1740 |
| aatcttcttg gagcctgcac acaggatggg cctctctatg tcatagttga gtatgcctct | 1800 |
| aaaggcaacc tccgagaata cctccgagcc cggaggccac ccgggatgga gtactcctat | 1860 |

```
gacattaacc gtgttcctga ggagcagatg accttcaagg acttggtgtc atgcacctac    1920
cagctggcca gaggcatgga gtacttggct tcccaaaaat gtattcatcg agatttagca    1980
gccagaaatg ttttggtaac agaaaacaat gtgatgaaaa tagcagactt tggactcgcc    2040
agagatatca acaatataga ctattacaaa aagaccacca atgggcggct tccagtcaag    2100
tggatggctc cagaagccct gtttgataga gtatacactc atcagagtga tgtctggtcc    2160
ttcggggtgt taatgtggga gatcttcact ttagggggct cgccctaccc agggattccc    2220
gtggaggaac tttttaagct gctgaaggaa ggacacagaa tggataagcc agccaactgc    2280
accaacgaac tgtacatgat gatgagggac tgttggcatg cagtgccctc ccagagacca    2340
acgttcaagc agttggtaga agacttggat cgaattctca ctctcacaac caatgaggaa    2400
tacttggacc tcagccaacc tctcgaacag tattcaccta gttaccctga cacaagaagt    2460
tcttgttctt caggagatga ttctgttttt tctccagacc ccatgcctta cgaaccatgc    2520
cttcctcagt atccacacat aaacggcagt gttaaaacat gaatgactgt gtctgcctgt    2580
ccccaaacag gacagcactg ggaacctagc tacactgagc agggagacca tgcctcccag    2640
agcttgttgt ctccacttgt atatatggat cagaggagta aataattgga aaagtaatca    2700
gcatatgtgt aaagatttat acagttgaaa acttgtaatc ttccccagga ggagaagaag    2760
gtttctggag cagtggactg ccacaagcca ccatgtaacc cctctcacct gccgtgcgta    2820
ctggctgtgg accagtagga ctcaaggtgg acgtgcgttc tgccttcctt gttaattttg    2880
taataattgg agaagattta tgtcagcaca cacttacaga gcacaaatgc agtatatagg    2940
tgctggatgt atgtaaatat attcaaatta tgtataaata tatattatat atttacaagg    3000
agttattttt tgtattgatt ttaaatggat gtcccaatgc acctagaaaa ttggtctctc    3060 ttttttttaat agctatttgc taaatgctgt tcttacacat aatttcttaa ttttcaccga    3120
gcagaggtgg aaaaatactt ttgctttcag ggaaaatggt ataacgttaa tttattaata    3180
aattggtaat atacaaaaca attaatcatt tatagttttt tttgtaattt aagtggcatt    3240
tctatgcagg cagcacagca gactagttaa tctattgctt ggacttaact agttatcaga    3300 tccttttgaaa agagaatatt tacaatatat gactaatttg gggaaaatga agttttgatt    3360
tatttgtgtt taaatgctgc tgtcagacga ttgttcttag acctcctaaa tgccccatat    3420
taaaagaact cattcatagg aaggtgtttc attttggtgt gcaaccctgt cattacgtca    3480
acgcaacgtc taactggact tcccaagata aatggtacca gcgtcctctt aaaagatgcc    3540
ttaatccatt ccttgaggac agaccttagt tgaaatgata gcagaatgtg cttctctctg    3600
gcagctggcc ttctgcttct gagttgcaca ttaatcagat tagcctgtat tctcttcagt    3660
gaattttgat aatggcttcc agactctttg gcgttggaga cgcctgttag gatcttcaag    3720
tcccatcata gaaaattgaa acacagagtt gttctgctga tagttttggg gatacgtcca    3780 tcttttttaag ggattgcttt catctaattc tggcaggacc tcaccaaaag atccagcctc    3840
atacctacat cagacaaaat atcgccgttg ttccttctgt actaaagtat tgtgttttgc    3900
tttggaaaca cccactcact ttgcaatagc cgtgcaagat gaatgcagat tacactgatc    3960
ttatgtgtta caaattgga gaaagtattt aataaaacct gttaattttt atactgacaa    4020
taaaaatgtt tctacagata ttaatgttaa caagacaaaa taaatgtcac gcaacttatt    4080
tttttaataa aaaaaaaaaa aaa                                            4103
```

<210> SEQ ID NO 136
<211> LENGTH: 4306

```
<212> TYPE: DNA
<213> ORGANISM: Homo sapiens

<400> SEQUENCE: 136
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctggcccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtcctttct tcctctcgtt ccccaaatcc gagggcagcc     300
cgcgggcgtc atgcccgcgc tcctccgcag cctggggtac gcgtgaagcc cgggaggctt     360
ggcgccggcg aagacccaag gaccactctt ctgcgtttgg agttgctccc cgcaaccccg     420
ggctcgtcgc tttctccatc ccgacccacg cggggcgcgg gacaacacag gtcgcggag      480
gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga agaggaccgg ggattggtac cgtaaccatg gtcagctggg     660
gtcgtttcat ctgcctggtc gtggtcacca tggcaacctt gtccctggcc cggccctcct     720
tcagtttagt tgaggatacc acattagagc cagaagagcc accaaccaaa taccaaatct     780
ctcaaccaga agtgtacgtg gctgcgccag gggagtcgct agaggtgcgc tgcctgttga     840
aagatgccgc cgtgatcagt tggactaagg atggggtgca cttggggccc aacaatagga     900
cagtgcttat tggggagtac ttgcagataa agggcgccac gcctagagac tccggcctct     960
atgcttgtac tgccagtagg actgtagaca gtgaaacttg gtacttcatg gtgaatgtca    1020
cagatgccat ctcatccgga gatgatgagg atgacaccga tggtgcggaa gattttgtca    1080
gtgagaacag taacaacaag agagcaccat actggaccaa cacagaaaag atggaaaagc    1140
ggctccatgc tgtgcctgcg gccaacactg tcaagtttcg ctgccagcc gggggaacc      1200
caatgccaac catgcggtgg ctgaaaaacg ggaaggagtt taagcaggag catcgcattg    1260
gaggctacaa ggtacgaaac cagcactgga gcctcattat ggaaagtgtg gtcccatctg    1320
acaagggaaa ttatacctgt gtagtggaga atgaatacgg gtccatcaat cacacgtacc    1380
acctggatgt tgtggagcga tcgcctcacc ggcccatcct ccaagccgga ctgccggcaa    1440
atgcctccac agtggtcgga ggagacgtag agtttgtctg caaggtttac agtgatgccc    1500
agccccacat ccagtggatc aagcacgtgg aaaagaacgg cagtaaatac gggcccgacg    1560
ggctgcccta cctcaaggtt ctcaaggttt cggctgagtc cagctcctcc atgaactcca    1620
acacccccgct ggtgaggata caacacgcc tctcttcaac ggcagacacc cccatgctgg    1680
cagggtctc cgagtatgaa cttccagagg acccaaaatg ggagtttcca agagataagc    1740
tgacactggg caagcccctg ggagaaggtt gctttgggca agtggtcatg gcggaagcag    1800
tgggaattga caaagacaag cccaaggagg cggtcaccgt ggccgtgaag atgttgaaag    1860
atgatgccac agagaaagac ctttctgatc tggtgtcaga gatggagatg atgaagatga    1920
ttgggaaaca caagaatatc ataaatcttc ttggagcctg cacacaggat gggcctctct    1980
atgtcatagt tgagtatgcc tctaaaggca acctccgaga ataccccga gccggaggc     2040
caccgggat ggagtactcc tatgacatta accgtgttcc tgaggagcag atgaccttca    2100
aggacttggt gtcatgcacc taccagctgg ccagaggcat ggagtacttg gcttcccaaa    2160
aatgtattca tcgagattta gcagccagaa atgttttggt aacagaaaac aatgtgatga    2220
```
aaatagcaga ctttggactc gccagagata tcaacaatat agactattac aaaaagacca      2280
ccaatgggcg gcttccagtc aagtggatgg ctccagaagc cctgtttgat agagtataca      2340
ctcatcagag tgatgtctgg tccttcgggg tgttaatgtg ggagatcttc actttagggg      2400
gctcgcccta cccagggatt cccgtggagg aacttttttaa gctgctgaag gaaggacaca     2460
gaatggataa gccagccaac tgcaccaacg aactgtacat gatgatgagg gactgttggc      2520
atgcagtgcc ctcccagaga ccaacgttca agcagttggt agaagacttg gatcgaattc      2580
tcactctcac aaccaatgag gaatacttgg acctcagcca acctctcgaa cagtattcac      2640
ctagttaccc tgacacaaga agttcttgtt cttcaggaga tgattctgtt ttttctccag      2700
accccatgcc ttacgaacca tgccttcctc agtatccaca cataaacggc agtgttaaaa      2760
catgaatgac tgtgtctgcc tgtccccaaa caggacagca ctgggaacct agctacactg      2820
agcagggaga ccatgcctcc cagagcttgt tgtctccact tgtatatatg gatcagagga      2880
gtaaataatt ggaaaagtaa tcagcatatg tgtaaagatt tatacagttg aaaacttgta      2940
atcttcccca ggaggagaag aaggtttctg gagcagtgga ctgccacaag ccaccatgta      3000 accctctca cctgccgtgc gtactggctg tggaccagta ggactcaagg tggacgtgcg       3060
ttctgccttc cttgttaatt ttgtaataat tggagaagat ttatgtcagc acacacttac      3120
agagcacaaa tgcagtatat aggtgctgga tgtatgtaaa tatattcaaa ttatgtataa      3180
atatatatta tatatttaca aggagttatt ttttgtattg attttaaatg gatgtcccaa      3240
tgcacctaga aaattggtct ctcttttttt aatagctatt tgctaaatgc tgttcttaca      3300
cataatttct taattttcac cgagcagagg tggaaaaata cttttgcttt cagggaaaat      3360
ggtataacgt taatttatta ataaattggt aatatacaaa acaattaatc atttatagtt      3420
ttttttgtaa tttaagtggc atttctatgc aggcagcaca gcagactagt taatctattg      3480
cttggactta actagttatc agatcctttg aaaagagaat atttacaata tatgactaat      3540
ttggggaaaa tgaagttttg atttatttgt gtttaaatgc tgctgtcaga cgattgttct      3600
tagacctcct aaatgcccca tattaaaaga actcattcat aggaaggtgt ttcattttgg      3660
tgtgcaaccc tgtcattacg tcaacgcaac gtcaactgg acttcccaag ataaatggta       3720
ccagcgtcct cttaaaagat gccttaatcc attccttgag gacagacctt agttgaaatg      3780
atagcagaat gtgcttctct ctggcagctg gccttctgct tctgagttgc acattaatca      3840
gattagcctg tattctcttc agtgaatttt gataatggct tccagactct ttggcgttgg      3900
agacgcctgt taggatcttc aagtcccatc atagaaaatt gaaacacaga gttgttctgc      3960
tgatagtttt ggggatacgt ccatcttttt aagggattgc tttcatctaa ttctggcagg      4020
acctcaccaa aagatccagc ctcataccta catcagacaa aatatcgccg ttgttccttc      4080
tgtactaaag tattgtgttt tgctttggaa acacccactc actttgcaat agccgtgcaa      4140
gatgaatgca gattacactg atcttatgtg ttacaaaatt ggagaaagta tttaataaaa      4200
cctgttaatt tttatactga caataaaaat gtttctacag atattaatgt taacaagaca      4260
aaataaatgt cacgcaactt attttttttaa taaaaaaaaa aaaaaa                   4306

<210> SEQ ID NO 137
<211> LENGTH: 4303
<212> TYPE: DNA
<213> ORGANISM: Homo sapiens

<400> SEQUENCE: 137
ggcggcggct ggaggagagc gcggtggaga gccgagcggg cggcggcgg gtgcggagcg        60

```
ggcgagggag cgcgcgcggc cgccacaaag ctcgggcgcc gcgggctgc atgcggcgta      120 cctggcccgg cgcggcgact gctctccggg ctggcggggg ccggccgcga gccccggggg      180
ccccgaggcc gcagcttgcc tgcgcgctct gagccttcgc aactcgcgag caaagtttgg      240
tggaggcaac gccaagcctg agtcctttct tcctctcgtt ccccaaatcc gagggcagcc      300
cgcgggcgtc atgcccgcgc tcctccgcag cctggggtac gcgtgaagcc cgggaggctt      360
ggcgccggcg aagacccaag gaccactctt ctgcgtttgg agttgctccc cgcaaccccg      420
ggctcgtcgc tttctccatc ccgacccacg cggggcgcgg gacaacaca ggtcgcggag       480 gagcgttgcc attcaagtga ctgcagcagc agcggcagcg cctcggttcc tgagcccacc      540
gcaggctgaa ggcattgcgc gtagtccatg cccgtagagg aagtgtgcag atgggattaa      600
cgtccacatg gagatatgga agaggaccgg ggattggtac cgtaaccatg gtcagctggg      660
gtcgtttcat ctgcctggtc gtggtcacca tggcaacctt gtccctggcc cggccctcct      720
tcagtttagt tgaggatacc acattagagc cagaaggagc accatactgg accaacacag      780
aaaagatgga aaagcggctc catgctgtgc ctgcggccaa cactgtcaag tttcgctgcc      840
cagccggggg gaacccaatg ccaaccatgc ggtggctgaa aaacgggaag gagtttaagc      900
aggagcatcg cattggaggc tacaaggtac gaaaccagca ctggagcctc attatggaaa      960
gtgtggtccc atctgacaag ggaaattata cctgtgtagt ggagaatgaa tacgggtcca     1020
tcaatcacac gtaccacctg gatgttgtgg agcgatcgcc tcaccggccc atcctccaag     1080
ccggactgcc ggcaaatgcc tccacagtgg tcggaggaga cgtagagttt gtctgcaagg     1140
tttacagtga tgcccagccc cacatccagt ggatcaagca cgtggaaaag aacggcagta     1200
aatacgggcc cgacgggctg ccctacctca aggttctcaa ggccgccggt gttaacacca     1260
cggacaaaga gattgaggtt ctctatattc ggaatgtaac ttttgaggac gctggggaat     1320
atacgtgctt ggcgggtaat tctattggga tatcctttca ctctgcatgg ttgacagttc     1380
tgccagcgcc tggaagagaa aaggagatta cagcttcccc agactacctg gagatagcca     1440
tttactgcat aggggtcttc ttaatcgcct gtatggtggt aacagtcatc ctgtgccgaa     1500
tgaagaacac gaccaagaag ccagacttca gcagccagcc ggctgtgcac aagctgacca     1560
aacgtatccc cctgcggaga caggtttcgg ctgagtccag ctcctccatg aactccaaca     1620
ccccgctggt gaggataaca acacgcctct cttcaacggc agacaccccc atgctggcag     1680
gggtctccga gtatgaactt ccagaggacc caaaatggga gtttccaaga gataagctga     1740
cactgggcaa gcccctggga gaaggttgct ttggcaagt ggtcatggcg gaagcagtgg      1800
gaattgacaa agacaagccc aaggaggcgg tcaccgtggc cgtgaagatg ttgaaagatg     1860
atgccacaga gaaagacctt tctgatctgg tgtcagagat ggagatgatg aagatgattg     1920
ggaaacacaa gaatatcata aatcttcttg gagcctgcac acaggatggg cctctctatg     1980
tcatagttga gtatgcctct aaaggcaacc tccgagaata cctccgagcc ggaggccac     2040 ccgggatgga gtactcctat gacattaacc gtgttcctga ggagcagatg accttcaagg     2100
acttggtgtc atgcacctac cagctggcca gaggcatgga gtactggctt cccaaaaat      2160 gtattcatcg agatttagca gccagaaatg ttttggtaac agaaaacaat gtgatgaaaa     2220
tagcagactt tggactcgcc agagatatca acaatataga ctattacaaa aagaccacca     2280
atgggcggct tccagtcaag tggatggctc cagaagccct gtttgataga gtatacactc     2340
atcagagtga tgtctggtcc ttcggggtgt taatgtggga gatcttcact ttaggggct      2400
```

| | | |
|---|---|---|
| cgccctaccc agggattccc gtggaggaac tttttaagct gctgaaggaa ggacacagaa | 2460 |
| tggataagcc agccaactgc accaacgaac tgtacatgat gatgagggac tgttggcatg | 2520 |
| cagtgccctc ccagagacca acgttcaagc agttggtaga agacttggat cgaattctca | 2580 |
| ctctcacaac caatgaggaa tacttggacc tcagccaacc tctcgaacag tattcaccta | 2640 |
| gttaccctga cacaagaagt tcttgttctt caggagatga ttctgttttt tctccagacc | 2700 |
| ccatgcctta cgaaccatgc cttcctcagt atccacacat aaacggcagt gttaaaacat | 2760 |
| gaatgactgt gtctgcctgt ccccaaacag gacagcactg ggaacctagc tacactgagc | 2820 |
| agggagacca tgcctcccag agcttgttgt ctccacttgt atatatggat cagaggagta | 2880 |
| aataattgga aaagtaatca gcatatgtgt aaagattat acagttgaaa acttgtaatc | 2940 |
| ttccccagga gggagaagaag gtttctggag cagtggactg ccacaagcca ccatgtaacc | 3000 |
| cctctcacct gccgtgcgta ctggctgtgg accagtagga ctcaaggtgg acgtgcgttc | 3060 |
| tgccttcctt gttaattttg taataattgg agaagattta tgtcagcaca cacttacaga | 3120 |
| gcacaaatgc agtatatagg tgctggatgt atgtaaatat attcaaatta tgtataaata | 3180 |
| tatattatat atttcaaagg agttatttt tgtattgatt taaatggat gtcccaatgc | 3240 |
| acctagaaaa ttggtctctc tttttttaat agctatttgc taaatgctgt tcttacacat | 3300 |
| aatttcttaa ttttcaccga gcagaggtgg aaaaatactt ttgctttcag ggaaaatggt | 3360 |
| ataacgttaa tttattaata aattggtaat atacaaaaca attaatcatt tatagttttt | 3420 |
| tttgtaattt aagtggcatt tctatgcagg cagcacagca gactagttaa tctattgctt | 3480 |
| ggacttaact agttatcaga tcctttgaaa agagaatatt tacaatatat gactaatttg | 3540 |
| gggaaaatga agttttgatt tatttgtgtt taaatgctgc tgtcagacga ttgttcttag | 3600 |
| acctcctaaa tgccccatat taaaagaact cattcatagg aaggtgtttc attttggtgt | 3660 |
| gcaaccctgt cattacgtca acgcaacgtc taactggact tcccaagata aatggtacca | 3720 |
| gcgtcctctt aaaagatgcc ttaatccatt ccttgaggac agaccttagt tgaaatgata | 3780 |
| gcagaatgtg cttctctctg gcagctggcc ttctgcttct gagttgcaca ttaatcagat | 3840 |
| tagcctgtat tctcttcagt gaattttgat aatggcttcc agactctttg gcgttggaga | 3900 |
| cgcctgttag gatcttcaag tcccatcata gaaaattgaa acacagagtt gttctgctga | 3960 |
| tagttttggg gatacgtcca tcttttaag ggattgcttt catctaattc tggcaggacc | 4020 |
| tcaccaaaag atccagcctc atacctacat cagacaaaat atcgccgttg ttccttctgt | 4080 |
| actaaagtat tgtgttttgc tttgaaaaca cccactcact ttgcaatagc cgtgcaagat | 4140 |
| gaatgcagat tacactgatc ttatgtgtta caaaattgga gaaagtattt aataaaacct | 4200 |
| gttaattttt atactgacaa taaaaatgtt tctacagata ttaatgttaa caagacaaaa | 4260 |
| taaatgtcac gcaacttatt tttttaataa aaaaaaaaaa aaa | 4303 |

```
<210> SEQ ID NO 138
<211> LENGTH: 3011
<212> TYPE: DNA
<213> ORGANISM: Homo sapiens

<400> SEQUENCE: 138
```

| | | |
|---|---|---|
| ggcggcggct ggaggagagc gcggtggaga gccgagcggg cgggcggcgg gtgcggagcg | 60 |
| ggcgagggag cgcgcgcggc cgccacaaag ctcgggcgcc gcggggctgc atgcggcgta | 120 |
| cctggccccgg cgcggcgact gctctccggg ctggcggggg ccggccgcga gccccggggg | 180 |
| ccccgaggcc gcagcttgcc tgcgcgctct gagccttcgc aactcgcgag caaagtttgg | 240 |

```
tggaggcaac gccaagcctg agtcctttct tcctctcgtt ccccaaatcc gagggcagcc      300
cgcgggcgtc atgcccgcgc tcctccgcag cctggggtac gcgtgaagcc cgggaggctt      360
ggcgccggcg aagacccaag gaccactctt ctgcgtttgg agttgctccc cgcaaccccg      420
ggctcgtcgc tttctccatc ccgacccacg cggggcgcgg gacaacaca ggtcgcggag       480 gagcgttgcc attcaagtga ctgcagcagc agcggcagcg cctcggttcc tgagcccacc      540
gcaggctgaa ggcattgcgc gtagtccatg cccgtagagg aagtgtgcag atgggattaa      600
cgtccacatg gagatatgga agaggaccgg ggattggtac cgtaaccatg gtcagctggg      660
gtcgtttcat ctgcctggtc gtggtcacca tggcaacctt gtccctggcc cggccctcct      720
tcagtttagt tgaggatacc acattagagc cagaagatgc catctcatcc ggagatgatg      780
aggatgacac cgatggtgcg gaagattttg tcagtgagaa cagtaacaac aagagagcac      840
catactggac caacacagaa aagatggaaa agcggctcca tgctgtgcct gcggccaaca      900
ctgtcaagtt tcgctgccca gccgggggga acccaatgcc aaccatgcgg tggctgaaaa      960
acgggaagga gtttaagcag gagcatcgca ttggaggcta caaggtacga aaccagcact     1020
ggagcctcat tatggaaagt gtggtcccat ctgacaaggg aaattatacc tgtgtagtgg     1080
agaatgaata cgggtccatc aatcacacgt accacctgga tgttgtggag cgatcgcctc     1140 accgcccat cctccaagcc ggactgccgg caaatgcctc cacagtggtc ggaggagacg      1200
tagagtttgt ctgcaaggtt tacagtgatg cccagcccca catccagtgg atcaagcacg     1260
tggaaaagaa cggcagtaaa tacgggcccg acgggctgcc ctacctcaag gttctcaagc     1320
actcggggat aaatagttcc aatgcagaag tgctggctct gttcaatgtg accgaggcgg     1380
atgctgggga atatatatgt aaggtctcca attatatagg gcaggccaac cagtctgcct     1440
ggctcactgt cctgccaaaa cagcaagcgc ctggaagaga aaggagatt acagcttccc      1500 cagactacct ggagatagcc atttactgca taggggtctt cttaatcgcc tgtatggtgg     1560
taacagtcat cctgtgccga atgaagaaca cgaccaagaa gccagacttc agcagccagc     1620
cggctgtgca caagctgacc aaacgtatcc ccctgcggag acaggtaaca gtttcggctg     1680
agtccagctc ctccatgaac tccaacaccc cgctggtgag gataacaaca cgcctctctt     1740
caacggcaga caccccatg ctggcagggg tctccgagta tgaacttcca gaggacccaa      1800
aatgggagtt tccaagagat aagctgacac tgggcaagcc cctgggagaa ggttgctttg     1860
ggcaagtggt catggcggaa gcagtgggaa ttgacaaaga caagcccaag gaggcggtca     1920
ccgtggccgt gaagatgttg aaagatgatg ccacagagaa agacctttct gatctggtgt     1980
cagagatgga gatgatgaag atgattggga acacaagaa tatcataaat cttcttggag      2040
cctgcacaca ggatgggcct ctctatgtca tagttgagta tgcctctaaa ggcaacctcc     2100
gagaatacct ccgagcccgg aggccacccg ggatggagta ctcctatgac attaaccgtg     2160
ttcctgagga gcagatgacc ttcaaggact tggtgtcatg cacctaccag ctggccagag     2220
gcatggagta cttggcttcc caaaaatgta ttcatcgaga tttagcagcc agaaatgttt     2280
tggtaacaga aaacaatgtg atgaaaatag cagactttgg actcgccaga gatatcaaca      2340
atatagacta ttacaaaaag accaccaatg gcggcttcc agtcaagtgg atggctccag      2400
aagccctgtt tgatagagta tacactcatc agagtgatgt ctggtccttc ggggtgttaa     2460
tgtgggagat cttcactta gggggctcgc cctaccagg gattcccgtg gaggaacttt        2520
ttaagctgct gaaggaagga cacagaatgg ataagccagc caactgcacc aacgaactgt     2580
```

```
acatgatgat gagggactgt tggcatgcag tgccctccca gagaccaacg ttcaagcagt    2640
tggtagaaga cttggatcga attctcactc tcacaaccaa tgagatctga aagtttatgg    2700
cttcattgag aaactgggaa aagttggtca ggcgcagtgg ctccatgcctg taatcccagc   2760 actttgggag gccgaggcag gcggatcatg aggtcaggag ttccagacca gcctggccaa    2820
catggtgaaa ccctgtctct actaaagata caaaaaatta gccgggcgtg ttggtgtgca    2880
cctgtaatcc cagctactcc gggaggctga ggcaggagag tcacttgaac cggggaggcg    2940
gaggttgcag tgagccgaga tcatgccatt gcattccagc cttggcgaca gagcgagact    3000
ccgtctcaaa a                                                         3011

<210> SEQ ID NO 139
<211> LENGTH: 4286
<212> TYPE: DNA
<213> ORGANISM: Homo sapiens

<400> SEQUENCE: 139
gtcgcgggca gctggcgccg cgcggtcctg ctctgccggt cgcacggacg caccggcggg      60
ccgccggccg gagggacggg cgggagctg ggcccgcgga cagcgagccg gagcgggagc     120
cgcgcgtagc gagccgggct ccggcgctcg ccagtctccc gagcggcgcc cgcctcccgc    180
cggtgcccgc gccgggccgt gggggggcagc atgcccgcgc gcgctgcctg aggacgccgc    240 ggccccccgcc cccgccatgg gcgcccctgc ctgcgccctc gcgctctgcg tggccgtggc    300
catcgtggcc ggcgcctcct cggagtcctt ggggacggag cagcgcgtcg tggggcgagc    360
ggcagaagtc ccgggcccag agcccggcca gcaggagcga ttggtcttcg gcagcgggga    420
tgctgtggag ctgagctgtc ccccgcccgg gggtggtccc atggggccca ctgtctgggt    480
caaggatggc acagggctgg tgcctcggga gcgtgtcctg gtggggcccc agcggctgca    540
ggtgctgaat gcctcccacg aggactccgg ggcctacagc tgccggcagc ggctcacgca    600
gcgcgtactg tgccacttca gtgtgcgggt gacagacgct ccatcctcgg gagatgacga    660
agacggggag gacgaggctg aggacacagg tgtggacaca ggggccccctt actggacacg    720 gcccgagcga atggacaaga agctgctggc cgtgccggcc gccaacaccg tccgcttccg    780
ctgcccagcc gctggcaacc ccactccctc catctcctgg ctgaagaacg gcagggagtt    840
ccgcggcgag caccgcattg gaggcatcaa gctgcggcat cagcagtgga gcctggtcat    900
ggaaagcgtg gtgccctcgg accgcggcaa ctacacctgc gtcgtggaga caagtttgg     960 cagcatccgg cagacgtaca cgctggacgt gctggagcgc tccccgcacc ggcccatcct   1020
gcaggcgggg ctgccggcca accagacggc ggtgctgggc agcgacgtgg agttccactg   1080
caaggtgtac agtgacgcac agccccacat ccagtggctc aagcacgtgg aggtgaatgg   1140
cagcaaggtg ggcccggacg gcacacccta cgttaccgtg ctcaagacgg cgggcgctaa   1200
caccaccgac aaggagctag aggttctctc cttgcacaac gtcacctttg aggacgccgg   1260
ggagtacacc tgcctggcgg gcaattctat tgggttttct catcactctg cgtggctggt   1320
ggtgctgcca gccgaggagg agctggtgga ggctgacgag gcgggcagtg tgtatgcagg   1380
catcctcagc tacggggtgg gcttcttcct gttcatcctg gtggtggcgg ctgtgacgct   1440
ctgccgcctg cgcagccccc caagaaagg cctgggctcc ccaccgtgc acaagatctc    1500 ccgcttcccg ctcaagcgac aggtgtccct ggagtccaac gcgtccatga gctccaacac   1560
accactggtg cgcatcgcaa ggctgtcctc aggggagggc cccacgctgg ccaatgtctc   1620
cgagctcgag ctgcctgccg accccaaatg ggagctgtct cgggccggc tgaccctggg   1680
```

```
caagccccttggggagggctgcttcggccaggtggtcatggcggaggccatcggcattga      1740
caaggaccgggccgccaagcctgtcaccgtagccgtgaagatgctgaaagacgatgccac      1800
tgacaaggacctgtcggacctggtgtctgagatggagatgatgaagatgatcgggaaaca      1860
caaaaacatcatcaacctgctgggcgcctgcacgcagggcgggcccctgtacgtgctggt      1920
ggagtacgcggccaagggtaacctgcgggagttctgcgggcgcggcggccccgggcct       1980
ggactactccttcgacacctgcaagccgcccgaggagcagctcaccttcaaggacctggt      2040
gtcctgtgcctaccaggtggcccggggcatggagtacttgcctcccagaagtgcatcca      2100
cagggacctggctgcccgcaatgtgctggtgaccgaggacaacgtgatgagatcgcaga      2160
cttcgggctggcccgggacgtgcacaacctcgactactacaagaagacgaccaacggccg      2220
gctgcccgtgaagtggatggcgcctgaggccttgtttgaccgagtctacactcaccagag      2280
tgacgtctggtcctttggggtcctgctctgggagatcttcacgctgggggctccccgta     2340
ccccggcatccctgtggaggagctcttcaagctgctgaaggagggccaccgcatggacaa      2400
gcccgccaactgcacacacgacctgtacatgatcatgcgggagtgctggcatgccgcgcc      2460
ctcccagaggcccaccttcaagcagctggtggaggacctgaccgtgtccttaccgtgac      2520
gtccaccgacgagtacctggacctgtcggcgcctttcgagcagtactcccgggtggcca      2580
ggacaccccagctccagctcctcaggggacgactccgtgtttgcccacgacctgctgcc      2640
cccggcccccccagcagtggggctcgcgacgtgaaggccactggtcccaacaatg        2700
tgaggggtccctagcagcccaccctgctgctggtgcacagccactccccgcatgagact      2760
cagtgcagatggagagacagctacacagagctttggtctgtgtgtgtgtgtgcgtgtg      2820
tgtgtgtgtgtgcacatccgcgtgtgcctgtgtgcgtgcgcatcttgcctccaggtgc      2880
agaggtaccctgggtgtcccgctgctgtgcaacggtctcctgactggtgctgcagcacc      2940
gaggggcctttgttctggggggaccccagtcagaatgtaagtgggcccaccggtgggac      3000
ccccgtggggcagggagctgggcccgacatggctccggcctctgcctttgcaccacggga      3060
catcacagggtgggcctcggcccctcccacacccaaagctgagcctgcaggaagcccca      3120
catgtccagcaccttgtgcctggggtgttagtggcaccgctccccacctccaggctttc      3180
ccacttcccaccctgcccctcagagactgaaattacgggtacctgaagatgggagccttt      3240
accttttatgcaaaaggttattccggaaactagtgtacatttctataaatagatgctgt      3300
gtatatggtatatatacatatatatataacatatatggaagaggaaaaggctggtaca      3360
acggaggcctgcgaccctggggggcacaggaggcaggcatggccctgggcggggcgtgggg      3420
gggcgtggaggaggccccaggggggtctcacccatgcaagcagaggaccagggcctttc       3480
tggcaccgcagttttgttttaaaactggacctgtatatttgtaaagctatttatgggccc      3540
ctggcactctgttcccacaccccaacactccagcatttagctggccacatggcggaga      3600
gttttaatttttaacttattgacaaccgagaaggtttatccgccgatagagggacggcc      3660
aagaatgtacgtccagcctgccccggagctggaggatccctccaagcctaaaaggttgt      3720
taatagttggaggtgattccagtgaagatattttatttcctttgtcctttttcaggagaa      3780
ttagatttctataggattttctcttaggagatttattttttggacttcaagcaagctgg      3840
tattttcatacaaattcttctaattgctgtgtgtcccaggcagggagacggtttccaggg      3900
aggggccggccctgtgtgcaggttccgatgttattagatgttacaagttttatatatatct      3960
atatatataatttattgagttttttacaagatgtatttgttgtagacttaacacttcttac      4020
```

```
gcaatgcttc tagagttta tagcctggac tgctaccttt caaagcttgg agggaagccg      4080
tgaattcagt tggttcgttc tgtactgtta ctgggccctg agtctgggca gctgtccctt      4140
gcttgcctgc agggccatgg ctcagggtgg tctcttcttg gggcccagtg catggtggcc      4200
agaggtgtca cccaaaaccgg caggtgcgat tttgttaacc cagcgacgaa ctttccgaaa      4260
aataaagaca cctggttgct aacctg                                           4286

<210> SEQ ID NO 140
<211> LENGTH: 3950
<212> TYPE: DNA
<213> ORGANISM: Homo sapiens

<400> SEQUENCE: 140
gtcgcgggca gctggcgccg cgcggtcctg ctctgccggt cgcacggacg caccggcggg        60
ccgccggccg gagggacggg gcgggagctg ggcccgcgga cagcgagccg gagcgggagc       120
cgcgcgtagc gagccgggct ccggcgctcg ccagtctccc gagcggcgcc cgcctcccgc       180
cggtgcccgc gccgggccgt ggggggcagc atgcccgcgc gcgctgcctg aggacgccgc       240
ggcccccgcc cccgccatgg gcgcccctgc ctgcgccctc gcgctctgcg tggccgtggc       300
catcgtggcc ggcgcctcct cggagtcctt ggggacggag cagcgcgtcg tggggcgagc       360
ggcagaagtc ccgggcccag agcccggcca gcaggagcag ttggtcttcg gcagcgggga       420
tgctgtggag ctgagctgtc ccccgccggg gggtggtccc atggggccca ctgtctgggt       480
caaggatggc acagggctgg tgccctcgga gcgtgtcctg gtggggcccc agcggctgca       540
ggtgctgaat gcctcccacg aggactccgg ggcctacagc tgccggcagc ggctcacgca       600
gcgcgtactg tgccacttca gtgtgcgggt gacagacgct ccatcctcgg agatgacga       660 agacggggag gacgaggctg aggacacagg tgtggacaca ggggcccctt actggacacg       720
gcccgagcgg atggacaaga agctgctggc cgtgccggcc gccaacaccg tccgcttccg       780
ctgcccagcc gctggcaacc ccactccctc catctcctgg ctgaagaacg caggggagtt       840
ccgcggcgag caccgcattg gaggcatcaa gctgcggcat cagcagtgga gcctggtcat       900
ggaaagcgtg gtgccctcgg accgcggcaa ctacacctgc gtcgtggaga caagtttgg       960 cagcatccgg cagacgtaca cgctggacgt gctggagcgc tccccgcacc ggcccatcct      1020
gcaggcgggg ctgccggcca accagacggc ggtgctgggc agcgacgtgg agttccactg      1080
caaggtgtac agtgacgcac agccccacat ccagtggctc aagcacgtgg aggtgaatgg      1140
cagcaaggtg ggcccggacg gcacacccta cgttaccgtg ctcaaggtgt ccctggagtc      1200
caacgcgtcc atgagctcca acaccaccac tggtgcgcatc gcaaggctgt cctcagggga      1260
gggccccacg ctggccaatg tctccgagct cgagctgcct gccgacccca atgggagct      1320 gtctcgggcc cggctgaccc tgggcaagcc ccttgggag ggctgcttcg gccaggtggt      1380
catggcggag gccatcggca ttgacaagga ccgggccgcc aagcctgtca ccgtagccgt      1440
gaagatgctg aaagacgatg ccactgacaa ggacctgtcg gacctggtgt ctgagatgga      1500
gatgatgaag atgatcggga acacaaaaaa catcatcaac ctgctgggcg cctgcacgca      1560
gggcgggccc ctgtacgtgc tggtggagta cgcggccaag ggtaacctgc gggagttct      1620 gcgggcgcgg cggccccggg gcctggacta ctccttcgac acctgcaagc cgcccgagga      1680
gcagctcacc ttcaaggacc tggtgtcctg tgcctaccag gtggcccggg gcatggagta      1740
cttggcctcc cagaagtgca tccacaggga cctggctgcc cgcaatgtgc tggtgaccga      1800
ggacaacgtg atgaagatcg cagacttcgg gctggcccgg gacgtgcaca acctcgacta      1860
```

```
ctacaagaag acgaccaacg gccggctgcc cgtgaagtgg atggcgcctg aggccttgtt      1920
tgaccgagtc tacactcacc agagtgacgt ctggtccttt ggggtcctgc tctgggagat      1980
cttcacgctg gggggctccc cgtacccegg catcctgtg gaggagctct tcaagctgct       2040
gaaggagggc caccgcatgg acaagccgc caactgcaca cacgaccgt acatgatcat       2100 gcgggagtgc tggcatgccg cgccctccca gaggcccacc ttcaagcagc tggtggagga      2160
cctggaccgt gtccttaccg tgacgtccac cgacagtac ctggaccgt cggcgccttt       2220 cgagcagtac tccccgggtg gccaggacac ccccagctcc agctcctcag ggacgactc       2280 cgtgtttgcc cacgacctgc tgcccccggc cccacccagc agtgggggct cgcggacgtg      2340
aagggccact ggtccccaac aatgtgaggg gtccctagca gcccacccctg ctgctggtgc     2400 acagccactc cccggcatga gactcagtgc agatggagag acagctacac agagctttgg      2460
tctgtgtgtg tgtgtgtgcg tgtgtgtgtg tgtgtgtgca catccgcgtg tgcctgtgtg      2520
cgtgcgcatc ttgcctccag gtgcagaggt accctgggtg tccccgctgc tgtgcaacgg      2580
tctcctgact ggtgctgcag caccgagggg cctttgttct gggggaccc agtgcagaat      2640 gtaagtgggc ccacccggtg ggaccccgt ggggcaggga gctgggcccg acatggctcc      2700
ggcctctgcc tttgcaccac gggacatcac agggtgggcc tcggcccctc ccacacccaa      2760
agctgagcct gcagggaagc cccacatgtc cagcaccttg tgcctggggt gttagtggca      2820
ccgcctcccc acctccaggc tttcccactt cccaccctgc ccctcagaga ctgaaattac      2880
gggtacctga agatgggagc ctttaccttt tatgcaaaag gtttattccg gaaactagtg      2940
tacatttcta taaatagatg ctgtgtatat ggtatatata catatatata tataacatat      3000
atggaagagg aaaaggctgg tacaacgag gcctgcgacc ctgggggcac aggaggcagg       3060
catggccctg ggcggggcgt gggggggcgt ggagggaggc cccagggggt ctcacccatg      3120
caagcagagg accagggcct tttctggcac cgcagttttg ttttaaaact ggacctgtat      3180
atttgtaaag ctatttatgg gcccctggca ctcttgttcc cacaccccaa cacttccagc      3240
atttagctgg ccacatggcg gagagtttta attttaact tattgacaac cgagaaggtt       3300
tatcccgccg atagagggac ggccaagaat gtacgtccag cctgccccgg agctggagga     3360 tccctccaa gcctaaaagg ttgttaatag ttggaggtga ttccagtgaa gatattttat       3420 ttccttgtc cttttcagg agaattagat ttctatagga ttttctttta ggagattat        3480 tttttggact tcaaagcaag ctggtatttt catacaaatt cttctaattg ctgtgtgtcc      3540
caggcaggga gacggtttcc agggaggggc cggccctgtg tgcaggttcc gatgttatta      3600
gatgttacaa gtttatatat atctatatat ataatttatt gagttttac aagatgtatt       3660 tgttgtagac ttaacacttc ttacgcaatg cttctagagt tttatagcct ggactgctac      3720
ctttcaaagc ttggagggaa gccgtgaatt cagttggttc gttctgtact gttactgggc      3780
cctgagtctg ggcagctgtc ccttgcttgc ctgcagggcc atggctcagg gtggtctctt      3840
cttggggccc agtgcatggt ggccagaggt gtcacccaaa ccggcaggtg cgattttgtt      3900
aacccagcga cgaactttcc gaaaaataaa gacacctggt tgctaacctg                3950
```

<210> SEQ ID NO 141
<211> LENGTH: 2085
<212> TYPE: DNA
<213> ORGANISM: Homo sapiens

<400> SEQUENCE: 141

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg gggatgctgt ggagctgagc     180
tgtccccgc ccgggggtgg tcccatgggg cccactgtct gggtcaagga tggcacaggg      240
ctggtgccct cggagcgtgt cctggtgggg ccccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga acggcagcaa ggtgggcccg     900
gacggcacac cctacgttac cgtgctcaag gtgtccctgg agtccaacgc gtccatgagc     960
tccaacacac cactggtgcg catcgcaagg ctgtcctcag ggagggccc cacgctggcc    1020
aatgtctccg agctcgagct gcctgccgac cccaaatggg agctgtctcg ggcccggctg    1080
accctgggca agcccttgg ggagggctgc ttcggccagg tggtcatggc ggaggccatc    1140
ggcattgaca aggaccgggc cgccaagcct gtcaccgtag ccgtgaagat gctgaaagac    1200
gatgccactg acaaggacct gtcggacctg gtgtctgaga tggagatgat gaagatgatc    1260
gggaaacaca aaacatcat caacctgctg ggcgcctgca cgcagggcgg gccctgtac     1320
gtgctggtgg agtacgcggc caagggtaac ctgcgggagt ttctgcgggc gcggcggccc    1380
ccgggcctgg actactcctt cgacacctgc aagccgcccg aggagcagct caccttcaag    1440
gacctggtgt cctgtgccta ccaggtggcc cggggcatgg agtacttggc ctcccagaag    1500
tgcatccaca gggacctggc tgcccgcaat gtgctggtga ccgaggacaa cgtgatgaag    1560
atcgcagact cgggctggcc ccgggacgtg cacaacctcg actactacaa gaagacaacc    1620
aacggccggc tgcccgtgaa gtggatggcg cctgaggcct gttttgaccg agtctacact    1680
caccagagtg acgtctggtc ctttggggtc ctgctctggg agatcttcac gctgggggc    1740
tccccgtacc ccggcatccc tgtggaggag ctcttcaagc tgctgaagga gggccaccgc    1800
atggacaagc cgccaactg cacacacgac ctgtacatga tcatgcggga gtgctggcat    1860
gccgcgccct cccagaggcc caccttcaag cagctggtgg aggacctgga ccgtgtcctt    1920
accgtgacgt ccaccgacga gtacctggac ctgtcggcgc ctttcgagca gtactccccg    1980
ggtggccagg acaccccag ctccagctcc tcaggggacg actccgtgtt tgcccacgac    2040
ctgctgcccc cggccccacc cagcagtggg ggctcgcgga cgtga                   2085
```

<210> SEQ ID NO 142
<211> LENGTH: 4431
<212> TYPE: DNA
<213> ORGANISM: Homo sapiens

<400> SEQUENCE: 142

```
aggcggggct ggagtggtgg aaggggggtg gcaggtctgc attgccgctt ccctggtgcc      60
```

```
gggagcagtc gccgctgccg cctccgcccg cggccgggac ccccgtcctc gcccgggact    120
ccttacccgg ggaacctaga ccaggtctcc agaggcttgt ggaagagaag caggcgaccc    180
ttcctgagtt atcctggctt agcctcccaa tctggctccc cttcccctc ccattccct     240
gctcccctg tcccttcccc atccacccaa ctgaactggg tataggtcaa agtcctctc     300
tttccttttc cttcctaggc actcattggc taggacctgt ttgctctttt ttttgtgccc    360
agagatactg gaacacgctt catctaagta actgtgggga ggggtctttt tgactctaca    420
agtccttgag caaaaagctg aaaagaagc aggaggtgga gaagacccag tgaagtgccc     480
caagccccat catggaagag ggcttccgag accgggcagc tttcatccgt ggggccaaag    540
acattgctaa ggaagtcaaa aagcatgcgg ccaagaaggt ggtgaagggc ctggacagag    600
tccaggacga atattcccga agatcgtact cccgctttga ggaggaggat gatgatgatg    660
acttccctgc tcccagtgat ggttattacc gaggagaagg gacccaggat gaggaggaag    720
gtggtgcatc cagtgatgct actgagggcc atgacgagga tgatgagatc tatgaagggg    780
aatatcaggg cattccccgg gcagagtctg ggggcaaagg cgagcggatg gcagatgggg    840
cgcccctggc tggagtaagg gggggcttga gtgatgggga gggtccccct ggggccgggg    900
gggaggcaca acgacggaaa gaacgagaag aactggccca acagtatgaa gccatcctac    960
gggagtgtgg ccacggccgc ttccagtgga cactgtattt tgtgcttggt ctggcgctga   1020
tggctgacgg tgtggaggtc tttgtggtgg gcttcgtgct gccccagcgct gagaaagaca   1080
tgtgcctgtc cgactccaac aaaggcatgc taggcctcat cgtctacctg ggcatgatgg   1140
tgggagcctt cctctgggga ggtctggctg accggctggg tcggaggcag tgtctgctca   1200
tctcgctctc agtcaacagc gtcttcgcct tcttctcatc ttttgtccag ggttacggca   1260
cttcctctt ctgccgccta ctttctgggg ttgggattgg agggtccatc cccattgtct    1320
tctcctattt ctccgagttt ctggcccagg agaaacgagg ggagcatttg agctggctct   1380
gcatgttttg gatgattggt ggcgtgtacg cagctgctat ggcctgggcc atcatccccc   1440
actatgggtg gagttttcag atgggttctg cctaccagtt ccacagctgg agggtcttcg   1500
tcctcgtctg cgcctttcct tctgtgtttg ccattggggc tctgaccacg cagcctgaga   1560
gccccgtt cttcctagag aatggaaagc atgatgaggc ctggatggtg ctgaagcagg     1620
tccatgatac caacatgcga gccaaaggac atcctgagcg agtgttctca gtaacccaca   1680
ttaagacgat tcatcaggag gatgaattga ttgagatcca gtcggacaca gggacctggt   1740
accagcgctg gggggtccgg gccttgagcc taggggggca ggtttggggg aattttctct   1800
cctgttttgg tcccgaatat cggcgcatca ctctgatgat gatgggtgtg tggttcacca   1860
tgtcattcag ctactatggc ctgaccgtct ggtttcctga catgatccgc catctccagg   1920
cagtggacta cgcatcccgc accaaagtgt tccccgggga gcgcgtagag catgtaactt   1980
ttaacttcac gttggagaat cagatccacc gaggcgggca gtacttcaat gacaagttca   2040
ttgggctgcg gctcaagtca gtgtcctttg aggattccct gtttgaagag tgttattttg   2100
aggatgtcac atccagcaac acgttttttcc gcaactgcac attcatcaac actgtgttct   2160
ataacactga cctgttcgag tacaagtttg tgaacagccg tctgataaac agtacattcc   2220
tgcacaacaa ggagggctgc ccgctagacg tgacagggac gggcgaaggt gcctacatgg   2280
tatactttgt gagcttcctg ggacactgg cagtgcttcc tgggaatatc gtgtctgccc    2340
tgctcatgga caagatcggc aggctcagaa tgcttgctgg ctccagcgtg atgtcctgtg   2400
```

```
tctcctgctt cttcctgtct tttgggaaca gtgagtcggc catgatcgct ctgctctgcc    2460 ttttttggcgg ggtcagcatt gcatcctgga atgcgctgga cgtgttgact gttgaactct    2520 accccctcaga caagaggacc acagcttttg gcttcctgaa tgccctgtgt aagctggcag    2580
ctgtgctggg gatcagcatc ttcacatcct tcgtgggaat caccaaggct gcacccatcc    2640
tctttgcctc agctgcccct tgcccttggca gctctctggc cctgaagctg cctgagaccc    2700
gggggcaggt gctgcagtga aggggtctct agggctttgg gattggcagg cacactgtga    2760
gaccaacaac tccttccttc ccctccctgc cctgccatcc tgacctccag agccctcact    2820
ccccactccc cgtgtttggt gtcttagctg tgtgtgcgtg tgcgtgtgca tgtgtgtaaa    2880
ccccgtgggc agggactaca gggaaggctc cttcatccca gttttgagat gaagctgtac    2940
tccccatttc ccactgccct tgactttgca aagagaagg ctgagcccca tccttctccc    3000
cctgttagag aggggccctt gcttccctgt tccagggggtt ccagaatagg cttcctgcct    3060
tccccatcat tccctctgcc taggccctgg tgaaaccaca ggtatgcaat tatgctaggg    3120 gctgggggctc tggtgtagac catggaccaa agaacttct tagagtctga agagtgggcc    3180
tcgggtgccc tctcacatct cctgttggat gctgggggag aagcaataaa cctcagccct    3240
ctggcctcca ctttcctctc aatttgggct gcaaatatga agcctgaatt ttatgaaatt    3300
agctttctga ttcttattta ttaatagatt aagttctgag gcagctccgc aggactgtgt    3360
gtgaatgtgt atgtatactt acatatgtgt gtgcatgtgc catggggcgg ggggtatcac    3420
tatactgtcc tcaaatataa gccaagggta atttcagcgg atgcacacac aaccctgcct    3480
cccacagttc ctcccctaat ctggtttctg tgttgagcct gggatggagg agccctaggc    3540
cagcctggga taagagtccc acagtctagg gagatctgag ggcatccgac aaggcccatc    3600
tccttccctc ctcaagaagc agaggcctcc tctggagtga gaggctccac ccactacagc    3660
acaggcggga atagcacagc tgccctccca tgctccctac ctgtcccctc acaggagggg    3720
gagcagggga gggaaagaaa ccaggcatct ggtcaaacca gcagatcaaa aagcacaaag    3780
agctggggca gaggcaggaa gcaggggccc tcctggcagc tcctctgagt ggggagaggt    3840
tgggcagtga gtgagggacc cctaatgcag ggactagaag cctcagtttc cccatttttac    3900 ccttccacac aatagcctct gtaggttagg ctgccccatc ccaccctact ctgtgtggct    3960
gctttctttg gtgccctccc ctcaccccac tgtagctgtg acgtgttgta gttttttagat    4020 gtttgtaaaa tgtttaaaaa aatgttaaaaa ggaaaaaagt gaaaataaca aaaagaaaa    4080 tcaaaattca ccttcgtcat gctgcgtcca gtgcccaac cctgtggtca ctctccccat    4140
tttgtaacac tgtaccaggt ggtgactgtt taactctttg gtgtctgtgc tcaaaagact    4200
gccttctcca gtgcccagtg tatgagtgtg tgccctgtgc ccttgtccct cactccccac    4260
atgctggacg tagccctctt cctcgcaccc ctgggaggga cccatccatc tcccttgctc    4320
tcctggggaa ccctaaaccc aactctgttg atgtgaaaaa tgcagtgaaa atatattgacg    4380 aaaaataaaa cggaaacaaa tcctcaaaat acaaaaaaaa aaaaaaaaa a              4431
```

<210> SEQ ID NO 143
<211> LENGTH: 5311
<212> TYPE: DNA
<213> ORGANISM: Homo sapiens

<400> SEQUENCE: 143

```
agcataaccct tcggtggcag gacaaatcag gccagcacgc agtctgccaa gtcctgctcg      60
ctccctgtca agaaaaacag ctggatccat ttctaatcaa cacttcccaa cgcaacactt     120
```

```
ctgagtctct gaaggagacc agagcttgaa actttccaga cttccaacag acatcgagtg    180
caaaaggata tttaggttgt ctttgcacaa atctggttga tttgagagat aaaggggggg    240
ggaaccagtg tgactttcac ctaagaagtc acatgaacat atttcacatt tgaactacat    300
aatgaatgat ggttattgaa atagcccaaa cctctaccac agagcgaggg atatagctca    360
aggggcaacc aggcagtcgc agaaccaagg aatggatgac tacaagtatc aggacaatta    420
tgggggctat gctcccagtg atggctatta ccgcggcaat gagtccaacc agaagaaga    480 tgcacagagt gatgtcaccg aaggccatga tgaggaagac gagatctatg agggcgagta    540
ccagggtatc cctcacccag atgatgtcaa ggccaagcag gccaagatgg cgccctccag    600
aatggacagc cttcggggcc agacagacct gatggctgag aggctggaag atgaggagca    660 gttgcccac cagtacgaga ccatcatgga tgagtgtggc catggccgct tccagtggat    720
cctctttttc gtcttgggtt tggccctgat ggccgatggg gtggaagtgt cgtggtgag    780 ttttgccctg cccagtgcag agaaggacat gtgtctgtcc agttccaaaa aaggaatgct    840
agggatgata gtctacttgg gaatgatggc gggcgccttc atcctgggag gcctggctga    900
taagctggga aggaagcgag tcctcagcat gtctctggcc gtcaatgcct ccttcgcctc    960
cctctcttcc ttcgtgcagg gatatggagc cttcctcttc tgccgactca tctcaggcat   1020
cggtattggg ggtgctctac cgattgtttt tgcctatttt tctgaattct tgtctcggga   1080
gaagcgagga gaacacctca gttggctggg catcttctgg atgactgggg gcctgtacgc   1140
atctgccatg gcctggagca tcatcccaca ctatggctgg ggcttcagca tggggaccaa   1200
ttaccacttc catagctgga gagtgtttgt catcgtctgt gctctgccct gcaccgtgtc   1260
catggtggcc ctgaagttca tgccagagag cccaaggttt ctgctagaga tgggcaaaca   1320
tgatgaagcc tggatgattc tcaagcaagt ccatgacacc aacatgagag ctaaggggac   1380
cccagagaaa gtgttcacgg tttccaacat caaaactccc aagcaaatgg atgaattcat   1440
tgagatccaa agttcaacag gaacctggta ccagcgctgg ctggtcagat tcaagaccat   1500
tttcaagcag gtctgggata atgccctgta ctgtgtgatg gggccctaca gaatgaatac   1560
actgattctg gccgtggttt ggtttgccat ggcattcagt tactatggac tgacagtttg   1620
gtttcctgat atgatccgct attttcaaga tgaagaatac aagtctaaaa tgaaggtgtt   1680
ttttggtgag catgtgtacg cgccacaat caacttcacg atggaaaatc agatccacca   1740
acatgggaaa cttgtgaatg ataagttcac aagaatgtac tttaaacatg tactctttga   1800
ggacacattc tttgacgagt gctatttga agacgtaaca tcaacagata cctacttcaa   1860
aaattgtacc attgaatcaa ccatctttta caacacagac ctctacgagc acaagttcat   1920
caactgtcgg tttatcaact ccaccttcct ggagcagaag gagggctgcc acatggactt   1980
ggagcaagat aatgacttcc tgatttacct cgtcagcttc ctgggcagcc tgtctgtctt   2040
acccgggaac atcatttctg ccctgctcat ggatagaatt ggaaggctca agatgattgg   2100
tggctccatg ctaatctctg cagtctgctg cttcttcctg ttttttggca acagtgagtc   2160
tgcaatgatc ggctggcagt gcctgttctg tgggacaagc attgcagcct ggaatgctct   2220
ggatgtgatc acagtggagc tgtatccac caaccagaga gcaacagcct tcggcattct   2280
caatggatta tgcaaatttg gcgccatcct gggaaacacc atctttgctt cttttgttgg   2340
gataaccaaa gtggtcccca tccttctggc tgctgcttct ctggttgggg gtggcctgat   2400
tgcccttcga ctgccagaga ctcgagaaca ggtcctgatg tgaacaacct atgggaaaag   2460
```

```
gaaaggtcga gagaatcttg tccaggacac tgaaatgcat ccacacttcc tgcctatcac    2520
ggtccggagg acaccttgga tagcacggga ggagaagttg actttgtgac ccctagttta    2580
ggacccactt cagctgtcaa tatgtttgta actcaggtga ctgatttggg ggtgccctga    2640 gccacccta  gaatcacaga gctgcgtgtt aacttcaag  tcttcccagt ccaaggcagg    2700
gagaggattc tccagtgagt gcacacacta tgcgaggagc aagcatttct ctaagtcaag    2760
tgcaaggact taacttgcgt ttgaaaagga attagagggt cagaaacacc caggttcctc    2820
cagaaagctc cttggagccc aacaacttaa caaatcaact tggctggaag ttagagtcat    2880
tatatgaaga ttgggcttga agtatatatt tttgcattta aaagtatcac ctatcatatt    2940
ttccactcga aaattgacat agtagcattg aggatactct gatctagaaa gccaagtatt    3000
tgagcaacat ctatagagat ctacttttct cctatgtctc ctaggctttc catgataatt    3060
aggtaataca tttaagaagg atatttattt ctgttttgct ctattcaaag aaacggaatg    3120
ggatagttat tctgtaaact aagtttgtat ataactttat ttgggtttaa tttccacaac    3180
tggtatctgc aaatattgcc agcattttag ccatattttg ggagaacttg gtgtttgagg    3240
tcccaggaaa tgaggtctga tcaaatgaaa tgcaagcaca atttcttaca gccatttaac    3300
tttctgttgg gaggatgaat taacaaactc acattgtgca gtctgcttaa tccaggcact    3360
tttctttgtg caggtgtagt gagtagttac ttctctccct tacacagatg acttgtgaaa    3420
ctcaagctca ccatcttcag tgctggcatt ttactttgcc actacccaaa acaatgtga    3480 gatgtgttca gtggcctctg gtactctttg caggcaagaa tcaaacaaca tggggactga    3540
gggaaggatg gggaagtgta gccacagttc ttccaaatgt aaatactttt tgtttgttct    3600
agtggtaaaa tgcaaatgca atccatattt gttaggatgg tcaggtctca tgagaaatct    3660
atgctatgtg tccagagctt ttgaaacaga gtccattgga gtgggagtta gggagtgtag    3720
tggatgccaa atatgttttt cttcagtgct taagagaact gttcctgaa  gtccagcttt    3780 gaacataaac aggggtgtgg gttgggggag gagcttagga caaacctctc tgatgaaggt    3840
cagcaataga ctgaagtctt gactgcatgg aagaggaaaa acatcagaac tgtctgacaa    3900 tggagggac  agtgagctac gcacaactgc cagcggaggt gaacttgcac ctgcccaggc    3960
cggatgaaca tcagcctgca agaactagtt gtttgagttg atttgcagtg ctctcaatgg    4020
gcaagtgcca cattttccct ggcagagatc tccaaaaatt taaaacagaa taataatggc    4080
tatatcgagt gtttctcag  tattggagaa atgcttaggt cctatgatag cttcgggaca    4140 tcttctgta  attttcctca attaacgggt tggtaggggt aaatcttatg acaccttcc    4200 accgtcgatt tgagatcagt tttaatggtt aaaatgttta ctctccttct gtcaaccctc    4260
acctttttat ttcacccct  cccttttttt ctgtacaggg agagaagaca tattgactct    4320
gactggacac cctgattcct ccaaatatat ataccactgt gtattaatct ttctctcagt    4380
gttttatagg agtactaaca tttattgctc tgtcaataat gaaaggctcg atgtaatata    4440
gctgtaattt actttccata tgaatacagt ggctaggttc ataaaagaga attgtgtgag    4500
tctgggatta ccacatctaa aacattattc tttaatggga taatacaatt cattgagcag    4560
ctaccactta aaaaacttgc aggacagtta gagcctgcat ttctagttaa gatggatctt    4620
gtaaatttaa aattggatta acattggagt gctggggtgg ctgcaataat ttgggggcta    4680
actccatttg gtttccaaga tctcacttct gcattatctt tatggctctt taaaccagcc    4740
acctagccaa tcagggcaa  ttcccatctc atccatcact caggtctttg taaagggtgc    4800
agccaagctc tgcagacttt tgcaggattg tctagcctga gtaccgggct acttcttaaa    4860
```

```
tgccgtcact cctgctgaga taaatgcgtc tttaaaaata gtctctgtgg caggtcactg    4920
ggggacaatg tacagcattc tggccatcca cttcttttc acttcatgtt ctaccccaag    4980
agactcccga tgtcggctgt ggagggttaa agggatgagg ctttcctttg tttagcaaat    5040
ctgttcacag ttcttgatga tgtattttat gatgcccagc ttggaaatag ttgctttcca    5100
tagtctcaac tgtattgtgt catctcctga tgctgatttt tgatcttttg ttttattaaa    5160
aataattagt gaaagaggtg tgcctatctg tgaagtttgt agtacatcat cctgaggtca    5220
tgtaacaagt aaaccccaac ccagcgttcc ctcctacgtt gtgttagttc attaaaacta    5280
aataataaaa ataactgtaa gaaaaccta a                                    5311

<210> SEQ ID NO 144
<211> LENGTH: 2362
<212> TYPE: DNA
<213> ORGANISM: Homo sapiens

<400> SEQUENCE: 144
cactcagggc aagggtgtcc gacggctgga gcgttctgtt ttgaacccaa agtggatgat      60
gctgtcagag ctgaactact gaaaggaggc tgtgaaaatt tcccatcttc tcattggcca    120
tcagttgaga taagatggaa gactcttaca aggataggac ttcactgatg aagggtgcca    180
aggacattgc cagagaggtg aagaaacaaa cagtaaagaa ggtgaatcaa gctgtggacc    240
gagcccagga tgaatacacc cagaggtcct acagtcggtt ccaagatgaa gaagatgatg    300
atgactacta cccggctgga gaaacctata tggtgaggc caacgatgac gaaggctcaa    360
gtgaagccac tgaggggcat gatgaagatg atgagatcta tgagggggag tatcagggca    420
tccccagtat gaaccaagcg aaggacagca tcgtgtcagt ggggcagccc aagggcgatg    480
agtacaagga ccgacgggag ctggaatcag aaaggagagc tgacgaggaa gagttagccc    540
agcagtatga gctgataatc caagaatgcg gtcatggtcg ttttcagtgg gcccttttct    600
tcgtcctggg catggctctt atggcagacg tgtagaggt gtttgtcgtt ggcttcgtgt    660
tacccagtgc tgagacagac ctctgcatcc caaattcagg atctggatgg ctaggcagca    720
tagtgtacct cgggatgatg gtgggggcgt tcttctgggg aggactggca gacaaagtgg    780
gaaggaaaca gtctcttctg atttgcatgt ctgtcaacgg attctttgcc ttcctttctt    840
catttgtcca aggttatggc ttctttctct tctgtcgctt actttctgga ttcgggattg    900
gaggagccat acccactgtg ttctcgtact tgctgaagt cctggcccgg aaaagcggg    960 gcgaacactt gagctggctc tgcatgttct ggatgatcgg tggcatctac gcctctgcca   1020
tggcctgggc catcatcccg cactacgggt ggagcttcag catgggatcg gcctaccagt   1080
ttcacagttg gcgtgtgttt gtcatcgtct gtgcactccc ctgtgtctcc tccgtggtgg   1140
ccctcacatt catgcctgaa agcccacgat tcttgttgga ggttggaaaa catgatgaag   1200
cttggatgat tctgaagtta attcatgaca ccaacatgag agcccggggt cagcctgaga   1260
aggtcttcac ggtaaacaaa ataaaaactc ctaaacaaat agatgagctg attgaaattg   1320
agagtgacac aggaacatgg tataggaggt gttttgttcg gatccgcacc gagctgtacg   1380
gaatttggtt gactttatg agatgtttca actacccagt cagggataat acaataaagc   1440
ttacaattgt ttggttcacc ctgtcctttg ggtactatgg attatccgtt tggttccctg   1500
atgtcattaa acctctgcag tccgatgaat atgcattgct aaccagaaat gtggagagag   1560
ataaatatgc aaatttcact attaacttta caatggaaaa tcagattcat actggaatgg   1620
```

| | |
|---|---:|
| aatacgacaa tggcagattc ataggggtca agttcaaatc tgtaactttc aaagactctg | 1680 |
| tttttaagtc ctgcacctt gaggatgtaa cttcagtgaa cacctacttc aagaactgca | 1740 |
| catttattga cactgttttt gacaacacag attttgagcc atataaattc attgacagtg | 1800 |
| aatttaaaaa ctgctcgttt tttcacaaca agacggatg tcagattacc tttgatgatg | 1860 |
| actatagtgc ctactggatt tattttgtca actttctggg gacattggca gtattgccag | 1920 |
| ggaacattgt gtctgctctg ctgatggaca gaattgggcg cttaacaatg ctaggtggct | 1980 |
| ctatggtgct ttcggggatc agctgtttct tcctttggtt cggcaccagt gaatccatga | 2040 |
| tgataggcat gctgtgtctg tacaatggat tgaccatctc agcctggaac tctcttgacg | 2100 |
| tggtcactgt ggaactgtac cccacagacc ggagggcaac aggctttggc ttcttaaatg | 2160 |
| cgctatgcaa ggcagcagcc gtcctgggaa acttaatatt tggctctctg gtcagcatca | 2220 |
| ccaaatcaat ccccatcctg ctggcttcta ctgtgctcgt gtgtggagga ctcgttgggc | 2280 |
| tgtgcctgcc tgacacacga acccaggttc tgatgtaatg ggaaaaaaag ccatccttcc | 2340 |
| tgcgtttctt cctcctgccc tg | 2362 |

<210> SEQ ID NO 145
<211> LENGTH: 2053
<212> TYPE: DNA
<213> ORGANISM: Homo sapiens

<400> SEQUENCE: 145

| | |
|---|---:|
| catctttgat gagggcagag ctcacgttgc attgaagacg aaacctcggg gaggtcaggc | 60 |
| gctgtctttc cttccctccc tgctcggcgg ctccaccaca gttgcaacct gcagaggccc | 120 |
| ggagaacaca accctcccga gaagcccagg tccagagcca acccgtcac tgacccccca | 180 |
| gcccaggcgc ccagccactc cccaccgcta ccatggccga agacgcagac atgcgcaatg | 240 |
| agctggagga gatgcagcga agggctgacc agttggctga tgagtcgctg gaaagcaccc | 300 |
| gtcgtatgct gcaactggtt gaagagagta aagatgctgg tatcaggact ttggttatgt | 360 |
| tggatgaaca aggagaacaa ctcgatcgtg tcgaagaagg catgaaccat atcaaccaag | 420 |
| acatgaagga ggctgagaaa aatttaaaag atttagggaa atgctgtggc ctttttcatat | 480 |
| gtccttgtaa caagcttaaa tcaagtgatg cttacaaaaa agcctggggc aataatcagg | 540 |
| acggagtggt ggccagccag cctgctcgtg tagtggacga acgggagcag atggccatca | 600 |
| gtggcggctt catccgcagg gtaacaaatg atgcccgaga aaatgaaatg gatgaaaacc | 660 |
| tagagcaggt gagcggcatc atcgggaacc tccgtcacat ggccctggat atgggcaatg | 720 |
| agatcgatac acagaatcgc cagatcgaca ggatcatgga gaaggctgat tccaacaaaa | 780 |
| ccagaattga tgaggccaac caacgtgcaa caaagatgct gggaagtggt taagtgtgcc | 840 |
| cacccgtgtt ctcctccaaa tgctgtcggg caagatagct ccttcatgct tttctcatgg | 900 |
| tattatctag taggtctgca cacataacac acatcagtcc acccccattg tgaatgttgt | 960 |
| cctgtgtcat ctgtcagctt cccaacaata ctttgtgtct tttgttctct cttggtctct | 1020 |
| ttctttccaa aggttgtaca tagtggtcat ttggtggctc taactccttg atgtcttgag | 1080 |
| tttcattttt cattttctct cctcggtggc atttgctgaa taacaacaat ttaggaatgc | 1140 |
| tcaatgtgct gttgattctt tcaatccaca gtattgttct tgtaaaactg tgacattcca | 1200 |
| cagagttact gccacggtcc tttgagtgtc aggctctgaa tctctcaaaa tgtgccgtct | 1260 |
| ttggttcctc atggctgtta tctgtcttta tgatttcatg attagacaat gtggaattac | 1320 |
| ataacaggca ttgcactaaa agtgatgtga tttatgcatt tatgcatgag aactaaatag | 1380 |

```
atttttagat tcctacttaa acaaaaactt tccatgacag tagcatactg atgagacaac    1440
acacacacac acaaaacaac agcaacaaca acagaacaac aacaaagcat gctcagtatt    1500
gagacactgt caagattaag ttataccagc aaaagtgcag tagtgtcact ttttcctgt     1560 caatatatag agacttctaa atcataatca tccttttta aaaaaagaa ttttaaaaaa      1620 gatggatttg acacactcac catttaatca tttccagcaa aatatatgtt tggctgaaat    1680
tatgtcaaat ggatgtaata tagggtttgt ttgctgcttt tgatggctac gttttggaga    1740
gagcaatctt gctgtgaaac agtgtggatg taaattttat aaggctgact cttactaacc    1800
accatttccc ctgtggtttg ttatcagtac aattctttgt tgcttaatct agagctatgc    1860
acaccaaatt gctgagatgt ttagtagctg ataaagaaac cttttaaaaa aataatataa    1920
atgaatgaaa tataaactgt gagataaata tcattatagc atgtaatatt aaattcctcc    1980
tgtctcctct gtcagtttgt gaagtgattg acattttgta gctagtttaa aattattaaa    2040
aattatagac tcc                                                      2053
```

<210> SEQ ID NO 146
<211> LENGTH: 2053
<212> TYPE: DNA
<213> ORGANISM: Homo sapiens

<400> SEQUENCE: 146

```
catctttgat gagggcagag ctcacgttgc attgaagacg aaacctcggg gaggtcaggc      60
gctgtctttc cttccctccc tgctcggcgg ctccaccaca gttgcaacct gcagaggccc     120
ggagaacaca accctcccga gaagcccagg tccagagcca aacccgtcac tgacccccca     180
gcccaggcgc ccagccactc cccaccgcta ccatggccga agacgcagac atgcgcaatg     240
agctggagga gatgcagcga agggctgacc agttggctga tgagtcgctg aaagcaccc      300 gtcgtatgct gcaactggtt gaagagagta aagatgctgg tatcaggact ttggttatgt     360
tggatgaaca aggagaacaa ctggaacgca ttgaggaagg gatggaccaa atcaataagg     420
acatgaaaga agcagaaaag aatttgacgg acctaggaaa attctgcggg ctttgtgtgt     480
gtccctgtaa caagcttaaa tcaagtgatg cttacaaaaa agcctgggc aataatcagg      540 acggagtggt ggccagccag cctgctcgtg tagtggacga acgggagcag atggccatca     600
gtggcggctt catccgcagg gtaacaaatg atgcccgaga aaatgaaatg gatgaaaacc     660
tagagcaggt gagcggcatc atcgggaacc tccgtcacat ggccctggat atgggcaatg     720
agatcgatac acagaatcgc cagatcgaca ggatcatgga aaggctgat tccaacaaaa      780 ccagaattga tgaggccaac caacgtgcaa caaagatgct gggaagtggt taagtgtgcc     840
cacccgtgtt ctcctccaaa tgctgtcggg caagatagc ccttcatgct tttctcatgg      900
tattatctag taggtctgca cacataacac acatcagtcc acccccattg tgaatgttgt     960
cctgtgtcat ctgtcagctt cccaacaata ctttgtgtct tttgttctct cttggtctct    1020
ttctttccaa aggttgtaca tagtggtcat ttggtggctc taactccttg atgtcttgag    1080
tttcattttt cattttctct cctcggtggc atttgctgaa taacaacaat ttaggaatgc    1140
tcaatgtgct gttgattctt tcaatccaca gtattgttct tgtaaaactg tgacattcca    1200
cagagttact gccacggtcc tttgagtgtc aggctctgaa tctctcaaaa tgtgccgtct    1260
ttggttcctc atggctgtta tctgtctttta tgatttcatg attagacaat gtggaattac    1320
ataacaggca ttgcactaaa agtgatgtga tttatgcatt tatgcatgag aactaaatag    1380
```

```
attttagat tcctacttaa acaaaaactt tccatgacag tagcatactg atgagacaac    1440
acacacacac acaaaacaac agcaacaaca acagaacaac aacaaagcat gctcagtatt    1500
gagacactgt caagattaag ttataccagc aaaagtgcag tagtgtcact tttttcctgt    1560
caatatatag agacttctaa atcataatca tcctttttta aaaaaaagaa ttttaaaaaa    1620
gatggatttg acacactcac catttaatca tttccagcaa aatatatgtt tggctgaaat    1680
tatgtcaaat ggatgtaata tagggtttgt ttgctgcttt tgatggctac gttttggaga    1740
gagcaatctt gctgtgaaac agtgtggatg taaattttat aaggctgact cttactaacc    1800
accatttccc ctgtggtttg ttatcagtac aattctttgt tgcttaatct agagctatgc    1860
acaccaaatt gctgagatgt ttagtagctg ataaagaaac cttttaaaaa aataatataa    1920
atgaatgaaa tataaactgt gagataaata tcattatagc atgtaatatt aaattcctcc    1980
tgtctcctct gtcagtttgt gaagtgattg acattttgta gctagtttaa aattattaaa    2040
aattatagac tcc                                                       2053

<210> SEQ ID NO 147
<211> LENGTH: 5
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 147

Asp Glu Ala Asn Gln
1               5

<210> SEQ ID NO 148
<211> LENGTH: 6
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A
      cleavage site

<400> SEQUENCE: 148

Ile Asp Glu Ala Asn Gln
1               5
```

The invention claimed is:

1. A process for manufacturing a botulinum toxin serotype A (BoNT/A) pharmaceutical product, comprising:
   a. contacting a sample of a BoNT/A pharmaceutical formulation reconstituted with an aqueous solution with differentiated mammalian neuroblastoma cells susceptible to intoxication by about 10 pM or less of BoNT/A, wherein the susceptibility to intoxication is the lower limit of quantification of cleaved BoNT/A substrate as determined by Western blot; and
   b. releasing the BoNT/A pharmaceutical formulation as a BoNT/A pharmaceutical product.

2. The process of claim 1, further comprising a step of determining BoNT/A activity in the sample and releasing the BoNT/A pharmaceutical product if the BoNT/A activity in the sample matches the BoNT/A activity of an accepted reference.

3. The process of claim 2, wherein determining BoNT/A activity in the sample is accomplished by detecting disappearance of an intact synaptosomal-associated protein of 25 kDa (SNAP-25) polypeptide in the differentiated mammalian neuroblastoma cells.

4. The process of claim 3, wherein the SNAP-25 polypeptide is a non-naturally occurring SNAP-25 polypeptide.

5. The process of claim 4, wherein the non-naturally occurring SNAP-25 polypeptide comprises a fluorophore or a fluorescent protein.

6. The process of claim 1, wherein the differentiated mammalian neuroblastoma cells are susceptible to intoxication by about 1 pM or less of BoNT/A.

7. The process of claim 1, wherein the BoNT/A pharmaceutical formulation is sodium-free.

8. The process of claim 7, wherein the sodium chloride-free BoNT/A pharmaceutical formulation comprises a dose of a non-complexed about 150 kDa BoNT/A suitable for use as a human cosmetic or medicinal BoNT/A therapy.

9. The process of claim 8, wherein the sodium chloride-free BoNT/A pharmaceutical formulation further comprises a TAT-derived peptide delivery agent.

10. The process of claim 9, further comprising diluting the sample of the reconstituted BoNT/A pharmaceutical formulation such that the sample has a BoNT/A concentration of less than 1 pM.

11. The process of claim 1, wherein the mammalian neuroblastoma cells are Neuro-2a cells.

12. A process for manufacturing a botulinum toxin serotype A (BoNT/A) pharmaceutical product, comprising:
   a. mixing a sodium chloride-free BoNT/A pharmaceutical formulation with an aqueous solution to form a reconstituted BoNT/A pharmaceutical formulation, said sodium chloride-free BoNT/A pharmaceutical formulation comprising:
      i. a dose of a non-complexed about 150 kDa BoNT/A suitable for use as a human cosmetic or medicinal BoNT/A therapy, and
      ii. a TAT-derived peptide delivery agent;
   b. preparing a sample by diluting the reconstituted BoNT/A pharmaceutical formulation;
   c. contacting the sample with differentiated mammalian neuroblastoma cells susceptible to intoxication by about 10 pM or less of BoNT/A, wherein the susceptibility to intoxication is the lower limit of quantitation of cleaved BoNT/A substrate as determined by Western blot;
   d. determining BoNT/A activity in the sample; and
   e. releasing the sodium chloride-free BoNT/A pharmaceutical formulation as a BoNT/A pharmaceutical product.

13. The process of claim 12, further comprising a step of determining the BoNT/A activity in an accepted reference and releasing the BoNT/A pharmaceutical formulation as a BoNT/A pharmaceutical product if the BoNT/A activity in the sample matches the BoNT/A activity in the accepted reference.

14. The process of claim 12, wherein the dose comprises less than 1 ng of the non-complexed about 150 kDa BoNT/A.

15. The process of claim 13, wherein the concentration of the non-complexed about 150 kDa BoNT/A in the sample is about 1 pM or less.

16. The process of claim 12, wherein determining BoNT/A activity in the sample is accomplished by detecting disappearance of an intact SNAP-25 polypeptide in the differentiated mammalian neuroblastoma cells.

17. The process of claim 16, wherein the SNAP-25 polypeptide is a non-naturally occurring SNAP-25 polypeptide.

18. The process of claim 17, wherein the non-naturally occurring SNAP-25 polypeptide comprises a fluorophore or a fluorescent protein.

19. The process of claim 12, wherein the differentiated mammalian neuroblastoma cells are susceptible to intoxication by about 1 pM or less of BoNT/A.

20. The process of claim 12, wherein preparing the sample comprises diluting the reconstituted BoNT/A pharmaceutical formulation with cell culture media.

21. The process of claim 20, wherein the differentiated mammalian neuroblastoma cells are incubated in the sample for between about 24 and 72 hours.

22. The process of claim 19, wherein the mammalian neuroblastoma cells are Neuro-2a cells.

23. A product produced by the process of claim 12.
24. A product produced by the process of claim 13.
25. A product produced by the process of claim 15.
26. A product produced by the process of claim 18.
27. A product produced by the process of claim 19.
28. A product produced by the process of claim 20.
29. A product produced by the process of claim 21.
30. A product produced by the process of claim 22.

* * * * *